United States Patent
Kalish et al.

(10) Patent No.: US 10,723,704 B2
(45) Date of Patent: Jul. 28, 2020

(54) PYRAZOLONE DERIVATIVES AS NITROXYL DONORS

(71) Applicant: Cardioxyl Pharmaceuticals, Inc., Chapel Hill, NC (US)

(72) Inventors: Vincent Jacob Kalish, Annapolis, MD (US); Lisa Marie Frost, Abingdon (GB); Frederick Arthur Brookfield, Abingdon (GB); Stephen Martin Courtney, Abingdon (GB); Carl Leslie North, Abingdon (GB); Matthew Robert Conroy, Abingdon (GB)

(73) Assignee: Cardioxyl Pharmaceuticals, Inc., Chapel Hill, NC (US)

( * ) Notice: Subject to any disclaimer, the term of this patent is extended or adjusted under 35 U.S.C. 154(b) by 0 days.

(21) Appl. No.: 15/769,160

(22) PCT Filed: Oct. 18, 2016

(86) PCT No.: PCT/US2016/057475
§ 371 (c)(1),
(2) Date: Apr. 18, 2018

(87) PCT Pub. No.: WO2017/070081
PCT Pub. Date: Apr. 27, 2017

(65) Prior Publication Data
US 2018/0318308 A1     Nov. 8, 2018

Related U.S. Application Data

(60) Provisional application No. 62/243,296, filed on Oct. 19, 2015.

(51) Int. Cl.
| | |
|---|---|
| *C07D 231/46* | (2006.01) |
| *C07D 231/54* | (2006.01) |
| *C07D 491/048* | (2006.01) |
| *C07D 491/052* | (2006.01) |
| *C07D 498/04* | (2006.01) |
| *A61K 31/416* | (2006.01) |
| *A61K 31/4162* | (2006.01) |
| *C07D 231/22* | (2006.01) |
| *C07D 401/04* | (2006.01) |
| *C07D 405/06* | (2006.01) |
| *C07D 405/12* | (2006.01) |
| *C07D 471/04* | (2006.01) |
| *C07D 487/04* | (2006.01) |
| *C07D 498/10* | (2006.01) |
| *C07D 498/18* | (2006.01) |

(52) U.S. Cl.
CPC ......... *C07D 231/22* (2013.01); *C07D 231/46* (2013.01); *C07D 231/54* (2013.01); *C07D 401/04* (2013.01); *C07D 405/06* (2013.01); *C07D 405/12* (2013.01); *C07D 471/04* (2013.01); *C07D 487/04* (2013.01); *C07D 491/048* (2013.01); *C07D 491/052* (2013.01); *C07D 498/04* (2013.01); *C07D 498/10* (2013.01); *C07D 498/18* (2013.01)

(58) Field of Classification Search
CPC combination set(s) only.
See application file for complete search history.

(56) References Cited

U.S. PATENT DOCUMENTS

| | | |
|---|---|---|
| 6,936,639 B2 | 8/2005 | Wink et al. |
| 7,696,373 B2 | 4/2010 | King |
| 7,863,262 B2 | 1/2011 | Wink et al. |
| 7,989,652 B2 | 8/2011 | King |
| 8,268,890 B2 | 9/2012 | Wink et al. |
| 8,269,034 B2 | 9/2012 | King |
| 8,569,536 B2 | 10/2013 | King |
| 9,181,213 B2 | 11/2015 | Toscano et al. |
| 9,499,511 B2 | 11/2016 | Toscano et al. |
| 9,682,938 B2 * | 6/2017 | Kalish .................. C07D 403/04 |
| 9,862,699 B2 | 1/2018 | Toscano et al. |
| 2012/0201907 A1 | 8/2012 | Wink et al. |
| 2015/0004259 A1 | 1/2015 | Wink et al. |
| 2016/0228460 A1 | 8/2016 | Wink et al. |

FOREIGN PATENT DOCUMENTS

| | | |
|---|---|---|
| WO | WO 2005/074598 | 8/2005 |
| WO | WO 2007/002444 | 1/2007 |
| WO | WO 2007/109175 | 9/2007 |
| WO | WO 2009/042970 | 4/2009 |
| WO | WO 2009/137717 | 11/2009 |
| WO | WO 2011/063400 | 5/2011 |
| WO | WO 2011/071947 | 6/2011 |

(Continued)

OTHER PUBLICATIONS

Guthrie, D.A. et al., ""Catch-and-Release" of HNO with Pyrazolones", In the Journal of Organic Chemistry, vol. 80, No. 3, Jan. 16, 2015, pp. 1338-1348.
International Preliminary Report on Patentability dated Apr. 24, 2018 in International Application No. PCT/US2016/057475.
International Search Report and Written Opinion dated Feb. 8, 2017 in International Patent Application No. PCT/US2016/057475.

*Primary Examiner* — Amanda L. Aguirre
(74) *Attorney, Agent, or Firm* — Byrne Poh LLP; Nina R. Horan

(57) ABSTRACT

The disclosed subject matter provides pyrazolone derivative compounds, pharmaceutical compositions comprising such compounds, kits comprising such compounds, and methods of using such compounds or pharmaceutical compositions. In particular, the disclosed subject matter provides methods of using such compounds or pharmaceutical compositions for treating heart failure.

19 Claims, No Drawings

(56) References Cited

FOREIGN PATENT DOCUMENTS

| WO | WO 2011/071951 | 6/2011 | |
|---|---|---|---|
| WO | WO 2013/059194 | 4/2013 | |
| WO | WO-2013059191 A1 * | 4/2013 | ......... B01D 53/1406 |
| WO | WO 2014/070919 | 5/2014 | |
| WO | WO 2014/113696 | 7/2014 | |
| WO | WO 2014/113700 | 7/2014 | |
| WO | WO 2015/109210 | 7/2015 | |
| WO | WO 2015/183838 | 12/2015 | |
| WO | WO 2015/183839 | 12/2015 | |
| WO | WO-2015183839 A1 * | 12/2015 | |
| WO | WO 2016/210392 | 12/2016 | |
| WO | WO 2017/070084 | 4/2017 | |
| WO | WO 2018/022899 | 2/2018 | |

* cited by examiner

PYRAZOLONE DERIVATIVES AS NITROXYL DONORS

JOINT RESEARCH AGREEMENT

The disclosure and claims herein were made as a result of activities undertaken within the scope of a joint research agreement between Cardioxyl Pharmaceuticals, Inc. and The Johns Hopkins University that was in effect on or before the effective filing date of the claimed invention.

1. BACKGROUND

Nitroxyl (HNO) has been shown to have positive cardiovascular effects in in vitro and in vivo models of failing hearts. However, at physiological pH, nitroxyl dimerizes to hyponitrous acid, which subsequently dehydrates to nitrous oxide. Owing to this metastability, nitroxyl for therapeutic use is typically generated in situ from donor compounds. A variety of compounds capable of donating nitroxyl have been described and proposed for use in treating disorders known or suspected to be responsive to nitroxyl. See, e.g., U.S. Pat. Nos. 6,936,639, 7,696,373, 8,030,356, 8,268,890, 8,227,639, and 8,318,705, U.S. pre-grant publication nos. 2009/0281067, 2009/0298795, 2011/0136827, and 2011/0144067, PCT international publication no. WO 2013/059194, and Paolocci et al., Pharmacol. Therapeutics 113: 442-458 (2007). Although compounds in these references are disclosed to be capable of donating nitroxyl, they differ in various physicochemical properties and there remains a need to identify nitroxyl donors that have physicochemical properties best suited for treating specific clinical conditions via specific routes of administration.

Additionally, while nitroxyl donors for parenteral (e.g., intravenous) administration are currently being developed for clinical use, non-ideal solid state stability of the nitroxyl donors has impeded the development of oral dosage forms.

Accordingly, there is a need to provide nitroxyl donating compounds and compositions that are useful for the treatment of heart failure and that have a suitable safety profile. Moreover, there exists a need to provide nitroxyl donors that have increased solid state stability and, thus, are more amenable for oral administration.

Citation of any reference in Section 1 of this application is not to be construed as an admission that such reference is prior art to the present application.

2. SUMMARY OF THE DISCLOSURE

The present disclosure relates to pyrazolone derivative compounds, pharmaceutical compositions comprising such compounds, kits comprising such compounds, and methods of using such compounds or pharmaceutical compositions.

In a particular embodiment, a pyrazolone derivative compound of the disclosure is compound of formula (Ia)

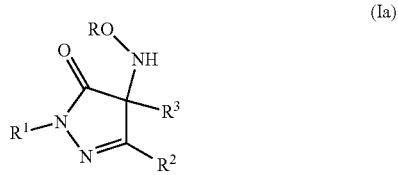

(Ia)

or a pharmaceutically acceptable salt thereof, wherein:
$R^1$ is phenyl, wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;
$R^4$, $R^5$, $R^6$ and $R^7$ are each independently H or $(C_1-C_6)$alkyl;
$R^8$ is H, —(C=O)(C$_1$-C$_6$)alkyl or —(C=O)(C$_1$-C$_4$)perhaloalkyl;
$R^2$ is $(C_1-C_6)$alkyl;
$R^3$ is —C(=NOR$^9$)R$^{10}$, wherein R$^9$ is (C$_1$-C$_6$)alkyl and R$^{10}$ is phenyl; and
R is hydrogen, —COH, —CO—(C$_1$-C$_6$)alkyl, —CO—(C$_2$-C$_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl or 5-methyl-2-oxo-2H-1,3-dioxol-4-ylmethyl.

In another particular embodiment, a pyrazolone derivative compound of the disclosure is compound of formula (Ib)

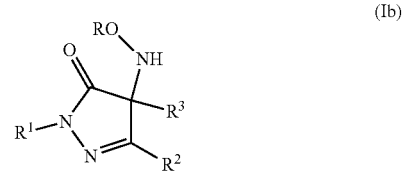

(Ib)

or a pharmaceutically acceptable salt thereof, wherein:
$R^1$ is H, (C$_1$-C$_6$)alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)O(5-methyl-2-oxo-2H-1,3-dioxol-4-ylmethyl), —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)

haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl;

R$^8$ is H, —(C=O)(C$_1$-C$_6$)alkyl or —(C=O)(C$_1$-C$_4$)perhaloalkyl;

R$^2$ is (C$_1$-C$_6$)alkyl or phenyl, wherein said alkyl and phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^3$ is (C$_1$-C$_6$)alkyl substituted with 1, 2 or 3 substituent(s) independently selected from —OH, —C(=O)OH, —C(=O)O(C$_1$-C$_6$)alkyl, —C(=O)O(5-methyl-2-oxo-2H-1,3-dioxol-4-ylmethyl), —C(=O)NR$^4$R$^5$, —NR$^4$R$^5$, (C$_1$-C$_6$)alkoxy, (C$_1$-C$_4$)haloalkoxy, (C$_1$-C$_4$)perhaloalkoxy, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, N—(C$_1$-C$_6$)alkylaminosulfonyl, N,N-di(C$_1$-C$_6$)alkylaminosulfonyl, (5- or 6-membered)heteroaryl or phenyl, wherein said heteroaryl or phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl; and R is hydrogen, —COH, —CO—(C$_1$-C$_6$)alkyl, —CO—(C$_2$-C$_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl or 5-methyl-2-oxo-2H-1,3-dioxol-4-ylmethyl.

In another particular embodiment, a pyrazolone derivative compound of the disclosure is compound of formula (Ic)

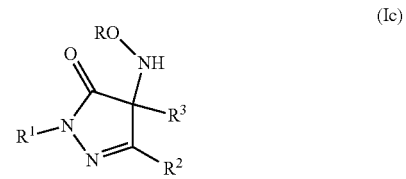

(Ic)

or a pharmaceutically acceptable salt thereof, wherein:

R$^1$ is H, (C$_1$-C$_6$)alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(5-methyl-2-oxo-2H-1,3-dioxol-4-ylmethyl), —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl;

R$^8$ is H, —(C=O)(C$_1$-C$_6$)alkyl or —(C=O)(C$_1$-C$_4$)perhaloalkyl;

R$^2$ is (C$_1$-C$_6$)alkyl substituted with 1, 2 or 3 substituent(s) independently selected from —OH, —C(=O)OH, —C(=O)O(C$_1$-C$_6$)alkyl, —C(=O)NR$^4$R$^5$, —NR$^4$R$^5$, (C$_1$-C$_6$)alkoxy, (C$_1$-C$_4$)haloalkoxy, (C$_1$-C$_4$)perhaloalkoxy, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, N—(C$_1$-C$_6$)alkylaminosulfonyl, N,N-di(C$_1$-C$_6$)alkylaminosulfonyl, (5- or 6-membered)heteroaryl or phenyl;

wherein said heteroaryl or phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-

$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl;

R$^4$, R$^5$, R$^6$ and R$^7$ are each independently H or ($C_1$-$C_6$)alkyl;

R$^8$ is H, —(C=O)($C_1$-$C_6$)alkyl or —(C=O)($C_1$-$C_4$)perhaloalkyl;

R$^3$ is ($C_1$-$C_6$)alkyl, (5- or 6-membered)heteroaryl, phenyl or —C(=NOR$^9$)R$^{10}$ wherein R$^9$ is ($C_1$-$C_6$)alkyl, ($C_1$-$C_6$)alkyl substituted with phenyl or phenyl and R$^{10}$ is selected from ($C_1$-$C_6$)alkyl; and R is hydrogen, —COH, —CO—($C_1$-$C_6$)alkyl, —CO—($C_2$-$C_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—($C_1$-$C_6$)alkyl, —CO—NH$_2$, —CO—NH—($C_1$-$C_4$)alkyl, or —CO—N(($C_1$-$C_4$)alkyl)$_2$, wherein said —($C_1$-$C_6$)alkyl, —($C_2$-$C_4$)alkenyl, phenyl, benzyl, cyclopentyl, cyclohexyl, -(5-, 6-, or 7-membered)heterocycloalkyl, benzyloxy, —O—($C_1$-$C_6$)alkyl, —NH—($C_1$-$C_4$)alkyl, or —N(($C_1$-$C_4$)alkyl)$_2$ can be unsubstituted or substituted with 1, 2 or 3 substituents selected from halo, —($C_1$-$C_6$)alkyl, —($C_2$-$C_4$)alkenyl, —($C_2$-$C_3$)alkynyl, -(5- or 6-membered)heteroaryl, —O—($C_1$-$C_6$)alkyl, —S—($C_1$-$C_6$)alkyl, —C(halo)$_3$, —CH(halo)$_2$, —CH$_2$(halo), —CN, —NO$_2$, —NH$_2$, —NH—($C_1$-$C_4$)alkyl, —N(—($C_1$-$C_4$)alkyl)$_2$, —C(O)($C_1$-$C_4$)alkyl, —C(O)O($C_1$-$C_4$)alkyl, —OC(O)($C_1$-$C_4$)alkyl, —OC(O)NH$_2$, —S(O)($C_1$-$C_4$)alkyl, —S(O)$_2$($C_1$-$C_4$)alkyl or 5-methyl-2-oxo-2H-1,3-dioxol-4-ylmethyl;

provided that when R$^1$ is H, R$^3$ is not ($C_1$-$C_6$)alkyl.

In another particular embodiment, a pyrazolone derivative compound of the disclosure is compound of formula (Id)

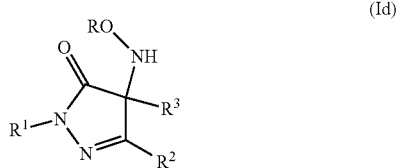

(Id)

or a pharmaceutically acceptable salt thereof, wherein:

R$^1$ is ($C_1$-$C_6$)alkyl substituted with 1, 2 or 3 substituent(s) independently selected from —OH, —C(=O)OH, —C(=O)O($C_1$-$C_6$)alkyl, —C(=O)O(5-methyl-2-oxo-2H-1,3-dioxol-4-ylmethyl), —C(=O)NR$^4$R$^5$, —NR$^4$R$^5$, ($C_1$-$C_6$)alkoxy, ($C_1$-$C_4$)haloalkoxy, ($C_1$-$C_4$)perhaloalkoxy, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$- phenyl, —S(O)$_2$-(5-, 6-, or 7-membered)heterocycloalkyl, —S(=O)(=NR$^8$)($C_1$-$C_6$)alkyl, N—($C_1$-$C_6$)alkylaminosulfonyl, N,N-di($C_1$-$C_6$)alkylaminosulfonyl, (5- or 6-membered)heteroaryl or phenyl, wherein said heteroaryl or phenyl are unsubstituted or substituted with 1, 2, 3, 4, or 5 substituent(s) independently selected from halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl;

R$^4$, R$^5$, R$^6$ and R$^7$ are each independently H or ($C_1$-$C_6$)alkyl;

R$^8$ is H, —(C=O)($C_1$-$C_6$)alkyl or —(C=O)($C_1$-$C_4$)perhaloalkyl;

R$^2$ is phenyl, wherein said phenyl is unsubstituted or substituted with 1, 2, 3, 4, or 5 substituent(s) independently selected from halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl;

R$^4$, R$^5$, R$^6$ and R$^7$ are each independently H or ($C_1$-$C_6$)alkyl;

R$^8$ is H, —(C=O)($C_1$-$C_6$)alkyl or —(C=O)($C_1$-$C_4$)perhaloalkyl;

R$^3$ is ($C_1$-$C_6$)alkyl, (5- or 6-membered)heteroaryl, phenyl or —C(=NOR$^9$)R$^{10}$ wherein R$^9$ is ($C_1$-$C_6$)alkyl, ($C_1$-$C_6$)alkyl substituted with phenyl or phenyl and R$^{10}$ is selected from ($C_1$-$C_6$)alkyl; and R is hydrogen, —COH, —CO—($C_1$-$C_6$)alkyl, —CO—($C_2$-$C_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—($C_1$-$C_6$)alkyl, —CO—NH$_2$, —CO—NH—($C_1$-$C_4$)alkyl, or —CO—N(($C_1$-$C_4$)alkyl)$_2$, wherein said —($C_1$-$C_6$)alkyl, —($C_2$-$C_4$)alkenyl, phenyl, benzyl, cyclopentyl, cyclohexyl, -(5-, 6-, or 7-membered)heterocycloalkyl, benzyloxy, —O—($C_1$-$C_6$)alkyl, —NH—($C_1$-$C_4$)alkyl, or —N(($C_1$-$C_4$)alkyl)$_2$ can be unsubstituted or substituted with 1, 2 or 3 substituents selected from halo, —($C_1$-$C_6$)alkyl, —($C_2$-$C_4$)alkenyl, —($C_2$-$C_3$)alkynyl, -(5- or 6-membered)heteroaryl, —O—($C_1$-$C_6$)alkyl, —S—($C_1$-$C_6$)alkyl, —C(halo)$_3$, —CH(halo)$_2$, —CH$_2$(halo), —CN, —NO$_2$, —NH$_2$, —NH—($C_1$-$C_4$)alkyl, —N(—($C_1$-$C_4$)alkyl)$_2$, —C(O)($C_1$-$C_4$)alkyl, —C(O)O($C_1$-$C_4$)alkyl, —OC(O)($C_1$-$C_4$)alkyl, —OC(O)NH$_2$, —S(O)($C_1$-$C_4$)alkyl, —S(O)$_2$($C_1$-$C_4$)alkyl or 5-methyl-2-oxo-2H-1,3-dioxol-4-ylmethyl;

provided that when R$^1$ is ($C_1$-$C_6$)alkyl substituted with —C(=O)OH and R$^3$ is ($C_1$-$C_6$)alkyl or —C(=NOR$^9$)R$^{10}$ and R$^9$ is ($C_1$-$C_6$)alkyl, R$^{10}$ is not ($C_1$-$C_6$)alkyl.

In another particular embodiment, a pyrazolone derivative compound of the disclosure is compound of formula (Ie)

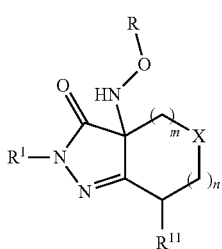

(Ie)

or a pharmaceutically acceptable salt thereof, wherein:

$R^1$ is H, $(C_1-C_6)$alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)O(5-methyl-2-oxo-2H-1,3-dioxol-4-ylmethyl), —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

X is CH$_2$, O, NH, N(C$_1$-C$_6$)alkyl, N(C=O)(C$_1$-C$_6$)alkyl, N(CO)phenyl, S, SO, or SO$_2$, wherein said phenyl is unsubstituted to substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

m is 0, 1, 2, 3, 4, or 5;

n is 0, 1, 2, 3, 4, or 5;

$R^{11}$ is H, (C$_1$-C$_6$)alkyl or phenyl, wherein said alkyl and said phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

$R^4$, $R^5$, $R^6$ and $R^7$ are each independently H or (C$_1$-C$_6$)alkyl; $R^8$ is H, —(C=O)(C$_1$-C$_6$)alkyl or —(C=O)(C$_1$-C$_4$)perhaloalkyl; and R is hydrogen, —COH, —CO—(C$_1$-C$_6$)alkyl, —CO—(C$_2$-C$_4$)alkenyl, —CO-phenyl, —CO-benzyl, —CO-cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl or 5-methyl-2-oxo-2H-1,3-dioxol-4-ylmethyl.

In another particular embodiment, a pyrazolone derivative compound of the disclosure is compound of formula (If)

(If)

or a pharmaceutically acceptable salt thereof, wherein:

$R^2$ is (C$_1$-C$_6$)alkyl or phenyl, wherein said phenyl is unsubstituted or substituted with 1, 2, 3, 4, or 5 substituent(s) independently selected from halo, cyano, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_6$-C$_{10}$)aryl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl, wherein said (5-, 6-, or 7-membered)heterocycloalkyl is unsubstituted or substituted with 1 or 2 substituent(s) independently selected from halo or (C$_1$-C$_6$)alkyl;

m is 1, 2 or 3; and

R is 5-methyl-2-oxo-2H-1,3-dioxol-4-ylmethyl.

In another particular embodiment, a pyrazolone derivative compound of the disclosure is compound of formula (Ig)

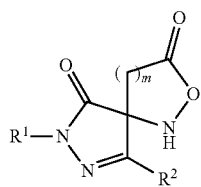

(Ig)

or a pharmaceutically acceptable salt thereof, wherein:
$R^1$ is H, $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)O(5-methyl-2-oxo-2H-1,3-dioxol-4-ylmethyl), —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl;

$R^4$, $R^5$, $R^6$ and $R^7$ are each independently H or $(C_1-C_6)$alkyl; and $R^8$ is H, —(C=O)$(C_1-C_6)$alkyl or —(C=O)$(C_1-C_4)$perhaloalkyl;

$R^2$ is $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl; and m is 1, 2 or 3.

In another particular embodiment, a pyrazolone derivative compound of the disclosure is compound of formula (Ih)

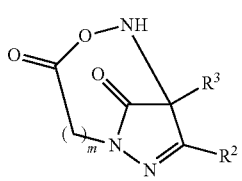

(Ih)

or a pharmaceutically acceptable salt thereof, wherein:
$R^2$ is $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl;

$R^4$, $R^5$, $R^6$ and $R^7$ are each independently H or $(C_1-C_6)$alkyl;

$R^8$ is H, —(C=O)$(C_1-C_6)$alkyl or —(C=O)$(C_1-C_4)$perhaloalkyl;

$R^3$ is $(C_1-C_6)$alkyl, (5- or 6-membered)heteroaryl, phenyl or —C(=NOR$^9$)R$^{10}$ wherein R$^9$ is $(C_1-C_6)$alkyl, $(C_1-C_6)$alkyl substituted with phenyl or phenyl and R$^{10}$ is selected from $(C_1-C_6)$alkyl; and m is 1, 2 or 3.

In another particular embodiment, a pyrazolone derivative compound of the disclosure is compound of formula (Ii)

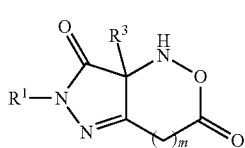

(Ii)

or a pharmaceutically acceptable salt thereof, wherein:
$R^1$ is H, $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)O(5-methyl-2-oxo-2H-1,3-dioxol-4-ylmethyl), —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl;

$R^4$, $R^5$, $R^6$ and $R^7$ are each independently H or $(C_1-C_6)$alkyl;

$R^8$ is H, —(C=O)$(C_1-C_6)$alkyl or —(C=O)$(C_1-C_4)$perhaloalkyl;

$R^3$ is $(C_1-C_6)$alkyl, (5- or 6-membered)heteroaryl, phenyl or —C(=NOR$^9$)R$^{10}$ wherein R$^9$ is $(C_1-C_6)$alkyl, $(C_1-C_6)$alkyl substituted with phenyl or phenyl and R$^{10}$ are independently selected from $(C_1-C_6)$alkyl; and m is 0, 1 or 2, wherein when m is 2, the lactone ring is optionally fused to a phenyl ring, wherein said fused phenyl ring is unsubstituted or substituted with 1, 2, 3, 4, or 5 substituent(s) independently selected from halo, $(C_1-C_6)$ alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1-C_6$)alkyl, —NR$^4$R$^5$, N—($C_1-C_6$)alkylaminosulfonyl, and N,N-di($C_1-C_6$)alkylaminosulfonyl.

In another particular embodiment, a pyrazolone derivative compound of the disclosure is compound of formula (Ij)

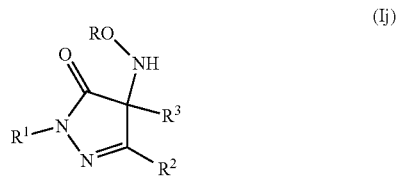

(Ij)

or a pharmaceutically acceptable salt thereof, wherein:
R$^1$ is ($C_1-C_6$)alkyl;
R$^2$ is phenyl, wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1-C_6$)alkyl, —NR$^4$R$^5$, N—($C_1-C_6$)alkylaminosulfonyl, and N,N-di($C_1-C_6$)alkylaminosulfonyl;

R$^4$, R$^5$, R$^6$ and R$^7$ are each independently H or ($C_1-C_6$)alkyl;
R$^8$ is H, —(C=O)($C_1-C_6$)alkyl or —(C=O)($C_1-C_4$)perhaloalkyl;
R$^3$ is ($C_1-C_6$)alkyl; and
R is 5-methyl-2-oxo-2H-1,3-dioxol-4-ylmethyl.

In another particular embodiment, a pyrazolone derivative compound of the disclosure is compound of formula (Ik)

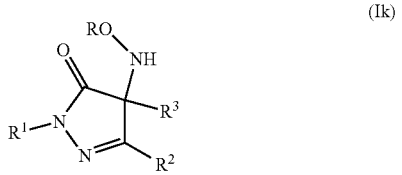

(Ik)

or a pharmaceutically acceptable salt thereof, wherein:
R$^1$ is (5-, 6- or 7-membered)heterocycloalkyl;
R$^2$ is phenyl, wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1-C_6$)alkyl, —NR$^4$R$^5$, N—($C_1-C_6$)alkylaminosulfonyl, and N,N-di($C_1-C_6$)alkylaminosulfonyl;

R$^4$, R$^5$, R$^6$ and R$^7$ are each independently H or ($C_1-C_6$)alkyl;
R$^8$ is H, —(C=O)($C_1-C_6$)alkyl or —(C=O)($C_1-C_4$)perhaloalkyl;
R$^3$ is ($C_1-C_6$)alkyl; and
R is hydrogen, —COH, —CO—($C_1-C_6$)alkyl, —CO—($C_2-C_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—($C_1-C_6$)alkyl, —CO—NH$_2$, —CO—NH—($C_1-C_4$)alkyl, or —CO—N(($C_1-C_4$)alkyl)$_2$, wherein said —($C_1-C_6$)alkyl, —($C_2-C_4$)alkenyl, phenyl, benzyl, cyclopentyl, cyclohexyl, -(5-, 6-, or 7-membered)heterocycloalkyl, benzyloxy, —O—($C_1-C_6$)alkyl, —NH—($C_1-C_4$)alkyl, or —N(($C_1-C_4$)alkyl)$_2$ can be unsubstituted or substituted with 1, 2 or 3 substituents selected from halo, —($C_1-C_6$)alkyl, —($C_2-C_4$)alkenyl, —($C_2-C_3$)alkynyl, -(5- or 6-membered)heteroaryl, —O—($C_1-C_6$)alkyl, —S—($C_1-C_6$)alkyl, —C(halo)$_3$, —CH(halo)$_2$, —CH$_2$(halo), —CN, —NO$_2$, —NH$_2$, —NH—($C_1-C_4$)alkyl, —N—($C_1-C_4$)alkyl)$_2$, —C(O)($C_1-C_4$)alkyl, —C(O)O($C_1-C_4$)alkyl, —OC(O)($C_1-C_4$)alkyl, —OC(O)NH$_2$, —S(O)($C_1-C_4$)alkyl, —S(O)$_2$($C_1-C_4$)alkyl or 5-methyl-2-oxo-2H-1,3-dioxol-4-ylmethyl.

3. DETAILED DESCRIPTION

The invention includes the following:
(1) A compound of formula (Ia)

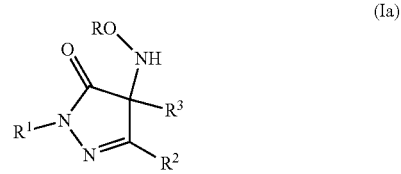

(Ia)

or a pharmaceutically acceptable salt thereof, wherein:
R$^1$ is phenyl, wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl;

R$^8$ is H, —(C=O)(C$_1$-C$_6$)alkyl or —(C=O)(C$_1$-C$_4$)perhaloalkyl;

R$^2$ is (C$_1$-C$_6$)alkyl;

R$^3$ is —C(=NOR$^9$)R$^{10}$, wherein R$^9$ is (C$_1$-C$_6$)alkyl and R$^{10}$ is phenyl; and R is hydrogen, —COH, —CO—(C$_1$-C$_6$)alkyl, —CO—(C$_2$-C$_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl or 5-methyl-2-oxo-2H-1,3-dioxol-4-ylmethyl.

(2) The compound of the above (1), wherein R$^1$ is unsubstituted phenyl.

(3) The compound of the above (1), wherein R$^1$ is phenyl substituted with 1, 2 or 3 independently selected substituent(s).

(4) The compound of any one of the above (1) to (3), wherein R$^2$ is (C$_1$-C$_4$)alkyl.

(5) The compound of the above (4), wherein R$^2$ is methyl.

(6) The compound of any one of the above (1) to (3), wherein R$^3$ is —C(=NOR$^9$)R$^{10}$ and R$^9$ is (C$_1$-C$_4$)alkyl.

(7) The compound of any one of the above (1) to (3), wherein R$^2$ is (C$_1$-C$_4$)alkyl and R$^3$ is —C(=NOR$^9$)R$^{10}$ and R$^9$ is (C$_1$-C$_4$)alkyl.

(8) The compound of the above (6), wherein R$^9$ is methyl.

(9) The compound of the above (7), wherein R$^9$ is methyl.

(10) The compound of any one of the above (1) to (3), wherein R is hydrogen, —CO—(C$_1$-C$_6$)alkyl, —CO-phenyl, —CO-benzyl, —CO—NH$_2$ or 5-methyl-2-oxo-2H-1,3-dioxol-4-ylmethyl.

(11) The compound of any one of the above (1) to (3), wherein R$^2$ is (C$_1$-C$_4$)alkyl and R is hydrogen, —CO—(C$_1$-C$_6$)alkyl, —CO-phenyl, —CO-benzyl, —CO—NH$_2$ or 5-methyl-2-oxo-2H-1,3-dioxol-4-ylmethyl.

(12) The compound of any one of the above (1) to (3), wherein R$^3$ is —C(=NOR$^9$)R$^{10}$, R$^9$ is (C$_1$-C$_4$)alkyl and R is hydrogen, —CO—(C$_1$-C$_6$)alkyl, —CO-phenyl, —CO-benzyl, —CO—NH$_2$ or 5-methyl-2-oxo-2H-1,3-dioxol-4-ylmethyl.

(13) The compound of any one of the above (1) to (3), wherein R$^2$ is (C$_1$-C$_4$)alkyl, R$^3$ is —C(=NOR$^9$)R$^{10}$, R$^9$ is (C$_1$-C$_4$)alkyl and R is hydrogen, —CO—(C$_1$-C$_6$)alkyl, —CO-phenyl, —CO-benzyl, —CO—NH$_2$ or 5-methyl-2-oxo-2H-1,3-dioxol-4-ylmethyl.

(14) The compound of any one of the above (1) to (3), wherein R is hydrogen.

(15) The compound of any one of the above (1) to (3), wherein R$^2$ is (C$_1$-C$_4$)alkyl and R is hydrogen.

(16) The compound of any one of the above (1) to (3), wherein R$^3$ is —C(=NOR$^9$)R$^{10}$, R$^9$ is (C$_1$-C$_4$)alkyl and R is hydrogen.

(17) The compound of any one of the above (1) to (3), wherein R$^2$ is (C$_1$-C$_4$)alkyl, R$^3$ is —C(=NOR$^9$)R$^{10}$, R$^9$ is (C$_1$-C$_4$)alkyl and R is hydrogen.

(18) A compound of formula (Ib)

(Ib)

or a pharmaceutically acceptable salt thereof, wherein:

R$^1$ is H, (C$_1$-C$_6$)alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)O(5-methyl-2-oxo-2H-1,3-dioxol-4-ylmethyl), —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl;

R$^8$ is H, —(C=O)(C$_1$-C$_6$)alkyl or —(C=O)(C$_1$-C$_4$)perhaloalkyl;

R$^2$ is (C$_1$-C$_6$)alkyl or phenyl, wherein said alkyl and phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^3$ is (C$_1$-C$_6$)alkyl substituted with 1, 2 or 3 substituent(s) independently selected from —OH, —C(=O)OH, —C(=O)O(C$_1$-C$_6$)alkyl, —C(=O)O(5-methyl-2-oxo-2H-1,3-dioxol-4-ylmethyl), —C(=O)NR$^4$R$^5$, —NR$^4$R$^5$, (C$_1$-C$_6$)alkoxy, (C$_1$-C$_4$)haloalkoxy, (C$_1$-C$_4$)perhaloalkoxy, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$-(5-, 6-, or 7-membered)heterocycloalkyl, —$S(=O)(=NR^8)(C_1-C_6)$alkyl, N—$(C_1-C_6)$alkylaminosulfonyl, N,N-di$(C_1-C_6)$alkylaminosulfonyl, (5- or 6-membered)heteroaryl or phenyl, wherein said heteroaryl or phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —$C(=O)OH$, —$C(=O)O(C_1-C_6)$alkyl, —$C(=O)NR^4R^5$, —$C(=O)$-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$-(5-, 6-, or 7-membered)heterocycloalkyl, —$S(=O)(=NR^8)(C_1-C_6)$alkyl, —$NR^4R^5$, N—$(C_1-C_6)$alkylaminosulfonyl, and N,N-di$(C_1-C_6)$alkylaminosulfonyl; and R is hydrogen, —COH, —CO—$(C_1-C_6)$alkyl, —CO—$(C_2-C_4)$alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—$(C_1-C_6)$alkyl, —CO—$NH_2$, —CO—NH—$(C_1-C_4)$alkyl, or —CO—N$((C_1-C_4)$alkyl$)_2$, wherein said —$(C_1-C_6)$alkyl, —$(C_2-C_4)$alkenyl, phenyl, benzyl, cyclopentyl, cyclohexyl, -(5-, 6-, or 7-membered)heterocycloalkyl, benzyloxy, —O—$(C_1-C_6)$alkyl, —NH—$(C_1-C_4)$alkyl, or —N$((C_1-C_4)$alkyl$)_2$ can be unsubstituted or substituted with 1, 2 or 3 substituents selected from halo, —$(C_1-C_6)$alkyl, —$(C_2-C_4)$alkenyl, —$(C_2-C_3)$alkynyl, -(5- or 6-membered)heteroaryl, —O—$(C_1-C_6)$alkyl, —S—$(C_1-C_6)$alkyl, —C(halo)$_3$, —CH(halo)$_2$, —$CH_2$(halo), —CN, —$NO_2$, —$NH_2$, —NH—$(C_1-C_4)$alkyl, —N(—$(C_1-C_4)$alkyl$)_2$, —$C(O)(C_1-C_4)$alkyl, —$C(O)O(C_1-C_4)$alkyl, —$OC(O)(C_1-C_4)$alkyl, —$OC(O)NH_2$, —$S(O)(C_1-C_4)$alkyl, —$S(O)_2(C_1-C_4)$alkyl or 5-methyl-2-oxo-2H-1,3-dioxol-4-ylmethyl.

(19) The compound of the above (18), wherein $R^1$ is H, $(C_1-C_4)$alkyl or unsubstituted phenyl.
(20) The compound of the above (19), wherein $R^1$ is H.
(21) The compound of the above (19), wherein $R^1$ is $(C_1-C_4)$alkyl.
(22) The compound of the above (19), wherein $R^1$ is methyl.
(23) The compound of the above (19), wherein $R^1$ is unsubstituted phenyl.
(24) The compound of any one of the above (18) to (23), wherein $R^2$ is $(C_1-C_4)$alkyl.
(25) The compound of the above (24), wherein $R^2$ is methyl.
(26) The compound of any one of the above (18) to (23), wherein $R^2$ is phenyl, wherein said phenyl is unsubstituted or substituted with 1, 2 or 3 independently selected substituent(s).
(27) The compound of the above (26), wherein the substituent(s) is selected from $(C_1-C_6)$alkylsulfanyl, $(C_1-C_6)$alkylsulfinyl, $(C_1-C_6)$alkylsulfonyl, —$S(O)_2$—$NH_2$, —$S(O)_2$—$NR^6R^7$, N—$(C_1-C_6)$alkylaminosulfonyl, and N,N-di$(C_1-C_6)$alkylaminosulfonyl.
(28) The compound of any one of the above (18) to (23), wherein $R^3$ is $(C_1-C_4)$alkyl substituted with $C(=O)OH$, —$C(=O)O(C_1-C_6)$alkyl, —$C(=O)O(5$-methyl-2-oxo-2H-1,3-dioxol-4-ylmethyl) or OH.
(29) The compound of the above (28), wherein $R^3$ is $(C_1-C_2)$alkyl substituted with $C(=O)OH$, —$C(=O)O(C_1-C_6)$alkyl, —$C(=O)O(5$-methyl-2-oxo-2H-1,3-dioxol-4-ylmethyl), or OH.
(30) The compound any one of the above (18) to (23), wherein $R^2$ is $(C_1-C_4)$alkyl and $R^3$ is $(C_1-C_4)$alkyl substituted with $C(=O)OH$, —$C(=O)O(C_1-C_6)$alkyl, —$C(=O)O(5$-methyl-2-oxo-2H-1,3-dioxol-4-ylmethyl), or OH.
(31) The compound of the above (30), wherein $R^3$ is $(C_1-C_2)$alkyl substituted with $C(=O)OH$, —$C(=O)O(C_1-C_6)$alkyl, —$C(=O)O(5$-methyl-2-oxo-2H-1,3-dioxol-4-ylmethyl), or OH.
(32) The compound of any one of the above (18) to (23), wherein R is hydrogen, —CO—$(C_1-C_6)$alkyl, —CO-phenyl, —CO-benzyl, —CO—$NH_2$ or 5-methyl-2-oxo-2H-1,3-dioxol-4-ylmethyl.
(33) The compound of any one of the above (18) to (23), wherein $R^2$ is $(C_1-C_4)$alkyl and R is hydrogen, —CO—$(C_1-C_6)$alkyl, —CO-phenyl, —CO-benzyl, —CO—$NH_2$ or 5-methyl-2-oxo-2H-1,3-dioxol-4-ylmethyl.
(34) The compound of any one of the above (18) to (23), wherein $R^3$ is $(C_1-C_4)$alkyl substituted with $C(=O)OH$, —$C(=O)O(C_1-C_6)$alkyl or OH and R is hydrogen, —CO—$(C_1-C_6)$alkyl, —CO-phenyl, —CO— benzyl, —CO—$NH_2$ or 5-methyl-2-oxo-2H-1,3-dioxol-4-ylmethyl.
(35) The compound of any one of the above (18) to (23), wherein $R^2$ is $(C_1-C_4)$alkyl, $R^3$ is $(C_1-C_4)$alkyl substituted $C(=O)OH$, —$C(=O)O(C_1-C_6)$alkyl or OH and R is hydrogen, —CO—$(C_1-C_6)$alkyl, —CO-phenyl, —CO-benzyl, —CO—$NH_2$ or 5-methyl-2-oxo-2H-1,3-dioxol-4-ylmethyl.
(36) The compound of the above any one of the above (18) to (23), wherein R is hydrogen.
(37) The compound of any one of the above (18) to (23), wherein $R^2$ is $(C_1-C_4)$alkyl and R is hydrogen.
(38) The compound of any one of the above (18) to (23), wherein $R^3$ is $(C_1-C_4)$alkyl substituted with $C(=O)OH$, —$C(=O)O(C_1-C_6)$alkyl, —$C(=O)O(5$-methyl-2-oxo-2H-1,3-dioxol-4-ylmethyl) or OH and R is hydrogen.
(39) The compound of any one of the above (18) to (23), wherein $R^2$ is $(C_1-C_4)$alkyl, $R^3$ is $(C_1-C_4)$alkyl substituted with $C(=O)OH$, —$C(=O)O(C_1-C_6)$alkyl, —$C(=O)O(5$-methyl-2-oxo-2H-1,3-dioxol-4-ylmethyl) or OH and R is hydrogen.
(40) A compound of formula (Ic)

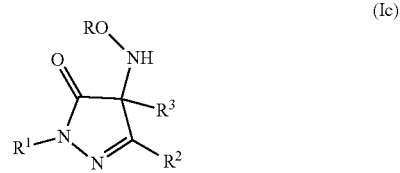

or a pharmaceutically acceptable salt thereof, wherein:
$R^1$ is H, $(C_1-C_6)$alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —$C(=O)OH$, —$C(=O)O$ (5-methyl-2-oxo-2H-1,3-dioxol-4-ylmethyl), —$C(=O)O$ $(C_1-C_6)$alkyl, —$C(=O)NR^4R^5$, —$C(=O)$-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-$ C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(═O)(═NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl;

R$^8$ is H, —(C═O)(C$_1$-C$_6$)alkyl or —(C═O)(C$_1$-C$_4$)perhaloalkyl;

R$^2$ is (C$_1$-C$_6$)alkyl substituted with 1, 2 or 3 substituent(s) independently selected from —OH, —C(═O)OH, —C(═O)O(C$_1$-C$_6$)alkyl, —C(═O)NR$^4$R$^5$, —NR$^4$R$^5$, (C$_1$-C$_6$)alkoxy, (C$_1$-C$_4$)haloalkoxy, (C$_1$-C$_4$)perhaloalkoxy, —C(═O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(═O)(═NR$^8$)(C$_1$-C$_6$)alkyl, N—(C$_1$-C$_6$)alkylaminosulfonyl, N,N-di(C$_1$-C$_6$)alkylaminosulfonyl, (5- or 6-membered)heteroaryl or phenyl;

wherein said heteroaryl or phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(═O)OH, —C(═O)O(C$_1$-C$_6$)alkyl, —C(═O)NR$^4$R$^5$, —C(═O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(═O)(═NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl;

R$^8$ is H, —(C═O)(C$_1$-C$_6$)alkyl or —(C═O)(C$_1$-C$_4$)perhaloalkyl;

R$^3$ is (C$_1$-C$_6$)alkyl, (5- or 6-membered)heteroaryl, phenyl or —C(═NOR$^9$)R$^{10}$ wherein R$^9$ is (C$_1$-C$_6$)alkyl, (C$_1$-C$_6$)alkyl substituted with phenyl or phenyl and R$^{10}$ is selected from (C$_1$-C$_6$)alkyl; and R is hydrogen, —COH, —CO—(C$_1$-C$_6$)alkyl, —CO—(C$_2$-C$_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl or 5-methyl-2-oxo-2H-1,3-dioxol-4-ylmethyl;

provided that when R$^1$ is H, R$^3$ is not (C$_1$-C$_6$)alkyl.

(41) The compound of the above (40), wherein R$^1$ is H or (C$_1$-C$_6$)alkyl.

(42) The compound of the above (40), wherein R$^1$ is H.

(43) The compound of the above (40), wherein R$^1$ is (C$_1$-C$_4$)alkyl.

(44) The compound of the above (40), wherein R$^1$ is methyl.

(45) The compound of any one of the above (40) to (44), wherein R$^2$ is (C$_1$-C$_4$)alkyl substituted with a substituent selected from —OH, —C(═O)OH, —C(═O)O(C$_1$-C$_6$)alkyl, —C(═O)NR$^4$R$^5$, —NR$^4$R$^5$, (C$_1$-C$_6$)alkoxy, (C$_1$-C$_4$)haloalkoxy, (C$_1$-C$_4$)perhaloalkoxy, —C(═O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(═O)(═NR$^8$)(C$_1$-C$_6$)alkyl, N—(C$_1$-C$_6$)alkylaminosulfonyl, N,N-di(C$_1$-C$_6$)alkylaminosulfonyl, (5- or 6-membered)heteroaryl or phenyl.

(46) The compound of the above (45), wherein R$^2$ is (C$_1$-C$_2$)alkyl substituted with a substituent selected from —OH, —C(═O)OH, —C(═O)O(C$_1$-C$_6$)alkyl, —C(═O)NR$^4$R$^5$, —NR$^4$R$^5$, (C$_1$-C$_6$)alkoxy, (C$_1$-C$_4$)haloalkoxy, (C$_1$-C$_4$)perhaloalkoxy, —C(═O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(═O)(═NR$^8$)(C$_1$-C$_6$)alkyl, N—(C$_1$-C$_6$)alkylaminosulfonyl, N,N-di(C$_1$-C$_6$)alkylaminosulfonyl, (5- or 6-membered)heteroaryl or phenyl.

(47) The compound of the above (46), wherein R$^2$ is (C$_1$-C$_2$)alkyl substituted with (5- or 6-membered)heteroaryl or phenyl.

(48) The compound of any one of the above (40) to (44), wherein R$^3$ is (C$_1$-C$_6$)alkyl.

(49) The compound of the above (48), wherein R$^3$ is (C$_1$-C$_4$)alkyl.

(50) The compound of the above (49), wherein R$^3$ is methyl.

(51) The compound of any one of the above (40) to (44), wherein R$^2$ is (C$_1$-C$_2$)alkyl substituted with (5- or 6-membered)heteroaryl or phenyl and R$^3$ is (C$_1$-C$_6$)alkyl.

(52) The compound of the above (51), wherein R$^3$ is (C$_1$-C$_4$)alkyl.

(53) The compound of the above (52), wherein R$^3$ is methyl.

(54) The compound of any one of the above (40) to (44), wherein R is hydrogen, —CO—(C$_1$-C$_6$)alkyl, —CO-phenyl, —CO-benzyl, —CO—NH$_2$ or 5-methyl-2-oxo-2H-1,3-dioxol-4-ylmethyl.

(55) The compound of any one of the above (40) to (44), wherein R$^2$ is (C$_1$-C$_2$)alkyl substituted with (5- or 6-membered)heteroaryl or phenyl; and R is hydrogen, —CO—(C$_1$-C$_6$)alkyl, —CO-phenyl, —CO— benzyl, —CO—NH$_2$ or 5-methyl-2-oxo-2H-1,3-dioxol-4-ylmethyl.

(56) The compound of any one of the above (40) to (44), wherein R$^3$ is (C$_1$-C$_6$)alkyl; and R is hydrogen, —CO—(C$_1$-

$C_6$)alkyl, —CO-phenyl, —CO-benzyl, —CO—$NH_2$ or 5-methyl-2-oxo-2H-1,3-dioxol-4-ylmethyl.

(57) The compound of any one of the above (40) to (44), wherein $R^2$ is ($C_1$-$C_2$)alkyl substituted with (5- or 6-membered)heteroaryl or phenyl; $R^3$ is ($C_1$-$C_6$)alkyl; and R is hydrogen, —CO—($C_1$-$C_6$)alkyl, —CO— phenyl, —CO-benzyl, —CO—$NH_2$ or 5-methyl-2-oxo-2H-1,3-dioxol-4-ylmethyl.

(58) The compound of the above any one of the above (40) to (44), wherein R is hydrogen.

(59) The compound of any one of the above (40) to (44), wherein $R^2$ is ($C_1$-$C_2$)alkyl substituted with (5- or 6-membered)heteroaryl or phenyl; and R is hydrogen.

(60) The compound of any one of the above (40) to (44), wherein $R^3$ is ($C_1$-$C_6$)alkyl and R is hydrogen.

(61) The compound of any one of the above (40) to (44), wherein $R^2$ is ($C_1$-$C_2$)alkyl substituted with (5- or 6-membered)heteroaryl or phenyl; $R^3$ is ($C_1$-$C_6$)alkyl; and R is hydrogen.

(62) A compound of formula (Id)

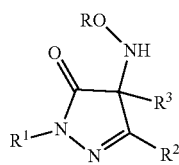

(Id)

or a pharmaceutically acceptable salt thereof, wherein:
$R^1$ is ($C_1$-$C_6$)alkyl substituted with 1, 2 or 3 substituent(s) independently selected from —OH, —C(=O)OH, —C(=O)O($C_1$-$C_6$)alkyl, —C(=O)O(5-methyl-2-oxo-2H-1,3-dioxol-4-ylmethyl), —C(=O)$NR^4R^5$, —$NR^4R^5$, ($C_1$-$C_6$)alkoxy, ($C_1$-$C_4$)haloalkoxy, ($C_1$-$C_4$)perhaloalkoxy, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1$-$C_6$)alkyl, N—($C_1$-$C_6$)alkylaminosulfonyl, N,N-di($C_1$-$C_6$)alkylaminosulfonyl, (5- or 6-membered)heteroaryl or phenyl, wherein said heteroaryl or phenyl are unsubstituted or substituted with 1, 2, 3, 4, or 5 substituent(s) independently selected from halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)$NR^4R^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1$-$C_6$)alkyl, —$NR^4R^5$, N—($C_1$-$C_6$)alkylaminosulfonyl, and N,N-di($C_1$-$C_6$)alkylaminosulfonyl;

$R^4$, $R^5$, $R^6$ and $R^7$ are each independently H or ($C_1$-$C_6$) alkyl;

$R^8$ is H, —(C=O)($C_1$-$C_6$)alkyl or —(C=O)($C_1$-$C_4$)perhaloalkyl;

$R^2$ is phenyl, wherein said phenyl is unsubstituted or substituted with 1, 2, 3, 4, or 5 substituent(s) independently selected from halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)$NR^4R^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1$-$C_6$)alkyl, —$NR^4R^5$, N—($C_1$-$C_6$)alkylaminosulfonyl, and N,N-di($C_1$-$C_6$)alkylaminosulfonyl;

$R^4$, $R^5$, $R^6$ and $R^7$ are each independently H or ($C_1$-$C_6$) alkyl;

$R^8$ is H, —(C=O)($C_1$-$C_6$)alkyl or —(C=O)($C_1$-$C_4$)perhaloalkyl;

$R^3$ is ($C_1$-$C_6$)alkyl, (5- or 6-membered)heteroaryl, phenyl or —C(=$NOR^9$)$R^{10}$ wherein $R^9$ is ($C_1$-$C_6$)alkyl, ($C_1$-$C_6$)alkyl substituted with phenyl or phenyl and $R^{10}$ is selected from ($C_1$-$C_6$)alkyl; and R is hydrogen, —COH, —CO—($C_1$-$C_6$)alkyl, —CO—($C_2$-$C_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—($C_1$-$C_6$)alkyl, —CO—$NH_2$, —CO—NH—($C_1$-$C_4$)alkyl, or —CO—N(($C_1$-$C_4$)alkyl)$_2$, wherein said —($C_1$-$C_6$)alkyl, —($C_2$-$C_4$)alkenyl, phenyl, benzyl, cyclopentyl, cyclohexyl, -(5-, 6-, or 7-membered)heterocycloalkyl, benzyloxy, —O—($C_1$-$C_6$) alkyl, —NH—($C_1$-$C_4$)alkyl, or —N(($C_1$-$C_4$)alkyl)$_2$ can be unsubstituted or substituted with 1, 2 or 3 substituents selected from halo, —($C_1$-$C_6$)alkyl, —($C_2$-$C_4$)alkenyl, —($C_2$-$C_3$)alkynyl, -(5- or 6-membered)heteroaryl, —O—($C_1$-$C_6$)alkyl, —S—($C_1$-$C_6$)alkyl, —C(halo)$_3$, —CH(halo)$_2$, —CH$_2$(halo), —CN, —NO$_2$, —NH$_2$, —NH—($C_1$-$C_4$)alkyl, —N(—($C_1$-$C_4$)alkyl)$_2$, —C(O)($C_1$-$C_4$)alkyl, —C(O)O($C_1$-$C_4$)alkyl, —OC(O)($C_1$-$C_4$)alkyl, —OC(O)$NH_2$, —S(O)($C_1$-$C_4$)alkyl, —S(O)$_2$($C_1$-$C_4$)alkyl or 5-methyl-2-oxo-2H-1,3-dioxol-4-ylmethyl provided that when $R^1$ is ($C_1$-$C_6$)alkyl substituted with —C(=O)OH and $R^3$ is ($C_1$-$C_6$)alkyl or —C(=$NOR^9$)$R^{10}$ and $R^9$ is ($C_1$-$C_6$)alkyl, $R^{10}$ is not ($C_1$-$C_6$)alkyl.

(63) The compound of the above (62), wherein $R^1$ is ($C_1$-$C_4$)alkyl substituted with a substituent selected from —OH, —C(=O)OH, —C(=O)O($C_1$-$C_6$)alkyl, —C(=O)O(5-methyl-2-oxo-2H-1,3-dioxol-4-ylmethyl), —C(=O)$NR^4R^5$, (5-, 6-, or 7-membered)heterocycloalkyl, (5- or 6-membered)heteroaryl or phenyl.

(64) The compound of the above (62), wherein $R^1$ is ($C_1$-$C_2$)alkyl substituted with a substituent selected from —OH, —C(=O)OH, —C(=O)O($C_1$-$C_6$)alkyl, —C(=O)O(5-methyl-2-oxo-2H-1,3-dioxol-4-ylmethyl), —C(=O)$NR^4R^5$, (5-, 6-, or 7-membered)heterocycloalkyl, (5- or 6-membered)heteroaryl or phenyl.

(65) The compound of the above (62), wherein $R^1$ is ($C_1$-$C_2$)alkyl substituted with —C(=O)O($C_1$-$C_6$)alkyl, —C(=O)O(5-methyl-2-oxo-2H-1,3-dioxol-4-ylmethyl), (5-, 6-, or 7-membered)heterocycloalkyl or —C(=O)$NR^4R^5$.

(66) The compound of the above (62), wherein $R^1$ is ($C_1$) alkyl substituted with —C(=O)O($C_1$-$C_4$)alkyl.

(67) The compound of the above (62), wherein $R^1$ is $(C_1)$ alkyl substituted with —C(=O)$NR^4R^5$.
(68) The compound of the above (62), wherein $R^1$ is $(C_1)$ alkyl substituted with —C(=O)O(5-methyl-2-oxo-2H-1,3-dioxol-4-ylmethyl).
(69) The compound of the above (62), wherein $R^1$ is $(C_1)$ alkyl substituted with (5-, 6-, or 7-membered)heterocycloalkyl.
(70) The compound of any one of the above (62) to (69), wherein $R^2$ is unsubstituted phenyl or phenyl substituted with 1, 2 or 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, —C(=O)OH, —C(=O)O$(C_1-C_6)$alkyl, —C(=O)$NR^4R^5$, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, —S(O)$_2$—$NH_2$, —S(O)$_2$—$NR^6R^7$, —$NR^4R^5$, N—$(C_1-C_6)$alkylaminosulfonyl, and N,N-di$(C_1-C_6)$alkylaminosulfonyl.
(71) The compound of the above (70), wherein $R^2$ is unsubstituted phenyl or phenyl substituted with a substituent selected from $(C_1-C_6)$alkylsulfanyl, $(C_1-C_6)$alkylsulfinyl, $(C_1-C_6)$alkylsulfonyl, —S(O)$_2$—$NH_2$, —S(O)$_2$—$NR^6R^7$, N—$(C_1-C_6)$alkylaminosulfonyl, and N,N-di$(C_1-C_6)$alkylaminosulfonyl.
(72) The compound of any one of the above (62) to (69), wherein $R^3$ is $(C_1-C_6)$alkyl.
(73) The compound of the above (72), wherein $R^3$ is methyl.
(74) The compound of any one of the above (62) to (69), wherein $R^2$ is unsubstituted phenyl or phenyl substituted with a substituent selected from $(C_1-C_6)$alkylsulfanyl, $(C_1-C_6)$alkylsulfinyl, $(C_1-C_6)$alkylsulfonyl, —S(O)$_2$—$NH_2$, —S(O)$_2$—$NR^6R^7$, N—$(C_1-C_6)$alkylaminosulfonyl, and N,N-di$(C_1-C_6)$alkylaminosulfonyl; and $R^3$ is $(C_1-C_6)$alkyl.
(75) The compound of any one of the above (62) to (69), wherein $R^2$ is unsubstituted phenyl or phenyl substituted with a substituent selected from $(C_1-C_6)$alkylsulfanyl, $(C_1-C_6)$alkylsulfinyl, $(C_1-C_6)$alkylsulfonyl, —S(O)$_2$—$NH_2$, —S(O)$_2$—$NR^6R^7$, N—$(C_1-C_6)$alkylaminosulfonyl, and N,N-di$(C_1-C_6)$alkylaminosulfonyl; and $R^3$ is methyl.
(76) The compound of any one of the above (62) to (69), wherein R is hydrogen, —CO—$(C_1-C_6)$alkyl, —CO-phenyl, —CO-benzyl, —CO—$NH_2$ or 5-methyl-2-oxo-2H-1,3-dioxol-4-ylmethyl.
(77) The compound of any one of the above (62) to (69), wherein $R^2$ is unsubstituted phenyl or phenyl substituted with a substituent selected from $(C_1-C_6)$alkylsulfanyl, $(C_1-C_6)$alkylsulfinyl, $(C_1-C_6)$alkylsulfonyl, —S(O)$_2$—$NH_2$, —S(O)$_2$—$NR^6R^7$, N—$(C_1-C_6)$alkylaminosulfonyl, and N,N-di$(C_1-C_6)$alkylaminosulfonyl; and R is hydrogen, —CO—$(C_1-C_6)$alkyl, —CO-phenyl, —CO-benzyl, —CO—$NH_2$ or 5-methyl-2-oxo-2H-1,3-dioxol-4-ylmethyl.
(78) The compound of any one of the above (62) to (69), wherein $R^3$ is $(C_1-C_6)$alkyl; and R is hydrogen, —CO—$(C_1-C_6)$alkyl, —CO-phenyl, —CO-benzyl, —CO—$NH_2$ or 5-methyl-2-oxo-2H-1,3-dioxol-4-ylmethyl.
(79) The compound of any one of the above (62) to (69), wherein $R^2$ is unsubstituted phenyl or phenyl substituted with a substituent selected from $(C_1-C_6)$alkylsulfanyl, $(C_1-C_6)$alkylsulfinyl, $(C_1-C_6)$alkylsulfonyl, —S(O)$_2$—$NH_2$, —S(O)$_2$—$NR^6R^7$, N—$(C_1-C_6)$alkylaminosulfonyl, and N,N-di$(C_1-C_6)$alkylaminosulfonyl; $R^3$ is $(C_1-C_6)$alkyl; and R is hydrogen, —CO—$(C_1-C_6)$alkyl, —CO-phenyl, —CO— benzyl, —CO—$NH_2$ or 5-methyl-2-oxo-2H-1,3-dioxol-4-ylmethyl.
(80) The compound of any one of the above (62) to (69), wherein R is hydrogen.
(81) The compound of any one of the above (62) to (69), wherein $R^2$ is unsubstituted phenyl or phenyl substituted with a substituent selected from $(C_1-C_6)$alkylsulfanyl, $(C_1-C_6)$alkylsulfinyl, $(C_1-C_6)$alkylsulfonyl, —S(O)$_2$—$NH_2$, —S(O)$_2$—$NR^6R^7$, N—$(C_1-C_6)$alkylaminosulfonyl, and N,N-di$(C_1-C_6)$alkylaminosulfonyl; and R is hydrogen.
(82) The compound of any one of the above (62) to (69), wherein $R^3$ is $(C_1-C_6)$alkyl; and R is hydrogen.
(83) The compound of any one of the above (62) to (69), wherein $R^2$ is unsubstituted phenyl or phenyl substituted with a substituent selected from $(C_1-C_6)$alkylsulfanyl, $(C_1-C_6)$alkylsulfinyl, $(C_1-C_6)$alkylsulfonyl, —S(O)$_2$—$NH_2$, —S(O)$_2$—$NR^6R^7$, N—$(C_1-C_6)$alkylaminosulfonyl, and N,N-di$(C_1-C_6)$alkylaminosulfonyl; $R^3$ is $(C_1-C_6)$alkyl; and R is hydrogen.
(84) A compound of formula (Ie)

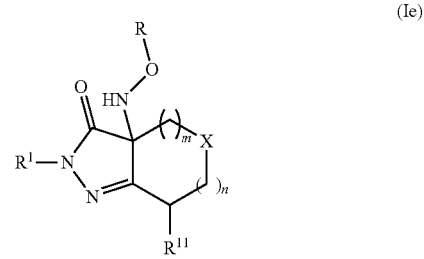

(Ie)

or a pharmaceutically acceptable salt thereof, wherein:
$R^1$ is H, $(C_1-C_6)$alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)O(5-methyl-2-oxo-2H-1,3-dioxol-4-ylmethyl), —C(=O)$NR^4R^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)$(C_1-C_6)$alkyl, —$NR^4R^5$, N—$(C_1-C_6)$alkylaminosulfonyl, and N,N-di$(C_1-C_6)$alkylaminosulfonyl;
X is $CH_2$, O, NH, N$(C_1-C_6)$alkyl, N(C=O)$(C_1-C_6)$alkyl, N(CO)phenyl, S, SO, or $SO_2$, wherein said phenyl is unsubstituted to substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)$NR^4R^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)$(C_1-C_6)$alkyl, —$NR^4R^5$, N—$(C_1-C_6)$alkylaminosulfonyl, and N,N-di$(C_1-C_6)$alkylaminosulfonyl;
m is 0, 1, 2, 3, 4, or 5;

n is 0, 1, 2, 3, 4, or 5;

$R^{11}$ is H, $(C_1-C_6)$alkyl or phenyl, wherein said alkyl and said phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1-C_6$)alkyl, —NR$^4$R$^5$, N—($C_1-C_6$)alkylaminosulfonyl, and N,N-di($C_1-C_6$)alkylaminosulfonyl;

$R^4$, $R^5$, $R^6$ and $R^7$ are each independently H or $(C_1-C_6)$alkyl; $R^8$ is H, —(C=O)($C_1-C_6$)alkyl or —(C=O)($C_1-C_4$)perhaloalkyl; and R is hydrogen, —COH, —CO—($C_1-C_6$)alkyl, —CO—($C_2-C_4$)alkenyl, —CO-phenyl, —CO-benzyl, —CO-cyclopentyl, —CO-cyclohexyl, —CO-(5-, 6-, or 7-membered)heterocycloalkyl, —CO-benzyloxy, —CO—O—($C_1-C_6$)alkyl, —CO—NH$_2$, —CO—NH—($C_1-C_4$)alkyl, or —CO—N(($C_1-C_4$)alkyl)$_2$, wherein said —($C_1-C_6$)alkyl, —($C_2-C_4$)alkenyl, phenyl, benzyl, cyclopentyl, cyclohexyl, -(5-, 6-, or 7-membered)heterocycloalkyl, benzyloxy, —O—($C_1-C_6$)alkyl, —NH—($C_1-C_4$)alkyl, or —N(($C_1-C_4$)alkyl)$_2$ can be unsubstituted or substituted with 1, 2 or 3 substituents selected from halo, —($C_1-C_6$)alkyl, —($C_2-C_4$)alkenyl, —($C_2-C_3$)alkynyl, -(5- or 6-membered)heteroaryl, —O—($C_1-C_6$)alkyl, —S—($C_1-C_6$)alkyl, —C(halo)$_3$, —CH(halo)$_2$, —CH$_2$(halo), —CN, —NO$_2$, —NH$_2$, —NH—($C_1-C_4$)alkyl, —N(—($C_1-C_4$)alkyl)$_2$, —C(O)($C_1-C_4$)alkyl, —C(O)O($C_1-C_4$)alkyl, —OC(O)($C_1-C_4$)alkyl, —OC(O)NH$_2$, —S(O)($C_1-C_4$)alkyl, —S(O)$_2$($C_1-C_4$)alkyl or 5-methyl-2-oxo-2H-1,3-dioxol-4-ylmethyl.

(85) The compound of the above (84), wherein $R^1$ is H or $(C_1-C_6)$alkyl.

(86) The compound of the above (84), wherein $R^1$ is H or methyl.

(87) The compound of the above (84), wherein $R^1$ is H.

(88) The compound of any one of the above (84) to (87), wherein X is CH$_2$, O, NH, N($C_1-C_6$)alkyl, S, SO, or SO$_2$.

(89) The compound of the above (88), wherein X is NH.

(90) The compound of the above (88), wherein X is CH$_2$.

(91) The compound of the above (88), wherein X is O.

(92) The compound of the above (88), wherein X is S.

(93) The compound of the above (88), wherein X is SO$_2$.

(94) The compound of any one of the above (84) to (87), wherein m is 0, 1 or 2.

(95) The compound of any one of the above (84) to (87), wherein m is 0.

(96) The compound of any one of the above (84) to (87), wherein m is 1.

(97) The compound of any one of the above (84) to (87), wherein m is 2.

(98) The compound of the above (88), wherein m is 0, 1 or 2.

(99) The compound of the above (98), wherein m is 0.

(100) The compound of the above (98), wherein m is 1.

(101) The compound of the above (98), wherein m is 2.

(102) The compound of any one of the above (84) to (87), wherein n is 0, 1 or 2.

(103) The compound of the above (102), wherein n is 0.

(104) The compound of the above (102), wherein n is 1.

(105) The compound of the above (102), wherein n is 2.

(106) The compound of any one of the above (84) to (87), wherein X is CH$_2$, O, NH, N($C_1-C_6$)alkyl, S, SO, or SO$_2$; and n is 0, 1 or 2.

(107) The compound of any one of the above (84) to (87), wherein m is 0, 1 or 2; and n is 0, 1 or 2.

(108) The compound of any one of the above (84) to (87), wherein X is CH$_2$, O, NH, N($C_1-C_6$)alkyl, S, SO, or SO$_2$; m is 0, 1 or 2; and n is 0, 1 or 2.

(109) The compound of any one of the above (84) to (87), wherein X is CH$_2$, O, S, SO, or SO$_2$; m is 0, 1 or 2; and n is 0, 1 or 2.

(110) The compound of any one of the above (84) to (87), wherein $R^{11}$ is H or $(C_1-C_6)$alkyl.

(111) The compound of any one of the above (84) to (87), wherein X is CH$_2$, O, NH, N($C_1-C_6$)alkyl, S, SO, or SO$_2$; and $R^{11}$ is H or $(C_1-C_6)$alkyl.

(112) The compound of any one of the above (84) to (87), wherein m is 0, 1 or 2; and $R^{11}$ is H or $(C_1-C_6)$alkyl.

(113) The compound of any one of the above (84) to (87), wherein n is 0, 1 or 2; and $R^{11}$ is H or $(C_1-C_6)$alkyl.

(114) The compound of any one of the above (84) to (87), wherein X is CH$_2$, O, NH, N($C_1-C_6$)alkyl, S, SO, or SO$_2$; m is 0, 1 or 2; and $R^{11}$ is H or $(C_1-C_6)$alkyl.

(115) The compound of any one of the above (84) to (87), wherein X is CH$_2$, O, NH, N($C_1-C_6$)alkyl, S, SO, or SO$_2$; n is 0, 1 or 2; and $R^{11}$ is H or $(C_1-C_6)$alkyl.

(116) The compound of any one of the above (84) to (87), wherein m is 0, 1 or 2; n is 0, 1 or 2; and $R^{11}$ is H or $(C_1-C_6)$alkyl.

(117) The compound of any one of the above (84) to (87), wherein X is CH$_2$, O, NH, N($C_1-C_6$)alkyl, S, SO, or SO$_2$; m is 0, 1 or 2; n is 0, 1 or 2; and $R^{11}$ is H or $(C_1-C_6)$alkyl.

(118) The compound of the above (110), wherein $R^{11}$ is H or methyl.

(119) The compound of the above (111), wherein $R^{11}$ is H or methyl.

(120) The compound of the above (112), wherein $R^{11}$ is H or methyl.

(121) The compound of the above (113), wherein $R^{11}$ is H or methyl.

(122) The compound of the above (114), wherein $R^{11}$ is H or methyl.

(123) The compound of the above (115), wherein $R^{11}$ is H or methyl.

(124) The compound of the above (116), wherein $R^{11}$ is H or methyl.

(125) The compound of the above (117), wherein $R^{11}$ is H or methyl.

(126) The compound of the above (110), wherein $R^{11}$ is H.

(127) The compound of the above (111), wherein $R^{11}$ is H.

(128) The compound of the above (112), wherein $R^{11}$ is H.

(129) The compound of the above (113), wherein $R^{11}$ is H.

(130) The compound of the above (114), wherein $R^{11}$ is H.

(131) The compound of the above (115), wherein $R^{11}$ is H.

(132) The compound of the above (116), wherein $R^{11}$ is H.

(133) The compound of the above (117), wherein $R^{11}$ is H.

(134) The compound of any one of the above (84) to (87), wherein R is hydrogen, —CO—($C_1-C_6$)alkyl, —CO-phenyl, —CO-benzyl, —CO—NH$_2$ or 5-methyl-2-oxo-2H-1,3-dioxol-4-ylmethyl.

(135) The compound of any one of the above (84) to (87), wherein X is CH$_2$, O, NH, N($C_1-C_6$)alkyl, S, SO, or SO$_2$; and R is hydrogen, —CO—($C_1-C_6$)alkyl, —CO-phenyl, —CO-benzyl, —CO—NH$_2$ or 5-methyl-2-oxo-2H-1,3-dioxol-4-ylmethyl.

(136) The compound of any one of the above (84) to (87), wherein m is 0, 1 or 2; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(137) The compound of any one of the above (84) to (87), wherein n is 0, 1 or 2; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(138) The compound of any one of the above (84) to (87), wherein $R^{11}$ is H or ($C_1$-$C_6$)alkyl; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(139) The compound of any one of the above (84) to (87), wherein X is $CH_2$, O, NH, N($C_1$-$C_6$)alkyl, S, SO, or $SO_2$; m is 0, 1 or 2; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(140) The compound of any one of the above (84) to (87), wherein X is $CH_2$, O, NH, N($C_1$-$C_6$)alkyl, S, SO, or $SO_2$; n is 0, 1 or 2; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(141) The compound of any one of the above (84) to (87), wherein X is $CH_2$, O, NH, N($C_1$-$C_6$)alkyl, S, SO, or $SO_2$; $R^{11}$ is H or ($C_1$-$C_6$)alkyl; and R is hydrogen, —CO—($C_1$-$C_6$)alkyl, —CO-phenyl, —CO— benzyl, —CO—$NH_2$ or 5-methyl-2-oxo-2H-1,3-dioxol-4-ylmethyl.
(142) The compound of any one of the above (84) to (87), wherein m is 0, 1 or 2; n is 0, 1 or 2; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(143) The compound of any one of the above (84) to (87), wherein m is 0, 1 or 2; $R^{11}$ is H or ($C_1$-$C_6$)alkyl; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(144) The compound of any one of the above (84) to (87), wherein n is 0, 1 or 2; $R^{11}$ is H or ($C_1$-$C_6$)alkyl; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(145) The compound of any one of the above (84) to (87), wherein X is $CH_2$, O, NH, N($C_1$-$C_6$)alkyl, S, SO, or $SO_2$; m is 0, 1 or 2; n is 0, 1 or 2; and R is hydrogen, —CO—($C_1$-$C_6$)alkyl, —CO-phenyl, —CO— benzyl, —CO—$NH_2$ or 5-methyl-2-oxo-2H-1,3-dioxol-4-ylmethyl.
(146) The compound of any one of the above (84) to (87), wherein X is $CH_2$, O, NH, N($C_1$-$C_6$)alkyl, S, SO, or $SO_2$; m is 0, 1 or 2; $R^{11}$ is H or ($C_1$-$C_6$)alkyl; and R is hydrogen, —CO—($C_1$-$C_6$)alkyl, —CO— phenyl, —CO-benzyl, —CO—$NH_2$ or 5-methyl-2-oxo-2H-1,3-dioxol-4-ylmethyl.
(147) The compound of any one of the above (84) to (87), wherein m is 0, 1 or 2; n is 0, 1 or 2; $R^{11}$ is H or ($C_1$-$C_6$)alkyl; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(148) The compound of any one of the above (84) to (87), wherein X is $CH_2$, O, NH, N($C_1$-$C_6$)alkyl, S, SO, or $SO_2$; m is 0, 1 or 2; n is 0, 1 or 2; $R^{11}$ is H or ($C_1$-$C_6$)alkyl; and R is hydrogen, —CO—($C_1$-$C_6$)alkyl, —CO-phenyl, —CO-benzyl, —CO—$NH_2$ or 5-methyl-2-oxo-2H-1,3-dioxol-4-ylmethyl.
(149) The compound of the above (134), wherein R is hydrogen.
(150) The compound of the above (135), wherein R is hydrogen.
(151) The compound of the above (136), wherein R is hydrogen.
(152) The compound of the above (137), wherein R is hydrogen.
(153) The compound of the above (138), wherein R is hydrogen.
(154) The compound of the above (139), wherein R is hydrogen.
(155) The compound of the above (140), wherein R is hydrogen.
(156) The compound of the above (141), wherein R is hydrogen.
(157) The compound of the above (142), wherein R is hydrogen.
(158) The compound of the above (143), wherein R is hydrogen.
(159) The compound of the above (144), wherein R is hydrogen.
(160) The compound of the above (145), wherein R is hydrogen.
(161) The compound of the above (146), wherein R is hydrogen.
(162) The compound of the above (147), wherein R is hydrogen.
(163) The compound of the above (148), wherein R is hydrogen.
(164) A compound of formula (If)

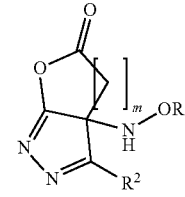

(If)

or a pharmaceutically acceptable salt thereof, wherein:
$R^2$ is ($C_1$-$C_6$)alkyl or phenyl, wherein said phenyl is unsubstituted or substituted with 1, 2, 3, 4, or 5 substituent(s) independently selected from halo, cyano, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)$NR^4R^5$, —C(=O)-(5-, 6-, or 7-membered)heterocycloalkyl, (5-, 6-, or 7-membered)heterocycloalkyl, ($C_6$-$C_{10}$)aryl, ($C_1$-$C_6$)alkylsulfanyl, ($C_1$-$C_4$)haloalkylsulfanyl, ($C_1$-$C_4$)perhaloalkylsulfanyl, ($C_1$-$C_6$)alkylsulfinyl, ($C_1$-$C_6$)alkylsulfonyl, ($C_3$-$C_6$)cycloalkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1$-$C_6$)alkyl, —$NR^4R^5$, N—($C_1$-$C_6$)alkylaminosulfonyl, and N,N-di($C_1$-$C_6$)alkylaminosulfonyl, wherein said (5-, 6-, or 7-membered)heterocycloalkyl is unsubstituted or substituted with 1 or 2 substituent(s) independently selected from halo or ($C_1$-$C_6$)alkyl;
m is 1, 2 or 3; and
R is 5-methyl-2-oxo-2H-1,3-dioxol-4-ylmethyl.
(165) The compound of the above (164), wherein $R^2$ is ($C_1$-$C_4$)alkyl substituted with phenyl, wherein said phenyl is unsubstituted or substituted with 1, 2 or 3 individually selected substituent(s).

(166) The compound of the above (164), wherein R² is (C₁-C₂)alkyl substituted with phenyl, wherein said phenyl is unsubstituted or substituted with 1, 2 or 3 individually selected substituent(s).

(167) The compound of the above (165) or (166), wherein said phenyl is unsubstituted.

(168) The compound of the above (165) or (166), wherein said phenyl is substituted with a substituent selected from (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, N—(C₁-C₆)alkylaminosulfonyl, and N,N-di(C₁-C₆)alkylaminosulfonyl.

(169) The compound of the above (168), wherein said phenyl is substituted with a substituent selected from (C₁-C₆)alkylsulfonyl, —S(O)₂—NR⁶R⁷, N—(C₁-C₆)alkylaminosulfonyl, and N,N-di(C₁-C₆)alkylaminosulfonyl.

(170) The compound of the above (169), wherein said substituent is selected from methylsulfonyl, N-methylaminosulfonyl, and N,N-dimethylaminosulfonyl.

(171) The compound of the above (165) or (166), wherein R² is benzyl, wherein said benzyl is unsubstituted or substituted with 1, 2 or 3 individually selected substituent(s).

(172) The compound of the above (171), wherein said benzyl is substituted with a substituent selected from (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, N—(C₁-C₆)alkylaminosulfonyl, and N,N-di(C₁-C₆)alkylaminosulfonyl.

(173) The compound of the above (172), wherein said benzyl is substituted with a substituent selected from (C₁-C₆)alkylsulfonyl, —S(O)₂—NR⁶R⁷, N—(C₁-C₆)alkylaminosulfonyl, and N,N-di(C₁-C₆)alkylaminosulfonyl.

(174) The compound of the above (173), wherein said substituent is selected from methylsulfonyl, N-methylaminosulfonyl, and N,N-dimethylaminosulfonyl.

(175) The compound of any one of the above (164) to (166), wherein m is 1.

(176) The compound of any one of the above (164) to (166), wherein m is 2.

(177) The compound of any one of the above (164) to (166), wherein m is 3.

(178) A compound of formula (Ig)

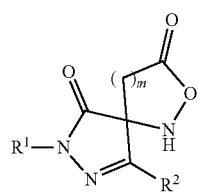

or a pharmaceutically acceptable salt thereof, wherein:
R¹ is H, (C₁-C₆)alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, (C₁-C₆)alkyl, (C₁-C₄)haloalkyl, (C₁-C₄)perhaloalkyl, (C₁-C₆)alkoxy, (C₁-C₄)haloalkoxy, (C₁-C₄)perhaloalkoxy, —C(=O)OH, —C(=O)O(C₁-C₆)alkyl, —C(=O)O(5-methyl-2-oxo-2H-1,3-dioxol-4-ylmethyl), —C(=O)NR⁴R⁵, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl;

R⁴, R⁵, R⁶ and R⁷ are each independently H or (C₁-C₆)alkyl; and

R⁸ is H, —(C=O)(C₁-C₆)alkyl or —(C=O)(C₁-C₄)perhaloalkyl;

R² is (C₁-C₆)alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, (C₁-C₆)alkyl, (C₁-C₄)haloalkyl, (C₁-C₄)perhaloalkyl, (C₁-C₆)alkoxy, (C₁-C₄)haloalkoxy, (C₁-C₄)perhaloalkoxy, —C(=O)OH, —C(=O)O(C₁-C₆)alkyl, —C(=O)NR⁴R⁵, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered) heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl;

m is 1, 2 or 3.

(179) The compound of the above (178), wherein R¹ is H, (C₁-C₆)alkyl, or phenyl, wherein said alkyl and phenyl are unsubstituted or substituted with 1, 2 or 3 independently selected substituent(s).

(180) The compound of the above (179), wherein R¹ is H, methyl, or phenyl, wherein said alkyl and phenyl are unsubstituted or substituted with 1, 2 or 3 independently selected substituent(s).

(181) The compound of the above (179), wherein R¹ is H.

(182) The compound of the above (179), wherein R¹ is methyl.

(183) The compound of the above (179), wherein R¹ is phenyl, wherein said phenyl is unsubstituted or substituted with 1, 2 or 3 independently selected substituent(s).

(184) The compound of any one of the above (178) to (183), wherein R² is (C₁-C₆)alkyl or phenyl, wherein said alkyl and phenyl are unsubstituted or substituted with 1, 2 or 3 independently selected substituent(s).

(185) The compound of the above (184), wherein R² is methyl or phenyl, wherein said alkyl and phenyl are unsubstituted or substituted with 1, 2 or 3 independently selected substituent(s).

(186) The compound of the above (184), wherein R² is methyl.

(187) The compound of the above (184), wherein R² is phenyl, wherein said phenyl is unsubstituted or substituted with 1, 2 or 3 independently selected substituent(s).

(188) The compound of the above (187), wherein R² is unsubstituted phenyl.

(189) The compound of the above (187), wherein R² is phenyl substituted with a substituent selected from (C₁-C₆)alkylsulfanyl, (C₁-C₆)alkylsulfinyl, (C₁-C₆)alkylsulfonyl, —S(O)₂—NH₂, —S(O)₂—NR⁶R⁷, N—(C₁-C₆)alkylaminosulfonyl, or N,N-di(C₁-C₆)alkylaminosulfonyl.

(190) The compound of any one of the above (178) to (183), wherein m is 1.
(191) The compound of any one of the above (178) to (183), wherein $R^2$ is $(C_1-C_6)$alkyl or phenyl, wherein said alkyl and phenyl are unsubstituted or substituted with 1, 2 or 3 independently selected substituent(s); and m is 1.
(192) The compound of any one of the above (178) to (183), wherein m is 2.
(193) The compound of any one of the above (178) to (183), wherein $R^2$ is $(C_1-C_6)$alkyl or phenyl, wherein said alkyl and phenyl are unsubstituted or substituted with 1, 2 or 3 independently selected substituent(s); and m is 2.
(194) The compound of any one of the above (178) to (183), wherein m is 3.
(195) The compound of any one of the above (178) to (183), wherein $R^2$ is $(C_1-C_6)$alkyl or phenyl, wherein said alkyl and phenyl are unsubstituted or substituted with 1, 2 or 3 independently selected substituent(s); and m is 3.
(196) A compound of formula (Ih)

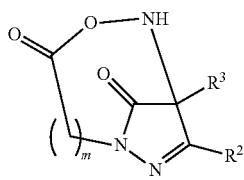

(Ih)

or a pharmaceutically acceptable salt thereof, wherein:
$R^2$ is $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl;
$R^4$, $R^5$, $R^6$ and $R^7$ are each independently H or $(C_1-C_6)$alkyl;
$R^8$ is H, —(C=O)$(C_1-C_6)$alkyl or —(C=O)$(C_1-C_4)$perhaloalkyl;
$R^3$ is $(C_1-C_6)$alkyl, (5- or 6-membered)heteroaryl, phenyl or —C(=NOR$^9$)R$^{10}$ wherein $R^9$ is $(C_1-C_6)$alkyl, $(C_1-C_6)$alkyl substituted with phenyl or phenyl and $R^{10}$ is selected from $(C_1-C_6)$alkyl; and
m is 1, 2 or 3.
(197) The compound of the above (196), wherein $R^2$ is $(C_1-C_6)$alkyl, or phenyl, wherein said alkyl and phenyl are unsubstituted or substituted with 1, 2 or 3 independently selected substituent(s).
(198) The compound of the above (196), wherein $R^2$ is methyl, or phenyl, wherein said alkyl and phenyl are unsubstituted or substituted with 1, 2 or 3 independently selected substituent(s).
(199) The compound of the above (196), wherein $R^2$ is methyl.

(200) The compound of the above (196), wherein $R^2$ is phenyl, wherein said phenyl is unsubstituted or substituted with 1, 2 or 3 independently selected substituent(s).
(201) The compound of the above (200), wherein $R^2$ is unsubstituted phenyl.
(202) The compound of the above (201), wherein $R^2$ is phenyl substituted with a substituent selected from $(C_1-C_6)$alkylsulfanyl, $(C_1-C_6)$alkylsulfinyl, $(C_1-C_6)$alkylsulfonyl, —S(O)$_2$—NH$_2$, —S(O)$_2$—NR$^6$R$^7$, N—$(C_1-C_6)$alkylaminosulfonyl, or N,N-di$(C_1-C_6)$alkylaminosulfonyl.
(203) The compound of any one of the above (196) to (202), wherein $R^3$ is $(C_1-C_6)$alkyl, phenyl or —C(=NOR$^9$)R$^{10}$.
(204) The compound of any one of the above (196) to (202), wherein $R^3$ is methyl, phenyl or —C(=NOR$^9$)R$^{10}$.
(205) The compound of the above (204), wherein $R^3$ is methyl.
(206) The compound of the above (204), wherein $R^3$ is phenyl.
(207) The compound of the above (204), wherein $R^3$ is —C(=NOR$^9$)R$^{10}$.
(208) The compound of the above (207), wherein $R^9$ is $(C_1-C_4)$alkyl, $(C_1-C_2)$alkyl substituted with phenyl or phenyl.
(209) The compound of the above (207), wherein $R^9$ is methyl, benzyl or phenyl.
(210) The compound of the above (207), wherein $R^{10}$ is $(C_1-C_4)$alkyl.
(211) The compound of the above (210), wherein $R^{10}$ is methyl.
(212) The compound of any one of the above (196) to (202), wherein m is 1.
(213) The compound of any one of the above (196) to (202), wherein $R^3$ is methyl, phenyl or —C(=NOR$^9$)R$^{10}$; and m is 1.
(214) The compound of any one of the above (196) to (202), wherein m is 2.
(215) The compound of any one of the above (196) to (202), wherein $R^3$ is methyl, phenyl or —C(=NOR$^9$)R$^{10}$; and m is 2.
(216) The compound of any one of the above (196) to (202), wherein m is 3.
(217) The compound of any one of the above (196) to (202), wherein $R^3$ is methyl, phenyl or —C(=NOR$^9$)R$^{10}$; and m is 2.
(218) A compound of formula (Ii)

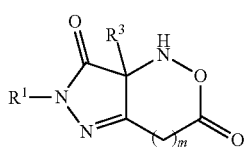

(Ii)

or a pharmaceutically acceptable salt thereof, wherein:
$R^1$ is H, $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)O(5-methyl-2-oxo-2H-1,3-dioxol-4-ylmethyl), —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1$-

C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl;

R$^8$ is H, —C(=O)(C$_1$-C$_6$)alkyl or —C(=O)(C$_1$-C$_4$)perhaloalkyl;

R$^3$ is (C$_1$-C$_6$)alkyl, (5- or 6-membered)heteroaryl, phenyl or —C(=NOR$^9$)R$^{10}$ wherein R$^9$ is (C$_1$-C$_6$)alkyl, (C$_1$-C$_6$)alkyl substituted with phenyl or phenyl and R$^{10}$ are independently selected from (C$_1$-C$_6$)alkyl; and m is 0, 1 or 2, wherein when m is 2, the lactone ring is optionally fused to a phenyl ring, wherein said fused phenyl ring is unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

(219) The compound of the above (218), wherein R$^1$ is H, (C$_1$-C$_6$)alkyl, or phenyl, wherein said alkyl and phenyl are unsubstituted or substituted with 1, 2 or 3 substituent(s).

(220) The compound of the above (218), wherein R$^1$ is H, methyl, or phenyl, wherein said alkyl and phenyl are unsubstituted or substituted with 1, 2 or 3 substituent(s).

(221) The compound of the above (218), wherein R$^1$ is H.

(222) The compound of the above (218), wherein R$^1$ is methyl.

(223) The compound of the above (218), wherein R$^1$ is phenyl, wherein said phenyl is unsubstituted or substituted with 1, 2 or 3 substituent(s).

(224) The compound of any one of the above (218) to (223), wherein R$^3$ is (C$_1$-C$_6$)alkyl, phenyl or —C(=NOR$^9$)R.

(225) The compound of the above (224), wherein R$^3$ is methyl, phenyl or —C(=NOR$^9$)R.

(226) The compound of the above (224), wherein R$^3$ is methyl.

(227) The compound of the above (224), wherein R$^3$ is phenyl.

(228) The compound of the above (224), wherein R$^3$ is —C(=NOR$^9$)R$^{10}$.

(229) The compound of the above (228), wherein R$^9$ is (C$_1$-C$_4$)alkyl, (C$_1$-C$_2$)alkyl substituted with phenyl or phenyl.

(230) The compound of the above (229), wherein R$^9$ is methyl, benzyl or phenyl.

(231) The compound of the above (228), wherein R$^{10}$ is (C$_1$-C$_4$)alkyl.

(232) The compound of the above (231), wherein R$^9$ is methyl, benzyl or phenyl.

(233) The compound of the above (231), wherein R$^{10}$ is methyl.

(234) The compound of the above (233), wherein R$^9$ is methyl, benzyl or phenyl.

(235) The compound of any one of the above (218) to (223), wherein m is 0.

(236) The compound of the above (235), wherein R$^3$ is methyl, phenyl or —C(=NOR$^9$)R$^{10}$.

(237) The compound of any one of the above (218) to (223), wherein m is 1.

(238) The compound of the above (237), wherein R$^3$ is methyl, phenyl or —C(=NOR$^9$)R$^{10}$.

(239) The compound of any one of the above (218) to (223), wherein m is 2.

(240) The compound of the above (239), wherein R$^3$ is methyl, phenyl or —C(=NOR$^9$)R$^{10}$.

(241) The compound of the above (239), wherein the lactone ring is fused to a phenyl ring, wherein the fused phenyl ring is unsubstituted or substituted with substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

(242) The compound of the above (241), wherein the fused phenyl ring is unsubstituted.

(243) The compound of the above (241), wherein the fused phenyl ring is substituted with 1, 2 or 3 independently selected substituent(s).

(244) The compound of the above (243), wherein the fused phenyl ring is substituted with a substituent selected from (C$_1$-C$_6$)alkylsulfanyl, (C$_1$-C$_6$)alkylsulfinyl, (C$_1$-C$_6$)alkylsulfonyl, —S(O)$_2$—NH$_2$, —S(O)$_2$—NR$^6$R$^7$, N—(C$_1$-C$_6$)alkylaminosulfonyl, or N,N-di(C$_1$-C$_6$)alkylaminosulfonyl.

(245) The compound of the above (241), wherein R$^3$ is methyl, phenyl or —C(=NOR$^9$)R$^{10}$.

(246) A compound of formula (Ij)

$$\text{(Ij)}$$

or a pharmaceutically acceptable salt thereof, wherein:

R$^1$ is (C$_1$-C$_6$)alkyl;

R$^2$ is phenyl, wherein said phenyl is unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)₂-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl;

R⁴, R⁵, R⁶ and R⁷ are each independently H or (C₁-C₆)alkyl;

R⁸ is H, —(C=O)(C₁-C₆)alkyl or —(C=O)(C₁-C₄)perhaloalkyl;

R³ is (C₁-C₆)alkyl; and

R is 5-methyl-2-oxo-2H-1,3-dioxol-4-ylmethyl.

(247) The compound of the above (246), wherein R¹ is (C₁-C₄)alkyl.

(248) The compound of the above (247), wherein R¹ is methyl.

(249) The compound of any one of the above (246) to (248), wherein R² is unsubstituted phenyl or phenyl substituted with 1, 2 or 3 independently selected substituent(s).

(250) The compound of the above (249), wherein R² is unsubstituted phenyl.

(251) The compound of the above (249), wherein R² is phenyl substituted with 1, 2 or 3 independently selected substituent(s).

(252) The compound of any one of the above (246) to (248), wherein R³ is (C₁-C₄)alkyl.

(253) The compound of the above (249), wherein R³ is (C₁-C₄)alkyl.

(254) The compound of the above (252), wherein R³ is methyl.

(255) The compound of the above (253), wherein R³ is methyl.

(256) A compound of formula (Ik)

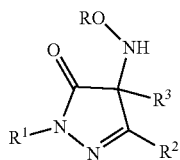

(Ik)

or a pharmaceutically acceptable salt thereof, wherein:

R¹ is (5-, 6- or 7-membered)heterocycloalkyl;

R² is phenyl, wherein said phenyl is unsubstituted or substituted with 1, 2, 3, 4, or 5 substituent(s) independently selected from halo, (C₁-C₆)alkyl, (C₁-C₄)haloalkyl, (C₁-C₄)perhaloalkyl, (C₁-C₆)alkoxy, (C₁-C₄)haloalkoxy, (C₁-C₄)perhaloalkoxy, —C(=O)OH, —C(=O)O(C₁-C₆)alkyl, —C(=O)NR⁴R⁵, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl;

R⁴, R⁵, R⁶ and R⁷ are each independently H or (C₁-C₆)alkyl;

R⁸ is H, —(C=O)(C₁-C₆)alkyl or —(C=O)(C₁-C₄)perhaloalkyl;

R³ is (C₁-C₆)alkyl; and

R is hydrogen, —COH, —CO—(C₁-C₆)alkyl, —CO—(C₂-C₄)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C₁-C₆)alkyl, —CO—NH₂, —CO—NH—(C₁-C₄)alkyl, or —CO—N((C₁-C₄)alkyl)₂, wherein said —(C₁-C₆)alkyl, —(C₂-C₄)alkenyl, phenyl, benzyl, cyclopentyl, cyclohexyl, -(5-, 6-, or 7-membered)heterocycloalkyl, benzyloxy, —O—(C₁-C₆)alkyl, —NH—(C₁-C₄)alkyl, or —N((C₁-C₄)alkyl)₂ can be unsubstituted or substituted with 1, 2 or 3 substituents selected from halo, —(C₁-C₆)alkyl, —(C₂-C₄)alkenyl, —(C₂-C₃)alkynyl, -(5- or 6-membered)heteroaryl, —O—(C₁-C₆)alkyl, —S—(C₁-C₆)alkyl, —C(halo)₃, —CH(halo)₂, —CH₂(halo), —CN, —NO₂, —NH₂, —NH—(C₁-C₄)alkyl, —N(—(C₁-C₄)alkyl)₂, —C(O)(C₁-C₄)alkyl, —C(O)O(C₁-C₄)alkyl, —OC(O)(C₁-C₄)alkyl, —OC(O)NH₂, —S(O)(C₁-C₄)alkyl, —S(O)₂(C₁-C₄)alkyl or 5-methyl-2-oxo-2H-1,3-dioxol-4-ylmethyl.

(257) The compound of the above (256), wherein R¹ is (5- or 6-membered)heterocycloalkyl.

(258) The compound of the above (256), wherein R¹ is (5-membered)heterocycloalkyl.

(259) The compound of the above (256), wherein R¹ is (6-membered)heterocycloalkyl.

(260) The compound of the above (256), wherein R¹ is (7-membered)heterocycloalkyl.

(261) The compound of the above (256), wherein R¹ is piperidinyl (262) The compound of any one of the above (256) to (261), wherein R² is unsubstituted phenyl or phenyl substituted with 1, 2 or 3 independently selected substituent(s).

(263) The compound of the above (262), wherein R² is unsubstituted phenyl.

(264) The compound of the above (262), wherein R² is phenyl substituted with 1, 2 or 3 independently selected substituent(s).

(265) The compound of any one of the above (256) to (261), wherein R³ is (C₁-C₄)alkyl.

(266) The compound of the above (262), wherein R³ is (C₁-C₄)alkyl.

(267) The compound of the above (265), wherein R³ is methyl.

(268) The compound of the above (266), wherein R³ is methyl.

(269) The compound of any one of the above (256) to (261), wherein R is hydrogen, —CO—(C₁-C₆)alkyl, —CO-phenyl, —CO-benzyl, —CO—NH₂ or 5-methyl-2-oxo-2H-1,3-dioxol-4-ylmethyl.

(270) The compound of the above (269), wherein R is hydrogen.

(271) The compound of the above (262), wherein R is hydrogen, —CO—(C₁-C₆)alkyl, —CO-phenyl, —CO-benzyl, —CO—NH₂ or 5-methyl-2-oxo-2H-1,3-dioxol-4-ylmethyl.

(272) The compound of the above (271), wherein R is hydrogen.

(273) The compound of the above (265), wherein R is hydrogen, —CO—(C₁-C₆)alkyl, —CO-phenyl, —CO-benzyl, —CO—NH₂ or 5-methyl-2-oxo-2H-1,3-dioxol-4-ylmethyl.

(274) The compound of the above (273), wherein R is hydrogen.

(275) The compound, which is selected from the group consisting of:

4-[(1)-(methoxyimino)(phenyl)methyl]-3-methyl-1-phenyl-1H-pyrazol-5-ol;

2-[4-(hydroxyamino)-3-methyl-5-oxo-1-phenyl-4,5-dihydro-1H-pyrazol-4-yl]acetic acid;

(1,4-dimethyl-5-oxo-3-phenyl-4,5-dihydro-1H-pyrazol-4-yl)amino 2,2-dimethylpropanoate;
(1,4-dimethyl-5-oxo-3-phenyl-4,5-dihydro-1H-pyrazol-4-yl)amino benzoate;
3-benzyl-4-(hydroxyamino)-1,4-dimethyl-4,5-dihydro-1H-pyrazol-5-one;
1,4-dimethyl-4-{[(5-methyl-2-oxo-2H-1,3-dioxol-4-yl)methoxy]amino}-3-phenyl-4,5-dihydro-1H-pyrazol-5-one;
ethyl 2-[4-(hydroxyamino)-3-methyl-5-oxo-4,5-dihydro-1H-pyrazol-4-yl]acetate;
3a-(hydroxyamino)-2H,3H,3aH,4H,5H,6H-cyclopenta[c]pyrazol-3-one;
ethyl 4-[4-(hydroxyamino)-3-methyl-5-oxo-4,5-dihydro-1H-pyrazol-4-yl]butanoate;
4-(hydroxyamino)-4-methyl-3-(pyridin-3-yl)-4,5-dihydro-1H-pyrazol-5-one;
2-{3-[4-(dimethylsulfamoyl)phenyl]-4-(hydroxyamino)-4-methyl-5-oxo-4,5-dihydro-1H-pyrazol-1-yl}acetic acid;
ethyl 2-{3-[4-(dimethylsulfamoyl)phenyl]-4-(hydroxyamino)-4-methyl-5-oxo-4,5-dihydro-1H-pyrazol-1-yl}acetate;
4-(hydroxyamino)-3-phenyl-4-(propan-2-yl)-4,5-dihydro-1H-pyrazol-5-one;
methyl 2-[4-(hydroxyamino)-3-(4-methane sulfonylphenyl)-4-methyl-5-oxo-4,5-dihydro-1H-pyrazol-1-yl]acetate;
4-(hydroxyamino)-1-methyl-3-phenyl-4-(propan-2-yl)-4,5-dihydro-1H-pyrazol-5-one;
ethyl 2-[4-(hydroxyamino)-3-(4-methanesulfonylphenyl)-4-methyl-5-oxo-4,5-dihydro-1H-pyrazol-1-yl]acetate;
3-[4-(hydroxyamino)-4-methyl-5-oxo-4,5-dihydro-1H-pyrazol-3-yl]pyridin-1-ium-1-olate;
1-(4-bromophenyl)-4-(hydroxyamino)-3,4-dimethyl-4,5-dihydro-1H-pyrazol-5-one;
4-(hydroxyamino)-1,4-dimethyl-3-(propan-2-yl)-4,5-dihydro-1H-pyrazol-5-one;
4-[4-(Hydroxyamino)-4-methyl-5-oxo-4,5-dihydro-1H-pyrazol-3-yl]-N-methylbenzene-1-sulfonamide;
4-(Hydroxyamino)-4-(2-hydroxyethyl)-1,3-dimethyl-4,5-dihydro-1H-pyrazol-5-one;
2-[4-(Hydroxyamino)-3-(4-methanesulfonylphenyl)-4-methyl-5-oxo-4,5-dihydro-1H-pyrazol-1-yl]acetamide;
4-(Hydroxyamino)-4-(2-hydroxyethyl)-3-methyl-4,5-dihydro-1H-pyrazol-5-one;
3a-(Hydroxyamino)-2H,3H,3aH,4H,6H,7H-thiopyrano[4,3-c]pyrazol-3-one;
3a-(Hydroxyamino)-2H,3H,3aH,4H,6H,7H-5λ$^6$-thiopyrano[4,3-c]pyrazole-3,5,5-trione;
3a-(Hydroxyamino)-2H,3H,3aH,4H,5H,7H-pyrano[3,4-c]pyrazol-3-one;
3a-(Hydroxyamino)-2H,3H,3aH,4H,6H-5λ$^6$-thieno[3,4-c]pyrazole-3,5,5-trione;
(5-methyl-2-oxo-1,3-dioxol-4-yl)methyl 2-(4-(hydroxyamino)-4-methyl-3-(4-(methylsulfonyl)phenyl)-5-oxo-4,5-dihydro-1H-pyrazol-1-yl)acetate;
(5-methyl-2-oxo-1,3-dioxol-4-yl)methyl 2-(4-methyl-4-(((5-methyl-2-oxo-1,3-dioxol-4-yl)methoxy)amino)-3-(4-(methylsulfonyl)phenyl)-5-oxo-4,5-dihydro-1H-pyrazol-1-yl)acetate;
4-[4-(hydroxyamino)-1,4-dimethyl-5-oxo-4,5-dihydro-1H-pyrazol-3-yl]-N-methylbenzene-1-sulfonamide;
3a-(hydroxyamino)-2H,3H,3aH,4H,5H,6H,7H-pyrazolo[3,4-c]pyridin-3-one;
methyl 2-[4-(hydroxyamino)-3-(4-methanesulfonylphenyl)-1-methyl-5-oxo-4,5-dihydro-1H-pyrazol-4-yl]acetate;
2-[4-(hydroxyamino)-3-(4-methanesulfonylphenyl)-1-methyl-5-oxo-4,5-dihydro-1H-pyrazol-4-yl]acetic acid;
2-{3-[4-(dimethylsulfamoyl)phenyl]-4-(hydroxyamino)-1-methyl-5-oxo-4,5-dihydro-1H-pyrazol-4-yl}acetic acid;
2-[4-(hydroxyamino)-1-methyl-5-oxo-3-phenyl-4,5-dihydro-1H-pyrazol-4-yl]acetic acid;
9-(4-methanesulfonylphenyl)-7-methyl-2-oxa-1,7,8-triazaspiro[4.4]non-8-ene-3,6-dione;
N,N-dimethyl-4-{8-methyl-3,9-dioxo-2-oxa-1,7,8-triazaspiro[4.4]non-6-en-6-yl}benzene-1-sulfonamide;
7-methyl-9-phenyl-2-oxa-1,7,8-triazaspiro[4.4]non-8-ene-3,6-dione;
2-[4-(hydroxyamino)-1,3-dimethyl-5-oxo-4,5-dihydro-1H-pyrazol-4-yl]acetic acid;
2-{4-[4-(hydroxyamino)-1,4-dimethyl-5-oxo-4,5-dihydro-1H-pyrazol-3-yl]benzenesulfonyl}-2-methylpropanoic acid;
2-[4-(hydroxyamino)-1,4-dimethyl-5-oxo-4,5-dihydro-1H-pyrazol-3-yl]-5-methanesulfonylbenzoic acid;
12-methanesulfonyl-4,6-dimethyl-8-oxa-3,4,7-triazatricyclo[8.4.0.0$^{2,6}$]tetradeca-1(14),2,10,12-tetraene-5,9-dione;
4,6-dimethyl-8-oxa-3,4,7-triazatricyclo[8.4.0.0$^{2,6}$]tetradeca-1(14),2,10,12-tetraene-5,9-dione;
8-(4-methanesulfonylphenyl)-7-methyl-5-oxa-1,6,9-triazabicyclo[5.2.1]dec-8-ene-4,10-dione;
N,N-dimethyl-4-{7-methyl-4,10-dioxo-5-oxa-1,6,9-triazabicyclo[5.2.1]dec-8-en-8-yl}benzene-1-sulfonamide;
2,3a-dimethyl-2H,3H,3aH,4H,6H,7H-pyrazolo[4,3-c][1,2]oxazine-3,6-dione;
3a-(((5-methyl-2-oxo-1,3-dioxol-4-yl)methoxy)amino)-3-phenyl-3aH-furo[2,3-c]pyrazol-5(4H)-one;
3a-(((5-methyl-2-oxo-1,3-dioxol-4-yl)methoxy)amino)-3-(4-(methylsulfonyl)phenyl)-3aH-furo[2,3-c]pyrazol-5(4H)-one;
N-methyl-4-(3a-(((5-methyl-2-oxo-1,3-dioxol-4-yl)methoxy)amino)-5-oxo-4,5-dihydro-3aH-furo[2,3-c]pyrazol-3-yl)benzene sulfonamide;
N,N-dimethyl-4-(3a-(((5-methyl-2-oxo-1,3-dioxol-4-yl)methoxy)amino)-5-oxo-4,5-dihydro-3aH-furo[2,3-c]pyrazol-3-yl)benzenesulfonamide;
3a-(((5-methyl-2-oxo-1,3-dioxol-4-yl)methoxy)amino)-3-phenyl-4,5-dihydropyrano[2,3-c]pyrazol-6(3aH)-one;
3a-(((5-methyl-2-oxo-1,3-dioxol-4-yl)methoxy)amino)-3-(4-(methylsulfonyl)phenyl)-4,5-dihydropyrano[2,3-c]pyrazol-6(3aH)-one;
N-methyl-4-(3a-(((5-methyl-2-oxo-1,3-dioxol-4-yl)methoxy)amino)-6-oxo-3a,4,5,6-tetrahydropyrano[2,3-c]pyrazol-3-yl)benzenesulfonamide;
N,N-dimethyl-4-(3a-(((5-methyl-2-oxo-1,3-dioxol-4-yl)methoxy)amino)-6-oxo-3a,4,5,6-tetrahydropyrano[2,3-c]pyrazol-3-yl)benzenesulfonamide;
4-(Hydroxyamino)-3-(4-methanesulfonylphenyl)-4-methyl-1-(piperidin-4-yl)-4,5-dihydro-1H-pyrazol-5-one; and
4-(Hydroxyamino)-3-(4-methanesulfonylphenyl)-4-methyl-1-(oxan-4-ylmethyl)-4,5-dihydro-1H-pyrazol-5-one;
or pharmaceutically acceptable salts thereof.

(276) The compound according to the above (275), wherein the compound is 2-[4-(hydroxyamino)-3-methyl-5-oxo-1-phenyl-4,5-dihydro-1H-pyrazol-4-yl]acetic acid.

(277) The compound according to the above (275), wherein the compound is ethyl 2-[4-(hydroxyamino)-3-methyl-5-oxo-4,5-dihydro-1H-pyrazol-4-yl]acetate.

(278) The compound according to the above (275), wherein the compound is ethyl 4-[4-(hydroxyamino)-3-methyl-5-oxo-4,5-dihydro-1H-pyrazol-4-yl]butanoate.

(279) The compound according to the above (275), wherein the compound is 2-{3-[4-(dimethylsulfamoyl)phenyl]-4-(hydroxyamino)-4-methyl-5-oxo-4,5-dihydro-1H-pyrazol-1-yl}acetic acid.
(280) The compound according to the above (275), wherein the compound is ethyl 2-{3-[4-(dimethylsulfamoyl)phenyl]-4-(hydroxyamino)-4-methyl-5-oxo-4,5-dihydro-1H-pyrazol-1-yl}acetate.
(281) The compound according to the above (275), wherein the compound is methyl 2-[4-(hydroxyamino)-3-(4-methanesulfonylphenyl)-4-methyl-5-oxo-4,5-dihydro-1H-pyrazol-1-yl]acetate.
(282) The compound according to the above (275), wherein the compound is ethyl 2-[4-(hydroxyamino)-3-(4-methanesulfonylphenyl)-4-methyl-5-oxo-4,5-dihydro-1H-pyrazol-1-yl]acetate.
(283) A pharmaceutical composition comprising the compound of any one of the above (1), (18), (40), (62), (84), (164), (178), (196), (218), (246), (256) or (275), and at least one pharmaceutically acceptable excipient.
(284) The pharmaceutical composition of the above (283), wherein the at least one pharmaceutically acceptable excipient is selected from lactose, microcrystalline cellulose, croscarmellose, or any mixture thereof.
(285) The pharmaceutical composition of the above (283), wherein the pharmaceutical composition is suitable for oral administration.
(286) The pharmaceutical composition of the above (283), wherein the pharmaceutical composition is formulated for administration in solid form.
(287) A method of treating a cardiovascular disease, comprising administering an effective amount of the compound of any one of the above (1), (18), (40), (62), (84), (164), (178), (196), (218), (246), (256) or (275) or the pharmaceutical composition of any of the above (283) to (286) to a patient in need thereof.
(288) The method of the above (287), wherein the cardiovascular disease is heart failure.
(289) The method of the above (287), wherein the cardiovascular disease is acute decompensated heart failure.
(290) The method of the above (287), wherein the compound or the pharmaceutical composition is administered orally.
(291) Use of the compound of any one of the above (1), (18), (40), (62), (84), (164), (178), (196), (218), (246), (256) or (275) or the pharmaceutical composition of any of the above (283) to (286) for the manufacture of a medicament useful for treating a cardiovascular disease.
(292) Use of the compound of any one of the above (1), (18), (40), (62), (84), (164), (178), (196), (218), (246), (256) or (275) or the pharmaceutical composition of any of the above (283) to (286) for the manufacture of a medicament useful for treating heart failure.
(293) Use of the compound of any one of the above (1), (18), (40), (62), (84), (164), (178), (196), (218), (246), (256) or (275) or the pharmaceutical composition of any of the above (283) to (286) for the manufacture of a medicament useful for treating acute decompensated heart failure.
(294) The use of any one of the above (149) to (151), wherein the compound or the pharmaceutical composition is administered orally.
(295) The compound of any one of the above (1), (18), (40), (62), (84), (164), (178), (196), (218), (246), (256) or (275) or the pharmaceutical composition of any of the above (283) to (286) for use in the treatment of a cardiovascular disease.
(296) The compound of any one of the above (1), (18), (40), (62), (84), (164), (178), (196), (218), (246), (256) or (275) or the pharmaceutical composition of any of the above (283) to (286) for use in the treatment of heart failure.
(297) The compound of any one of the above (1), (18), (40), (62), (84), (164), (178), (196), (218), (246), (256) or (275) or the pharmaceutical composition of any of the above (283) to (286) for use in the treatment of acute decompensated heart failure.
(298) A kit for treating and/or preventing a disease or condition responsive to nitroxyl therapy comprising a compound of any one of the above (1), (18), (40), (62), (84), (164), (178), (196), (218), (246), (256) or (275), or a pharmaceutical composition of any of the above (283) to (286); and instructions for use of the kit.
(299) The kit of the above (298), wherein the disease or condition is selected from cardiovascular diseases, ischemia/reperfusion injury, cancerous disease, and pulmonary hypertension.
(300) The kit of the above (299), wherein the cardiovascular disease is heart failure.

3.1 Definitions

Unless clearly indicated otherwise, the following terms as used herein have the meanings indicated below.

A "pharmaceutically acceptable salt" refers to a salt of any therapeutic agent disclosed herein, which salt can include any of a variety of organic and inorganic counter ions known in the art and which salt is pharmaceutically acceptable. When the therapeutic agent contains an acidic functionality, various exemplary embodiments of counter ions are sodium, potassium, calcium, magnesium, ammonium, tetraalkylammonium, and the like. When the therapeutic agent contains a basic functionality, a pharmaceutically acceptable salt can include as a counter ion, by way of example, an organic or inorganic acid, such as hydrochloride, hydrobromide, tartrate, mesylate, acetate, maleate, oxalate, and the like. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. Accordingly, a salt can be prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl-N-ethylamine; diethylamine; triethylamine; mono-, bis-, or tris-(2-hydroxy-lower-alkyl amines), such as mono-, bis-, or tris-(2-hydroxyethyl)amine, 2-hydroxy-tert-butylamine, or tris-(hydroxymethyl)methylamine, N,N-di-lower-alkyl-N-(hydroxy-lower-alkyl)-amines, such as N,N-dimethyl-N-(2-hydroxyethyl) amine, or tri-(2-hydroxyethyl)amine; N-methyl-D-glucamine; and amino acids such as arginine, lysine, and the like. A salt can also be prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

"Pharmaceutically acceptable excipient" refers to any substance, not itself a therapeutic agent, used as a carrier, diluent, adjuvant, binder, and/or vehicle for delivery of a therapeutic agent to a patient, or added to a pharmaceutical composition to improve its handling or storage properties or to permit or facilitate formation of a compound or pharmaceutical composition into a unit dosage form for administration. Pharmaceutically acceptable excipients are known in the pharmaceutical arts and are disclosed, for example, in Gennaro, Ed., *Remington: The Science and Practice of Pharmacy*, 20$^{th}$ Ed. (Lippincott Williams & Wilkins, Baltimore, Md., 2000) and *Handbook of Pharmaceutical Excipients*, American Pharmaceutical Association, Washington, D.C., (e.g., 1$^{st}$, 2$^{nd}$ and 3$^{rd}$ Eds., 1986, 1994 and 2000, respectively). As will be known to those in the art, pharmaceutically acceptable excipients can provide a variety of functions and can be described as wetting agents, buffering agents, suspending agents, lubricating agents, emulsifiers, disintegrants, absorbents, preservatives, surfactants, colorants, flavorants, and sweeteners. Examples of pharmaceutically acceptable excipients include without limitation: (1) sugars, such as lactose, glucose and sucrose, (2) starches, such as corn starch and potato starch, (3) cellulose and its derivatives, such as sodium carboxymethyl cellulose, ethyl cellulose, cellulose acetate, hydroxypropylmethylcellulose, hydroxypropylcellulose, microcrystalline cellulose, and croscarmellose, such as or croscarmellose sodium, (4) powdered tragacanth, (5) malt, (6) gelatin, (7) talc, (8) excipients, such as cocoa butter and suppository waxes, (9) oils, such as peanut oil, cottonseed oil, safflower oil, sesame oil, olive oil, corn oil and soybean oil, (10) glycols, such as propylene glycol, (11) polyols, such as glycerin, sorbitol, mannitol and polyethylene glycol, (12) esters, such as ethyl oleate and ethyl laurate, (13) agar, (14) buffering agents, such as magnesium hydroxide and aluminum hydroxide, (15) alginic acid, (16) pyrogen-free water, (17) isotonic saline, (18) Ringer's solution, (19) ethyl alcohol, (20) pH buffered solutions, (21) polyesters, polycarbonates and/or polyanhydrides, and (22) other non-toxic compatible substances employed in pharmaceutical formulations.

"Unit dosage form" refers to a physically discrete unit suitable as a unitary dosage for a human or an animal. Each unit dosage form can contain a predetermined amount of a therapeutic agent calculated to produce a desired effect.

Unless clearly indicated otherwise, a "patient" refers to an animal, such as a mammal, including but not limited to a human. Hence, the methods disclosed herein can be useful in human therapy and veterinary applications. In particular embodiments, the patient is a mammal. In certain embodiments, the patient is a human.

"Effective amount" refers to such amount of a therapeutic agent or a pharmaceutically acceptable salt thereof, which in combination with its parameters of efficacy and potential for toxicity, as well as based on the knowledge of the practicing specialist, should be effective in a given therapeutic form. As is understood in the art, an effective amount can be administered in one or more doses.

"Treatment", "treating" and the like is an approach for obtaining a beneficial or desired result, including clinical results. For purposes of this disclosure, beneficial or desired results include but are not limited to inhibiting and/or suppressing the onset and/or development of a condition or reducing the severity of such condition, such as reducing the number and/or severity of symptoms associated with the condition, increasing the quality of life of those suffering from the condition, decreasing the dose of other medications required to treat the condition, enhancing the effect of another medication a patient is taking for the condition, and/or prolonging survival of patients having the condition.

"Prevent", "preventing" and the like refers to reducing the probability of developing a condition in a patient who does not have, but is at risk of developing a condition. A patient "at risk" may or may not have a detectable condition, and may or may not have displayed a detectable condition prior to the treatment methods disclosed herein. "At risk" denotes that a patient has one or more so-called risk factors, which are measurable parameters that correlate with development of a condition and are known in the art. A patient having one or more of these risk factors has a higher probability of developing the condition than a patient without such risk factor(s).

"Positive inotrope" refers to an agent that causes an increase in myocardial contractile function. Exemplary positive inotropes are a beta-adrenergic receptor agonist, an inhibitor of phosphodiesterase activity, and calcium-sensitizers. Beta-adrenergic receptor agonists include, among others, dopamine, dobutamine, terbutaline, and isoproterenol. Analogs and derivatives of such compounds are also included within positive inotropes. For example, U.S. Pat. No. 4,663,351 discloses a dobutamine prodrug that can be administered orally.

A condition that is "responsive to nitroxyl therapy" includes any condition in which administration of a compound that donates an effective amount of nitroxyl under physiological conditions treats and/or prevents the condition, as those terms are defined herein. A condition whose symptoms are suppressed or diminished upon administration of nitroxyl donor is a condition responsive to nitroxyl therapy.

"Pulmonary hypertension" or "PH" refers to a condition in which the pulmonary arterial pressure is elevated. The current hemodynamic definition of PH is a mean pulmonary arterial pressure ("MPAP") at rest of greater than or equal to 25 mmHg. Badesch et al., *J. Amer. Coll. Cardiol.* 54 (Suppl.):S55-S66 (2009).

"N/A" means not assessed.

"($C_1$-$C_6$)alkyl" refers to saturated linear and branched hydrocarbon structures having 1, 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of ($C_1$-$C_6$)alkyl groups include methyl, ethyl, n-propyl, iso-propyl, n-butyl, tert-butyl, n-hexyl, and the like.

"($C_2$-$C_6$)alkyl" refers to saturated linear and branched hydrocarbon structures having 2, 3, 4, 5, or 6 carbon atoms. When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of ($C_2$-$C_6$)alkyl groups include ethyl, n-propyl, iso-propyl, n-butyl, tert-butyl, n-hexyl, and the like.

"($C_1$-$C_4$)alkyl" refers to saturated linear and branched hydrocarbon structures having 1, 2, 3, or 4 carbon atoms.

When an alkyl residue having a specific number of carbons is named, all geometric isomers having that number of carbons are intended to be encompassed; thus, for example, "propyl" includes n-propyl and iso-propyl and "butyl" includes n-butyl, sec-butyl, iso-butyl and tert-butyl. Examples of $(C_1-C_4)$alkyl groups include methyl, ethyl, n-propyl, iso-propyl, n-butyl, tert-butyl, and the like.

"$(C_2-C_4)$alkenyl" refers to a straight-chain or branched unsaturated hydrocarbon radical having 2, 3, or 4 carbon atoms and a double bond in any position, e.g., ethenyl, 1-propenyl, 2-propenyl (allyl), 1-butenyl, 2-butenyl, 3-butenyl, 1-methylethenyl, 1-methyl-1-propenyl, 2-methyl-2-propenyl, 2-methyl-1-propenyl, 1-methyl-2-propenyl, and the like.

"$(C_3-C_6)$cycloalkyl" refers to a saturated cyclic hydrocarbon containing 3, 4, 5, or 6 ring carbon atoms. Examples of $(C_3-C_6)$cycloalkyl groups include cyclopropyl, cyclobutyl, cyclopentyl, cyclohexyl, and the like.

"$(C_1-C_4)$perhaloalkyl" refers to a $(C_1-C_4)$alkyl group wherein every hydrogen atom is replaced by halo, each halo being independently selected. Examples of $(C_1-C_4)$perhaloalkyl groups include —$CF_3$, —$CCl_3$, —$CF_2CF_3$, —$CCl_2CF_3$, —$CClFCClF_2$, —$CF(CF_3)_2$, —$CBr(CF_3)(CFCl_2)$, and the like.

"$(C_1-C_4)$haloalkyl" refers to a $(C_1-C_4)$alkyl group wherein at least one hydrogen atom is replaced by halo but wherein the $(C_1-C_4)$haloalkyl contains few halos than a $(C_1-C_4)$perhaloalkyl having the same number of carbon atoms as the $(C_1-C_4)$haloalkyl. Each halo of a $(C_1-C_4)$haloalkyl is independently selected. Examples of $(C_1-C_4)$haloalkyl groups include —$CHF_2$, —$CH_2F$, —$CHFCl$, —$CH_2CF_3$, —$CHClCHF_2$, —$CHFCHClF$, —$CH(CF_3)_2$, —$CH(CF_3)(CH_3)$, —$CBr(CHF_2)(CHCl_2)$, and the like.

"$(C_1-C_6)$alkoxy" refers to —O—$(C_1-C_6)$alkyl. Examples of $(C_1-C_6)$alkoxy groups include methoxy, ethoxy, propoxy, n-propoxy, iso-propoxy, butoxy, n-butoxy, sec-butoxy, tert-butoxy, pentoxy, hexyloxy, and the like.

"$(C_1-C_4)$alkoxy" refers to —O—$(C_1-C_4)$alkyl. Examples of $(C_1-C_4)$alkoxy groups include methoxy, ethoxy, propoxy, n-propoxy, iso-propoxy, butoxy, n-butoxy, sec-butoxy, tert-butoxy, and the like.

"$(C_1-C_4)$haloalkoxy" refers to —O—$(C_1-C_4)$haloalkyl. Examples of $(C_1-C_4)$haloalkoxy groups include —$OCHF_2$, —$OCH_2F$, —$OCHFCl$, —$OCH_2CF_3$, —$OCHClCHF_2$, —$OCHFCHClF$, —$OCH(CF_3)_2$, —$OCH(CF_3)(CH_3)$, —$OCBr(CHF_2)(CHCl_2)$, and the like.

"$(C_1-C_4)$perhaloalkoxy" refers to —O—$(C_1-C_4)$perhaloalkyl. Examples of $(C_1-C_4)$perhaloalkoxy groups include —$OCF_3$, —$OCCl_3$, —$OCF_2CF_3$, —$OCCl_2CF_3$, —$OCClFCClF_2$, —$OCF(CF_3)_2$, —$OCBr(CF_3)(CFCl_2)$, and the like.

"$(C_1-C_6)$alkylsulfanyl" refers to —S—$(C_1-C_6)$alkyl. Examples of $(C_1-C_6)$alkylsulfanyl groups include methylsulfanyl, ethylsulfanyl, propylsulfanyl, n-propylsulfanyl, iso-propylsulfanyl, butylsulfanyl, n-butylsulfanyl, sec-butylsulfanyl, tert-butylsulfanyl, pentylsulfanyl, hexylsulfanyl, and the like.

"$(C_1-C_4)$haloalkylsulfanyl" refers to —S—$(C_1-C_4)$haloalkyl. Examples of $(C_1-C_4)$haloalkylsulfanyl groups include —$SCHF_2$, —$SCH_2F$, —$SCHFCl$, —$SCH_2CF_3$, —$SCHClCHF_2$, —$SCHFCHClF$, —$SCH(CF_3)_2$, —$SCH(CF_3)(CH_3)$, —$SCBr(CHF_2)(CHCl_2)$, and the like.

"$(C_1-C_4)$perhaloalkylsulfanyl" refers to —S—$(C_1-C_4)$perhaloalkyl. Examples of $(C_1-C_4)$perhaloalkylsulfanyl groups include —$SCF_3$, —$SCCl_3$, —$SCF_2CF_3$, —$SCCl_2CF_3$, —$SCClFCClF_2$, —$SCF(CF_3)_2$, —$SCBr(CF_3)(CFCl_2)$, and the like.

"$(C_1-C_6)$alkylsulfinyl" refers to —S(O)—$(C_1-C_6)$alkyl. Examples of $(C_1-C_6)$alkylsulfinyl groups include methylsulfinyl, ethylsulfinyl, propylsulfinyl, n-propylsulfinyl, iso-propylsulfinyl, butylsulfinyl, n-butylsulfinyl, sec-butylsulfinyl, tert-butylsulfinyl, pentylsulfinyl, hexylsulfinyl, and the like.

"$(C_1-C_6)$alkylsulfonyl" refers to —$S(O)_2$—$(C_1-C_6)$alkyl. Examples of $(C_1-C_6)$alkylsulfonyl groups include methylsulfonyl, ethylsulfonyl, propylsulfonyl, n-propylsulfonyl, iso-propylsulfonyl, butylsulfonyl, n-butylsulfonyl, sec-butylsulfonyl, tert-butylsulfonyl, pentylsulfonyl, hexylsulfonyl, and the like.

"$(C_3-C_6)$cycloalkylsulfonyl" refers to —$S(O)_2$—$(C_3-C_6)$cycloalkyl. Examples of $(C_3-C_6)$cycloalkylsulfonyl groups include —$S(O)_2$-cyclopropyl, —$S(O)_2$-cyclobutyl, —$S(O)_2$-cyclopentyl, —$S(O)_2$-cyclohexyl, and the like.

"$(C_1-C_4)$perhaloalkylsulfinyl" refers to —S(O)—$(C_1-C_4)$perhaloalkyl. Examples of $(C_1-C_4)$perhaloalkylsulfinyl groups include —S(O)—$CF_3$, —S(O)—$CCl_3$, —S(O)—$CF_2CF_3$, —S(O)—$CCl_2CF_3$, —S(O)—$CClFCClF_2$, —S(O)—$CClFCClF_2$, —S(O)—$CClFCClF_2$, —S(O)—$CF(CF_3)_2$, —S(O)—$CBr(CF_3)(CFCl_2)$, and the like.

"$(C_1-C_4)$perhaloalkylsulfonyl" refers to —$S(O)_2$—$(C_1-C_4)$perhaloalkyl. Examples of $(C_1-C_4)$perhaloalkylsulfonyl groups include —$S(O)_2$—$CF_3$, —$S(O)_2$—$CCl_3$, —$S(O)_2$—$CF_2CF_3$, —$S(O)_2$—$CCl_2CF_3$, —$S(O)_2$—$CClFCClF_2$, —$S(O)_2$—$CClFCClF_2$, —$S(O)_2$—$CClFCClF_2$, —$S(O)_2$—$CF(CF_3)_2$, —$S(O)_2$—$CBr(CF_3)(CFCl_2)$, and the like.

"$(C_1-C_4)$haloalkylsulfinyl" refers to —S(O)—$(C_1-C_4)$haloalkyl. Examples of $(C_1-C_4)$haloalkylsulfinyl groups include —S(O)—$CHF_2$, —S(O)—$CH_2F$, —S(O)—$CHFCl$, —S(O)—$CH_2CF_3$, —S(O)—$CHClCHF_2$, —S(O)—$CHFCHClF$, —S(O)—$CH(CF_3)_2$, —S(O)—$CH(CF_3)(CH_3)$, —S(O)—$CBr(CHF_2)(CHCl_2)$, and the like.

"$(C_1-C_4)$haloalkylsulfonyl" refers to —$S(O)_2$—$(C_1-C_4)$haloalkyl. Examples of $(C_1-C_4)$haloalkylsulfonyl groups include —$S(O)_2$—$CHF_2$, —$S(O)_2$—$CH_2F$, —$S(O)_2$—$CHFCl$, —$S(O)_2$—$CH_2CF_3$, —$S(O)_2$—$CHClCHF_2$, —$S(O)_2$—$CHFCHClF$, —$S(O)_2$—$CH(CF_3)_2$, —$S(O)_2$—$CH(CF_3)(CH_3)$, —$S(O)_2$—$CBr(CHF_2)(CHCl_2)$, and the like.

"N—$(C_1-C_6)$alkylaminosulfonyl" refers to —$S(O)_2$—NH—$(C_1-C_6)$alkyl. Examples of N—$(C_1-C_6)$alkylaminosulfonyl groups include —$S(O)_2$—NH-methyl, —$S(O)_2$—NH-ethyl, —$S(O)_2$—NH-n-propyl, —$S(O)_2$—NH-iso-propyl, —$S(O)_2$—NH-n-butyl, —$S(O)_2$—NH-sec-butyl, —$S(O)_2$—NH-iso-butyl, —$S(O)_2$—NH-tert-butyl, —$S(O)_2$—NH-n-hexyl, and the like.

"N,N-di$(C_1-C_6)$alkylaminosulfonyl" refers to —$S(O)_2$—N—$((C_1-C_6)$alkyl$)_2$ wherein each $(C_1-C_6)$alkyl is independently selected. Examples of N,N-di$(C_1-C_6)$alkylaminosulfonyl groups include —$S(O)_2$—N(methyl)$_2$, —$S(O)_2$—N(methyl)(ethyl), —$S(O)_2$—N(ethyl)$_2$, —$S(O)_2$—N(methyl)(n-propyl), —$S(O)_2$—N(ethyl)(iso-propyl), —$S(O)_2$—N(methyl)(n-butyl), —$S(O)_2$—N(ethyl)(sec-butyl), —$S(O)_2$—N(iso-propyl)(iso-butyl), —$S(O)_2$—N(tert-butyl)$_2$, —$S(O)_2$—N(methyl)(n-hexyl), and the like.

"(5-, 6-, or 7-membered)heterocycloalkyl" refers to a saturated or partially unsaturated, monocyclic-heterocycle ring of 5, 6, or 7 members, comprising 1, 2, 3, or 4 ring heteroatoms each independently selected from nitrogen, oxygen, and sulfur, wherein said nitrogen and sulfur heteroatoms may optionally be oxidized and the nitrogen heteroatom may optionally be quaternized. A heterocycloalkyl group can be attached to the parent structure through a carbon or a heteroatom. Examples of (5-, 6-, or 7-membered)heterocycloalkyl groups include pyrrolidinyl, piperidinyl, piperazinyl, tetrahydro-oxazinyl, tetrahydrofuranyl, thiolanyl, dithiolanyl, pyrrolinyl, pyrazolinyl, pyrazolidinyl, imidazolinyl, imidazolidinyl, tetrahydrofuranone, γ-butyrolactone, 2H-pyranyl, 4H-pyranyl, dioxolanyl, tetrahydropyranyl, dioxanyl, dihydrothiophenyl, morpholinyl, thiomorpholinyl, oxazinyl, tetrahydro-oxazinyl, 1,2,3-triazinanyl, and the like.

"(5- or 6-membered)heteroaryl" refers to a monocyclic aromatic heterocycle ring of 5 or 6 members, i.e., a monocyclic aromatic ring comprising at least one ring heteroatom, e.g., 1, 2, 3, or 4 ring heteroatoms, each independently selected from nitrogen, oxygen, and sulfur. When the (5- or 6-membered)heteroaryl comprises a nitrogen or sulfur atom(s), the nitrogen atom or sulfur atom(s) are optionally oxidized to form the N-oxide or S-oxide(s). A (5- or 6-membered)heteroaryl group can be attached to the parent structure through a carbon or heteroatom. Examples of (5- or 6-membered)heteroaryls include pyridyl, pyrrolyl, pyrazolyl, furyl, imidazolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, thiophenyl, and the like.

"$(C_6-C_{10})$aryl" refers to a monovalent aromatic hydrocarbon group which may be monocyclic, bicyclic or tricyclic, wherein at least one ring in the system is aromatic and wherein each ring in the system contains 3, 4, 5, 6 or 7 ring members. Examples of $(C_6-C_{10})$aryl groups include without limitation phenyl, naphthyl, indanyl, indenyl and tetralinyl. In some embodiments, the aryl is phenyl.

Unless clearly indicated otherwise, each substituent of a "substituted phenyl", "phenyl substituted with 1, 2, or 3 independently selected substituent(s)", "monosubstituted phenyl", "disubstituted phenyl", "trisubstituted phenyl", and the like is independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, C(=O)OH, C(=O)O$(C_1-C_6)$alkyl, C(=O)NR$^4$R$^5$, C(=O)-(5-, 6-, or 7-membered)heterocycloalkyl, (5-, 6-, or 7-membered)heterocycloalkyl, $(C_1-C_6)$alkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, S(O)$_2$—NR$^6$R$^7$, S(O)$_2$-phenyl, S(O)$_2$-(5-, 6-, or 7-membered)heterocycloalkyl, S(=O)(=NR$^8$)(C$_1$-C$_6$)alkyl, NR$^4$R$^5$, N—(C$_1$-C$_6$)alkylaminosulfonyl, and N,N-di(C$_1$-C$_6$)alkylaminosulfonyl, wherein said (5-, 6-, or 7-membered)heterocycloalkyl is unsubstituted or substituted with 1 or 2 substituent(s) independently selected from halo or $(C_1-C_6)$alkyl.

"Halo" or "halogen" refers to fluoro (—F), chloro (—Cl), bromo (—Br) and iodo (—I).

A compound of the disclosure can contain one, two, or more asymmetric centers and thus can give rise to enantiomers, diastereomers, and other stereoisomeric forms. The disclosure encompasses compounds with all such possible forms, as well as their racemic and resolved forms or any mixture thereof, unless specifically otherwise indicated. When a compound of the disclosure contains an olefinic double bond, a C=N double bond, or any other center of geometric asymmetry, it is intended to include all "geometric isomers", e.g., both Z and E geometric isomers, unless specifically otherwise indicated. All "tautomers", e.g., amine-imine, enamine-enimine, enamine-imine, urea-isourea, ketone-enol, amide-imidic acid, lactam-lactim, are intended to be encompassed by the disclosure as well unless specifically otherwise indicated.

Unless otherwise stated, structures depicted herein are also meant to include compounds that differ only in the presence of one or more isotopically enriched or isotopically-labeled atoms. Examples of isotopes present in the compounds of the disclosure include isotopes of hydrogen (e.g., $^2$H and $^3$H), carbon (e.g., $^{13}$C and $^{14}$C), nitrogen (e.g., $^{15}$N) and oxygen (e.g., $^{17}$O and $^{18}$O).

3.2 Compounds of the Disclosure

One aspect of the disclosure provides a compound of formula (Ia)

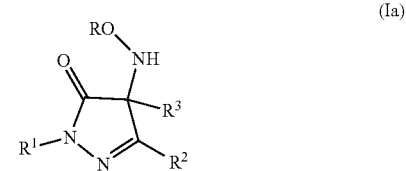

(Ia)

or a pharmaceutically acceptable salt thereof, wherein:
R$^1$ is phenyl, wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;
R$^4$, R$^5$, R$^6$ and R$^7$ are each independently H or $(C_1-C_6)$alkyl;
R$^8$ is H, —(C=O)(C$_1$-C$_6$)alkyl or —(C=O)(C$_1$-C$_4$)perhaloalkyl;
R$^2$ is $(C_1-C_6)$alkyl;
R$^3$ is —C(=NOR$^9$)R$^{10}$, wherein R$^9$ is $(C_1-C_6)$alkyl and R$^{10}$ is phenyl; and
R is hydrogen, —COH, —CO—(C$_1$-C$_6$)alkyl, —CO—(C$_2$-C$_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl or 5-methyl-2-oxo-2H-1,3-dioxol-4-ylmethyl.

In one embodiment, the present disclosure relates to a compound of formula (Ia) and the attendant definitions, wherein R$^1$ is unsubstituted phenyl. In another embodiment, $R^1$ is phenyl substituted with 1, 2 or 3 independently selected substituent(s), the substitutents being selected from among those disclosed above for $R^1$ in connection with formula (Ia). In another embodiment, $R^1$ is phenyl substituted with 1, 2, or 3 independently selected substituent(s), at least one of which is halo. In another embodiment, $R^1$ is phenyl substituted with 1, 2, or 3 independently selected substituent(s), at least one of which is $(C_1-C_6)$alkyl. In another embodiment, $R^1$ is phenyl substituted with 1, 2, or 3 independently selected substituent(s), at least one of which is $(C_1-C_4)$haloalkyl. In another embodiment, $R^1$ is phenyl substituted with 1, 2, or 3 independently selected substituent(s), at least one of which is $(C_1-C_4)$perhaloalkyl. In another embodiment, $R^1$ is phenyl substituted with 1, 2, or 3 independently selected substituent(s), at least one of which is $(C_1-C_6)$alkoxy. In another embodiment, $R^1$ is phenyl substituted with 1, 2, or 3 independently selected substituent(s), at least one of which is $(C_1-C_4)$perhaloalkoxy. In another embodiment, $R^1$ is phenyl substituted with 1, 2, or 3 independently selected substituent(s), at least one of which is —C(=O)OH. In another embodiment, $R^1$ is phenyl substituted with 1, 2, or 3 independently selected substituent(s), at least one of which is —C(=O)O($C_1-C_6$)alkyl. In another embodiment, $R^1$ is phenyl substituted with 1, 2, or 3 independently selected substituent(s), at least one of which is —C(=O)$NR^4R^5$. In another embodiment, $R^1$ is phenyl substituted with 1, 2, or 3 independently selected substituent(s), at least one of which is —C(=O)NH($C_1-C_6$)alkyl, wherein said alkyl is substituted with COOH. In another embodiment, $R^1$ is phenyl substituted with 1, 2, or 3 independently selected substituent(s), at least one of which is —C(=O)NH—($C_1-C_6$)alkylsulfonyl. In another embodiment, $R^1$ is phenyl substituted with 1, 2, or 3 independently selected substituent(s), at least one of which is —C(=O)-(5-, 6-, or 7-membered)heterocycloalkyl. In another embodiment, $R^1$ is phenyl substituted with 1, 2, or 3 independently selected substituent(s), at least one of which is (5-, 6-, or 7-membered)heterocycloalkyl. In another embodiment, $R^1$ is phenyl substituted with 1, 2, or 3 independently selected substituent(s), at least one of which is $(C_1-C_6)$alkylsulfanyl. In another embodiment, $R^1$ is phenyl substituted with 1, 2, or 3 independently selected substituent(s), at least one of which is methylsulfanyl. In another embodiment, $R^1$ is phenyl substituted with 1, 2, or 3 independently selected substituent(s), at least one of which is $(C_1-C_4)$perhaloalkylsulfanyl. In another embodiment, $R^1$ is phenyl substituted with 1, 2, or 3 independently selected substituent(s), at least one of which is trifluoromethylsulfanyl. In another embodiment, $R^1$ is phenyl substituted with 1, 2, or 3 independently selected substituent(s), at least one of which is $(C_1-C_6)$alkylsulfinyl. In another embodiment, $R^1$ is phenyl substituted with 1, 2, or 3 independently selected substituent(s), at least one of which is methylsulfinyl. In another embodiment, $R^1$ is phenyl substituted with 1, 2, or 3 independently selected substituent(s), at least one of which is $(C_1-C_6)$alkylsulfonyl. In another embodiment, $R^1$ is phenyl substituted with 1, 2, or 3 independently selected substituent(s), at least one of which is methylsulfonyl. In another embodiment, $R^1$ is phenyl substituted with 1, 2, or 3 independently selected substituent(s), at least one of which is $(C_3-C_6)$cycloalkylsulfonyl. In another embodiment, $R^1$ is phenyl substituted with 1, 2, or 3 independently selected substituent(s), at least one of which is cyclopropylsulfonyl. In another embodiment, $R^1$ is phenyl substituted with 1, 2, or 3 independently selected substituent(s), at least one of which is $(C_1-C_4)$haloalkylsulfinyl. In another embodiment, $R^1$ is phenyl substituted with 1, 2, or 3 independently selected substituent(s), at least one of which is $(C_1-C_4)$haloalkylsulfonyl. In another embodiment, $R^1$ is phenyl substituted with 1, 2, or 3 independently selected substituent(s), at least one of which is $(C_1-C_4)$perhaloalkylsulfinyl. In another embodiment, $R^1$ is phenyl substituted with 1, 2, or 3 independently selected substituent(s), at least one of which is $(C_1-C_4)$perhaloalkylsulfonyl. In another embodiment, $R^1$ is phenyl substituted with 1, 2, or 3 independently selected substituent(s), at least one of which is —$S(O)_2$—$NR^6R^7$. In another embodiment, $R^1$ is phenyl substituted with 1, 2, or 3 independently selected substituent(s), at least one of which is —$S(O)_2$-phenyl. In another embodiment, $R^1$ is phenyl substituted with 1, 2, or 3 independently selected substituent(s), at least one of which is —$S(O)_2$-(5-, 6-, or 7-membered)heterocycloalkyl. In another embodiment, $R^1$ is phenyl substituted with 1, 2, or 3 independently selected substituent(s), at least one of which is —S(=O)(=$NR^8$)($C_1-C_6$)alkyl. In another embodiment, $R^1$ is phenyl substituted with 1, 2, or 3 independently selected substituent(s), at least one of which is N,N-di($C_1-C_6$)alkylaminosulfonyl. In another embodiment, $R^1$ is phenyl substituted with 1, 2, or 3 independently selected substituent(s), at least one of which is N,N-dimethylaminosulfonyl.

In another embodiment, the present disclosure relates to a compound of formula (Ia) and the attendant definitions, wherein $R^1$ is monosubstituted phenyl substituted with halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)$NR^4R^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$-(5-, 6-, or 7-membered)heterocycloalkyl, —S(=O)(=$NR^8$)($C_1-C_6$)alkyl, —$NR^4R^5$, N—($C_1-C_6$)alkylaminosulfonyl, or N,N-di($C_1-C_6$)alkylaminosulfonyl.

In another embodiment, the present disclosure relates to a compound of formula (Ia) and the attendant definitions, wherein $R^1$ is disubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)$NR^4R^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$-(5-, 6-, or 7-membered)heterocycloalkyl, —S(=O)(=$NR^8$)($C_1-C_6$)alkyl, —$NR^4R^5$, N—($C_1-C_6$)alkylaminosulfonyl, and N,N-di($C_1-C_6$)alkylaminosulfonyl.

In another embodiment, the present disclosure relates to a compound of formula (Ia) and the attendant definitions, wherein $R^1$ is trisubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)$NR^4R^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl.

In one embodiment, the present disclosure relates to a compound of formula (Ia) and the attendant definitions, wherein R² is (C₁-C₄)alkyl. In another embodiment, R² is methyl, ethyl, propyl, or butyl. In another embodiment, R² is methyl, ethyl, or propyl. In another embodiment, R² is methyl, ethyl, or butyl. In another embodiment, R² is methyl, propyl, or butyl. In another embodiment, R² is ethyl, propyl, or butyl. In another embodiment, R² is methyl or ethyl. In another embodiment, R² is methyl or propyl. In another embodiment, R² is methyl or butyl. In another embodiment, R² is ethyl or propyl. In another embodiment, R² is ethyl or butyl. In another embodiment, R² is propyl or butyl. In another embodiment, R² is methyl. In another embodiment, R² is ethyl. In another embodiment, R² is propyl. In another embodiment, R² is iso-propyl. In another embodiment, R² is butyl. In another embodiment, R² is tert-butyl.

In one embodiment, the present disclosure relates to a compound of formula (Ia) and the attendant definitions, wherein R³ is —C(=NOR⁹)R¹⁰ wherein R⁹ is (C₁-C₄)alkyl and R¹⁰ is phenyl. In another embodiment, R⁹ is phenyl is methyl, ethyl or propyl. In another embodiment, R⁹ is methyl or ethyl. In another embodiment, R⁹ is methyl. In another embodiment, R⁹ is ethyl.

In one embodiment, the present disclosure relates to a compound of formula (Ia) and the attendant definitions, wherein R is hydrogen, —CO-methyl, —CO-ethyl, —CO-benzyl, —CO-phenyl or 5-methyl-2-oxo-2H-1,3-dioxol-4-ylmethyl. In another embodiment, R is hydrogen or 5-methyl-2-oxo-2H-1,3-dioxol-4-ylmethyl. In another embodiment, R is hydrogen. In another embodiment, R is 5-methyl-2-oxo-2H-1,3-dioxol-4-ylmethyl. In another embodiment, R is —CO-methyl or —CO-ethyl. In another embodiment, R is —CO-methyl. In another embodiment, R is —CO-ethyl. In another embodiment, R is —CO-benzyl or —CO-phenyl. In another embodiments, R is —CO-benzyl. In another embodiment, R is —CO-phenyl. In another embodiment, R is —CO—NH₂. In each of the above embodiments in this paragraph, R is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is -halo, —NH₂, —NHCH₃, —CF₃ or —OCH₃ or the substituents are independently selected from -halo, —NH₂, —NHCH₃, —CF₃ or —OCH₃.

Another aspect of the disclosure provides a compound of formula (Ib)

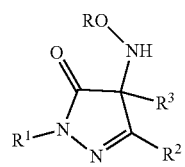

(Ib)

or a pharmaceutically acceptable salt thereof, wherein:
R¹ is H, (C₁-C₆)alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, (C₁-C₆)alkyl, (C₁-C₄)haloalkyl, (C₁-C₄)perhaloalkyl, (C₁-C₆)alkoxy, (C₁-C₄)haloalkoxy, (C₁-C₄)perhaloalkoxy, —C(=O)OH, —C(=O)O(C₁-C₆)alkyl, —C(=O)O(5-methyl-2-oxo-2H-1,3-dioxol-4-ylmethyl), —C(=O)NR⁴R⁵, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl;

R⁴, R⁵, R⁶ and R⁷ are each independently H or (C₁-C₆)alkyl;

R⁸ is H, —(C=O)(C₁-C₆)alkyl or —(C=O)(C₁-C₄)perhaloalkyl;

R² is (C₁-C₆)alkyl or phenyl, wherein said alkyl and phenyl are unsubstituted or substituted with 1, 2, 3, 4, or 5 substituent(s) independently selected from halo, (C₁-C₆)alkyl, (C₁-C₄)haloalkyl, (C₁-C₄)perhaloalkyl, (C₁-C₆)alkoxy, (C₁-C₄)haloalkoxy, (C₁-C₄)perhaloalkoxy, —C(=O)OH, —C(=O)O(C₁-C₆)alkyl, —C(=O)NR⁴R⁵, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl;

R³ is (C₁-C₆)alkyl substituted with 1, 2 or 3 substituent(s) independently selected from —OH, —C(=O)OH, —C(=O)O(C₁-C₆)alkyl, —C(=O)O(5-methyl-2-oxo-2H-1,3-dioxol-4-ylmethyl), —C(=O)NR⁴R⁵, —NR⁴R⁵, (C₁-C₆)alkoxy, (C₁-C₄)haloalkoxy, (C₁-C₄)perhaloalkoxy, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, N—(C₁-C₆)alkylaminosulfonyl, N,N-di(C₁-C₆)alkylaminosulfonyl, (5- or 6-membered)heteroaryl or phenyl, wherein said heteroaryl or phenyl are unsubstituted or substituted with 1, 2, 3, 4, or 5 substituent(s) independently selected from halo, (C₁-C₆)alkyl, (C₁-C₄)haloalkyl, (C₁-C₄)perhaloalkyl, (C₁-C₆)alkoxy, (C₁-C₄)haloalkoxy, (C₁-C₄)perhaloalkoxy, —C(=O)OH, —C(=O)O(C₁-C₆)alkyl, —C(=O)NR⁴R⁵, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl; and R is hydrogen, —COH, —CO—($C_1$-$C_6$)alkyl, —CO—($C_2$-$C_4$)alkenyl, —CO-phenyl, —CO-benzyl, —CO— cyclopentyl, —CO-cyclohexyl, —CO-(5-, 6-, or 7-membered) heterocycloalkyl, —CO-benzyloxy, —CO—O—($C_1$-$C_6$) alkyl, —CO—$NH_2$, —CO—NH—($C_1$-$C_4$)alkyl, or —CO—N(($C_1$-$C_4$)alkyl)$_2$, wherein said —($C_1$-$C_6$)alkyl, —($C_2$-$C_4$) alkenyl, phenyl, benzyl, cyclopentyl, cyclohexyl, -(5-, 6-, or 7-membered)heterocycloalkyl, benzyloxy, —O—($C_1$-$C_6$) alkyl, —NH—($C_1$-$C_4$)alkyl, or —N(($C_1$-$C_4$)alkyl)$_2$ can be unsubstituted or substituted with 1, 2 or 3 substituents selected from halo, —($C_1$-$C_6$)alkyl, —($C_2$-$C_4$)alkenyl, —($C_2$-$C_3$)alkynyl, -(5- or 6-membered)heteroaryl, —O—($C_1$-$C_6$)alkyl, —S—($C_1$-$C_6$)alkyl, —C(halo)$_3$, —CH(halo)$_2$, —$CH_2$(halo), —CN, —$NO_2$, —$NH_2$, —NH—($C_1$-$C_4$)alkyl, —N(—($C_1$-$C_4$)alkyl)$_2$, —C(O)($C_1$-$C_4$)alkyl, —C(O)O($C_1$-$C_4$)alkyl, —OC(O)($C_1$-$C_4$)alkyl, —OC(O)$NH_2$, —S(O)($C_1$-$C_4$)alkyl, —S(O)$_2$($C_1$-$C_4$)alkyl or 5-methyl-2-oxo-2H-1,3-dioxol-4-ylmethyl.

In one embodiment, the present disclosure relates to a compound of formula (Ib) and the attendant definitions, wherein $R^1$ is H. In another embodiment, $R^1$ is ($C_1$-$C_6$)alkyl, wherein the alkyl is unsubstituted or substituted with 1, 2 or 3 independently selected substituents. In another embodiment, $R^1$ is (5- or 6-membered)heteroaryl, wherein the heteroaryl is unsubstituted or substituted with 1, 2, 3, 4, or 5 independently selected substituents. In another embodiment, $R^1$ is phenyl, wherein the phenyl is unsubstituted or substituted with 1, 2, 3, 4, or 5 independently selected substituents. In each of the embodiments listed in this paragraph, the substitutents are selected from among those disclosed above for $R^1$ in connection with formula (Ib).

In another embodiment, the present disclosure relates to a compound of formula (Ib) and the attendant definitions, wherein $R^1$ is ($C_1$-$C_4$)alkyl. In another embodiment, $R^1$ is methyl, ethyl, propyl, or butyl. In another embodiment, $R^1$ is methyl, ethyl, or propyl. In another embodiment, $R^1$ is methyl, ethyl, or butyl. In another embodiment, $R^1$ is methyl, propyl, or butyl. In another embodiment, $R^1$ is ethyl, propyl, or butyl. In another embodiment, $R^1$ is methyl or ethyl. In another embodiment, $R^1$ is methyl or propyl. In another embodiment, $R^1$ is methyl or butyl. In another embodiment, $R^1$ is ethyl or propyl. In another embodiment, $R^1$ is ethyl or butyl. In another embodiment, $R^1$ is propyl or butyl. In another embodiment, $R^1$ is methyl. In another embodiment, $R^1$ is ethyl. In another embodiment, $R^1$ is propyl. In another embodiment, $R^1$ is iso-propyl. In another embodiment, $R^1$ is butyl. In another embodiment, $R^1$ is tert-butyl. In each of the embodiments listed in this paragraph, the alkyl is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is —C(=O)OH, —C(=O)O($C_1$-$C_6$)alkyl, —C(=O)$OCH_3$, —C(=O)$OCH_2CH_3$, —C(=O)O(5-methyl-2-oxo-2H-1,3-dioxol-4-ylmethyl), —C(=O)$NR^4R^5$, —C(=O)$NH_2$, —C(=O)$NHCH_3$, —C(=O)N($CH_3$)$_2$, —$NR^4R^5$, —$NH_2$, —$NHCH_3$, ($C_1$-$C_6$)alkylsulfanyl, ($C_1$-$C_6$)alkylsulfinyl, ($C_1$-$C_6$)alkylsulfonyl, —S(O)$_2$—$NH_2$, —N—($C_1$-$C_6$)alkylaminosulfonyl, or N,N-di($C_1$-$C_6$)alkylaminosulfonyl or the substituents are independently selected from —C(=O)OH, —C(=O)O($C_1$-$C_6$)alkyl, —C(=O)$OCH_3$, —C(=O)$OCH_2CH_3$, —C(=O)O(5-methyl-2-oxo-2H-1,3-dioxol-4-ylmethyl), —C(=O)$NR^4R^5$, —C(=O)$NH_2$, —C(=O)$NHCH_3$, —C(=O)N($CH_3$)$_2$, —$NR^4R^5$, —$NH_2$, —$NHCH_3$, ($C_1$-$C_6$)alkylsulfanyl, ($C_1$-$C_6$)alkylsulfinyl, ($C_1$-$C_6$)alkylsulfonyl, —S(O)$_2$—$NH_2$, —N—($C_1$-$C_6$)alkylaminosulfonyl, or N,N-di($C_1$-$C_6$)alkylaminosulfonyl.

In another embodiment, the present disclosure relates to a compound of formula (Ib) and the attendant definitions, wherein $R^1$ is (5- or 6-membered)heteroaryl, wherein the heteroaryl is unsubstituted or substituted with 1, 2 or 3 independently selected substituents, the substitutents being selected from among those disclosed above for $R^1$ in connection with formula (Ib). In another embodiment, $R^1$ is unsubstituted (5- or 6-membered)heteroaryl. In another embodiment, $R^1$ is monosubstituted (5- or 6-membered) heteroaryl. In another embodiment, $R^1$ is disubstituted (5- or 6-membered)heteroaryl. In another embodiment, $R^1$ is trisubstituted (5- or 6-membered)heteroaryl. In various embodiments of each of the above embodiments in this paragraph, the substituent is halo, ($C_1$-$C_6$)alkyl, ($C_1$-$C_6$)alkoxy, phenyl, —C(=O)$NR^4R^5$, ($C_1$-$C_6$)alkylsulfinyl, ($C_1$-$C_6$)alkylsulfonyl, and N,N-di($C_1$-$C_6$)alkylaminosulfonyl.

In another embodiment, the present disclosure relates to a compound of formula (Ib) and the attendant definitions, wherein $R^1$ is unsubstituted phenyl. In another embodiment, $R^1$ is phenyl substituted with 1, 2 or 3 independently selected substituent(s), the substitutents being selected from among those disclosed above for $R^1$ in connection with formula (Ib). In another embodiment, $R^1$ is phenyl substituted with 1, 2, or 3 independently selected substituent(s), at least one of which is halo. In another embodiment, $R^1$ is phenyl substituted with 1, 2, or 3 independently selected substituent(s), at least one of which is ($C_1$-$C_6$)alkyl. In another embodiment, $R^1$ is phenyl substituted with 1, 2, or 3 independently selected substituent(s), at least one of which is ($C_1$-$C_4$)haloalkyl. In another embodiment, $R^1$ is phenyl substituted with 1, 2, or 3 independently selected substituent(s), at least one of which is ($C_1$-$C_4$)perhaloalkyl. In another embodiment, $R^1$ is phenyl substituted with 1, 2, or 3 independently selected substituent(s), at least one of which is ($C_1$-$C_6$)alkoxy. In another embodiment, $R^1$ is phenyl substituted with 1, 2, or 3 independently selected substituent(s), at least one of which is ($C_1$-$C_4$)perhaloalkoxy. In another embodiment, $R^1$ is phenyl substituted with 1, 2, or 3 independently selected substituent(s), at least one of which is —C(=O) OH. In another embodiment, $R^1$ is phenyl substituted with 1, 2, or 3 independently selected substituent(s), at least one of which is —C(=O)O($C_1$-$C_6$)alkyl. In another embodiment, $R^1$ is phenyl substituted with 1, 2, or 3 independently selected substituent(s), at least one of which is —C(=O)$NR^4R^5$. In another embodiment, $R^1$ is phenyl substituted with 1, 2, or 3 independently selected substituent(s), at least one of which is —C(=O)NH($C_1$-$C_6$)alkyl, wherein said alkyl is substituted with COOH. In another embodiment, $R^1$ is phenyl substituted with 1, 2, or 3 independently selected substituent(s), at least one of which is —C(=O)NH—($C_1$-$C_6$)alkylsulfonyl. In another embodiment, $R^1$ is phenyl substituted with 1, 2, or 3 independently selected substituent(s), at least one of which is —C(=O)-(5-, 6-, or 7-membered)heterocycloalkyl. In another embodiment, $R^1$ is phenyl substituted with 1, 2, or 3 independently selected substituent(s), at least one of which is (5-, 6-, or 7-membered)heterocycloalkyl. In another embodiment, $R^1$ is phenyl substituted with 1, 2, or 3 independently selected substituent(s), at least one of which is ($C_1$-$C_6$)alkylsulfanyl. In another embodiment, $R^1$ is phenyl substituted with 1, 2, or 3 independently selected substituent(s), at least one of which is ($C_1$-$C_4$)perhaloalkylsulfanyl. In another embodiment, $R^1$ is phenyl substituted with 1, 2, or 3 independently selected k substituent(s), at least one of which is $(C_1$-$C_6)$alkylsulfinyl. In another embodiment, $R^1$ is phenyl substituted with 1, 2, or 3 independently selected substituent(s), at least one of which is $(C_1$-$C_6)$alkylsulfonyl. In another embodiment, $R^1$ is phenyl substituted with 1, 2, or 3 independently selected substituent(s), at least one of which is $(C_3$-$C_6)$cycloalkylsulfonyl. In another embodiment, $R^1$ is phenyl substituted with 1, 2, or 3 independently selected substituent(s), at least one of which is $(C_1$-$C_4)$haloalkylsulfinyl. In another embodiment, $R^1$ is phenyl substituted with 1, 2, or 3 independently selected substituent(s), at least one of which is $(C_1$-$C_4)$haloalkylsulfonyl. In another embodiment, $R^1$ is phenyl substituted with 1, 2, or 3 independently selected substituent(s), at least one of which is $(C_1$-$C_4)$perhaloalkylsulfinyl. In another embodiment, $R^1$ is phenyl substituted with 1, 2, or 3 independently selected substituent(s), at least one of which is $(C_1$-$C_4)$perhaloalkylsulfonyl. In another embodiment, $R^1$ is phenyl substituted with 1, 2, or 3 independently selected substituent(s), at least one of which is —S(O)$_2$—NR$^6$R$^7$. In another embodiment, $R^1$ is phenyl substituted with 1, 2, or 3 independently selected substituent(s), at least one of which is —S(O)$_2$-phenyl. In another embodiment, $R^1$ is phenyl substituted with 1, 2, or 3 independently selected substituent(s), at least one of which is —S(O)$_2$-(5-, 6-, or 7-membered)heterocycloalkyl. In another embodiment, $R^1$ is phenyl substituted with 1, 2, or 3 independently selected substituent(s), at least one of which is —S(=O)(=NR$^8$)(C$_1$-C$_6$)alkyl. In another embodiment, $R^1$ is phenyl substituted with 1, 2, or 3 independently selected substituent(s), at least one of which is N,N-di(C$_1$-C$_6$)alkylaminosulfonyl.

In another embodiment, the present disclosure relates to a compound of formula (Ib) and the attendant definitions, wherein $R^1$ is monosubstituted phenyl substituted with halo, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, $(C_1$-$C_6)$alkylsulfanyl, $(C_1$-$C_4)$perhaloalkylsulfanyl, $(C_1$-$C_6)$alkylsulfinyl, $(C_1$-$C_6)$alkylsulfonyl, $(C_1$-$C_4)$haloalkylsulfinyl, $(C_1$-$C_4)$haloalkylsulfonyl, $(C_1$-$C_4)$perhaloalkylsulfinyl, $(C_1$-$C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$) alkylaminosulfonyl, or N,N-di(C$_1$-C$_6$)alkylaminosulfonyl.

In another embodiment, the present disclosure relates to a compound of formula (Ib) and the attendant definitions, wherein $R^1$ is disubstituted phenyl, each substituent being independently selected from halo, $(C_1$-$C_6)$alkyl, $(C_1$-$C_4)$perhaloalkyl, $(C_1$-$C_6)$alkoxy, $(C_1$-$C_4)$haloalkoxy, $(C_1$-$C_4)$perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, $(C_1$-$C_6)$alkylsulfanyl, $(C_1$-$C_4)$perhaloalkylsulfanyl, $(C_1$-$C_6)$alkylsulfinyl, $(C_1$-$C_6)$alkylsulfonyl, $(C_1$-$C_4)$haloalkylsulfinyl, $(C_1$-$C_4)$haloalkylsulfonyl, $(C_1$-$C_4)$perhaloalkylsulfinyl, $(C_1$-$C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$) alkylaminosulfonyl, and N,N-di(C$_1$-C$_6$)alkylaminosulfonyl.

In another embodiment, the present disclosure relates to a compound of formula (Ib) and the attendant definitions, wherein $R^1$ is trisubstituted phenyl, each substituent being independently selected from halo, $(C_1$-$C_6)$alkyl, $(C_1$-$C_4)$perhaloalkyl, $(C_1$-$C_6)$alkoxy, $(C_1$-$C_4)$haloalkoxy, $(C_1$-$C_4)$perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, $(C_1$-$C_6)$alkylsulfanyl, $(C_1$-$C_4)$perhaloalkylsulfanyl, $(C_1$-$C_6)$alkylsulfinyl, $(C_1$-$C_6)$alkylsulfonyl, $(C_1$-$C_4)$haloalkylsulfinyl, $(C_1$-$C_4)$haloalkylsulfonyl, $(C_1$-$C_4)$perhaloalkylsulfinyl, $(C_1$-$C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$) alkylaminosulfonyl, and N,N-di(C$_1$-C$_6$)alkylaminosulfonyl.

In one embodiment, the present disclosure relates to a compound of formula (Ib) and the attendant definitions, wherein $R^2$ is $(C_1$-$C_4)$ alkyl. In another embodiment, $R^2$ is methyl, ethyl, propyl, or butyl. In another embodiment, $R^2$ is methyl, ethyl, or propyl. In another embodiment, $R^2$ is methyl, ethyl, or butyl. In another embodiment, $R^2$ is methyl, propyl, or butyl. In another embodiment, $R^2$ is ethyl, propyl, or butyl. In another embodiment, $R^2$ is methyl or ethyl. In another embodiment, $R^2$ is methyl or propyl. In another embodiment, $R^2$ is methyl or butyl. In another embodiment, $R^2$ is ethyl or propyl. In another embodiment, $R^2$ is ethyl or butyl. In another embodiment, $R^2$ is propyl or butyl. In another embodiment, $R^2$ is methyl. In another embodiment, $R^2$ is ethyl. In another embodiment, $R^2$ is propyl. In another embodiment, $R^2$ is iso-propyl. In another embodiment, $R^2$ is butyl. In another embodiment, $R^2$ is tert-butyl. In each of the embodiments listed in this paragraph, the alkyl is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is —C(=O)OH, —C(=O)O(C$_1$-C$_6$)alkyl, —C(=O)OCH$_3$, —C(=O)OCH$_2$CH$_3$, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, $(C_1$-$C_6)$alkylsulfanyl, $(C_1$-$C_6)$alkylsulfinyl, $(C_1$-$C_6)$alkylsulfonyl, —S(O)$_2$—NH$_2$, —N—(C$_1$-C$_6$)alkylaminosulfonyl, or N,N-di(C$_1$-C$_6$)alkylaminosulfonyl or the substituents are independently selected from —C(=O)OH, —C(=O)O(C$_1$-C$_6$)alkyl, —C(=O)OCH$_3$, —C(=O)OCH$_2$CH$_3$, —C(=O) O(5-methyl-2-oxo-2H-1,3-dioxol-4-ylmethyl), —C(=O) NR$^4$R$^5$, —C(=O)NH$_2$, —C(=O)NHCH$_3$, —C(=O)N (CH$_3$)$_2$, —NR$^4$R$^5$, —NH$_2$, —NHCH$_3$, $(C_1$-$C_6)$ alkylsulfanyl, $(C_1$-$C_6)$alkylsulfinyl, $(C_1$-$C_6)$alkylsulfonyl, —S(O)$_2$—NH$_2$, —N—(C$_1$-C$_6$)alkylaminosulfonyl, or N,N-di(C$_1$-C$_6$)alkylaminosulfonyl.

In another embodiment, the present disclosure relates to a compound of formula (Ib) and the attendant definitions, wherein $R^2$ is unsubstituted phenyl. In another embodiment, $R^2$ is phenyl substituted with 1, 2 or 3 independently selected substituent(s), the substituents being selected from among those disclosed above for $R^2$ in connection with formula (Ib). In another embodiment, $R^2$ is phenyl substituted with 1, 2, or 3 independently selected substituent(s), at least one of which is halo. In another embodiment, $R^2$ is phenyl substituted with 1, 2, or 3 independently selected substituent(s), at least one of which is $(C_1$-$C_6)$alkyl. In another embodiment, $R^2$ is phenyl substituted with 1, 2, or 3 independently selected substituent(s), at least one of which is $(C_1$-$C_4)$ haloalkyl. In another embodiment, $R^2$ is phenyl substituted with 1, 2, or 3 independently selected substituent(s), at least one of which is $(C_1$-$C_4)$perhaloalkyl. In another embodiment, $R^2$ is phenyl substituted with 1, 2, or 3 independently selected substituent(s), at least one of which is $(C_1$-$C_6)$ alkoxy. In another embodiment, $R^2$ is phenyl substituted with 1, 2, or 3 independently selected substituent(s), at least one of which is $(C_1-C_4)$perhaloalkoxy. In another embodiment, $R^2$ is phenyl substituted with 1, 2, or 3 independently selected substituent(s), at least one of which is —C(=O)OH. In another embodiment, $R^2$ is phenyl substituted with 1, 2, or 3 independently selected substituent(s), at least one of which is —C(=O)O($C_1-C_6$)alkyl. In another embodiment, $R^2$ is phenyl substituted with 1, 2, or 3 independently selected substituent(s), at least one of which is —C(=O)NR$^4$R$^5$. In another embodiment, $R^2$ is phenyl substituted with 1, 2, or 3 independently selected substituent(s), at least one of which is —C(=O)NH($C_1-C_6$)alkyl, wherein said alkyl is substituted with COOH. In another embodiment, $R^2$ is phenyl substituted with 1, 2, or 3 independently selected substituent(s), at least one of which is —C(=O)NH—($C_1$-$C_6$)alkylsulfonyl. In another embodiment, $R^2$ is phenyl substituted with 1, 2, or 3 independently selected substituent(s), at least one of which is —C(=O)-(5-, 6-, or 7-membered)heterocycloalkyl. In another embodiment, $R^2$ is phenyl substituted with 1, 2, or 3 independently selected substituent(s), at least one of which is (5-, 6-, or 7-membered)heterocycloalkyl. In another embodiment, $R^2$ is phenyl substituted with 1, 2, or 3 independently selected substituent(s), at least one of which is ($C_1$-$C_6$)alkylsulfanyl. In another embodiment, $R^2$ is phenyl substituted with 1, 2, or 3 independently selected substituent(s), at least one of which is methylsulfanyl. In another embodiment, $R^2$ is phenyl substituted with 1, 2, or 3 independently selected substituent(s), at least one of which is ($C_1$-$C_4$)perhaloalkylsulfanyl. In another embodiment, $R^2$ is phenyl substituted with 1, 2, or 3 independently selected substituent(s), at least one of which is ($C_1$-$C_6$)alkylsulfinyl. In another embodiment, $R^2$ is phenyl substituted with 1, 2, or 3 independently selected substituent(s), at least one of which is ($C_1$-$C_6$)alkylsulfonyl. In another embodiment, $R^2$ is phenyl substituted with 1, 2, or 3 independently selected substituent(s), at least one of which is ($C_3$-$C_6$)cycloalkylsulfonyl. In another embodiment, $R^2$ is phenyl substituted with 1, 2, or 3 independently selected substituent(s), at least one of which is ($C_1$-$C_4$)haloalkylsulfinyl. In another embodiment, $R^2$ is phenyl substituted with 1, 2, or 3 independently selected substituent(s), at least one of which is ($C_1$-$C_4$)haloalkylsulfonyl. In another embodiment, $R^2$ is phenyl substituted with 1, 2, or 3 independently selected substituent(s), at least one of which is ($C_1$-$C_4$)perhaloalkylsulfinyl. In another embodiment, $R^2$ is phenyl substituted with 1, 2, or 3 independently selected substituent(s), at least one of which is ($C_1$-$C_4$)perhaloalkylsulfonyl. In another embodiment, $R^2$ is phenyl substituted with 1, 2, or 3 independently selected substituent(s), at least one of which is —S(O)$_2$—NR$^6$R$^7$. In another embodiment, $R^2$ is phenyl substituted with 1, 2, or 3 independently selected substituent(s), at least one of which is —S(O)$_2$-phenyl. In another embodiment, $R^2$ is phenyl substituted with 1, 2, or 3 independently selected substituent(s), at least one of which is —S(O)$_2$-(5-, 6-, or 7-membered)heterocycloalkyl. In another embodiment, $R^2$ is phenyl substituted with 1, 2, or 3 independently selected substituent(s), at least one of which is —S(=O)(=NR$^8$)($C_1$-$C_6$)alkyl. In another embodiment, $R^2$ is phenyl substituted with 1, 2, or 3 independently selected substituent(s), at least one of which is N,N-di($C_1$-$C_6$)alkylaminosulfonyl.

In another embodiment, the present disclosure relates to a compound of formula (Ib) and the attendant definitions, wherein $R^2$ is monosubstituted phenyl substituted with halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$) alkylaminosulfonyl, or N,N-di($C_1$-$C_6$)alkylaminosulfonyl.

In another embodiment, the present disclosure relates to a compound of formula (Ib) and the attendant definitions, wherein $R^2$ is disubstituted phenyl, each substituent being independently selected from halo, ($C_1$-$C_6$)alkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$) alkylaminosulfonyl, and N,N-di($C_1$-$C_6$)alkylaminosulfonyl.

In another embodiment, the present disclosure relates to a compound of formula (Ib) and the attendant definitions, wherein $R^2$ is trisubstituted phenyl, each substituent being independently selected from halo, ($C_1$-$C_6$)alkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$) alkylaminosulfonyl, and N,N-di($C_1$-$C_6$)alkylaminosulfonyl.

In one embodiment, the present disclosure relates to a compound of formula (Ib) and the attendant definitions, wherein $R^3$ is ($C_1$-$C_6$)alkyl substituted with 1, 2 or 3 independently selected substituent(s), the substitutents being selected from among those disclosed above for $R^3$ in connection with formula (Ib). In another embodiment, $R^3$ is ($C_1$-$C_6$)alkyl substituted with a substituent selected from among those disclosed above for $R^3$ in connection with formula (Ib). In another embodiment, $R^3$ is ($C_1$-$C_4$)alkyl substituted with 1, 2 or 3 independently selected substituent(s), the substitutents being selected from among those disclosed above for $R^3$ in connection with formula (Ib). In another embodiment, $R^3$ is ($C_1$-$C_4$)alkyl substituted with a substitutent selected from among those disclosed above for $R^3$ in connection with formula (Ib). In another embodiment, $R^3$ is ($C_1$-$C_2$)alkyl substituted with 1, 2 or 3 independently selected substituent(s), the substitutents being selected from among those disclosed above for $R^3$ in connection with formula (Ib). In another embodiment, $R^3$ is ($C_1$-$C_2$)alkyl substituted with a substituent selected from among those disclosed above for $R^3$ in connection with formula (Ib). In various embodiments of each of the above embodiments in this paragraph, the substituent is —C(=O) OH, —C(=O)O($C_1$-$C_6$)alkyl, —C(=O)OCH$_3$, —C(=O) OCH$_2$CH$_3$, —C(=O)O(5-methyl-2-oxo-2H-1,3-dioxol-4-ylmethyl), —C(=O)NR$^4$R$^5$, —C(=O)NH$_2$, —C(=O)

NHCH₃, —C(=O)N(CH₃)₂, —NR⁴R⁵, —NH₂, —NHCH₃, (C₁-C₆)alkylsulfanyl, (C₁-C₆)alkylsulfinyl, (C₁-C₆)alkylsulfonyl, —S(O)₂—NH₂, —N—(C₁-C₆)alkylaminosulfonyl, or N,N-di(C₁-C₆)alkylaminosulfonyl or the substituents are independently selected from —C(=O)OH, —C(=O)O(C₁-C₆)alkyl, —C(=O)OCH₃, —C(=O)OCH₂CH₃, —C(=O)O(5-methyl-2-oxo-2H-1,3-dioxol-4-ylmethyl), —C(=O)NR⁴R⁵, —C(=O)NH₂, —C(=O)NHCH₃, —C(=O)N(CH₃)₂, —NR⁴R⁵, —NH₂, —NHCH₃, (C₁-C₆)alkylsulfanyl, (C₁-C₆)alkylsulfinyl, (C₁-C₆)alkylsulfonyl, —S(O)₂—NH₂, —N—(C₁-C₆)alkylaminosulfonyl, or N,N-di(C₁-C₆)alkylaminosulfonyl.

In one embodiment, the present disclosure relates to a compound of formula (Ib) and the attendant definitions, wherein R is hydrogen, —CO-methyl, —CO-ethyl, —CO-benzyl, —CO-phenyl or 5-methyl-2-oxo-2H-1,3-dioxol-4-ylmethyl. In another embodiment, R is hydrogen or 5-methyl-2-oxo-2H-1,3-dioxol-4-ylmethyl. In another embodiment, R is hydrogen. In another embodiment, R is 5-methyl-2-oxo-2H-1,3-dioxol-4-ylmethyl. In another embodiment, R is —CO-methyl or —CO-ethyl. In another embodiment, R is —CO-methyl. In another embodiment, R is —CO-ethyl. In another embodiment, R is —CO-benzyl or —CO-phenyl. In another embodiments, R is —CO-benzyl. In another embodiment, R is —CO-phenyl. In another embodiment, R is —CO—NH₂. In each of the above embodiments in this paragraph, R is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is -halo, —NH₂, —NHCH₃, —CF₃ or —OCH₃ or the substituents are independently selected from -halo, —NH₂, —NHCH₃, —CF₃ or —OCH₃.

Another aspect of the disclosure provides a compound of formula (Ic)

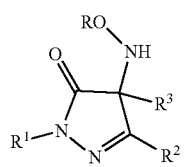

(Ic)

or a pharmaceutically acceptable salt thereof, wherein:
R¹ is H, (C₁-C₆)alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, (C₁-C₆)alkyl, (C₁-C₄)haloalkyl, (C₁-C₄)perhaloalkyl, (C₁-C₆)alkoxy, (C₁-C₄)haloalkoxy, (C₁-C₄)perhaloalkoxy, —C(=O)OH, —C(=O)O(5-methyl-2-oxo-2H-1,3-dioxol-4-ylmethyl), —C(=O)O(C₁-C₆)alkyl, —C(=O)NR⁴R⁵, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl;

R⁴, R⁵, R⁶ and R⁷ are each independently H or (C₁-C₆)alkyl;

R⁸ is H, —(C=O)(C₁-C₆)alkyl or —(C=O)(C₁-C₄)perhaloalkyl;

R² is (C₁-C₆)alkyl substituted with 1, 2 or 3 substituent(s) independently selected from —OH, —C(=O)OH, —C(=O)O(C₁-C₆)alkyl, —C(=O)NR⁴R⁵, —NR⁴R⁵, (C₁-C₆)alkoxy, (C₁-C₄)haloalkoxy, (C₁-C₄)perhaloalkoxy, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, N—(C₁-C₆)alkylaminosulfonyl, N,N-di(C₁-C₆)alkylaminosulfonyl, (5- or 6-membered)heteroaryl or phenyl;

wherein said heteroaryl or phenyl are unsubstituted or substituted with 1, 2, 3, 4, or 5 substituent(s) independently selected from halo, (C₁-C₆)alkyl, (C₁-C₄)haloalkyl, (C₁-C₄)perhaloalkyl, (C₁-C₆)alkoxy, (C₁-C₄)haloalkoxy, (C₁-C₄)perhaloalkoxy, —C(=O)OH, —C(=O)O(C₁-C₆)alkyl, —C(=O)NR⁴R⁵, —C(=O)-(5-, 6-, or 7-membered)heterocycloalkyl, (5-, 6-, or 7-membered)heterocycloalkyl, (C₁-C₆)alkylsulfanyl, (C₁-C₄)haloalkylsulfanyl, (C₁-C₄)perhaloalkylsulfanyl, (C₁-C₆)alkylsulfinyl, (C₁-C₆)alkylsulfonyl, (C₃-C₆)cycloalkylsulfonyl, (C₁-C₄)haloalkylsulfinyl, (C₁-C₄)haloalkylsulfonyl, (C₁-C₄)perhaloalkylsulfinyl, (C₁-C₄)perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)(C₁-C₆)alkyl, —NR⁴R⁵, N—(C₁-C₆)alkylaminosulfonyl, and N,N-di(C₁-C₆)alkylaminosulfonyl;

R⁴, R⁵, R⁶ and R⁷ are each independently H or (C₁-C₆)alkyl;

R⁸ is H, —(C=O)(C₁-C₆)alkyl or —(C=O)(C₁-C₄)perhaloalkyl;

R³ is (C₁-C₆)alkyl, (5- or 6-membered)heteroaryl, phenyl or —C(=NOR⁹)R¹⁰ wherein R⁹ is (C₁-C₆)alkyl, (C₁-C₆)alkyl substituted with phenyl or phenyl and R¹⁰ is selected from (C₁-C₆)alkyl; and R is hydrogen, —COH, —CO—(C₁-C₆)alkyl, —CO—(C₂-C₄)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C₁-C₆)alkyl, —CO—NH₂, —CO—NH—(C₁-C₄)alkyl, or —CO—N((C₁-C₄)alkyl)₂, wherein said —(C₁-C₆)alkyl, —(C₂-C₄)alkenyl, phenyl, benzyl, cyclopentyl, cyclohexyl, -(5-, 6-, or 7-membered)heterocycloalkyl, benzyloxy, —O—(C₁-C₆)alkyl, —NH—(C₁-C₄)alkyl, or —N((C₁-C₄)alkyl)₂ can be unsubstituted or substituted with 1, 2 or 3 substituents selected from halo, —(C₁-C₆)alkyl, —(C₂-C₄)alkenyl, —(C₂-C₃)alkynyl, -(5- or 6-membered)heteroaryl, —O—(C₁-C₆)alkyl, —S—(C₁-C₆)alkyl, —C(halo)₃, —CH(halo)₂, —CH₂(halo), —CN, —NO₂, —NH₂, —NH—(C₁-C₄)alkyl, —N(—(C₁-C₄)alkyl)₂, —C(O)(C₁-C₄)alkyl, —C(O)O(C₁-C₄)alkyl, —OC(O)(C₁-C₄)alkyl, —OC(O)NH₂, —S(O)(C₁-C₄)alkyl, —S(O)₂(C₁-C₄)alkyl or 5-methyl-2-oxo-2H-1,3-dioxol-4-ylmethyl;

provided that when R¹ is H, R³ is not (C₁-C₆)alkyl.

In one embodiment, the present disclosure relates to a compound of formula (Ic) and the attendant definitions, wherein R¹ is H. In another embodiment, R¹ is (C₁-C₆)alkyl, wherein the alkyl is unsubstituted or substituted with 1, 2 or 3 independently selected substituents. In another embodiment, $R^1$ is (5- or 6-membered)heteroaryl, wherein the heteroaryl is unsubstituted or substituted with 1, 2, 3, 4, or 5 independently selected substituents. In another embodiment, $R^1$ is phenyl, wherein the phenyl is unsubstituted or substituted with 1, 2, 3, 4, or 5 independently selected substituents. In each of the embodiments listed in this paragraph, the substituents are selected from among those disclosed above for $R^1$ in connection with formula (Ic).

In another embodiment, the present disclosure relates to a compound of formula (Ic) and the attendant definitions, wherein $R^1$ is $(C_1-C_4)$alkyl. In another embodiment, $R^1$ is methyl, ethyl, propyl, or butyl. In another embodiment, $R^1$ is methyl, ethyl, or propyl. In another embodiment, $R^1$ is methyl, ethyl, or butyl. In another embodiment, $R^1$ is methyl, propyl, or butyl. In another embodiment, $R^1$ is ethyl, propyl, or butyl. In another embodiment, $R^1$ is methyl or ethyl. In another embodiment, $R^1$ is methyl or propyl. In another embodiment, $R^1$ is methyl or butyl. In another embodiment, $R^1$ is ethyl or propyl. In another embodiment, $R^1$ is ethyl or butyl. In another embodiment, $R^1$ is propyl or butyl. In another embodiment, $R^1$ is methyl. In another embodiment, $R^1$ is ethyl. In another embodiment, $R^1$ is propyl. In another embodiment, $R^1$ is iso-propyl. In another embodiment, $R^1$ is butyl. In another embodiment, $R^1$ is tert-butyl. In each of the embodiments listed in this paragraph, the alkyl is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is —C(=O)OH, —C(=O)O($C_1$-$C_6$)alkyl, —C(=O)OCH$_3$, —C(=O)OCH$_2$CH$_3$, —C(=O)O(5-methyl-2-oxo-2H-1,3-dioxol-4-ylmethyl), —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1$-$C_6$)alkylsulfanyl, ($C_1$-$C_6$)alkylsulfinyl, ($C_1$-$C_6$)alkylsulfonyl, —S(O)$_2$—NH$_2$, —N—($C_1$-$C_6$)alkylaminosulfonyl, or N,N-di($C_1$-$C_6$)alkylaminosulfonyl or the substituents are independently selected from —C(=O)OH, —C(=O)O($C_1$-$C_6$)alkyl, —C(=O)OCH$_3$, —C(=O)OCH$_2$CH$_3$, —C(=O)O(5-methyl-2-oxo-2H-1,3-dioxol-4-ylmethyl), —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1$-$C_6$)alkylsulfanyl, ($C_1$-$C_6$)alkylsulfinyl, ($C_1$-$C_6$)alkylsulfonyl, —S(O)$_2$—NH$_2$, —N—($C_1$-$C_6$)alkylaminosulfonyl, or N,N-di($C_1$-$C_6$)alkylaminosulfonyl.

In another embodiment, the present disclosure relates to a compound of formula (Ic) and the attendant definitions, wherein $R^1$ is (5- or 6-membered)heteroaryl, wherein the heteroaryl is unsubstituted or substituted with 1, 2 or 3 independently selected substituents, the substitutents being selected from among those disclosed above for $R^1$ in connection with formula (Ic). In another embodiment, $R^1$ is unsubstituted (5- or 6-membered)heteroaryl. In another embodiment, $R^1$ is monosubstituted (5- or 6-membered) heteroaryl. In another embodiment, $R^1$ is disubstituted (5- or 6-membered)heteroaryl. In another embodiment, $R^1$ is trisubstituted (5- or 6-membered)heteroaryl. In various embodiments of each of the above embodiments in this paragraph, the substituent is halo, $(C_1-C_6)$alkyl, $(C_1-C_6)$alkoxy, phenyl, —C(=O)NR$^4$R$^5$, ($C_1$-$C_6$)alkylsulfinyl, ($C_1$-$C_6$)alkylsulfonyl, and N,N-di($C_1$-$C_6$)alkylaminosulfonyl.

In another embodiment, the present disclosure relates to a compound of formula (Ic) and the attendant definitions, wherein $R^1$ is unsubstituted phenyl. In another embodiment, $R^1$ is phenyl substituted with 1, 2 or 3 independently selected substituent(s), the substitutents being selected from among those disclosed above for $R^1$ in connection with formula (Ic). In another embodiment, $R^1$ is phenyl substituted with 1, 2, or 3 independently selected substituent(s), at least one of which is halo. In another embodiment, $R^1$ is phenyl substituted with 1, 2, or 3 independently selected substituent(s), at least one of which is $(C_1-C_6)$alkyl. In another embodiment, $R^1$ is phenyl substituted with 1, 2, or 3 independently selected substituent(s), at least one of which is $(C_1-C_4)$haloalkyl. In another embodiment, $R^1$ is phenyl substituted with 1, 2, or 3 independently selected substituent(s), at least one of which is $(C_1-C_4)$perhaloalkyl. In another embodiment, $R^1$ is phenyl substituted with 1, 2, or 3 independently selected substituent(s), at least one of which is $(C_1-C_6)$alkoxy. In another embodiment, $R^1$ is phenyl substituted with 1, 2, or 3 independently selected substituent(s), at least one of which is $(C_1-C_4)$perhaloalkoxy. In another embodiment, $R^1$ is phenyl substituted with 1, 2, or 3 independently selected substituent(s), at least one of which is —C(=O)OH. In another embodiment, $R^1$ is phenyl substituted with 1, 2, or 3 independently selected substituent(s), at least one of which is —C(=O)O($C_1$-$C_6$)alkyl. In another embodiment, $R^1$ is phenyl substituted with 1, 2, or 3 independently selected substituent(s), at least one of which is —C(=O)NR$^4$R$^5$. In another embodiment, $R^1$ is phenyl substituted with 1, 2, or 3 independently selected substituent(s), at least one of which is —C(=O)NH($C_1$-$C_6$)alkyl, wherein said alkyl is substituted with COOH. In another embodiment, $R^1$ is phenyl substituted with 1, 2, or 3 independently selected substituent(s), at least one of which is —C(=O)NH—($C_1$-$C_6$)alkylsulfonyl. In another embodiment, $R^1$ is phenyl substituted with 1, 2, or 3 independently selected substituent(s), at least one of which is —C(=O)-(5-, 6-, or 7-membered)heterocycloalkyl. In another embodiment, $R^1$ is phenyl substituted with 1, 2, or 3 independently selected substituent(s), at least one of which is (5-, 6-, or 7-membered)heterocycloalkyl. In another embodiment, $R^1$ is phenyl substituted with 1, 2, or 3 independently selected substituent(s), at least one of which is $(C_1-C_6)$alkylsulfanyl. In another embodiment, $R^1$ is phenyl substituted with 1, 2, or 3 independently selected substituent(s), at least one of which is $(C_1-C_4)$perhaloalkylsulfanyl. In another embodiment, $R^1$ is phenyl substituted with 1, 2, or 3 independently selected substituent(s), at least one of which is $(C_1-C_6)$alkylsulfinyl. In another embodiment, $R^1$ is phenyl substituted with 1, 2, or 3 independently selected substituent(s), at least one of which is $(C_1-C_6)$alkylsulfonyl. In another embodiment, $R^1$ is phenyl substituted with 1, 2, or 3 independently selected substituent(s), at least one of which is $(C_3-C_6)$cycloalkylsulfonyl. In another embodiment, $R^1$ is phenyl substituted with 1, 2, or 3 independently selected substituent(s), at least one of which is $(C_1-C_4)$haloalkylsulfinyl. In another embodiment, $R^1$ is phenyl substituted with 1, 2, or 3 independently selected substituent(s), at least one of which is $(C_1-C_4)$haloalkylsulfonyl. In another embodiment, $R^1$ is phenyl substituted with 1, 2, or 3 independently selected substituent(s), at least one of which is $(C_1-C_4)$perhaloalkylsulfinyl. In another embodiment, $R^1$ is phenyl substituted with 1, 2, or 3 independently selected substituent(s), at least one of which is $(C_1-C_4)$perhaloalkylsulfonyl. In another embodiment, $R^1$ is phenyl substituted with 1, 2, or 3 independently selected substituent(s), at least one of which is —S(O)$_2$—NR$^6$R$^7$. In another embodiment, $R^1$ is phenyl substituted with 1, 2, or 3 independently selected j substituent(s), at least one of which is —S(O)$_2$-phenyl. In another embodiment, $R^1$ is phenyl substituted with 1, 2, or 3 independently selected substituent(s), at least one of which is —S(O)$_2$-(5-, 6-, or 7-membered)heterocycloalkyl. In another embodiment, $R^1$ is phenyl substituted with 1, 2, or 3 independently selected substituent(s), at least one of which is —S(=O)(=NR$^8$)(C$_1$-C$_6$)alkyl. In another embodiment, $R^1$ is phenyl substituted with 1, 2, or 3 independently selected substituent(s), at least one of which is N,N-di(C$_1$-C$_6$)alkylaminosulfonyl.

In another embodiment, the present disclosure relates to a compound of formula (Ic) and the attendant definitions, wherein $R^1$ is monosubstituted phenyl substituted with halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, or N,N-di(C$_1$-C$_6$)alkylaminosulfonyl.

In another embodiment, the present disclosure relates to a compound of formula (Ic) and the attendant definitions, wherein $R^1$ is disubstituted phenyl, each substituent being independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In another embodiment, the present disclosure relates to a compound of formula (Ic) and the attendant definitions, wherein $R^1$ is trisubstituted phenyl, each substituent being independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In one embodiment, the present disclosure relates to a compound of formula (Ic) and the attendant definitions, wherein $R^2$ is (C$_1$-C$_6$)alkyl substituted with 1, 2 or 3 independently selected substituent(s), the substitutents being selected from among those disclosed above for $R^2$ in connection with formula (Ic). In another embodiment, $R^2$ is (C$_1$-C$_6$)alkyl substituted with a substituent selected from among those disclosed above for $R^2$ in connection with formula (Ic). In another embodiment, $R^2$ is (C$_1$-C$_4$)alkyl substituted with 1, 2 or 3 independently selected substituent(s), the substitutents being selected from among those disclosed above for $R^2$ in connection with formula (Ic). In another embodiment, $R^2$ is (C$_1$-C$_4$)alkyl substituted with a substitutent selected from among those disclosed above for $R^2$ in connection with formula (Ic). In another embodiment, $R^2$ is (C$_1$-C$_2$)alkyl substituted with 1, 2 or 3 independently selected substituent(s), the substitutents being selected from among those disclosed above for $R^2$ in connection with formula (Ic). In another embodiment, $R^2$ is (C$_1$-C$_2$)alkyl substituted with a substituent selected from among those disclosed above for $R^2$ in connection with formula (Ic). In various embodiments of each of the above embodiments in this paragraph, the substituent is —C(=O)OH, —C(=O)O(C$_1$-C$_6$)alkyl, —C(=O)OCH$_3$, —C(=O)OCH$_2$CH$_3$, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, (C$_1$-C$_6$)alkylsulfanyl, (C$_1$-C$_6$)alkylsulfinyl, (C$_1$-C$_6$)alkylsulfonyl, —S(O)$_2$—NH$_2$, —N—(C$_1$-C$_6$)alkylaminosulfonyl, or N,N-di(C$_1$-C$_6$)alkylaminosulfonyl or the substituents are independently selected from —C(=O)OH, —C(=O)O(C$_1$-C$_6$)alkyl, —C(=O)OCH$_3$, —C(=O)OCH$_2$CH$_3$, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, (C$_1$-C$_6$)alkylsulfanyl, (C$_1$-C$_6$)alkylsulfinyl, (C$_1$-C$_6$)alkylsulfonyl, —S(O)$_2$—NH$_2$, —N—(C$_1$-C$_6$)alkylaminosulfonyl, or N,N-di(C$_1$-C$_6$)alkylaminosulfonyl.

In one embodiment, the present disclosure relates to a compound of formula (Ic) and the attendant definitions, wherein $R^3$ is (C$_1$-C$_6$)alkyl. In another embodiment, $R^3$ is (5- or 6-membered)heteroaryl. In another embodiment, $R^3$ is phenyl. In another embodiment, $R^3$ is —C(=NOR$^9$)R$^{10}$ wherein $R^9$ is (C$_1$-C$_6$)alkyl, (C$_1$-C$_6$)alkyl substituted with phenyl or phenyl and $R^{10}$ is selected from (C$_1$-C$_6$)alkyl.

In another embodiment, the present disclosure relates to a compound of formula (Ic) and the attendant definitions, wherein $R^3$ is (C$_1$-C$_4$)alkyl. In another embodiment, $R^3$ is methyl, ethyl, propyl, or butyl. In another embodiment, $R^3$ is methyl, ethyl, or propyl. In another embodiment, $R^3$ is methyl, ethyl, or butyl. In another embodiment, $R^3$ is methyl, propyl, or butyl. In another embodiment, $R^3$ is ethyl, propyl, or butyl. In another embodiment, $R^3$ is methyl or ethyl. In another embodiment, $R^3$ is methyl or propyl. In another embodiment, $R^3$ is methyl or butyl. In another embodiment, $R^3$ is ethyl or propyl. In another embodiment, $R^3$ is ethyl or butyl. In another embodiment, $R^3$ is propyl or butyl. In another embodiment, $R^3$ is methyl. In another embodiment, $R^3$ is ethyl. In another embodiment, $R^3$ is propyl. In another embodiment, $R^3$ is iso-propyl. In another embodiment, $R^3$ is butyl. In another embodiment, $R^3$ is tert-butyl.

In another embodiment, the present disclosure relates to a compound of formula (Ic) and the attendant definitions, wherein $R^3$ is —C(=NOR$^9$)R$^{10}$ wherein $R^9$ is (C$_1$-C$_6$)alkyl and $R^{10}$ is (C$_1$-C$_6$)alkyl. In another embodiment, $R^3$ is —C(=NOR$^9$)R$^{10}$ wherein $R^9$ is (C$_1$-C$_6$)alkyl and $R^{10}$ is (C$_1$-C$_4$)alkyl. In another embodiment, $R^3$ is —C(=NOR$^9$)R$^{10}$ wherein $R^9$ is (C$_1$-C$_6$)alkyl and $R^{10}$ is methyl, ethyl or propyl. In another embodiment, $R^3$ is —C(=NOR$^9$)R$^{10}$ wherein $R^9$ is (C$_1$-C$_6$)alkyl and $R^{10}$ is methyl or ethyl. In another embodiment, $R^3$ is —C(=NOR$^9$)R$^{10}$ wherein $R^9$ is (C$_1$-C$_6$)alkyl and $R^{10}$ is methyl. In another embodiment, $R^3$ is —C(=NOR$^9$)R$^{10}$ wherein $R^9$ is (C$_1$-C$_6$)alkyl and $R^{10}$ is ethyl.

In another embodiment, the present disclosure relates to a compound of formula (Ic) and the attendant definitions, wherein $R^3$ is —C(=NOR$^9$)R$^{10}$ wherein $R^9$ is methyl, ethyl, propyl or butyl and $R^{10}$ is (C$_1$-C$_6$)alkyl. In another embodiment, $R^3$ is —C(=NOR$^9$)R$^{10}$ wherein $R^9$ is methyl, ethyl, propyl or butyl and $R^{10}$ is (C$_1$-C$_4$)alkyl. In another embodiment, $R^3$ is —C(=NOR$^9$)R$^{10}$ wherein $R^9$ is methyl, ethyl, propyl or butyl and $R^{10}$ is methyl, ethyl or propyl. In another embodiment, $R^3$ is —C(=NOR$^9$)R$^{10}$ wherein $R^9$ is methyl, ethyl, propyl or butyl and $R^{10}$ is methyl or ethyl. In another embodiment, $R^3$ is —C(=NOR$^9$)R$^{10}$ wherein $R^9$ is methyl, ethyl, propyl or butyl and $R^{10}$ is methyl. In another embodiment, $R^3$ is —C(=NOR$^9$)R$^{10}$ wherein $R^9$ is methyl, ethyl, propyl or butyl and $R^{10}$ is ethyl. In one embodiment, $R^3$ is —C(=NOR$^9$)R$^{10}$ wherein $R^9$ is methyl and $R^{10}$ is $(C_1$-$C_6)$alkyl. In another embodiment, $R^3$ is —C(=NOR$^9$)R$^{10}$ wherein $R^9$ is methyl and $R^{10}$ is $(C_1$-$C_4)$alkyl. In another embodiment, $R^3$ is —C(=NOR$^9$)R$^{10}$ wherein $R^9$ is methyl and $R^{10}$ is methyl, ethyl or propyl. In another embodiment, $R^3$ is —C(=NOR$^9$)R$^{10}$ wherein $R^9$ is methyl and $R^{10}$ is methyl or ethyl. In another embodiment, $R^3$ is —C(=NOR$^9$)R$^{10}$ wherein $R^9$ is methyl and $R^{10}$ is methyl. In another embodiment, $R^3$ is —C(=NOR$^9$)R$^{10}$ wherein $R^9$ is methyl and $R^{10}$ is ethyl. In one embodiment, $R^3$ is —C(=NOR$^9$)R$^{10}$ wherein $R^9$ is ethyl and $R^{10}$ is $(C_1$-$C_6)$alkyl. In another embodiment, $R^3$ is —C(=NOR$^9$)R$^{10}$ wherein $R^9$ is ethyl and $R^{10}$ is $(C_1$-$C_4)$alkyl. In another embodiment, $R^3$ is —C(=NOR$^9$)R$^{10}$ wherein $R^9$ is ethyl and $R^{10}$ is methyl, ethyl or propyl. In another embodiment, $R^3$ is —C(=NOR$^9$)R$^{10}$ wherein $R^9$ is ethyl and $R^{10}$ is methyl or ethyl. In another embodiment, $R^3$ is —C(=NOR$^9$)R$^{10}$ wherein $R^9$ is ethyl and $R^{10}$ is methyl. In another embodiment, $R^3$ is —C(=NOR$^9$)R$^{10}$ wherein $R^9$ is ethyl and $R^{10}$ is ethyl. In one embodiment, $R^3$ is —C(=NOR$^9$)R$^{10}$ wherein $R^9$ is propyl and $R^{10}$ is $(C_1$-$C_6)$alkyl. In another embodiment, $R^3$ is —C(=NOR$^9$)R$^{10}$ wherein $R^9$ is propyl and $R^{10}$ is $(C_1$-$C_4)$alkyl. In another embodiment, $R^3$ is —C(=NOR$^9$)R$^{10}$ wherein $R^9$ is propyl and $R^{10}$ is methyl, ethyl or propyl. In another embodiment, $R^3$ is —C(=NOR$^9$)R$^{10}$ wherein $R^9$ is propyl and $R^{10}$ is methyl or ethyl. In another embodiment, $R^3$ is —C(=NOR$^9$)R$^{10}$ wherein $R^9$ is propyl and $R^{10}$ is methyl. In another embodiment, $R^3$ is —C(=NOR$^9$)R$^{10}$ wherein $R^9$ is propyl and $R^{10}$ is ethyl. In one embodiment, $R^3$ is —C(=NOR$^9$)R$^{10}$ wherein $R^9$ is butyl and $R^{10}$ is $(C_1$-$C_6)$alkyl. In another embodiment, $R^3$ is —C(=NOR$^9$)R$^{10}$ wherein $R^9$ is butyl and $R^{10}$ is $(C_1$-$C_4)$alkyl. In another embodiment, $R^3$ is —C(=NOR$^9$)R$^{10}$ wherein $R^9$ is butyl and $R^{10}$ is methyl, ethyl or propyl. In another embodiment, $R^3$ is —C(=NOR$^9$)R$^{10}$ wherein $R^9$ is butyl and $R^{10}$ is methyl or ethyl. In another embodiment, $R^3$ is —C(=NOR$^9$)R$^{10}$ wherein $R^9$ is butyl and $R^{10}$ is methyl. In another embodiment, $R^3$ is —C(=NOR$^9$)R$^{10}$ wherein $R^9$ is butyl and $R^{10}$ is ethyl. In one embodiment, $R^3$ is —C(=NOR$^9$)R$^{10}$ wherein $R^9$ is tert-butyl and $R^{10}$ is $(C_1$-$C_6)$alkyl. In another embodiment, $R^3$ is —C(=NOR$^9$)R$^{10}$ wherein $R^9$ is tert-butyl and $R^{10}$ is $(C_1$-$C_4)$alkyl. In another embodiment, $R^3$ is —C(=NOR$^9$)R$^{10}$ wherein $R^9$ is tert-butyl and $R^{10}$ is methyl, ethyl or propyl. In another embodiment, $R^3$ is —C(=NOR$^9$)R$^{10}$ wherein $R^9$ is tert-butyl and $R^{10}$ is methyl or ethyl. In another embodiment, $R^3$ is —C(=NOR$^9$)R$^{10}$ wherein $R^9$ is tert-butyl and $R^{10}$ is methyl. In another embodiment, $R^3$ is —C(=NOR$^9$)R$^{10}$ wherein $R^9$ is tert-butyl and $R^{10}$ is ethyl. In one embodiment, $R^3$ is —C(=NOR$^9$)R$^{10}$ wherein $R^9$ is iso-butyl and $R^{10}$ is $(C_1$-$C_6)$alkyl. In another embodiment, $R^3$ is —C(=NOR$^9$)R$^{10}$ wherein $R^9$ is iso-butyl and $R^{10}$ is $(C_1$-$C_4)$alkyl. In another embodiment, $R^3$ is —C(=NOR$^9$)R$^{10}$ wherein $R^9$ is iso-butyl and $R^{10}$ is methyl, ethyl or propyl. In another embodiment, $R^3$ is —C(=NOR$^9$)R$^{10}$ wherein $R^9$ is iso-butyl and $R^{10}$ is methyl or ethyl. In another embodiment, $R^3$ is —C(=NOR$^9$)R$^{10}$ wherein $R^9$ is iso-butyl and $R^{10}$ is methyl. In another embodiment, $R^3$ is —C(=NOR$^9$)R$^{10}$ wherein $R^9$ is iso-butyl and $R^{10}$ is ethyl.

In another embodiment, the present disclosure relates to a compound of formula (Ic) and the attendant definitions, wherein $R^3$ is —C(=NOR$^9$)R$^{10}$ wherein at least one of $R^9$ and $R^{10}$ is methyl. In another embodiment, $R^3$ is —C(=NOR$^9$)R$^{10}$ wherein each of $R^9$ and $R^{10}$ is methyl. In another embodiment, $R^3$ is —C(=NOR$^9$)R$^{10}$ wherein one of $R^9$ and $R^{10}$ is methyl and the other is ethyl.

In another embodiment, the present disclosure relates to a compound of formula (Ic) and the attendant definitions, wherein $R^3$ is —C(=NOR$^9$)R$^{10}$ wherein $R^9$ is $(C_1$-$C_6)$alkyl substituted with phenyl and $R^{10}$ is $(C_1$-$C_6)$alkyl. In another embodiment, $R^3$ is —C(=NOR$^9$)R$^{10}$ wherein $R^9$ is $(C_1$-$C_6)$alkyl substituted with phenyl and $R^{10}$ is $(C_1$-$C_4)$alkyl. In another embodiment, $R^3$ is —C(=NOR$^9$)R$^{10}$ wherein $R^9$ is $(C_1$-$C_6)$alkyl substituted with phenyl and $R^{10}$ is methyl, ethyl or propyl. In another embodiment, $R^3$ is —C(=NOR$^9$)R$^{10}$ wherein $R^9$ is $(C_1$-$C_6)$alkyl substituted with phenyl and $R^{10}$ is methyl or ethyl. In another embodiment, $R^3$ is —C(=NOR$^9$)R$^{10}$ wherein $R^9$ is $(C_1$-$C_6)$alkyl substituted with phenyl and $R^{10}$ is methyl. In another embodiment, $R^3$ is —C(=NOR$^9$)R$^{10}$ wherein $R^9$ is phenyl and $R^{10}$ is ethyl.

In another embodiment, the present disclosure relates to a compound of formula (Ic) and the attendant definitions, wherein $R^3$ is —C(=NOR$^9$)R$^{10}$ wherein $R^9$ is $(C_1$-$C_4)$alkyl substituted with phenyl and $R^{10}$ is $(C_1$-$C_6)$alkyl. In one embodiment, $R^3$ is —C(=NOR$^9$)R$^{10}$ wherein $R^9$ is $(C_1)$alkyl substituted with phenyl and $R^{10}$ is $(C_1$-$C_6)$alkyl. In one embodiment, $R^3$ is —C(=NOR$^9$)R$^{10}$ wherein $R^9$ is $(C_2)$alkyl substituted with phenyl and $R^{10}$ is $(C_1$-$C_6)$alkyl. In one embodiment, $R^3$ is —C(=NOR$^9$)R$^{10}$ wherein $R^9$ is $(C_1$-$C_4)$alkyl substituted with phenyl and $R^{10}$ is $(C_1$-$C_4)$alkyl. In one embodiment, $R^3$ is —C(=NOR$^9$)R$^{10}$ wherein $R^9$ is $(C_1)$alkyl substituted with phenyl and $R^{10}$ is $(C_1$-$C_4)$alkyl. In one embodiment, $R^3$ is —C(=NOR$^9$)R$^{10}$ wherein $R^9$ is $(C_2)$alkyl substituted with phenyl and $R^{10}$ is $(C_1$-$C_4)$alkyl. In one embodiment, $R^3$ is —C(=NOR$^9$)R$^{10}$ wherein $R^9$ is $(C_1$-$C_4)$alkyl substituted with phenyl and $R^{10}$ is methyl, ethyl or propyl. In one embodiment, $R^3$ is —C(=NOR$^9$)R$^{10}$ wherein $R^9$ is $(C_1)$alkyl substituted with phenyl and $R^{10}$ is methyl, ethyl or propyl. In one embodiment, $R^3$ is —C(=NOR$^9$)R$^{10}$ wherein $R^9$ is $(C_2)$alkyl substituted with phenyl and $R^{10}$ is methyl, ethyl or propyl. In one embodiment, $R^3$ is —C(=NOR$^9$)R$^{10}$ wherein $R^9$ is $(C_1$-$C_4)$alkyl substituted with phenyl and $R^{10}$ is methyl or ethyl. In one embodiment, $R^3$ is —C(=NOR$^9$)R$^{10}$ wherein $R^9$ is $(C_1)$alkyl substituted with phenyl and $R^{10}$ is methyl or ethyl. In one embodiment, $R^3$ is —C(=NOR$^9$)R$^{10}$ wherein $R^9$ is $(C_2)$alkyl substituted with phenyl and $R^{10}$ is methyl or ethyl. In one embodiment, $R^3$ is —C(=NOR$^9$)R$^{10}$ wherein $R^9$ is $(C_1$-$C_4)$alkyl substituted with phenyl and $R^{10}$ is methyl. In one embodiment, $R^3$ is —C(=NOR$^9$)R$^{10}$ wherein $R^9$ is $(C_1)$alkyl substituted with phenyl and $R^{10}$ is methyl. In one embodiment, $R^3$ is —C(=NOR$^9$)R$^{10}$ wherein $R^9$ is $(C_2)$alkyl substituted with phenyl and $R^{10}$ is methyl. In one embodiment, $R^3$ is —C(=NOR$^9$)R$^{10}$ wherein $R^9$ is $(C_1$-$C_4)$alkyl substituted with phenyl and $R^{10}$ is ethyl. In one embodiment, $R^3$ is —C(=NOR$^9$)R$^{10}$ wherein $R^9$ is $(C_1)$alkyl substituted with phenyl and $R^{10}$ is ethyl. In one embodiment, $R^3$ is —C(=NOR$^9$)R$^{10}$ wherein $R^9$ is $(C_2)$alkyl substituted with phenyl and $R^{10}$ is ethyl.

In another embodiment, the present disclosure relates to a compound of formula (Ic) and the attendant definitions, wherein $R^3$ is —C(=NOR$^9$)R$^{10}$ wherein $R^9$ is phenyl and $R^{10}$ is $(C_1$-$C_6)$alkyl. In another embodiment, $R^3$ is —C(=NOR$^9$)R$^{10}$ wherein $R^9$ is phenyl and $R^{10}$ is $(C_1$-$C_4)$alkyl. In another embodiment, $R^3$ is —C(=NOR$^9$)R$^{10}$ wherein $R^9$ is phenyl and $R^{10}$ is methyl, ethyl or propyl. In another embodiment, $R^3$ is —C(=NOR$^9$)R$^{10}$ wherein $R^9$ is phenyl and $R^{10}$ is methyl or ethyl. In another embodiment, $R^3$ is —C(=NOR$^9$)R$^{10}$ wherein R$^9$ is phenyl and R$^{10}$ is methyl. In another embodiment, R$^3$ is —C(=NOR$^9$)R$^{10}$ wherein R$^9$ is phenyl and R$^{10}$ is ethyl.

In one embodiment, the present disclosure relates to a compound of formula (Ic) and the attendant definitions, wherein R is hydrogen, —CO-methyl, —CO-ethyl, —CO-benzyl, —CO-phenyl or 5-methyl-2-oxo-2H-1,3-dioxol-4-ylmethyl. In another embodiment, R is hydrogen or 5-methyl-2-oxo-2H-1,3-dioxol-4-ylmethyl. In another embodiment, R is hydrogen. In another embodiment, R is 5-methyl-2-oxo-2H-1,3-dioxol-4-ylmethyl. In another embodiment, R is —CO-methyl or —CO-ethyl. In another embodiment, R is —CO-methyl. In another embodiment, R is —CO-ethyl. In another embodiment, R is —CO-benzyl or —CO-phenyl. In another embodiments, R is —CO-benzyl. In another embodiment, R is —CO-phenyl. In another embodiment, R is —CO—NH$_2$. In each of the above embodiments in this paragraph, R is unsubstituted in one embodiment, monosubstituted in another embodiment, disubstituted with two independently selected substituents in an additional embodiment, or trisubstituted with three independently selected substituents in a further embodiment. In various embodiments of each of the above embodiments in this paragraph, the substituent is -halo, —NH$_2$, —NHCH$_3$, —CF$_3$ or —OCH$_3$ or the substituents are independently selected from -halo, —NH$_2$, —NHCH$_3$, —CF$_3$ or —OCH$_3$.

Another aspect of the disclosure provides a compound of formula (Id)

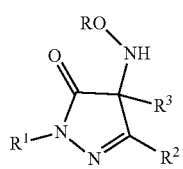

(Id)

or a pharmaceutically acceptable salt thereof, wherein:
$R^1$ is (C$_1$-C$_6$)alkyl substituted with 1, 2 or 3 substituent(s) independently selected from —OH, —C(=O)OH, —C(=O)O(C$_1$-C$_6$)alkyl, —C(=O)O(5-methyl-2-oxo-2H-1,3-dioxol-4-ylmethyl), —C(=O)NR$^4$R$^5$, —NR$^4$R$^5$, (C$_1$-C$_6$)alkoxy, (C$_1$-C$_4$)haloalkoxy, (C$_1$-C$_4$)perhaloalkoxy, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, N—(C$_1$-C$_6$)alkylaminosulfonyl, N,N-di(C$_1$-C$_6$)alkylaminosulfonyl, (5- or 6-membered)heteroaryl or phenyl,
wherein said heteroaryl or phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;
$R^4$, $R^5$, $R^6$ and $R^7$ are each independently H or (C$_1$-C$_6$)alkyl;
$R^8$ is H, —(C=O)(C$_1$-C$_6$)alkyl or —(C=O)(C$_1$-C$_4$)perhaloalkyl;
$R^2$ is phenyl, wherein said phenyl is unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;
$R^4$, $R^5$, $R^6$ and $R^7$ are each independently H or (C$_1$-C$_6$)alkyl;
$R^8$ is H, —(C=O)(C$_1$-C$_6$)alkyl or —(C=O)(C$_1$-C$_4$)perhaloalkyl;
$R^3$ is (C$_1$-C$_6$)alkyl, (5- or 6-membered)heteroaryl, phenyl or —C(=NOR$^9$)R$^{10}$ wherein R$^9$ is (C$_1$-C$_6$)alkyl, (C$_1$-C$_6$)alkyl substituted with phenyl or phenyl and R$^{10}$ is selected from (C$_1$-C$_6$)alkyl; and
R is hydrogen, —COH, —CO—(C$_1$-C$_6$)alkyl, —CO—(C$_2$-C$_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl or 5-methyl-2-oxo-2H-1,3-dioxol-4-ylmethyl;
provided that when $R^1$ is (C$_1$-C$_6$)alkyl substituted with —C(=O)OH and $R^3$ is (C$_1$-C$_6$)alkyl or —C(=NOR$^9$)R$^{10}$ and $R^9$ is (C$_1$-C$_6$)alkyl, $R^{10}$ is not (C$_1$-C$_6$)alkyl.

In one embodiment, the present disclosure relates to a compound of formula (Id) and the attendant definitions, wherein $R^1$ is (C$_1$-C$_6$)alkyl substituted with 1, 2 or 3 independently selected substituent(s), the substituents being selected from among those disclosed above for $R^1$ in connection with formula (Id). In another embodiment, $R^1$ is (C$_1$-C$_6$)alkyl substituted with a substituent selected from among those disclosed above for $R^1$ in connection with formula (Id). In another embodiment, $R^1$ is (C$_1$-C$_4$)alkyl substituted with 1, 2 or 3 independently selected substituent(s), the substituents being selected from among those disclosed above for $R^1$ in connection with formula (Id). In another embodiment, $R^1$ is (C$_1$-C$_4$)alkyl substituted with a substituent selected from among those disclosed above for $R^1$ in connection with formula (Id). In another embodiment, $R^1$ is $(C_1-C_2)$alkyl substituted with 1, 2 or 3 independently selected substituent(s), the substituents being selected from among those disclosed above for $R^1$ in connection with formula (Id). In another embodiment, $R^1$ is $(C_1-C_2)$alkyl substituted with a substituent selected from among those disclosed above for $R^1$ in connection with formula (Id). In various embodiments of each of the above embodiments in this paragraph, the substituent is —C(=O)OH, —C(=O)O($C_1-C_6$)alkyl, —C(=O)OCH$_3$, —C(=O)OCH$_2$CH$_3$, —C(=O)O(5-methyl-2-oxo-2H-1,3-dioxol-4-ylmethyl), (5-, 6-, or 7-membered)heterocycloalkyl, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1-C_6$)alkylsulfanyl, ($C_1-C_6$)alkylsulfinyl, ($C_1-C_6$)alkylsulfonyl, —S(O)$_2$—NH$_2$, —N—($C_1-C_6$)alkylaminosulfonyl, or N,N-di($C_1-C_6$)alkylaminosulfonyl or the substituents are independently selected from —C(=O)OH, —C(=O)O($C_1-C_6$)alkyl, —C(=O)OCH$_3$, —C(=O)OCH$_2$CH$_3$, —C(=O)O(5-methyl-2-oxo-2H-1,3-dioxol-4-ylmethyl), (5-, 6-, or 7-membered)heterocycloalkyl, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1-C_6$)alkylsulfanyl, ($C_1-C_6$)alkylsulfinyl, ($C_1-C_6$)alkylsulfonyl, —S(O)$_2$—NH$_2$, —N—($C_1-C_6$)alkylaminosulfonyl, or N,N-di($C_1-C_6$)alkylaminosulfonyl.

In one embodiment, the present disclosure relates to a compound of formula (Id) and the attendant definitions, wherein $R^2$ is unsubstituted phenyl. In another embodiment, $R^2$ is phenyl substituted with 1, 2 or 3 independently selected substituent(s), the substitutents being selected from among those disclosed above for $R^2$ in connection with formula (Id). In another embodiment, $R^2$ is phenyl substituted with 1, 2, or 3 independently selected substituent(s), at least one of which is halo. In another embodiment, $R^2$ is phenyl substituted with 1, 2, or 3 independently selected substituent(s), at least one of which is ($C_1-C_6$)alkyl. In another embodiment, $R^2$ is phenyl substituted with 1, 2, or 3 independently selected substituent(s), at least one of which is ($C_1-C_4$)haloalkyl. In another embodiment, $R^2$ is phenyl substituted with 1, 2, or 3 independently selected substituent(s), at least one of which is ($C_1-C_4$)perhaloalkyl. In another embodiment, $R^2$ is phenyl substituted with 1, 2, or 3 independently selected substituent(s), at least one of which is ($C_1-C_6$)alkoxy. In another embodiment, $R^2$ is phenyl substituted with 1, 2, or 3 independently selected substituent(s), at least one of which is ($C_1-C_4$)perhaloalkoxy. In another embodiment, $R^2$ is phenyl substituted with 1, 2, or 3 independently selected substituent(s), at least one of which is —C(=O)OH. In another embodiment, $R^2$ is phenyl substituted with 1, 2, or 3 independently selected substituent(s), at least one of which is —C(=O)O($C_1-C_6$)alkyl. In another embodiment, $R^2$ is phenyl substituted with 1, 2, or 3 independently selected substituent(s), at least one of which is —C(=O)NR$^4$R$^5$. In another embodiment, $R^2$ is phenyl substituted with 1, 2, or 3 independently selected substituent(s), at least one of which is —C(=O)NH($C_1-C_6$)alkyl, wherein said alkyl is substituted with COOH. In another embodiment, $R^2$ is phenyl substituted with 1, 2, or 3 independently selected substituent(s), at least one of which is —C(=O)NH—($C_1-C_6$)alkylsulfonyl. In another embodiment, $R^2$ is phenyl substituted with 1, 2, or 3 independently selected substituent(s), at least one of which is —C(=O)-(5-, 6-, or 7-membered)heterocycloalkyl. In another embodiment, $R^2$ is phenyl substituted with 1, 2, or 3 independently selected substituent(s), at least one of which is (5-, 6-, or 7-membered)heterocycloalkyl. In another embodiment, $R^2$ is phenyl substituted with 1, 2, or 3 independently selected substituent(s), at least one of which is ($C_1-C_6$)alkylsulfanyl. In another embodiment, $R^2$ is phenyl substituted with 1, 2, or 3 independently selected substituent(s), at least one of which is ($C_1-C_4$)perhaloalkylsulfanyl. In another embodiment, $R^2$ is phenyl substituted with 1, 2, or 3 independently selected substituent(s), at least one of which is ($C_1-C_6$)alkylsulfinyl. In another embodiment, $R^2$ is phenyl substituted with 1, 2, or 3 independently selected substituent(s), at least one of which is ($C_1-C_6$)alkylsulfonyl. In another embodiment, $R^2$ is phenyl substituted with 1, 2, or 3 independently selected substituent(s), at least one of which is ($C_3-C_6$)cycloalkylsulfonyl. In another embodiment, $R^2$ is phenyl substituted with 1, 2, or 3 independently selected substituent(s), at least one of which is ($C_1-C_4$)haloalkylsulfinyl. In another embodiment, $R^2$ is phenyl substituted with 1, 2, or 3 independently selected substituent(s), at least one of which is ($C_1-C_4$)haloalkylsulfonyl. In another embodiment, $R^2$ is phenyl substituted with 1, 2, or 3 independently selected substituent(s), at least one of which is ($C_1-C_4$)perhaloalkylsulfinyl. In another embodiment, $R^2$ is phenyl substituted with 1, 2, or 3 independently selected substituent(s), at least one of which is ($C_1-C_4$)perhaloalkylsulfonyl. In another embodiment, $R^2$ is phenyl substituted with 1, 2, or 3 independently selected substituent(s), at least one of which is —S(O)$_2$—NR$^6$R$^7$. In another embodiment, $R^2$ is phenyl substituted with 1, 2, or 3 independently selected substituent(s), at least one of which is —S(O)$_2$-phenyl. In another embodiment, $R^2$ is phenyl substituted with 1, 2, or 3 independently selected substituent(s), at least one of which is —S(O)$_2$-(5-, 6-, or 7-membered)heterocycloalkyl. In another embodiment, $R^2$ is phenyl substituted with 1, 2, or 3 independently selected substituent(s), at least one of which is —S(=O)(=NR$^8$)($C_1-C_6$)alkyl. In another embodiment, $R^2$ is phenyl substituted with 1, 2, or 3 independently selected substituent(s), at least one of which is N,N-di($C_1-C_6$)alkylaminosulfonyl.

In another embodiment, the present disclosure relates to a compound of formula (Id) and the attendant definitions, wherein $R^2$ is monosubstituted phenyl substituted with halo, ($C_1-C_6$)alkyl, ($C_1-C_4$)haloalkyl, ($C_1-C_4$)perhaloalkyl, ($C_1-C_6$)alkoxy, ($C_1-C_4$)haloalkoxy, ($C_1-C_4$)perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1-C_6$)alkylsulfanyl, ($C_1-C_4$)perhaloalkylsulfanyl, ($C_1-C_6$)alkylsulfinyl, ($C_1-C_6$)alkylsulfonyl, ($C_1-C_4$)haloalkylsulfinyl, ($C_1-C_4$)haloalkylsulfonyl, ($C_1-C_4$)perhaloalkylsulfinyl, ($C_1-C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1-C_6$)alkyl, —NR$^4$R$^5$, N—($C_1-C_6$)alkylaminosulfonyl, or N,N-di($C_1-C_6$)alkylaminosulfonyl.

In another embodiment, the present disclosure relates to a compound of formula (Id) and the attendant definitions, wherein $R^2$ is disubstituted phenyl, each substituent being independently selected from halo, ($C_1-C_6$)alkyl, ($C_1-C_4$)perhaloalkyl, ($C_1-C_6$)alkoxy, ($C_1-C_4$)haloalkoxy, ($C_1-C_4$)perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1-C_6$)alkylsulfanyl, ($C_1-C_4$)perhaloalkylsulfanyl, ($C_1-C_6$)alkylsulfinyl, ($C_1-C_6$)alkylsulfonyl, ($C_1-C_4$)haloalkylsulfinyl, ($C_1-C_4$)haloalkylsulfonyl, ($C_1-C_4$)perhaloalkylsulfinyl, ($C_1-C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1-C_6$)alkyl, —NR$^4$R$^5$, N—($C_1-C_6$)alkylaminosulfonyl, and N,N-di($C_1-C_6$)alkylaminosulfonyl.

In another embodiment, the present disclosure relates to a compound of formula (Id) and the attendant definitions, wherein $R^2$ is trisubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, $-C(=O)OH$, $-C(=O)O(C_1-C_6)$alkyl, $-C(=O)NR^4R^5$, $-C(=O)$-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, $-S(O)_2-NH_2$, $-S(O)_2-NR^6R^7$, $-S(O)_2$-phenyl, $-S(O)_2$-(5-, 6-, or 7-membered)heterocycloalkyl, $-S(=O)(=NR^8)(C_1-C_6)$alkyl, $-NR^4R^5$, $N-(C_1-C_6)$alkylaminosulfonyl, and N,N-di$(C_1-C_6)$alkylaminosulfonyl.

In one embodiment, the present disclosure relates to a compound of formula (Id) and the attendant definitions, wherein $R^3$ is $(C_1-C_6)$alkyl. In another embodiment, $R^3$ is (5- or 6-membered)heteroaryl. In another embodiment, $R^3$ is phenyl. In another embodiment, $R^3$ is $-C(=NOR^9)R^{10}$ wherein $R^9$ is $(C_1-C_6)$alkyl, $(C_1-C_6)$alkyl substituted with phenyl or phenyl and $R^{10}$ is selected from $(C_1-C_6)$alkyl.

In another embodiment, the present disclosure relates to a compound of formula (Id) and the attendant definitions, wherein $R^3$ is $(C_1-C_4)$alkyl. In another embodiment, $R^3$ is methyl, ethyl, propyl, or butyl. In another embodiment, $R^3$ is methyl, ethyl, or propyl. In another embodiment, $R^3$ is methyl, ethyl, or butyl. In another embodiment, $R^3$ is methyl, propyl, or butyl. In another embodiment, $R^3$ is ethyl, propyl, or butyl. In another embodiment, $R^3$ is methyl or ethyl. In another embodiment, $R^3$ is methyl or propyl. In another embodiment, $R^3$ is methyl or butyl. In another embodiment, $R^3$ is ethyl or propyl. In another embodiment, $R^3$ is ethyl or butyl. In another embodiment, $R^3$ is propyl or butyl. In another embodiment, $R^3$ is methyl. In another embodiment, $R^3$ is ethyl. In another embodiment, $R^3$ is propyl. In another embodiment, $R^3$ is iso-propyl. In another embodiment, $R^3$ is butyl. In another embodiment, $R^3$ is tert-butyl.

In another embodiment, the present disclosure relates to a compound of formula (Id) and the attendant definitions, wherein $R^3$ is $-C(=NOR^9)R^{10}$ wherein $R^9$ is $(C_1-C_6)$alkyl and $R^{10}$ is $(C_1-C_6)$alkyl. In another embodiment, $R^3$ is $-C(=NOR^9)R^{10}$ wherein $R^9$ is $(C_1-C_6)$alkyl and $R^{10}$ is $(C_1-C_4)$alkyl. In another embodiment, $R^3$ is $-C(=NOR^9)R^{10}$ wherein $R^9$ is $(C_1-C_6)$alkyl and $R^{10}$ is methyl, ethyl or propyl. In another embodiment, $R^3$ is $-C(=NOR^9)R^{10}$ wherein $R^9$ is $(C_1-C_6)$alkyl and $R^{10}$ is methyl or ethyl. In another embodiment, $R^3$ is $-C(=NOR^9)R^{10}$ wherein $R^9$ is $(C_1-C_6)$alkyl and $R^{10}$ is methyl. In another embodiment, $R^3$ is $-C(=NOR^9)R^{10}$ wherein $R^9$ is $(C_1-C_6)$alkyl and $R^{10}$ is ethyl.

In another embodiment, the present disclosure relates to a compound of formula (Id) and the attendant definitions, wherein $R^3$ is $-C(=NOR^9)R^{10}$ wherein $R^9$ is methyl, ethyl, propyl or butyl and $R^{10}$ is $(C_1-C_6)$alkyl. In another embodiment, $R^3$ is $-C(=NOR^9)R^{10}$ wherein $R^9$ is methyl, ethyl, propyl or butyl and $R^{10}$ is $(C_1-C_4)$alkyl. In another embodiment, $R^3$ is $-C(=NOR^9)R^{10}$ wherein $R^9$ is methyl, ethyl, propyl or butyl and $R^{10}$ is methyl, ethyl or propyl. In another embodiment, $R^3$ is $-C(=NOR^9)R^{10}$ wherein $R^9$ is methyl, ethyl, propyl or butyl and $R^{10}$ is methyl or ethyl. In another embodiment, $R^3$ is $-C(=NOR^9)R^{10}$ wherein $R^9$ is methyl, ethyl, propyl or butyl and $R^{10}$ is methyl. In another embodiment, $R^3$ is $-C(=NOR^9)R^{10}$ wherein $R^9$ is methyl, ethyl, propyl or butyl and $R^{10}$ is ethyl. In one embodiment, $R^3$ is $-C(=NOR^9)R^{10}$ wherein $R^9$ is methyl and $R^{10}$ is $(C_1-C_6)$alkyl. In another embodiment, $R^3$ is $-C(=NOR^9)R^{10}$ wherein $R^9$ is methyl and $R^{10}$ is $(C_1-C_4)$alkyl. In another embodiment, $R^3$ is $-C(=NOR^9)R^{10}$ wherein $R^9$ is methyl and $R^{10}$ is methyl, ethyl or propyl. In another embodiment, $R^3$ is $-C(=NOR^9)R^{10}$ wherein $R^9$ is methyl and $R^{10}$ is methyl or ethyl. In another embodiment, $R^3$ is $-C(=NOR^9)R^{10}$ wherein $R^9$ is methyl and $R^{10}$ is methyl. In another embodiment, $R^3$ is $-C(=NOR^9)R^{10}$ wherein $R^9$ is methyl and $R^{10}$ is ethyl. In one embodiment, $R^3$ is $-C(=NOR^9)R^{10}$ wherein $R^9$ is ethyl and $R^{10}$ is $(C_1-C_6)$alkyl. In another embodiment, $R^3$ is $-C(=NOR^9)R^{10}$ wherein $R^9$ is ethyl and $R^{10}$ is $(C_1-C_4)$alkyl. In another embodiment, $R^3$ is $-C(=NOR^9)R^{10}$ wherein $R^9$ is ethyl and $R^{10}$ is methyl, ethyl or propyl. In another embodiment, $R^3$ is $-C(=NOR^9)R^{10}$ wherein $R^9$ is ethyl and $R^{10}$ is methyl or ethyl. In another embodiment, $R^3$ is $-C(=NOR^9)R^{10}$ wherein $R^9$ is ethyl and $R^{10}$ is methyl. In another embodiment, $R^3$ is $-C(=NOR^9)R^{10}$ wherein $R^9$ is ethyl and $R^{10}$ is ethyl. In one embodiment, $R^3$ is $-C(=NOR^9)R^{10}$ wherein $R^9$ is propyl and $R^{10}$ is $(C_1-C_6)$alkyl. In another embodiment, $R^3$ is $-C(=NOR^9)R^{10}$ wherein $R^9$ is propyl and $R^{10}$ is $(C_1-C_4)$alkyl. In another embodiment, $R^3$ is $-C(=NOR^9)R^{10}$ wherein $R^9$ is propyl and $R^{10}$ is methyl, ethyl or propyl. In another embodiment, $R^3$ is $-C(=NOR^9)R^{10}$ wherein $R^9$ is propyl and $R^{10}$ is methyl or ethyl. In another embodiment, $R^3$ is $-C(=NOR^9)R^{10}$ wherein $R^9$ is propyl and $R^{10}$ is methyl. In another embodiment, $R^3$ is $-C(=NOR^9)R^{10}$ wherein $R^9$ is propyl and $R^{10}$ is ethyl. In one embodiment, $R^3$ is $-C(=NOR^9)R^{10}$ wherein $R^9$ is butyl and $R^{10}$ is $(C_1-C_6)$alkyl. In another embodiment, $R^3$ is $-C(=NOR^9)R^{10}$ wherein $R^9$ is butyl and $R^{10}$ is $(C_1-C_4)$alkyl. In another embodiment, $R^3$ is $-C(=NOR^9)R^{10}$ wherein $R^9$ is butyl and $R^{10}$ is methyl, ethyl or propyl. In another embodiment, $R^3$ is $-C(=NOR^9)R^{10}$ wherein $R^9$ is butyl and $R^{10}$ is methyl or ethyl. In another embodiment, $R^3$ is $-C(=NOR^9)R^{10}$ wherein $R^9$ is butyl and $R^{10}$ is methyl. In another embodiment, $R^3$ is $-C(=NOR^9)R^{10}$ wherein $R^9$ is butyl and $R^{10}$ is ethyl. In one embodiment, $R^3$ is $-C(=NOR^9)R^{10}$ wherein $R^9$ is tert-butyl and $R^{10}$ is $(C_1-C_6)$alkyl. In another embodiment, $R^3$ is $-C(=NOR^9)R^{10}$ wherein $R^9$ is tert-butyl and $R^{10}$ is $(C_1-C_4)$alkyl. In another embodiment, $R^3$ is $-C(=NOR^9)R^{10}$ wherein $R^9$ is tert-butyl and $R^{10}$ is methyl, ethyl or propyl. In another embodiment, $R^3$ is $-C(=NOR^9)R^{10}$ wherein $R^9$ is tert-butyl and $R^{10}$ is methyl or ethyl. In another embodiment, $R^3$ is $-C(=NOR^9)R^{10}$ wherein $R^9$ is tert-butyl and $R^{10}$ is methyl. In another embodiment, $R^3$ is $-C(=NOR^9)R^{10}$ wherein $R^9$ is tert-butyl and $R^{10}$ is ethyl. In one embodiment, $R^3$ is $-C(=NOR^9)R^{10}$ wherein $R^9$ is iso-butyl and $R^{10}$ is $(C_1-C_6)$alkyl. In another embodiment, $R^3$ is $-C(=NOR^9)R^{10}$ wherein $R^9$ is iso-butyl and $R^{10}$ is $(C_1-C_4)$alkyl. In another embodiment, $R^3$ is $-C(=NOR^9)R^{10}$ wherein $R^9$ is iso-butyl and $R^{10}$ is methyl, ethyl or propyl. In another embodiment, $R^3$ is $-C(=NOR^9)R^{10}$ wherein $R^9$ is iso-butyl and $R^{10}$ is methyl or ethyl. In another embodiment, $R^3$ is $-C(=NOR^9)R^{10}$ wherein $R^9$ is iso-butyl and $R^{10}$ is methyl. In another embodiment, $R^3$ is $-C(=NOR^9)R^{10}$ wherein $R^9$ is iso-butyl and $R^{10}$ is ethyl.

In another embodiment, the present disclosure relates to a compound of formula (Id) and the attendant definitions, wherein $R^3$ is $-C(=NOR^9)R^{10}$ wherein at least one of $R^9$ and $R^{10}$ is methyl. In another embodiment, $R^3$ is $-C(=NOR^9)R^{10}$ wherein each of $R^9$ and $R^{10}$ is methyl. In another embodiment, $R^3$ is $-C(=NOR^9)R^{10}$ wherein one of $R^9$ and $R^{10}$ is methyl and the other is ethyl.

In another embodiment, the present disclosure relates to a compound of formula (Id) and the attendant definitions, wherein $R^3$ is —C(=NOR$^9$)R$^{10}$ wherein $R^9$ is $(C_1\text{-}C_6)$alkyl substituted with phenyl and $R^{10}$ is $(C_1\text{-}C_6)$alkyl. In another embodiment, $R^3$ is —C(=NOR$^9$)R$^{10}$ wherein $R^9$ is $(C_1\text{-}C_6)$alkyl substituted with phenyl and $R^{10}$ is $(C_1\text{-}C_4)$alkyl. In another embodiment, $R^3$ is —C(=NOR$^9$)R$^{10}$ wherein $R^9$ is $(C_1\text{-}C_6)$alkyl substituted with phenyl and $R^{10}$ is methyl, ethyl or propyl. In another embodiment, $R^3$ is —C(=NOR$^9$)R$^{10}$ wherein $R^9$ is $(C_1\text{-}C_6)$alkyl substituted with phenyl and $R^{10}$ is methyl or ethyl. In another embodiment, $R^3$ is —C(=NOR$^9$)R$^{10}$ wherein $R^9$ is $(C_1\text{-}C_6)$alkyl substituted with phenyl and $R^{10}$ is methyl. In another embodiment, $R^3$ is —C(=NOR$^9$)R$^{10}$ wherein $R^9$ is phenyl and $R^{10}$ is ethyl.

In another embodiment, the present disclosure relates to a compound of formula (Id) and the attendant definitions, wherein $R^3$ is —C(=NOR$^9$)R$^{10}$ wherein $R^9$ is $(C_1\text{-}C_4)$alkyl substituted with phenyl and $R^{10}$ is $(C_1\text{-}C_6)$alkyl. In one embodiment, $R^3$ is —C(=NOR$^9$)R$^{10}$ wherein $R^9$ is $(C_1)$alkyl substituted with phenyl and $R^{10}$ is $(C_1\text{-}C_6)$alkyl. In one embodiment, $R^3$ is —C(=NOR$^9$)R$^{10}$ wherein $R^9$ is $(C_2)$alkyl substituted with phenyl and $R^{10}$ is $(C_1\text{-}C_6)$alkyl. In one embodiment, $R^3$ is —C(=NOR$^9$)R$^{10}$ wherein $R^9$ is $(C_1\text{-}C_4)$alkyl substituted with phenyl and $R^{10}$ is $(C_1\text{-}C_4)$alkyl. In one embodiment, $R^3$ is —C(=NOR$^9$)R$^{10}$ wherein $R^9$ is $(C_1)$alkyl substituted with phenyl and $R^{10}$ is $(C_1\text{-}C_4)$alkyl. In one embodiment, $R^3$ is —C(=NOR$^9$)R$^{10}$ wherein $R^9$ is $(C_2)$alkyl substituted with phenyl and $R^{10}$ is $(C_1\text{-}C_4)$alkyl. In one embodiment, $R^3$ is —C(=NOR$^9$)R$^{10}$ wherein $R^9$ is $(C_1\text{-}C_4)$alkyl substituted with phenyl and $R^{10}$ is methyl, ethyl or propyl. In one embodiment, $R^3$ is —C(=NOR$^9$)R$^{10}$ wherein $R^9$ is $(C_1)$alkyl substituted with phenyl and $R^{10}$ is methyl, ethyl or propyl. In one embodiment, $R^3$ is —C(=NOR$^9$)R$^{10}$ wherein $R^9$ is $(C_2)$alkyl substituted with phenyl and $R^{10}$ is methyl, ethyl or propyl. In one embodiment, $R^3$ is —C(=NOR$^9$)R$^{10}$ wherein $R^9$ is $(C_1\text{-}C_4)$alkyl substituted with phenyl and $R^{10}$ is methyl or ethyl. In one embodiment, $R^3$ is —C(=NOR$^9$)R$^{10}$ wherein $R^9$ is $(C_1)$alkyl substituted with phenyl and $R^{10}$ is methyl or ethyl. In one embodiment, $R^3$ is —C(=NOR$^9$)R$^{10}$ wherein $R^9$ is $(C_2)$alkyl substituted with phenyl and $R^{10}$ is methyl or ethyl. In one embodiment, $R^3$ is —C(=NOR$^9$)R$^{10}$ wherein $R^9$ is $(C_1\text{-}C_4)$alkyl substituted with phenyl and $R^{10}$ is methyl. In one embodiment, $R^3$ is —C(=NOR$^9$)R$^{10}$ wherein $R^9$ is $(C_1)$alkyl substituted with phenyl and $R^{10}$ is methyl. In one embodiment, $R^3$ is —C(=NOR$^9$)R$^{10}$ wherein $R^9$ is $(C_2)$alkyl substituted with phenyl and $R^{10}$ is methyl. In one embodiment, $R^3$ is —C(=NOR$^9$)R$^{10}$ wherein $R^9$ is $(C_1\text{-}C_4)$alkyl substituted with phenyl and $R^{10}$ is ethyl. In one embodiment, $R^3$ is —C(=NOR$^9$)R$^{10}$ wherein $R^9$ is $(C_1)$alkyl substituted with phenyl and $R^{10}$ is ethyl. In one embodiment, $R^3$ is —C(=NOR$^9$)R$^{10}$ wherein $R^9$ is $(C_2)$alkyl substituted with phenyl and $R^{10}$ is ethyl.

In another embodiment, the present disclosure relates to a compound of formula (Id) and the attendant definitions, wherein $R^3$ is —C(=NOR$^9$)R$^{10}$ wherein $R^9$ is phenyl and $R^{10}$ is $(C_1\text{-}C_6)$alkyl. In another embodiment, $R^3$ is —C(=NOR$^9$)R$^{10}$ wherein $R^9$ is phenyl and $R^{10}$ is $(C_1\text{-}C_4)$alkyl. In another embodiment, $R^3$ is —C(=NOR$^9$)R$^{10}$ wherein $R^9$ is phenyl and $R^{10}$ is methyl, ethyl or propyl. In another embodiment, $R^3$ is —C(=NOR$^9$)R$^{10}$ wherein $R^9$ is phenyl and $R^{10}$ is methyl or ethyl. In another embodiment, $R^3$ is —C(=NOR$^9$)R$^{10}$ wherein $R^9$ is phenyl and $R^{10}$ is methyl. In another embodiment, $R^3$ is —C(=NOR$^9$)R$^{10}$ wherein $R^9$ is phenyl and $R^{10}$ is ethyl.

In one embodiment, the present disclosure relates to a compound of formula (Id) and the attendant definitions, wherein R is hydrogen, —CO-methyl, —CO-ethyl, —CO-benzyl, —CO-phenyl or 5-methyl-2-oxo-2H-1,3-dioxol-4-ylmethyl. In another embodiment, R is hydrogen or 5-methyl-2-oxo-2H-1,3-dioxol-4-ylmethyl. In another embodiment, R is hydrogen. In another embodiment, R is 5-methyl-2-oxo-2H-1,3-dioxol-4-ylmethyl. In another embodiment, R is —CO-methyl or —CO-ethyl. In another embodiment, R is —CO-methyl. In another embodiment, R is —CO-ethyl. In another embodiment, R is —CO-benzyl or —CO-phenyl. In another embodiments, R is —CO-benzyl. In another embodiment, R is —CO-phenyl. In another embodiment, R is —CO—NH$_2$. In each of the above embodiments in this paragraph, R is unsubstituted in one embodiment, monosubstituted in another embodiment, disubstituted with two independently selected substituents in an additional embodiment, or trisubstituted with three independently selected substituents in a further embodiment. In various embodiments of each of the above embodiments in this paragraph, the substituent is -halo, —NH$_2$, —NHCH$_3$, —CF$_3$ or —OCH$_3$ or the substituents are independently selected from -halo, —NH$_2$, —NHCH$_3$, —CF$_3$ or —OCH$_3$.

Another aspect of the disclosure provides a compound of formula (Ie)

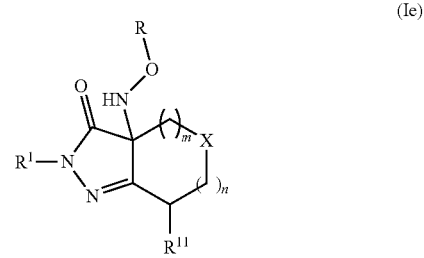

(Ie)

or a pharmaceutically acceptable salt thereof, wherein:
$R^1$ is H, $(C_1\text{-}C_6)$alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, $(C_1\text{-}C_6)$alkyl, $(C_1\text{-}C_4)$haloalkyl, $(C_1\text{-}C_4)$perhaloalkyl, $(C_1\text{-}C_6)$alkoxy, $(C_1\text{-}C_4)$haloalkoxy, $(C_1\text{-}C_4)$perhaloalkoxy, —C(=O)OH, —C(=O)O$(C_1\text{-}C_6)$alkyl, —C(=O)O(5-methyl-2-oxo-2H-1,3-dioxol-4-ylmethyl), —C(=O)NR$^4$R$^5$, —C(=O)-(5-, 6-, or 7-membered)heterocycloalkyl, (5-, 6-, or 7-membered)heterocycloalkyl, $(C_1\text{-}C_6)$alkylsulfanyl, $(C_1\text{-}C_4)$haloalkylsulfanyl, $(C_1\text{-}C_4)$perhaloalkylsulfanyl, $(C_1\text{-}C_6)$alkylsulfinyl, $(C_1\text{-}C_6)$alkylsulfonyl, $(C_3\text{-}C_6)$cycloalkylsulfonyl, $(C_1\text{-}C_4)$haloalkylsulfinyl, $(C_1\text{-}C_4)$haloalkylsulfonyl, $(C_1\text{-}C_4)$perhaloalkylsulfinyl, $(C_1\text{-}C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;
X is CH$_2$, O, NH, N(C$_1$-C$_6$)alkyl, N(C=O)(C$_1$-C$_6$)alkyl, N(CO)phenyl, S, SO, or SO$_2$, wherein said phenyl is unsubstituted to substituted with 1, 2, 3, 4, or 5 substituent(s) independently selected from halo, $(C_1\text{-}C_6)$alkyl, $(C_1\text{-}C_4)$haloalkyl, $(C_1\text{-}C_4)$perhaloalkyl, $(C_1\text{-}C_6)$alkoxy, $(C_1\text{-}C_4)$haloalkoxy, $(C_1\text{-}C_4)$perhaloalkoxy, —C(=O)OH, —C(=O)O$(C_1\text{-}C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1\text{-}C_6)$alkylsulfanyl, $(C_1\text{-}C_4)$haloalkylsulfanyl, $(C_1\text{-}C_4)$perhaloalkylsulfanyl, $(C_1\text{-}C_6)$alkylsulfinyl, $(C_1\text{-}C_6)$alkylsulfonyl, $(C_3\text{-}C_6)$cycloalkylsulfonyl, $(C_1\text{-}C_4)$ haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

m is 0, 1, 2, 3, 4, or 5;

n is 0, 1, 2, 3, 4, or 5;

R$^{11}$ is H, (C$_1$-C$_6$)alkyl or phenyl, wherein said alkyl and said phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl; R$^8$ is H, —(C=O)(C$_1$-C$_6$)alkyl or —(C=O)(C$_1$-C$_4$)perhaloalkyl; and R is hydrogen, —COH, —CO—(C$_1$-C$_6$)alkyl, —CO—(C$_2$-C$_4$)alkenyl, —CO-phenyl, —CO-benzyl, —CO—cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl or 5-methyl-2-oxo-2H-1,3-dioxol-4-ylmethyl.

In one embodiment, the present disclosure relates to a compound of formula (Ie) and the attendant definitions, wherein R$^1$ is H. In another embodiment, R$^1$ is (C$_1$-C$_6$)alkyl, wherein the alkyl is unsubstituted or substituted with 1, 2 or 3 independently selected substituents. In another embodiment, R$^1$ is (5- or 6-membered)heteroaryl, wherein the heteroaryl is unsubstituted or substituted with 1, 2, 3, 4, or 5 independently selected substituents. In another embodiment, R$^1$ is phenyl, wherein the phenyl is unsubstituted or substituted with 1, 2, 3, 4, or 5 independently selected substituents. In each of the embodiments listed in this paragraph, the substitutents are selected from among those disclosed above for R$^1$ in connection with formula (Ie).

In another embodiment, the present disclosure relates to a compound of formula (Ie) and the attendant definitions, wherein R$^1$ is (C$_1$-C$_4$)alkyl. In another embodiment, R$^1$ is methyl, ethyl, propyl, or butyl. In another embodiment, R$^1$ is methyl, ethyl, or propyl. In another embodiment, R$^1$ is methyl, ethyl, or butyl. In another embodiment, R$^1$ is methyl, propyl, or butyl. In another embodiment, R$^1$ is ethyl, propyl, or butyl. In another embodiment, R$^1$ is methyl or ethyl. In another embodiment, R$^1$ is methyl or propyl. In another embodiment, R$^1$ is methyl or butyl. In another embodiment, R$^1$ is ethyl or propyl. In another embodiment, R$^1$ is ethyl or butyl. In another embodiment, R$^1$ is propyl or butyl. In another embodiment, R$^1$ is methyl. In another embodiment, R$^1$ is ethyl. In another embodiment, R$^1$ is propyl. In another embodiment, R$^1$ is iso-propyl. In another embodiment, R$^1$ is butyl. In another embodiment, R$^1$ is tert-butyl. In each of the embodiments listed in this paragraph, the alkyl is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is —C(=O)OH, —C(=O)O(C$_1$-C$_6$)alkyl, —C(=O)OCH$_3$, —C(=O)OCH$_2$CH$_3$, —C(=O)O(5-methyl-2-oxo-2H-1,3-dioxol-4-ylmethyl), —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, (C$_1$-C$_6$)alkylsulfanyl, (C$_1$-C$_6$)alkylsulfinyl, (C$_1$-C$_6$)alkylsulfonyl, —S(O)$_2$—NH$_2$, —N—(C$_1$-C$_6$)alkylaminosulfonyl, or N,N-di(C$_1$-C$_6$)alkylaminosulfonyl or the substituents are independently selected from —C(=O)OH, —C(=O)O(C$_1$-C$_6$)alkyl, —C(=O)OCH$_3$, —C(=O)OCH$_2$CH$_3$, —C(=O)O(5-methyl-2-oxo-2H-1,3-dioxol-4-ylmethyl), —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, (C$_1$-C$_6$)alkylsulfanyl, (C$_1$-C$_6$)alkylsulfinyl, (C$_1$-C$_6$)alkylsulfonyl, —S(O)$_2$—NH$_2$, —N—(C$_1$-C$_6$)alkylaminosulfonyl, or N,N-di(C$_1$-C$_6$)alkylaminosulfonyl.

In another embodiment, the present disclosure relates to a compound of formula (Ie) and the attendant definitions, wherein R$^1$ is (5- or 6-membered)heteroaryl, wherein the heteroaryl is unsubstituted or substituted with 1, 2 or 3 independently selected substituents, the substitutents being selected from among those disclosed above for R$^1$ in connection with formula (Ie). In another embodiment, R$^1$ is unsubstituted (5- or 6-membered)heteroaryl. In another embodiment, R$^1$ is monosubstituted (5- or 6-membered) heteroaryl. In another embodiment, R$^1$ is disubstituted (5- or 6-membered)heteroaryl. In another embodiment, R$^1$ is trisubstituted (5- or 6-membered)heteroaryl. In various embodiments of each of the above embodiments in this paragraph, the substituent is halo, (C$_1$-C$_6$)alkyl, (C$_1$-C$_6$)alkoxy, phenyl, —C(=O)NR$^4$R$^5$, (C$_1$-C$_6$)alkylsulfinyl, (C$_1$-C$_6$)alkylsulfonyl, and N,N-di(C$_1$-C$_6$)alkylaminosulfonyl.

In another embodiment, the present disclosure relates to a compound of formula (Ie) and the attendant definitions, wherein R$^1$ is unsubstituted phenyl. In another embodiment, R$^1$ is phenyl substituted with 1, 2 or 3 independently selected substituent(s), the substitutents being selected from among those disclosed above for R$^1$ in connection with formula (Ie). In another embodiment, R$^1$ is phenyl substituted with 1, 2, or 3 independently selected substituent(s), at least one of which is halo. In another embodiment, R$^1$ is phenyl substituted with 1, 2, or 3 independently selected substituent(s), at least one of which is (C$_1$-C$_6$)alkyl. In another embodiment, R$^1$ is phenyl substituted with 1, 2, or 3 independently selected substituent(s), at least one of which is (C$_1$-C$_4$)haloalkyl. In another embodiment, R$^1$ is phenyl substituted with 1, 2, or 3 independently selected substituent(s), at least one of which is (C$_1$-C$_4$)perhaloalkyl. In another embodiment, R$^1$ is phenyl substituted with 1, 2, or 3 independently selected substituent(s), at least one of which is (C$_1$-C$_6$)alkoxy. In another embodiment, R$^1$ is phenyl substituted with 1, 2, or 3 independently selected substituent(s), at least one of which is (C$_1$-C$_4$)perhaloalkoxy. In another embodiment, R$^1$ is phenyl substituted with 1, 2, or 3 independently selected substituent(s), at least one of which is —C(=O) OH. In another embodiment, $R^1$ is phenyl substituted with 1, 2, or 3 independently selected substituent(s), at least one of which is —C(=O)O($C_1$-$C_6$)alkyl. In another embodiment, $R^1$ is phenyl substituted with 1, 2, or 3 independently selected substituent(s), at least one of which is —C(=O) $NR^4R^5$. In another embodiment, $R^1$ is phenyl substituted with 1, 2, or 3 independently selected substituent(s), at least one of which is —C(=O)NH($C_1$-$C_6$)alkyl, wherein said alkyl is substituted with COOH. In another embodiment, $R^1$ is phenyl substituted with 1, 2, or 3 independently selected substituent(s), at least one of which is —C(=O)NH—($C_1$-$C_6$)alkylsulfonyl. In another embodiment, $R^1$ is phenyl substituted with 1, 2, or 3 independently selected substituent(s), at least one of which is —C(=O)-(5-, 6-, or 7-membered)heterocycloalkyl. In another embodiment, $R^1$ is phenyl substituted with 1, 2, or 3 independently selected substituent(s), at least one of which is (5-, 6-, or 7-membered)heterocycloalkyl. In another embodiment, $R^1$ is phenyl substituted with 1, 2, or 3 independently selected substituent(s), at least one of which is ($C_1$-$C_6$)alkylsulfanyl. In another embodiment, $R^1$ is phenyl substituted with 1, 2, or 3 independently selected substituent(s), at least one of which is ($C_1$-$C_4$) perhaloalkylsulfanyl. In another embodiment, $R^1$ is phenyl substituted with 1, 2, or 3 independently selected substituent(s), at least one of which is ($C_1$-$C_6$)alkylsulfinyl. In another embodiment, $R^1$ is phenyl substituted with 1, 2, or 3 independently selected substituent(s), at least one of which is ($C_1$-$C_6$)alkylsulfonyl. In another embodiment, $R^1$ is phenyl substituted with 1, 2, or 3 independently selected substituent(s), at least one of which is ($C_3$-$C_6$)cycloalkylsulfonyl. In another embodiment, $R^1$ is phenyl substituted with 1, 2, or 3 independently selected substituent(s), at least one of which is ($C_1$-$C_4$)haloalkylsulfinyl. In another embodiment, $R^1$ is phenyl substituted with 1, 2, or 3 independently selected substituent(s), at least one of which is ($C_1$-$C_4$)haloalkylsulfonyl. In another embodiment, $R^1$ is phenyl substituted with 1, 2, or 3 independently selected substituent(s), at least one of which is ($C_1$-$C_4$)perhaloalkylsulfinyl. In another embodiment, $R^1$ is phenyl substituted with 1, 2, or 3 independently selected substituent(s), at least one of which is ($C_1$-$C_4$)perhaloalkylsulfonyl. In another embodiment, $R^1$ is phenyl substituted with 1, 2, or 3 independently selected substituent(s), at least one of which is —S(O)$_2$—$NR^6R^7$. In another embodiment, $R^1$ is phenyl substituted with 1, 2, or 3 independently selected substituent(s), at least one of which is —S(O)$_2$-phenyl. In another embodiment, $R^1$ is phenyl substituted with 1, 2, or 3 independently selected substituent(s), at least one of which is —S(O)$_2$-(5-, 6-, or 7-membered)heterocycloalkyl. In another embodiment, $R^1$ is phenyl substituted with 1, 2, or 3 independently selected substituent(s), at least one of which is —S(=O)(=$NR^8$)($C_1$-$C_6$)alkyl. In another embodiment, $R^1$ is phenyl substituted with 1, 2, or 3 independently selected substituent(s), at least one of which is N,N-di($C_1$-$C_6$)alkylaminosulfonyl.

In another embodiment, the present disclosure relates to a compound of formula (Ie) and the attendant definitions, wherein $R^1$ is monosubstituted phenyl substituted with halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)$NR^4R^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1$-$C_6$)alkyl, —$NR^4R^5$, N—($C_1$-$C_6$)alkylaminosulfonyl, or N,N-di($C_1$-$C_6$)alkylaminosulfonyl.

In another embodiment, the present disclosure relates to a compound of formula (Ie) and the attendant definitions, wherein $R^1$ is disubstituted phenyl, each substituent being independently selected from halo, ($C_1$-$C_6$)alkyl, ($C_1$-$C_4$) perhaloalkyl, ($C_1$-$C_6$)alkoxy, ($C_1$-$C_4$)haloalkoxy, ($C_1$-$C_4$) perhaloalkoxy, —C(=O)OH, —C(=O)O($C_1$-$C_6$)alkyl, —C(=O)$NR^4R^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$) alkylsulfinyl, ($C_1$-$C_6$)alkylsulfonyl, ($C_1$-$C_4$) haloalkylsulfinyl, ($C_1$-$C_4$)haloalkylsulfonyl, ($C_1$-$C_4$) perhaloalkylsulfinyl, ($C_1$-$C_4$)perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1$-$C_6$)alkyl, —$NR^4R^5$, N—($C_1$-$C_6$) alkylaminosulfonyl, and N,N-di($C_1$-$C_6$)alkylaminosulfonyl.

In another embodiment, the present disclosure relates to a compound of formula (Ie) and the attendant definitions, wherein $R^1$ is trisubstituted phenyl, each substituent being independently selected from halo, ($C_1$-$C_6$)alkyl, ($C_1$-$C_4$) perhaloalkyl, ($C_1$-$C_6$)alkoxy, ($C_1$-$C_4$)haloalkoxy, ($C_1$-$C_4$) perhaloalkoxy, —C(=O)OH, —C(=O)O($C_1$-$C_6$)alkyl, —C(=O)$NR^4R^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$) alkylsulfinyl, ($C_1$-$C_6$)alkylsulfonyl, ($C_1$-$C_4$) haloalkylsulfinyl, ($C_1$-$C_4$)haloalkylsulfonyl, ($C_1$-$C_4$) perhaloalkylsulfinyl, ($C_1$-$C_4$)perhaloalkylsulfonyl, —S(O)$_2$—$NH_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1$-$C_6$)alkyl, —$NR^4R^5$, N—($C_1$-$C_6$) alkylaminosulfonyl, and N,N-di($C_1$-$C_6$)alkylaminosulfonyl.

In one embodiment, the present disclosure relates to a compound of formula (Ie) and the attendant definitions, wherein X is $CH_2$, O, S, SO, or $SO_2$. In another embodiment, X is $CH_2$, O, S, or SO. In another embodiment, X is $CH_2$, S, SO, or $SO_2$. In another embodiment, X is $CH_2$, O, SO, or $SO_2$. In another embodiment, X is $CH_2$, O, S, or $SO_2$. In another embodiment, X is O, S, SO or $SO_2$. In another embodiment, X is $CH_2$. In another embodiment, X is O. In another embodiment, X is S. In another embodiment, X is SO. In another embodiment, X is $SO_2$. In one embodiment, X is NH, N($C_1$-$C_6$)alkyl, N(C=O)($C_1$-$C_6$)alkyl, N(CO) phenyl. In one embodiment, X is NH. In another embodiment, X is N($C_1$-$C_6$)alkyl. In another embodiment, X is N(C=O)($C_1$-$C_6$)alkyl. In another embodiment, X is N(CO) phenyl.

In one embodiment, the present disclosure relates to a compound of formula (Ie) and the attendant definitions, wherein m is 1. In another embodiment, m is 2. In another embodiment, m is 3. In another embodiment, m is 4. In another embodiment, m is 5.

In one embodiment, the present disclosure relates to a compound of formula (Ie) and the attendant definitions, wherein n is 1. In another embodiment, n is 2. In another embodiment, n is 3. In another embodiment, n is 4. In another embodiment, n is 5.

In one embodiment, the present disclosure relates to a compound of formula (Ie) and the attendant definitions, wherein m+n is 1. In another embodiment, m+n is 2. In another embodiment, m+n is 3.

In one embodiment, the present disclosure relates to a compound of formula (Ie) and the attendant definitions, wherein $R^{11}$ is H. In another embodiment, $R^{11}$ is ($C_1$-$C_6$)

alkyl, wherein the alkyl is unsubstituted or substituted with 1, 2 or 3 independently selected substituents. In another embodiment, $R^{11}$ is phenyl, wherein the phenyl is unsubstituted or substituted with 1, 2, 3, 4, or 5 independently selected substituents. In each of the embodiments listed in this paragraph, the substitutents are selected from among those disclosed above for $R^{11}$ in connection with formula (Ie).

In another embodiment, the present disclosure relates to a compound of formula (Ie) and the attendant definitions, wherein $R^{11}$ is $(C_1-C_4)$alkyl. In another embodiment, $R^{11}$ is methyl, ethyl, propyl, or butyl. In another embodiment, $R^{11}$ is methyl, ethyl, or propyl. In another embodiment, $R^{11}$ is methyl, ethyl, or butyl. In another embodiment, $R^{11}$ is methyl, propyl, or butyl. In another embodiment, $R^{11}$ is ethyl, propyl, or butyl. In another embodiment, $R^{11}$ is methyl or ethyl. In another embodiment, $R^{11}$ is methyl or propyl. In another embodiment, $R^{11}$ is methyl or butyl. In another embodiment, $R^{11}$ is ethyl or propyl. In another embodiment, $R^{11}$ is ethyl or butyl. In another embodiment, $R^{11}$ is propyl or butyl. In another embodiment, $R^{11}$ is methyl. In another embodiment, $R^{11}$ is ethyl. In another embodiment, $R^{11}$ is propyl. In another embodiment, $R^{11}$ is iso-propyl. In another embodiment, $R^{11}$ is butyl. In another embodiment, $R^{11}$ is tert-butyl. In each of the embodiments listed in this paragraph, the alkyl is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is —C(=O)OH, —C(=O)O($C_1$-$C_6$)alkyl, —C(=O)OCH$_3$, —C(=O)OCH$_2$CH$_3$, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1$-$C_6$)alkylsulfanyl, ($C_1$-$C_6$)alkylsulfinyl, ($C_1$-$C_6$)alkylsulfonyl, —S(O)$_2$—NH$_2$, —N—($C_1$-$C_6$)alkylaminosulfonyl, or N,N-di($C_1$-$C_6$)alkylaminosulfonyl or the substituents are independently selected from —C(=O)OH, —C(=O)O($C_1$-$C_6$)alkyl, —C(=O)OCH$_3$, —C(=O)OCH$_2$CH$_3$, —C(=O)O(5-methyl-2-oxo-2H-1,3-dioxol-4-ylmethyl), —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1$-$C_6$)alkylsulfanyl, ($C_1$-$C_6$)alkylsulfinyl, ($C_1$-$C_6$)alkylsulfonyl, —S(O)$_2$—NH$_2$, —N—($C_1$-$C_6$)alkylaminosulfonyl, or N,N-di($C_1$-$C_6$)alkylaminosulfonyl.

In another embodiment, the present disclosure relates to a compound of formula (Ie) and the attendant definitions, wherein $R^{11}$ is unsubstituted phenyl. In another embodiment, $R^{11}$ is phenyl substituted with 1, 2 or 3 independently selected substituent(s), the substitutents being selected from among those disclosed above for $R^{11}$ in connection with formula (Ie). In another embodiment, $R^{11}$ is phenyl substituted with 1, 2, or 3 independently selected substituent(s), at least one of which is halo. In another embodiment, $R^{11}$ is phenyl substituted with 1, 2, or 3 independently selected substituent(s), at least one of which is ($C_1$-$C_6$)alkyl. In another embodiment, $R^{11}$ is phenyl substituted with 1, 2, or 3 independently selected substituent(s), at least one of which is ($C_1$-$C_4$)haloalkyl. In another embodiment, $R^{11}$ is phenyl substituted with 1, 2, or 3 independently selected substituent(s), at least one of which is ($C_1$-$C_4$)perhaloalkyl. In another embodiment, $R^{11}$ is phenyl substituted with 1, 2, or 3 independently selected substituent(s), at least one of which is ($C_1$-$C_6$)alkoxy. In another embodiment, $R^{11}$ is phenyl substituted with 1, 2, or 3 independently selected substituent(s), at least one of which is ($C_1$-$C_4$)perhaloalkoxy.

In another embodiment, $R^{11}$ is phenyl substituted with 1, 2, or 3 independently selected substituent(s), at least one of which is —C(=O)OH. In another embodiment, $R^{11}$ is phenyl substituted with 1, 2, or 3 independently selected substituent(s), at least one of which is —C(=O)O($C_1$-$C_6$)alkyl. In another embodiment, $R^{11}$ is phenyl substituted with 1, 2, or 3 independently selected substituent(s), at least one of which is —C(=O)NR$^4$R$^5$. In another embodiment, $R^{11}$ is phenyl substituted with 1, 2, or 3 independently selected substituent(s), at least one of which is —C(=O)NH($C_1$-$C_6$)alkyl, wherein said alkyl is substituted with COOH. In another embodiment, $R^{11}$ is phenyl substituted with 1, 2, or 3 independently selected substituent(s), at least one of which is —C(=O)NH—($C_1$-$C_6$)alkylsulfonyl. In another embodiment, $R^{11}$ is phenyl substituted with 1, 2, or 3 independently selected substituent(s), at least one of which is —C(=O)-(5-, 6-, or 7-membered)heterocycloalkyl. In another embodiment, $R^{11}$ is phenyl substituted with 1, 2, or 3 independently selected substituent(s), at least one of which is (5-, 6-, or 7-membered)heterocycloalkyl. In another embodiment, $R^{11}$ is phenyl substituted with 1, 2, or 3 independently selected substituent(s), at least one of which is ($C_1$-$C_6$)alkylsulfanyl. In another embodiment, $R^{11}$ is phenyl substituted with 1, 2, or 3 independently selected substituent(s), at least one of which is ($C_1$-$C_4$)perhaloalkylsulfanyl. In another embodiment, $R^{11}$ is phenyl substituted with 1, 2, or 3 independently selected substituent(s), at least one of which is ($C_1$-$C_6$)alkylsulfinyl. In another embodiment, $R^{11}$ is phenyl substituted with 1, 2, or 3 independently selected substituent(s), at least one of which is ($C_1$-$C_6$)alkylsulfonyl. In another embodiment, $R^{11}$ is phenyl substituted with 1, 2, or 3 independently selected substituent(s), at least one of which is ($C_3$-$C_6$)cycloalkylsulfonyl. In another embodiment, $R^{11}$ is phenyl substituted with 1, 2, or 3 independently selected substituent(s), at least one of which is ($C_1$-$C_4$)haloalkylsulfinyl. In another embodiment, $R^{11}$ is phenyl substituted with 1, 2, or 3 independently selected substituent(s), at least one of which is ($C_1$-$C_4$)haloalkylsulfonyl. In another embodiment, $R^{11}$ is phenyl substituted with 1, 2, or 3 independently selected substituent(s), at least one of which is ($C_1$-$C_4$)perhaloalkylsulfinyl. In another embodiment, $R^{11}$ is phenyl substituted with 1, 2, or 3 independently selected substituent(s), at least one of which is ($C_1$-$C_4$)perhaloalkylsulfonyl. In another embodiment, $R^{11}$ is phenyl substituted with 1, 2, or 3 independently selected substituent(s), at least one of which is —S(O)$_2$—NR$^6$R$^7$. In another embodiment, $R^{11}$ is phenyl substituted with 1, 2, or 3 independently selected substituent(s), at least one of which is —S(O)$_2$-phenyl. In another embodiment, $R^{11}$ is phenyl substituted with 1, 2, or 3 independently selected substituent(s), at least one of which is —S(O)$_2$-(5-, 6-, or 7-membered)heterocycloalkyl. In another embodiment, $R^{11}$ is phenyl substituted with 1, 2, or 3 independently selected substituent(s), at least one of which is —S(=O)(=NR$^8$)($C_1$-$C_6$)alkyl. In another embodiment, $R^{11}$ is phenyl substituted with 1, 2, or 3 independently selected substituent(s), at least one of which is N,N-di($C_1$-$C_6$)alkylaminosulfonyl.

In another embodiment, the present disclosure relates to a compound of formula (Ie) and the attendant definitions, wherein $R^{11}$ is monosubstituted phenyl substituted with halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$-(5-, 6-, or 7-membered)heterocycloalkyl, —$S(=O)(=NR^8)(C_1-C_6)$alkyl, —$NR^4R^5$, N—$(C_1-C_6)$alkylaminosulfonyl, or N,N-di$(C_1-C_6)$alkylaminosulfonyl.

In another embodiment, the present disclosure relates to a compound of formula (Ie) and the attendant definitions, wherein $R^{11}$ is disubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —$C(=O)OH$, —$C(=O)O(C_1-C_6)$alkyl, —$C(=O)NR^4R^5$, —$C(=O)$-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$-(5-, 6-, or 7-membered)heterocycloalkyl, —$S(=O)(=NR^8)(C_1-C_6)$alkyl, —$NR^4R^5$, N—$(C_1-C_6)$alkylaminosulfonyl, and N,N-di$(C_1-C_6)$alkylaminosulfonyl.

In another embodiment, the present disclosure relates to a compound of formula (Ie) and the attendant definitions, wherein $R^{11}$ is trisubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —$C(=O)OH$, —$C(=O)O(C_1-C_6)$alkyl, —$C(=O)NR^4R^5$, —$C(=O)$-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$-(5-, 6-, or 7-membered)heterocycloalkyl, —$S(=O)(=NR^8)(C_1-C_6)$alkyl, —$NR^4R^5$, N—$(C_1-C_6)$alkylaminosulfonyl, and N,N-di$(C_1-C_6)$alkylaminosulfonyl.

In one embodiment, the present disclosure relates to a compound of formula (Ie) and the attendant definitions, wherein R is hydrogen, —CO-methyl, —CO-ethyl, —CO-benzyl, —CO-phenyl or 5-methyl-2-oxo-2H-1,3-dioxol-4-ylmethyl. In another embodiment, R is hydrogen or 5-methyl-2-oxo-2H-1,3-dioxol-4-ylmethyl. In another embodiment, R is hydrogen. In another embodiment, R is 5-methyl-2-oxo-2H-1,3-dioxol-4-ylmethyl. In another embodiment, R is —CO-methyl or —CO-ethyl. In another embodiment, R is —CO-methyl. In another embodiment, R is —CO-ethyl. In another embodiment, R is —CO-benzyl or —CO-phenyl. In another embodiments, R is —CO-benzyl. In another embodiment, R is —CO-phenyl. In another embodiment, R is —CO—$NH_2$. In each of the above embodiments in this paragraph, R is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is -halo, —$NH_2$, —$NHCH_3$, —$CF_3$ or —$OCH_3$ or the substituents are independently selected from -halo, —$NH_2$, —$NHCH_3$, —$CF_3$ or —$OCH_3$.

Another aspect of the disclosure provides a compound of formula (If)

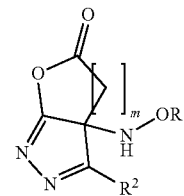

(If)

or a pharmaceutically acceptable salt thereof, wherein:
$R^2$ is $(C_1-C_6)$alkyl or phenyl, wherein said phenyl is unsubstituted or substituted with 1, 2, 3, 4, or 5 substituent(s) independently selected from halo, cyano, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —$C(=O)OH$, —$C(=O)O(C_1-C_6)$alkyl, —$C(=O)NR^4R^5$, —$C(=O)$-(5-, 6-, or 7-membered)heterocycloalkyl, (5-, 6-, or 7-membered)heterocycloalkyl, $(C_6-C_{10})$aryl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —$S(O)_2$—$NH_2$, —$S(O)_2$—$NR^6R^7$, —$S(O)_2$-phenyl, —$S(O)_2$-(5-, 6-, or 7-membered)heterocycloalkyl, —$S(=O)(=NR^8)(C_1-C_6)$alkyl, —$NR^4R^5$, N—$(C_1-C_6)$alkylaminosulfonyl, and N,N-di$(C_1-C_6)$alkylaminosulfonyl, wherein said (5-, 6-, or 7-membered)heterocycloalkyl is unsubstituted or substituted with 1 or 2 substituent(s) independently selected from halo or $(C_1-C_6)$alkyl;
m is 1, 2 or 3; and
R is 5-methyl-2-oxo-2H-1,3-dioxol-4-ylmethyl.

In one embodiment, the present disclosure relates to a compound of formula (If) and the attendant definitions, wherein m is 1. In another embodiment, m is 2. In another embodiment, m is 3.

In one embodiment, the present disclosure relates to a compound of formula (If) and the attendant definitions, wherein $R^2$ is methyl, ethyl, propyl, or butyl. In another embodiment, $R^2$ is methyl, ethyl, or propyl. In another embodiment, $R^2$ is methyl, ethyl, or butyl. In another embodiment, $R^2$ is methyl, propyl, or butyl. In another embodiment, $R^2$ is ethyl, propyl, or butyl. In another embodiment, $R^2$ is methyl or ethyl. In another embodiment, $R^2$ is methyl or propyl. In another embodiment, $R^2$ is methyl or butyl. In another embodiment, $R^2$ is ethyl or propyl. In another embodiment, $R^2$ is ethyl or butyl. In another embodiment, $R^2$ is propyl or butyl. In another embodiment, $R^2$ is methyl. In another embodiment, $R^2$ is ethyl. In another embodiment, $R^2$ is propyl. In another embodiment, $R^2$ is iso-propyl. In another embodiment, $R^2$ is butyl. In another embodiment, $R^2$ is tert-butyl.

In another embodiment, the present disclosure relates to a compound of formula (If) and the attendant definitions, wherein $R^2$ is unsubstituted phenyl. In another embodiment, $R^2$ is phenyl substituted with 1, 2, or 3 independently selected substituent(s), at least one of which is halo. In another embodiment, $R^2$ is phenyl substituted with 1, 2, or 3 independently selected substituent(s), at least one of which is chloro. In another embodiment, $R^2$ is phenyl substituted with 1, 2, or 3 independently selected substituent(s), at least one of which is fluoro. In another embodiment, $R^2$ is phenyl substituted with 1, 2, or 3 independently selected substituent(s), at least one of which is $(C_1-C_6)$alkyl. In another embodiment, $R^2$ is phenyl substituted with 1, 2, or 3 independently selected substituent(s), at least one of which is methyl. In another embodiment, $R^2$ is phenyl substituted with 1, 2, or 3 independently selected substituent(s), at least one of which is $(C_1-C_4)$haloalkyl. In another embodiment, $R^2$ is phenyl substituted with 1, 2, or 3 independently selected substituent(s), at least one of which is $(C_1-C_4)$perhaloalkyl. In another embodiment, $R^2$ is phenyl substituted with 1, 2, or 3 independently selected substituent(s), at least one of which is perfluoromethyl. In another embodiment, $R^2$ is phenyl substituted with 1, 2, or 3 independently selected substituent(s), at least one of which is $(C_1-C_6)$alkoxy. In another embodiment, $R^2$ is phenyl substituted with 1, 2, or 3 independently selected substituent(s), at least one of which is methoxy. In another embodiment, $R^2$ is phenyl substituted with 1, 2, or 3 independently selected substituent(s), at least one of which is $(C_1-C_4)$perhaloalkoxy. In another embodiment, $R^2$ is phenyl substituted with 1, 2, or 3 independently selected substituent(s), at least one of which is $(C_1-C_4)$perfluoroalkoxy.

In another embodiment, the present disclosure relates to a compound of formula (If) and the attendant definitions, wherein $R^2$ is phenyl substituted with 1, 2, or 3 independently selected substituent(s), at least one of which is —C(=O)OH. In another embodiment, $R^2$ is phenyl substituted with 1, 2, or 3 independently selected substituent(s), at least one of which is —C(=O)O($C_1$-$C_6$)alkyl. In another embodiment, $R^2$ is phenyl substituted with 1, 2, or 3 independently selected substituent(s), at least one of which is —C(=O)OCH$_3$. In another embodiment, $R^2$ is phenyl substituted with 1, 2, or 3 independently selected substituent(s), at least one of which is —C(=O)NR$^4$R$^5$. In another embodiment, $R^2$ is phenyl substituted with 1, 2, or 3 independently selected substituent(s), at least one of which is —C(=O)N(CH$_3$)$_2$. In another embodiment, $R^2$ is phenyl substituted with 1, 2, or 3 independently selected substituent(s), at least one of which is —C(=O)NH$_2$. In another embodiment, $R^2$ is phenyl substituted with 1, 2, or 3 independently selected substituent(s), at least one of which is —C(=O)NH($C_1$-$C_6$)alkyl, wherein said alkyl is substituted with COOH. In another embodiment, $R^2$ is phenyl substituted with 1, 2, or 3 independently selected substituent(s), at least one of which is —C(=O)NH—($C_1$-$C_6$)alkylsulfonyl.

In another embodiment, the present disclosure relates to a compound of formula (If) and the attendant definitions, wherein $R^2$ is phenyl substituted with 1, 2, or 3 independently selected substituent(s), at least one of which is —C(=O)-(5-, 6-, or 7-membered)heterocycloalkyl. In another embodiment, $R^2$ is phenyl substituted with 1, 2, or 3 independently selected substituent(s), at least one of which is —C(=O)-morpholinyl, —C(=O)-piperidinyl or —C(=O)-piperazinyl. In another embodiment, $R^2$ is phenyl substituted with 1, 2, or 3 independently selected substituent(s), at least one of which is —C(=O)-morpholinyl. In another embodiment, $R^2$ is phenyl substituted with 1, 2, or 3 independently selected substituent(s), at least one of which is —C(=O)-piperidinyl. In another embodiment, $R^2$ is phenyl substituted with 1, 2, or 3 independently selected substituent(s), at least one of which is —C(=O)-piperazinyl.

In another embodiment, the present disclosure relates to a compound of formula (If) and the attendant definitions, wherein $R^2$ is phenyl substituted with 1, 2, or 3 independently selected substituent(s), at least one of which is (5-, 6-, or 7-membered)heterocycloalkyl. In another embodiment, $R^2$ is phenyl substituted with 1, 2, or 3 independently selected substituent(s), at least one of which is morpholinyl, piperidinyl or piperazinyl. In another embodiment, $R^2$ is phenyl substituted with 1, 2, or 3 independently selected substituent(s), at least one of which is morpholinyl. In another embodiment, $R^2$ is phenyl substituted with 1, 2, or 3 independently selected substituent(s), at least one of which is piperidinyl. In another embodiment, $R^2$ is phenyl substituted with 1, 2, or 3 independently selected substituent(s), at least one of which is piperazinyl.

In another embodiment, the present disclosure relates to a compound of formula (If) and the attendant definitions, wherein $R^2$ is phenyl substituted with 1, 2, or 3 independently selected substituent(s), at least one of which is $(C_1-C_6)$alkylsulfanyl. In another embodiment, $R^2$ is phenyl substituted with 1, 2, or 3 independently selected substituent(s), at least one of which is methylsulfanyl. In another embodiment, $R^2$ is phenyl substituted with 1, 2, or 3 independently selected substituent(s), at least one of which is $(C_1-C_4)$perhaloalkylsulfanyl. In another embodiment, $R^2$ is phenyl substituted with 1, 2, or 3 independently selected substituent(s), at least one of which is trifluoromethylsulfanyl. In another embodiment, $R^2$ is phenyl substituted with 1, 2, or 3 independently selected substituent(s), at least one of which is $(C_1-C_6)$alkylsulfinyl. In another embodiment, $R^2$ is phenyl substituted with 1, 2, or 3 independently selected substituent(s), at least one of which is methylsulfinyl. In another embodiment, $R^2$ is phenyl substituted with 1, 2, or 3 independently selected substituent(s), at least one of which is $(C_1-C_6)$alkylsulfonyl. In another embodiment, $R^2$ is phenyl substituted with 1, 2, or 3 independently selected substituent(s), at least one of which is methylsulfonyl. In another embodiment, $R^2$ is phenyl substituted with 1, 2, or 3 independently selected substituent(s), at least one of which is $(C_3-C_6)$cycloalkylsulfonyl. In another embodiment, $R^2$ is phenyl substituted with 1, 2, or 3 independently selected substituent(s), at least one of which is cyclopropylsulfonyl.

In another embodiment, the present disclosure relates to a compound of formula (If) and the attendant definitions, wherein $R^2$ is phenyl substituted with 1, 2, or 3 independently selected substituent(s), at least one of which is $(C_1-C_4)$haloalkylsulfinyl. In another embodiment, $R^2$ is phenyl substituted with 1, 2, or 3 independently selected substituent(s), at least one of which is $(C_1-C_4)$haloalkylsulfonyl. In another embodiment, $R^2$ is phenyl substituted with 1, 2, or 3 independently selected substituent(s), at least one of which is $(C_1-C_4)$perhaloalkylsulfinyl. In another embodiment, $R^2$ is phenyl substituted with 1, 2, or 3 independently selected substituent(s), at least one of which is perhalomethylsulfinyl. In another embodiment, $R^2$ is phenyl substituted with 1, 2, or 3 independently selected substituent(s), at least one of which is perfluoromethylsulfinyl. In another embodiment, $R^2$ is phenyl substituted with 1, 2, or 3 independently selected substituent(s), at least one of which is $(C_1-C_4)$perhaloalkylsulfonyl. In another embodiment, $R^2$ is phenyl substituted with 1, 2, or 3 independently selected substituent(s), at least one of which is perhalomethylsulfonyl. In another embodiment, $R^2$ is phenyl substituted with 1, 2, or 3 independently selected substituent(s), at least one of which is perfluoromethylsulfonyl.

In another embodiment, the present disclosure relates to a compound of formula (If) and the attendant definitions, wherein $R^2$ is phenyl substituted with 1, 2, or 3 independently selected substituent(s), at least one of which is —S(O)$_2$—NR$^6$R$^7$. In another embodiment, $R^2$ is phenyl substituted with 1, 2, or 3 independently selected substituent(s), at least one of which is —S(O)$_2$—N(CH$_3$)(CH$_2$CH$_2$OCH$_3$), —S(O)$_2$—NH(CH$_2$CH$_2$OCH$_3$), —S(O)$_2$—N(CH$_3$)$_2$ or —S(O)$_2$—NH(CH$_3$).

In another embodiment, the present disclosure relates to a compound of formula (If) and the attendant definitions, wherein $R^2$ is phenyl substituted with 1, 2, or 3 independently selected substituent(s), at least one of which is —S(O)$_2$-phenyl. In another embodiment, R$^2$ is phenyl substituted with 1, 2, or 3 independently selected substituent(s), at least one of which is —S(O)$_2$-(5-, 6-, or 7-membered)heterocycloalkyl. In another embodiment, R$^2$ is phenyl substituted with 1, 2, or 3 independently selected substituent(s), at least one of which is —S(O)$_2$-morpholinyl, —S(O)$_2$-piperidinyl or —S(O)$_2$-piperazinyl. In another embodiment, R$^2$ is phenyl substituted with 1, 2, or 3 independently selected substituent(s), at least one of which is —S(O)$_2$-morpholinyl. In another embodiment, R$^2$ is phenyl substituted with 1, 2, or 3 independently selected substituent(s), at least one of which is —S(O)$_2$-piperidinyl. In another embodiment, R$^2$ is phenyl substituted with 1, 2, or 3 independently selected substituent(s), at least one of which is —S(O)$_2$-piperazinyl.

In another embodiment, the present disclosure relates to a compound of formula (If) and the attendant definitions, wherein R$^2$ is phenyl substituted with 1, 2, or 3 independently selected substituent(s), at least one of which is —S(=O)(=NR$^8$)(C$_1$-C$_6$)alkyl. In another embodiment, R$^2$ is phenyl substituted with 1, 2, or 3 independently selected substituent(s), at least one of which is —S(=O)(=NR$^8$)(CH$_3$). In another embodiment, R$^2$ is phenyl substituted with 1, 2, or 3 independently selected substituent(s), at least one of which is —S(=O)(=NH)(C$_1$-C$_6$)alkyl or —S(=O)(=NC(=O)CF$_3$)(C$_1$-C$_6$)alkyl. In another embodiment, R$^2$ is phenyl substituted with 1, 2, or 3 independently selected substituent(s), at least one of which is —S(=O)(=NH)(CH$_3$) or —S(=O)(=NC(=O)CF$_3$)(CH$_3$).

In another embodiment, the present disclosure relates to a compound of formula (If) and the attendant definitions, wherein R$^2$ is phenyl substituted with 1, 2, or 3 independently selected substituent(s), at least one of which is N,N-di(C$_1$-C$_6$)alkylaminosulfonyl. In another embodiment, R$^2$ is phenyl substituted with 1, 2, or 3 independently selected substituent(s), at least one of which is N,N-dimethylaminosulfonyl.

In another embodiment, the present disclosure relates to a compound of formula (If) and the attendant definitions, wherein R$^2$ is phenyl wherein the phenyl is unsubstituted or substituted with 1, 2, or 3 substituent(s) independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl. In another embodiment, R$^2$ is phenyl wherein the phenyl is unsubstituted or substituted with 1, 2, or 3 substituent(s) independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, and N,N-di(C$_1$-C$_6$)alkylaminosulfonyl. In another embodiment, R$^2$ is phenyl wherein the phenyl is unsubstituted or substituted with 1, 2, or 3 substituent(s) independently selected from chloro, fluoro, bromo, trifluoromethyl, methyl, butyl, methylsulfanyl, methylsulfinyl, methylsulfonyl, ethylsulfonyl, propylsulfonyl, phenylsulfonyl, methylsulfonylcarbamyl, methoxy, carboxyl, methylsulfonylcarbamyl, formamidopropanoic acid, formamidoacetic acid, methoxycarbonyl, morpholinylcarbonyl, 4,4-difluoropiperidinylcarbonyl, trifluoromethoxy, trifluoromethylsulfinyl, trifluoromethylsulfonyl, trifluoromethylsulfanyl, morpholinylsulfonyl, 4,4-difluoropiperidinylsulfonyl, N,N-dimethylcarbamyl, (methyl)oxo-λ$^6$-sulfanylidene-2,2,2-trifluoroacetamide, methylsulfonimidoyl, isopropylsulfonimidoyl, (methoxyethyl)methylamino, (methoxyethyl)-N-methyl-aminosulfonyl, dimethylcarbamyl, carbamyl, and N,N-dimethylaminosulfonyl. In another embodiment, R$^2$ is phenyl wherein the phenyl is unsubstituted or substituted with 1, 2, or 3 substituent(s) independently selected from 2-chloro, 3-chloro, 4-chloro, 5-chloro, 2-fluoro, 3-fluoro, 4-fluoro, 5-fluoro, 2-bromo, 3-bromo, 4-bromo, 5-bromo, 2-trifluoromethyl, 3-trifluoromethyl, 4-trifluoromethyl, 2-methyl, 3-methyl, 4-methyl, 5-methyl, 2-butyl, 3-butyl, 4-butyl, 5-butyl, 4-methylsulfanyl, 2-methylsulfinyl, 4-methylsulfinyl, 3-methylsulfonyl, 4-methylsulfonyl, 4-ethylsulfonyl, 4-propylsulfonyl, 2-methoxy, 4-methoxy, 2-trifluoromethoxy, 4-trifluoromethoxy, 4-carboxyl, 4-methylsulfonylcarbamyl, 4-formamidopropanoic acid, 4-formamidoacetic acid, 4-methoxycarbonyl, 4-morpholinylcarbonyl, 4-(4,4-difluoropiperidinylcarbonyl), 4-isopropylsulfonyl, 4-trifluoromethylsulfanyl, 4-trifluoromethylsulfinyl, 4-trifluoromethylsulfonyl, 4-phenylsulfonyl, 4-morpholinylsulfonyl, 4-(4,4-difluoropiperidinyl)sulfonyl, 4-dimethylcarbamyl, 4-(methyl)oxo-λ$^6$-sulfanylidene-2,2,2-trifluoroacetamide, 4-methylsulfonimidoyl, 4-isopropylsulfonimidoyl, 4-(methoxyethyl)-N-methyl-aminosulfonyl, 4-carbamyl, and 4-N,N-dimethylaminosulfonyl.

In another embodiment, the present disclosure relates to a compound of formula (If) and the attendant definitions, wherein R$^2$ is monosubstituted phenyl substituted with halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, N—(C$_1$-C$_6$)alkylaminosulfonyl, or N,N-di(C$_1$-C$_6$)alkylaminosulfonyl. In another embodiment, R$^2$ is monosubstituted phenyl substituted with halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, or N,N-di(C$_1$-C$_6$)alkylaminosulfonyl. In another embodiment, R$^2$ is monosubstituted phenyl substituted with chloro, fluoro, bromo, methyl, butyl, trifluoromethyl, methoxy, trifluoromethoxy, morpholinyl, piperazinyl, methylpiperazinyl, carboxyl, methylsulfonylcarbamyl, formamidopropanoic acid, formamidoacetic acid, methoxycarbonyl, morpholinylcarbonyl, 4,4-difluoropiperidinylcarbonyl, methylsulfanyl, methylsulfinyl, methylsulfonyl, ethylsulfonyl, propylsulfonyl, trifluoromethylsulfanyl, trifluoromethylsulfinyl, trifluoromethylsulfonyl, phenylsulfonyl, morpholinylsulfonyl, 4,4-difluoropiperidinylsulfonyl, dimethylcarbamyl, (methyl)oxo-$\lambda^6$-sulfanylidene-2,2,2-trifluoroacetamide, methylsulfonimidoyl, isopropylsulfonimidoyl, (methoxyethyl)-N-methyl-aminosulfonyl, carbamyl, methoxyethyl(methyl)amino and dimethylamino or N,N-dimethylaminosulfonyl. In another embodiment, $R^2$ is monosubstituted phenyl substituted with 2-chloro, 3-chloro, 4-chloro, 5-chloro, 2-fluoro, 3-fluoro, 4-fluoro, 5-fluoro, 4-bromo, 2-methyl, 3-methyl, 4-methyl, 5-methyl, 4-butyl, 4-t-butyl, 2-trifluoromethyl, 3-trifluoromethyl, 4-trifluoromethyl, 5-trifluoromethyl, 2-methoxy, 3-methoxy, 4-methoxy, 2-trifluoromethoxy, 4-trifluoromethoxy, 3-morpholin-4-yl, 3-(piperazin-1-yl), 3-(4-methylpiperazin-1-yl), 4-carboxyl, 4-methylsulfonylcarbamyl, 4-formamidopropanoic acid, 4-formamidoacetic acid, 4-methoxycarbonyl, 4-morpholinylcarbonyl, 4-(4,4-difluoropiperidinylcarbonyl), 4-methylsulfanyl, 2-methylsulfinyl, 4-methylsulfinyl, 3-methylsulfonyl, 4-methylsulfonyl, 4-ethylsulfonyl, 4-propylsulfonyl, 4-isopropylsulfonyl, 4-trifluoromethylsulfanyl, 4-trifluoromethylsulfinyl, 4-trifluoromethylsulfonyl, 4-phenylsulfonyl, 4-morpholinylsulfonyl, 4-(4,4-difluoropiperidinyl)sulfonyl, 4-dimethylcarbamyl, 4-(methyl)oxo-$\lambda^6$-sulfanylidene-2,2,2-trifluoroacetamide, 4-methylsulfonimidoyl, 4-isopropylsulfonimidoyl, 4-(methoxyethyl)-N-methyl-aminosulfonyl, 4-carbamyl, 4-methoxyethyl(methyl)amino, 3-dimethylamino or 4-N,N-dimethylaminosulfonyl.

In another embodiment, the present disclosure relates to a compound of formula (If) and the attendant definitions, wherein $R^2$ is disubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl. In another embodiment, $R^2$ is disubstituted phenyl, each substituent being independently selected from halo, $(C_1-C_6)$alkyl, $(C_1-C_4)$perhaloalkyl, $(C_1-C_6)$alkoxy, (5-, 6-, or 7-membered)heterocycloalkyl, $(C_1-C_6)$alkylsulfinyl, $(C_1-C_6)$alkylsulfonyl and —NR$^4$R$^5$. In another embodiment, $R^2$ is disubstituted phenyl, each substituent being independently selected from chloro, fluoro, methyl, trifluoromethyl, methoxy, morpholinyl, piperazinyl, methylpiperazinyl, methylsulfinyl, methylsulfonyl, methoxyethyl(methyl)amino and dimethylamino. In another embodiment, $R^2$ is disubstituted phenyl, each substituent being independently selected from 2-chloro, 3-chloro, 4-chloro, 5-chloro, 3-fluoro, 4-fluoro, 5-fluoro, 3-methyl, 5-methyl, 3-trifluoromethyl, 5-trifluoromethyl, 2-methoxy, 3-methoxy, 4-methoxy, 3-morpholin-4-yl, 3-(piperazin-1-yl), 3-(4-methylpiperazin-1-yl), 4-methylsulfinyl, 3-methylsulfonyl, 4-methylsulfonyl, 4-methoxyethyl(methyl)amino and 3-dimethylamino.

In another embodiment, the present disclosure relates to a compound of formula (If) and the attendant definitions, wherein $R^2$ is trisubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl. In another embodiment, $R^2$ is trisubstituted phenyl, each substituent being independently selected from halo, $(C_1-C_6)$alkyl, and $(C_1-C_6)$alkylsulfonyl. In another embodiment, $R^2$ is trisubstituted phenyl, each substituent being independently selected from fluoro, methyl and methylsulfonyl.

In another embodiment, the present disclosure relates to a compound of formula (If) and the attendant definitions, wherein $R^2$ is selected from unsubstituted phenyl, 4-chlorophenyl, 2-chlorophenyl, 3-chlorophenyl, 2,3-dichlorophenyl, 2,4-dichlorophenyl, 3,5-dichlorophenyl, 2-fluorophenyl, 4-fluorophenyl, 4-bromophenyl, 2-chloro-4-fluorophenyl, 2-methylphenyl, 4-butylphenyl, 4-t-butylphenyl, 3,5-dimethylphenyl, 4-methoxyphenyl, 2-methoxyphenyl, 2-trifluoromethoxyphenyl, 4-trifluoromethoxyphenyl, 4-methoxycarbonylphenyl, 4-carboxyl, 4-carbamylphenyl, 4-phenyl(formamido)propanoic acid, 4-phenyl(formamido)acetic acid, 4-N,N-dimethylcarbamylphenyl, 4-cyclopropylsulfonylphenyl, 4-phenylsulfonyl, 4-(4-4-difluoropiperidin-1-yl)sulfonylphenyl, 4-(isopropylsulfonimidoyl)phenyl, 4-morpholine-4-sulfonylphenyl, 4-morpholine-4-carbonylphenyl, 4-(4,4-difluoropiperidine-1-carbonyl)phenyl, 3-morpholinyl-4-methylsulfonylphenyl, 3-(methoxyethyl)methylamino-4-methylsulfonylphenyl, 3,5-difluoro-4-methylsulfonylphenyl, 2-ethoxy-4-fluorophenyl, 3-fluoro-4-methoxyphenyl, 2-trifluoromethylphenyl, 3-trifluoromethylphenyl, 4-trifluoromethylphenyl, 3,5-bis(trifluoromethyl)phenyl, 3-methylsulfonylphenyl, 4-methylsulfanylphenyl, 4-trifluoromethylsulfanylphenyl, 2-methylsulfinylphenyl, 4-methylsulfinylphenyl, 3-fluoro-4-methylsulfinylphenyl, 3-methyl-4-methylsulfinylphenyl, 4-methylsulfonylphenyl, 4-ethylsulfonylphenyl, 4-isopropylsulfonylphenyl, 4-morpholine-4-methylsulfonylphenyl, 3-(4-methylpiperazin-1-yl)-4-methylsulfonylphenyl, 3-piperazin-1-yl-4-methylsulfonylphenyl, 3-methoxy-4-methylsulfonylphenyl, 3-trifluoromethyl-4-methylsulfonylphenyl, 3-fluoro-4-methylsulfonylphenyl, 3-chloro-4-methylsulfonylphenyl, 3-methyl-4-methylsulfonylphenyl, 3,4-dimethylsulfonylphenyl, 3,5-dimethyl-4-methylsulfonylphenyl, 3-(dimethylamino)-4-methylsulfonylphenyl, 4-trifluoromethylsulfinylphenyl, 4-trifluoromethylsulfonylphenyl, 4-phenyl(methyl)oxo-$\lambda^6$-sulfanylidene-2,2,2-trifluoroacetamide, 4-methylsulfonimidoylphenyl, 4-isopropylsulfonimidoylphenyl, and 4-N,N-dimethylaminosulfonylphenyl. In another embodiment, $R^2$ is unsubstituted phenyl. In another embodiment, $R^2$ is 4-chlorophenyl. In another embodiment, $R^2$ is 2-chlorophenyl. In another embodiment, $R^2$ is 3-chlorophenyl. In another embodiment, $R^2$ is 2,3-dichlorophenyl. In another embodiment, $R^2$ is 2,4-dichlorophenyl. In another embodiment, $R^2$ is 3,5-dichlorophenyl. In another embodiment, $R^2$ is 2-fluorophenyl. In another embodiment, $R^2$ is 4-fluorophenyl. In another embodiment, $R^2$ is 4-bromophenyl. In another embodiment, $R^2$ is 2-chloro-4-fluorophenyl. In another embodiment, $R^2$ is 2-methylphenyl. In another embodiment, $R^2$ is 4-butylphenyl. In another embodiment, $R^2$ is 4-t-butylphenyl. In another embodiment, $R^2$ is 3,5-dimethylphenyl. In another embodiment, $R^2$ is 4-methoxyphenyl. In another embodiment, $R^2$ is 2-methoxyphenyl. In another embodiment, $R^2$ is 2-trifluoromethoxyphenyl. In another embodiment, $R^2$ is 4-trifluoromethoxyphenyl. In another embodiment, $R^2$ is 4-methoxycarbonylphenyl. In another embodiment, $R^2$ is 4-carboxyphenyl. In another embodiment, $R^2$ is 4-carbamylphenyl. In another embodiment, $R^2$ is 4-phenyl(formamido)propanoic acid. In another embodiment, $R^2$ is 4-phenyl(formamido)acetic acid. In another embodiment, $R^2$ is 4-N,N-dimethylcarbamylphenyl. In another embodiment, $R^2$ is 4-cyclopropylsulfonylphenyl. In another embodiment, $R^2$ is 4-phenylsulfonyl. In another embodiment, $R^2$ is 4-(4,4-difluoropiperidin-1-yl)sulfonylphenyl. In another embodiment, $R^2$ is 4-(isopropylsulfonimidoyl)phenyl. In another embodiment, $R^2$ is 4-morpholine-4-sulfonylphenyl. In another embodiment, $R^2$ is 4-morpholine-4-carbonylphenyl. In another embodiment, $R^2$ is 4-(4,4-difluoropiperidine-1-carbonyl)phenyl. In another embodiment, $R^2$ is 3-morpholinyl-4-methylsulfonylphenyl. In another embodiment, $R^2$ is 3-(methoxyethyl)methylamino-4-methylsulfonylphenyl. In another embodiment, $R^2$ is 3,5-difluoro-4-methylsulfonylphenyl. In another embodiment, $R^2$ is 3,5-difluoro-4-methylsulfonylphenyl. In another embodiment, $R^2$ is 2-ethoxy-4-fluorophenyl. In another embodiment, $R^2$ is 3-fluoro-4-methoxyphenyl. In another embodiment, $R^2$ is 2-trifluoromethylphenyl. In another embodiment, $R^2$ is 3-trifluoromethylphenyl. In another embodiment, $R^2$ is 4-trifluoromethylphenyl. In another embodiment, $R^2$ is 3,5-bis(trifluoromethyl)phenyl. In another embodiment, $R^2$ is 3-methylsulfonylphenyl. In another embodiment, $R^2$ is 4-methylsulfanylphenyl. In another embodiment, $R^2$ is 4-trifluoromethylsulfanylphenyl. In another embodiment, $R^2$ is 2-methylsulfinylphenyl. In another embodiment, $R^2$ is 4-methylsulfinylphenyl. In another embodiment, $R^2$ is 3-fluoro-4-methylsulfinylphenyl. In another embodiment, $R^2$ is 3-methyl-4-methylsulfinylphenyl. In another embodiment, $R^2$ is 4-methylsulfonylphenyl. In another embodiment, $R^2$ is 4-ethylsulfonylphenyl. In another embodiment, $R^2$ is 4-isopropylsulfonylphenyl. In another embodiment, $R^2$ is 4-morpholine-4-methylsulfonylphenyl. In another embodiment, $R^2$ is 3-(4-methylpiperazin-1-yl)-4-methylsulfonylphenyl. In another embodiment, $R^2$ is 3-piperazin-1-yl-4-methylsulfonylphenyl. In another embodiment, $R^2$ is 3-methoxy-4-methylsulfonylphenyl. In another embodiment, $R^2$ is 3-trifluoromethyl-4-methylsulfonylphenyl. In another embodiment, $R^2$ is 3-fluoro-4-methylsulfonylphenyl. In another embodiment, $R^2$ is 3-chloro-4-methylsulfonylphenyl. In another embodiment, $R^2$ is 3-methyl-4-methylsulfonylphenyl. In another embodiment, $R^2$ is 3,5-dimethyl-4-methylsulfonylphenyl. In another embodiment, $R^2$ is 3-(dimethylamino)-4-methylsulfonylphenyl. In another embodiment, $R^2$ is 4-trifluoromethylsulfinylphenyl. In another embodiment, $R^2$ is 4-trifluoromethylsulfonylphenyl. In another embodiment, $R^2$ is 4-phenyl(methyl)oxo-$\lambda^6$-sulfanylidene-2,2,2-trifluoroacetamide. In another embodiment, $R^2$ is 4-methylsulfonimidoylphenyl. In another embodiment, $R^2$ is 4-isopropylsulfonimidoylphenyl. In another embodiment, $R^2$ is 4-N,N-dimethylaminosulfonylphenyl.

In another embodiment, the present disclosure relates to a compound of formula (If) and the attendant definitions, wherein m is 1 and $R^2$ is unsubstituted phenyl. In another embodiment, m is 2 and $R^2$ is unsubstituted phenyl. In another embodiment, m is 3 and $R^2$ is unsubstituted phenyl. In another embodiment, m is 1 and $R^2$ is monosubstituted phenyl, e.g., selected from among the monosubstituted $R^2$ phenyl groups disclosed above in connection with the compounds of formula (If). In another embodiment, m is 2 and $R^2$ is monosubstituted phenyl, e.g., selected from among the monosubstituted $R^2$ phenyl groups disclosed above in connection with the compounds of formula (If). In another embodiment, m is 3 and $R^2$ is monosubstituted phenyl, e.g., selected from among the monosubstituted $R^2$ phenyl groups disclosed above in connection with the compounds of formula (If). In another embodiment, m is 1 and $R^2$ is disubstituted phenyl, e.g., selected from among the disubstituted $R^2$ phenyl groups disclosed above in connection with the compounds of formula (If). In another embodiment, m is 2 and $R^2$ is disubstituted phenyl, e.g., selected from among the disubstituted $R^2$ phenyl groups disclosed above in connection with the compounds of formula (If). In another embodiment, m is 3 and $R^2$ is disubstituted phenyl, e.g., selected from among the disubstituted $R^2$ phenyl groups disclosed above in connection with the compounds of formula (If). In another embodiment, m is 1 and $R^2$ is trisubstituted phenyl, e.g., selected from among the trisubstituted $R^2$ phenyl groups disclosed above in connection with the compounds of formula (If). In another embodiment, m is 2 and $R^2$ is trisubstituted phenyl, e.g., selected from among the trisubstituted $R^2$ phenyl groups disclosed above in connection with the compounds of formula (If). In another embodiment, $R^1$ is m is 3 and $R^2$ is trisubstituted phenyl, e.g., selected from among the trisubstituted $R^2$ phenyl groups disclosed above in connection with the compounds of formula (If).

In another embodiment, the present disclosure relates to a compound of formula (If) and the attendant definitions, wherein m is 1 and $R^2$ is methyl. In another embodiment, m is 1 and $R^2$ is ethyl. In another embodiment, m is 1 and $R^2$ is propyl. In another embodiment, m is 1 and $R^2$ is iso-propyl. In another embodiment, m is 1 and $R^2$ is butyl. In another embodiment, m is 1 and $R^2$ is tert-butyl. In another embodiment, m is 2 and $R^2$ is methyl. In another embodiment, m is 2 and $R^2$ is ethyl. In another embodiment, m is 2 and $R^2$ is propyl. In another embodiment, m is 2 and $R^2$ is iso-propyl. In another embodiment, m is 2 and $R^2$ is butyl. In another embodiment, m is 2 and $R^2$ is tert-butyl. In another embodiment, m is 3 and $R^2$ is methyl. In another embodiment, m is 3 and $R^2$ is ethyl. In another embodiment, m is 3 and $R^2$ is propyl. In another embodiment, m is 3 and $R^2$ is iso-propyl. In another embodiment, m is 3 and $R^2$ is butyl. In another embodiment, m is 3 and $R^2$ is tert-butyl.

Another aspect of the disclosure provides a compound of formula (Ig)

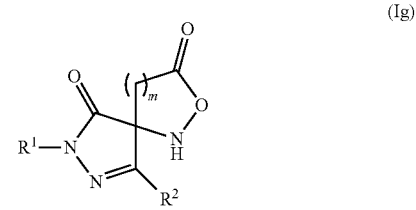

(Ig)

or a pharmaceutically acceptable salt thereof, wherein:
$R^1$ is H, $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s)

independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)O(5-methyl-2-oxo-2H-1,3-dioxol-4-ylmethyl), —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or $(C_1-C_6)$alkyl; and

R$^8$ is H, —C(=O)(C$_1$-C$_6$)alkyl or —C(=O)(C$_1$-C$_4$)perhaloalkyl;

R$^2$ is $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl; and m is 1, 2 or 3.

In one embodiment, the present disclosure relates to a compound of formula (Ig) and the attendant definitions, wherein R$^1$ is H. In another embodiment, R$^1$ is $(C_1-C_6)$alkyl, wherein the alkyl is unsubstituted or substituted with 1, 2 or 3 independently selected substituents. In another embodiment, R$^1$ is (5- or 6-membered)heteroaryl, wherein the heteroaryl is unsubstituted or substituted with 1, 2, 3, 4, or 5 independently selected substituents. In another embodiment, R$^1$ is phenyl, wherein the phenyl is unsubstituted or substituted with 1, 2, 3, 4, or 5 independently selected substituents. In each of the embodiments listed in this paragraph, the substituents are selected from among those disclosed above for R$^1$ in connection with formula (Ig).

In another embodiment, the present disclosure relates to a compound of formula (Ig) and the attendant definitions, wherein R$^1$ is $(C_1-C_4)$alkyl. In another embodiment, R$^1$ is methyl, ethyl, propyl, or butyl. In another embodiment, R$^1$ is methyl, ethyl, or propyl. In another embodiment, R$^1$ is methyl, ethyl, or butyl. In another embodiment, R$^1$ is methyl, propyl, or butyl. In another embodiment, R$^1$ is ethyl, propyl, or butyl. In another embodiment, R$^1$ is methyl or ethyl. In another embodiment, R$^1$ is methyl or propyl. In another embodiment, R$^1$ is methyl or butyl. In another embodiment, R$^1$ is ethyl or propyl. In another embodiment, R$^1$ is ethyl or butyl. In another embodiment, R$^1$ is propyl or butyl. In another embodiment, R$^1$ is methyl. In another embodiment, R$^1$ is ethyl. In another embodiment, R$^1$ is propyl. In another embodiment, R$^1$ is iso-propyl. In another embodiment, R$^1$ is butyl. In another embodiment, R$^1$ is tert-butyl. In each of the embodiments listed in this paragraph, the alkyl is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is —C(=O)OH, —C(=O)O(C$_1$-C$_6$)alkyl, —C(=O)OCH$_3$, —C(=O)OCH$_2$CH$_3$, —C(=O)O(5-methyl-2-oxo-2H-1,3-dioxol-4-ylmethyl), —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, $(C_1-C_6)$alkylsulfanyl, $(C_1-C_6)$alkylsulfinyl, $(C_1-C_6)$alkylsulfonyl, —S(O)$_2$—NH$_2$, —N—(C$_1$-C$_6$)alkylaminosulfonyl, or N,N-di(C$_1$-C$_6$)alkylaminosulfonyl or the substituents are independently selected from —C(=O)OH, —C(=O)O(C$_1$-C$_6$)alkyl, —C(=O)OCH$_3$, —C(=O)OCH$_2$CH$_3$, —C(=O)O(5-methyl-2-oxo-2H-1,3-dioxol-4-ylmethyl), —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, $(C_1-C_6)$alkylsulfanyl, $(C_1-C_6)$alkylsulfinyl, $(C_1-C_6)$alkylsulfonyl, —S(O)$_2$—NH$_2$, —N—(C$_1$-C$_6$)alkylaminosulfonyl, or N,N-di(C$_1$-C$_6$)alkylaminosulfonyl.

In another embodiment, the present disclosure relates to a compound of formula (Ig) and the attendant definitions, wherein R$^1$ is (5- or 6-membered)heteroaryl, wherein the heteroaryl is unsubstituted or substituted with 1, 2 or 3 independently selected substituents, the substitutents being selected from among those disclosed above for R$^1$ in connection with formula (Ig). In another embodiment, R$^1$ is unsubstituted (5- or 6-membered)heteroaryl. In another embodiment, R$^1$ is monosubstituted (5- or 6-membered) heteroaryl. In another embodiment, R$^1$ is disubstituted (5- or 6-membered)heteroaryl. In another embodiment, R$^1$ is trisubstituted (5- or 6-membered)heteroaryl. In various embodiments of each of the above embodiments in this paragraph, the substituent is halo, $(C_1-C_6)$alkyl, $(C_1-C_6)$alkoxy, phenyl, —C(=O)NR$^4$R$^5$, $(C_1-C_6)$alkylsulfinyl, $(C_1-C_6)$alkylsulfonyl, and N,N-di(C$_1$-C$_6$)alkylaminosulfonyl.

In another embodiment, the present disclosure relates to a compound of formula (Ig) and the attendant definitions, wherein R$^1$ is unsubstituted phenyl. In another embodiment, R$^1$ is phenyl substituted with 1, 2 or 3 independently selected substituent(s), the substitutents being selected from among those disclosed above for R$^1$ in connection with formula (Ig). In another embodiment, R$^1$ is phenyl substituted with 1, 2, or 3 independently selected substituent(s), at least one of which is halo. In another embodiment, R$^1$ is phenyl substituted with 1, 2, or 3 independently selected substituent(s), at least one of which is $(C_1-C_6)$alkyl. In another embodiment, R$^1$ is phenyl substituted with 1, 2, or 3 independently selected substituent(s), at least one of which is $(C_1-C_4)$haloalkyl. In another embodiment, R$^1$ is phenyl substituted with 1, 2, or 3 independently selected substituent(s), at least one of which is $(C_1-C_4)$perhaloalkyl. In another embodiment, R$^1$ is phenyl substituted with 1, 2, or 3 independently selected substituent(s), at least one of which is $(C_1-C_6)$alkoxy. In another embodiment, R$^1$ is phenyl substituted with 1, 2, or 3 independently selected substituent(s), at least one of which is $(C_1-C_4)$perhaloalkoxy. In another embodiment, R$^1$ is phenyl substituted with 1, 2, or 3 independently selected substituent(s), at least one of which is —C(=O)OH. In another embodiment, R$^1$ is phenyl substituted with 1, 2, or 3 independently selected substituent(s), at least one of which is —C(=O)O(C$_1$-C$_6$)alkyl. In another embodiment, R$^1$ is phenyl substituted with 1, 2, or 3 independently selected substituent(s), at least one of which is —C(=O)NR$^4$R$^5$. In another embodiment, R$^1$ is phenyl substituted with 1, 2, or 3 independently selected substituent(s), at least one of which is —C(=O)NH($C_1$-$C_6$)alkyl, wherein said alkyl is substituted with COOH. In another embodiment, $R^1$ is phenyl substituted with 1, 2, or 3 independently selected substituent(s), at least one of which is —C(=O)NH—($C_1$-$C_6$)alkylsulfonyl. In another embodiment, $R^1$ is phenyl substituted with 1, 2, or 3 independently selected substituent(s), at least one of which is —C(=O)-(5-, 6-, or 7-membered)heterocycloalkyl. In another embodiment, $R^1$ is phenyl substituted with 1, 2, or 3 independently selected substituent(s), at least one of which is (5-, 6-, or 7-membered)heterocycloalkyl. In another embodiment, $R^1$ is phenyl substituted with 1, 2, or 3 independently selected substituent(s), at least one of which is ($C_1$-$C_6$)alkylsulfanyl. In another embodiment, $R^1$ is phenyl substituted with 1, 2, or 3 independently selected substituent(s), at least one of which is ($C_1$-$C_4$)perhaloalkylsulfanyl. In another embodiment, $R^1$ is phenyl substituted with 1, 2, or 3 independently selected substituent(s), at least one of which is ($C_1$-$C_6$)alkylsulfinyl. In another embodiment, $R^1$ is phenyl substituted with 1, 2, or 3 independently selected substituent(s), at least one of which is ($C_1$-$C_6$)alkylsulfonyl. In another embodiment, $R^1$ is phenyl substituted with 1, 2, or 3 independently selected substituent(s), at least one of which is ($C_3$-$C_6$)cycloalkylsulfonyl. In another embodiment, $R^1$ is phenyl substituted with 1, 2, or 3 independently selected substituent(s), at least one of which is ($C_1$-$C_4$)haloalkylsulfinyl. In another embodiment, $R^1$ is phenyl substituted with 1, 2, or 3 independently selected substituent(s), at least one of which is ($C_1$-$C_4$)haloalkylsulfonyl. In another embodiment, $R^1$ is phenyl substituted with 1, 2, or 3 independently selected substituent(s), at least one of which is ($C_1$-$C_4$)perhaloalkylsulfinyl. In another embodiment, $R^1$ is phenyl substituted with 1, 2, or 3 independently selected substituent(s), at least one of which is ($C_1$-$C_4$)perhaloalkylsulfonyl. In another embodiment, $R^1$ is phenyl substituted with 1, 2, or 3 independently selected substituent(s), at least one of which is —S(O)$_2$—NR$^6$R$^7$. In another embodiment, $R^1$ is phenyl substituted with 1, 2, or 3 independently selected substituent(s), at least one of which is —S(O)$_2$-phenyl. In another embodiment, $R^1$ is phenyl substituted with 1, 2, or 3 independently selected substituent(s), at least one of which is —S(O)$_2$-(5-, 6-, or 7-membered)heterocycloalkyl. In another embodiment, $R^1$ is phenyl substituted with 1, 2, or 3 independently selected substituent(s), at least one of which is —S(=O)(=NR$^8$)($C_1$-$C_6$)alkyl. In another embodiment, $R^1$ is phenyl substituted with 1, 2, or 3 independently selected substituent(s), at least one of which is N,N-di($C_1$-$C_6$)alkylaminosulfonyl.

In another embodiment, the present disclosure relates to a compound of formula (Ig) and the attendant definitions, wherein $R^1$ is monosubstituted phenyl substituted with halo, ($C_1$-$C_6$)alkyl, ($C_1$-$C_4$)haloalkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$)alkylaminosulfonyl, or N,N-di($C_1$-$C_6$)alkylaminosulfonyl.

In another embodiment, the present disclosure relates to a compound of formula (Ig) and the attendant definitions, wherein $R^1$ is disubstituted phenyl, each substituent being independently selected from halo, ($C_1$-$C_6$)alkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl.

In another embodiment, the present disclosure relates to a compound of formula (Ig) and the attendant definitions, wherein $R^1$ is trisubstituted phenyl, each substituent being independently selected from halo, ($C_1$-$C_6$)alkyl, ($C_1$-$C_4$)perhaloalkyl, ($C_1$-$C_6$)alkoxy, ($C_1$-$C_4$)haloalkoxy, ($C_1$-$C_4$)perhaloalkoxy, —C(=O)OH, —C(=O)O($C_1$-$C_6$)alkyl, —C(=O)NR$^4$R$^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl.

In one embodiment, the present disclosure relates to a compound of formula (Ig) and the attendant definitions, wherein $R^2$ is ($C_1$-$C_6$)alkyl, wherein the alkyl is unsubstituted or substituted with 1, 2 or 3 independently selected substituents. In another embodiment, $R^2$ is (5- or 6-membered)heteroaryl, wherein the heteroaryl is unsubstituted or substituted with 1, 2, 3, 4, or 5 independently selected substituents. In another embodiment, $R^2$ is phenyl, wherein the phenyl is unsubstituted or substituted with 1, 2, 3, 4, or 5 independently selected substituents. In each of the embodiments listed in this paragraph, the substitutents are selected from among those disclosed above for $R^2$ in connection with formula (Ig).

In another embodiment, the present disclosure relates to a compound of formula (Ig) and the attendant definitions, wherein $R^2$ is ($C_1$-$C_4$)alkyl. In another embodiment, $R^2$ is methyl, ethyl, propyl, or butyl. In another embodiment, $R^2$ is methyl, ethyl, or propyl. In another embodiment, $R^2$ is methyl, ethyl, or butyl. In another embodiment, $R^2$ is methyl, propyl, or butyl. In another embodiment, $R^2$ is ethyl, propyl, or butyl. In another embodiment, $R^2$ is methyl or ethyl. In another embodiment, $R^2$ is methyl or propyl. In another embodiment, $R^2$ is methyl or butyl. In another embodiment, $R^2$ is ethyl or propyl. In another embodiment, $R^2$ is ethyl or butyl. In another embodiment, $R^2$ is propyl or butyl. In another embodiment, $R^2$ is methyl. In another embodiment, $R^2$ is ethyl. In another embodiment, $R^2$ is propyl. In another embodiment, $R^2$ is iso-propyl. In another embodiment, $R^2$ is butyl. In another embodiment, $R^2$ is tert-butyl. In each of the embodiments listed in this paragraph, the alkyl is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is —C(=O)OH, —C(=O)O($C_1$-$C_6$)alkyl, —C(=O)OCH$_3$, —C(=O)OCH$_2$CH$_3$, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1$-$C_6$)alkylsulfanyl, ($C_1$-$C_6$)alkylsulfinyl, ($C_1$-$C_6$)alkylsulfonyl, —S(O)$_2$—NH$_2$, —N—(C$_1$-C$_6$)alkylaminosulfonyl, or N,N-di(C$_1$-C$_6$)alkylaminosulfonyl or the substituents are independently selected from —C(=O)OH, —C(=O)O(C$_1$-C$_6$)alkyl, —C(=O)OCH$_3$, —C(=O)OCH$_2$CH$_3$, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, (C$_1$-C$_6$)alkylsulfanyl, (C$_1$-C$_6$)alkylsulfinyl, (C$_1$-C$_6$)alkylsulfonyl, —S(O)$_2$—NH$_2$, —N—(C$_1$-C$_6$)alkylaminosulfonyl, or N,N-di(C$_1$-C$_6$)alkylaminosulfonyl.

In another embodiment, the present disclosure relates to a compound of formula (Ig) and the attendant definitions, wherein R$^2$ is (5- or 6-membered)heteroaryl, wherein the heteroaryl is unsubstituted or substituted with 1, 2 or 3 independently selected substituents, the substitutents being selected from among those disclosed above for R$^2$ in connection with formula (Ig). In another embodiment, R$^2$ is unsubstituted (5- or 6-membered)heteroaryl. In another embodiment, R$^2$ is monosubstituted (5- or 6-membered)heteroaryl. In another embodiment, R$^2$ is disubstituted (5- or 6-membered)heteroaryl. In another embodiment, R$^2$ is trisubstituted (5- or 6-membered)heteroaryl. In various embodiments of each of the above embodiments in this paragraph, the substituent is halo, (C$_1$-C$_6$)alkyl, (C$_1$-C$_6$)alkoxy, phenyl, —C(=O)NR$^4$R$^5$, (C$_1$-C$_6$)alkylsulfinyl, (C$_1$-C$_6$)alkylsulfonyl, and N,N-di(C$_1$-C$_6$)alkylaminosulfonyl.

In another embodiment, the present disclosure relates to a compound of formula (Ig) and the attendant definitions, wherein R$^2$ is unsubstituted phenyl. In another embodiment, R$^2$ is phenyl substituted with 1, 2 or 3 independently selected substituent(s), the substitutents being selected from among those disclosed above for R$^2$ in connection with formula (Ig). In another embodiment, R$^2$ is phenyl substituted with 1, 2, or 3 independently selected substituent(s), at least one of which is halo. In another embodiment, R$^2$ is phenyl substituted with 1, 2, or 3 independently selected substituent(s), at least one of which is (C$_1$-C$_6$)alkyl. In another embodiment, R$^2$ is phenyl substituted with 1, 2, or 3 independently selected substituent(s), at least one of which is (C$_1$-C$_4$)haloalkyl. In another embodiment, R$^2$ is phenyl substituted with 1, 2, or 3 independently selected substituent(s), at least one of which is (C$_1$-C$_4$)perhaloalkyl. In another embodiment, R$^2$ is phenyl substituted with 1, 2, or 3 independently selected substituent(s), at least one of which is (C$_1$-C$_6$)alkoxy. In another embodiment, R$^2$ is phenyl substituted with 1, 2, or 3 independently selected substituent(s), at least one of which is (C$_1$-C$_4$)perhaloalkoxy. In another embodiment, R$^2$ is phenyl substituted with 1, 2, or 3 independently selected substituent(s), at least one of which is —C(=O)OH. In another embodiment, R$^2$ is phenyl substituted with 1, 2, or 3 independently selected substituent(s), at least one of which is —C(=O)O(C$_1$-C$_6$)alkyl. In another embodiment, R$^2$ is phenyl substituted with 1, 2, or 3 independently selected substituent(s), at least one of which is —C(=O)NR$^4$R$^5$. In another embodiment, R$^2$ is phenyl substituted with 1, 2, or 3 independently selected substituent(s), at least one of which is —C(=O)NH(C$_1$-C$_6$)alkyl, wherein said alkyl is substituted with COOH. In another embodiment, R$^2$ is phenyl substituted with 1, 2, or 3 independently selected substituent(s), at least one of which is —C(=O)NH—(C$_1$-C$_6$)alkylsulfonyl. In another embodiment, R$^2$ is phenyl substituted with 1, 2, or 3 independently selected substituent(s), at least one of which is —C(=O)-(5-, 6-, or 7-membered)heterocycloalkyl. In another embodiment, R$^2$ is phenyl substituted with 1, 2, or 3 independently selected substituent(s), at least one of which is (5-, 6-, or 7-membered)heterocycloalkyl. In another embodiment, R$^2$ is phenyl substituted with 1, 2, or 3 independently selected substituent(s), at least one of which is (C$_1$-C$_6$)alkylsulfanyl. In another embodiment, R$^2$ is phenyl substituted with 1, 2, or 3 independently selected substituent(s), at least one of which is (C$_1$-C$_4$)perhaloalkylsulfanyl. In another embodiment, R$^2$ is phenyl substituted with 1, 2, or 3 independently selected substituent(s), at least one of which is (C$_1$-C$_6$)alkylsulfinyl. In another embodiment, R$^2$ is phenyl substituted with 1, 2, or 3 independently selected substituent(s), at least one of which is (C$_1$-C$_6$)alkylsulfonyl. In another embodiment, R$^2$ is phenyl substituted with 1, 2, or 3 independently selected substituent(s), at least one of which is (C$_3$-C$_6$)cycloalkylsulfonyl. In another embodiment, R$^2$ is phenyl substituted with 1, 2, or 3 independently selected substituent(s), at least one of which is (C$_1$-C$_4$)haloalkylsulfinyl. In another embodiment, R$^2$ is phenyl substituted with 1, 2, or 3 independently selected substituent(s), at least one of which is (C$_1$-C$_4$)haloalkylsulfonyl. In another embodiment, R$^2$ is phenyl substituted with 1, 2, or 3 independently selected substituent(s), at least one of which is (C$_1$-C$_4$)perhaloalkylsulfinyl. In another embodiment, R$^2$ is phenyl substituted with 1, 2, or 3 independently selected substituent(s), at least one of which is (C$_1$-C$_4$)perhaloalkylsulfonyl. In another embodiment, R$^2$ is phenyl substituted with 1, 2, or 3 independently selected substituent(s), at least one of which is —S(O)$_2$—NR$^6$R$^7$. In another embodiment, R$^2$ is phenyl substituted with 1, 2, or 3 independently selected substituent(s), at least one of which is —S(O)$_2$-phenyl. In another embodiment, R$^2$ is phenyl substituted with 1, 2, or 3 independently selected substituent(s), at least one of which is —S(O)$_2$-(5-, 6-, or 7-membered)heterocycloalkyl. In another embodiment, R$^2$ is phenyl substituted with 1, 2, or 3 independently selected substituent(s), at least one of which is —S(=O)(=NR$^8$)(C$_1$-C$_6$)alkyl. In another embodiment, R$^2$ is phenyl substituted with 1, 2, or 3 independently selected substituent(s), at least one of which is N,N-di(C$_1$-C$_6$)alkylaminosulfonyl.

In another embodiment, the present disclosure relates to a compound of formula (Ig) and the attendant definitions, wherein R$^2$ is monosubstituted phenyl substituted with halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_6$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, or N,N-di(C$_1$-C$_6$)alkylaminosulfonyl.

In another embodiment, the present disclosure relates to a compound of formula (Ig) and the attendant definitions, wherein R$^2$ is disubstituted phenyl, each substituent being independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In another embodiment, the present disclosure relates to a compound of formula (Ig) and the attendant definitions, wherein $R^2$ is trisubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_4)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl.

In one embodiment, the present disclosure relates to a compound of formula (Ig) and the attendant definitions, wherein m is 1. In another embodiment, m is 2. In another embodiment, m is 3.

Another aspect of the disclosure provides a compound of formula (Ih)

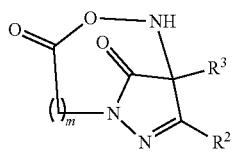

(Ih)

or a pharmaceutically acceptable salt thereof, wherein:
$R^2$ is $(C_1-C_6)$alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)($C_1$-$C_6$)alkyl, —NR$^4$R$^5$, N—($C_1$-$C_6$)alkylaminosulfonyl, and N,N-di($C_1$-$C_6$)alkylaminosulfonyl;
$R^4$, $R^5$, $R^6$ and $R^7$ are each independently H or $(C_1-C_6)$alkyl;
$R^8$ is H, —(C=O)($C_1-C_6$)alkyl or —(C=O)($C_1-C_4$)perhaloalkyl;
$R^3$ is $(C_1-C_6)$alkyl, (5- or 6-membered)heteroaryl, phenyl or —C(=NOR$^9$)R$^{10}$ wherein $R^9$ is $(C_1-C_6)$alkyl, $(C_1-C_6)$alkyl substituted with phenyl or phenyl and $R^{10}$ is selected from $(C_1-C_6)$alkyl; and
m is 1, 2 or 3.

In one embodiment, the present disclosure relates to a compound of formula (Ih) and the attendant definitions, wherein $R^2$ is $(C_1-C_6)$alkyl, wherein the alkyl is unsubstituted or substituted with 1, 2 or 3 independently selected substituents. In another embodiment, $R^2$ is (5- or 6-membered)heteroaryl, wherein the heteroaryl is unsubstituted or substituted with 1, 2, 3, 4, or 5 independently selected substituents. In another embodiment, $R^2$ is phenyl, wherein the phenyl is unsubstituted or substituted with 1, 2, 3, 4, or 5 independently selected substituents. In each of the embodiments listed in this paragraph, the substituents are selected from among those disclosed above for $R^2$ in connection with formula (Ih).

In another embodiment, the present disclosure relates to a compound of formula (Ih) and the attendant definitions, wherein $R^2$ is $(C_1-C_4)$alkyl. In another embodiment, $R^2$ is methyl, ethyl, propyl, or butyl. In another embodiment, $R^2$ is methyl, ethyl, or propyl. In another embodiment, $R^2$ is methyl, ethyl, or butyl. In another embodiment, $R^2$ is methyl, propyl, or butyl. In another embodiment, $R^2$ is ethyl, propyl, or butyl. In another embodiment, $R^2$ is methyl or ethyl. In another embodiment, $R^2$ is methyl or propyl. In another embodiment, $R^2$ is methyl or butyl. In another embodiment, $R^2$ is ethyl or propyl. In another embodiment, $R^2$ is ethyl or butyl. In another embodiment, $R^2$ is propyl or butyl. In another embodiment, $R^2$ is methyl. In another embodiment, $R^2$ is ethyl. In another embodiment, $R^2$ is propyl. In another embodiment, $R^2$ is iso-propyl. In another embodiment, $R^2$ is butyl. In another embodiment, $R^2$ is tert-butyl. In each of the embodiments listed in this paragraph, the alkyl is unsubstituted in one embodiment, monosubstituted in another embodiment, disubstituted with two independently selected substituents in an additional embodiment, or trisubstituted with three independently selected substituents in a further embodiment. In various embodiments of each of the above embodiments in this paragraph, the substituent is —C(=O)OH, —C(=O)O($C_1-C_6$)alkyl, —C(=O)OCH$_3$, —C(=O)OCH$_2$CH$_3$, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1-C_6$)alkylsulfanyl, ($C_1-C_6$)alkylsulfinyl, ($C_1-C_6$)alkylsulfonyl, —S(O)$_2$—NH$_2$, —N—($C_1-C_6$)alkylaminosulfonyl, or N,N-di($C_1-C_6$)alkylaminosulfonyl or the substituents are independently selected from —C(=O)OH, —C(=O)O($C_1$-$C_6$)alkyl, —C(=O)OCH$_3$, —C(=O)OCH$_2$CH$_3$, —C(=O)NR$^4$R$^5$, —C(=O)NH$_2$, —C(=O)NHCH$_3$, —C(=O)N(CH$_3$)$_2$, —NR$^4$R$^5$, —NH$_2$, —NHCH$_3$, ($C_1-C_6$)alkylsulfanyl, ($C_1-C_6$)alkylsulfinyl, ($C_1-C_6$)alkylsulfonyl, —S(O)$_2$—NH$_2$, —N—($C_1-C_6$)alkylaminosulfonyl, or N,N-di($C_1-C_6$)alkylaminosulfonyl.

In another embodiment, the present disclosure relates to a compound of formula (Ih) and the attendant definitions, wherein $R^2$ is (5- or 6-membered)heteroaryl, wherein the heteroaryl is unsubstituted or substituted with 1, 2 or 3 independently selected substituents, the substituents being selected from among those disclosed above for $R^2$ in connection with formula (Ih). In another embodiment, $R^2$ is unsubstituted (5- or 6-membered)heteroaryl. In another embodiment, $R^2$ is monosubstituted (5- or 6-membered)heteroaryl. In another embodiment, $R^2$ is disubstituted (5- or 6-membered)heteroaryl. In another embodiment, $R^2$ is trisubstituted (5- or 6-membered)heteroaryl. In various embodiments of each of the above embodiments in this paragraph, the substituent is halo, $(C_1-C_6)$alkyl, $(C_1-C_6)$alkoxy, phenyl, —C(=O)NR$^4$R$^5$, ($C_1-C_6$)alkylsulfinyl, ($C_1-C_6$)alkylsulfonyl, and N,N-di($C_1-C_6$)alkylaminosulfonyl.

In another embodiment, the present disclosure relates to a compound of formula (Ih) and the attendant definitions, wherein $R^2$ is unsubstituted phenyl. In another embodiment, $R^2$ is phenyl substituted with 1, 2 or 3 independently selected substituent(s), the substituents being selected from among those disclosed above for $R^2$ in connection with formula (Ih). In another embodiment, $R^2$ is phenyl substituted with 1, 2, or 3 independently selected substituent(s), at least one of which is halo. In another embodiment, $R^2$ is phenyl substituted with 1, 2, or 3 independently selected substituent(s), at least one of which is $(C_1$-$C_6)$alkyl. In another embodiment, $R^2$ is phenyl substituted with 1, 2, or 3 independently selected substituent(s), at least one of which is $(C_1$-$C_4)$haloalkyl. In another embodiment, $R^2$ is phenyl substituted with 1, 2, or 3 independently selected substituent(s), at least one of which is $(C_1$-$C_4)$perhaloalkyl. In another embodiment, $R^2$ is phenyl substituted with 1, 2, or 3 independently selected substituent(s), at least one of which is $(C_1$-$C_6)$ alkoxy. In another embodiment, $R^2$ is phenyl substituted with 1, 2, or 3 independently selected substituent(s), at least one of which is $(C_1$-$C_4)$perhaloalkoxy. In another embodiment, $R^2$ is phenyl substituted with 1, 2, or 3 independently selected substituent(s), at least one of which is —C(=O) OH. In another embodiment, $R^2$ is phenyl substituted with 1, 2, or 3 independently selected substituent(s), at least one of which is —C(=O)O$(C_1$-$C_6)$alkyl. In another embodiment, $R^2$ is phenyl substituted with 1, 2, or 3 independently selected substituent(s), at least one of which is —C(=O) $NR^4R^5$. In another embodiment, $R^2$ is phenyl substituted with 1, 2, or 3 independently selected substituent(s), at least one of which is —C(=O)NH$(C_1$-$C_6)$alkyl, wherein said alkyl is substituted with COOH. In another embodiment, $R^2$ is phenyl substituted with 1, 2, or 3 independently selected substituent(s), at least one of which is —C(=O)NH—$(C_1$-$C_6)$alkylsulfonyl. In another embodiment, $R^2$ is phenyl substituted with 1, 2, or 3 independently selected substituent(s), at least one of which is —C(=O)-(5-, 6-, or 7-membered) heterocycloalkyl. In another embodiment, $R^2$ is phenyl substituted with 1, 2, or 3 independently selected substituent(s), at least one of which is (5-, 6-, or 7-membered)heterocycloalkyl. In another embodiment, $R^2$ is phenyl substituted with 1, 2, or 3 independently selected substituent(s), at least one of which is $(C_1$-$C_6)$alkylsulfanyl. In another embodiment, $R^2$ is phenyl substituted with 1, 2, or 3 independently selected substituent(s), at least one of which is $(C_1$-$C_4)$ perhaloalkylsulfanyl. In another embodiment, $R^2$ is phenyl substituted with 1, 2, or 3 independently selected substituent(s), at least one of which is $(C_1$-$C_6)$alkylsulfinyl. In another embodiment, $R^2$ is phenyl substituted with 1, 2, or 3 independently selected substituent(s), at least one of which is $(C_1$-$C_6)$alkylsulfonyl. In another embodiment, $R^2$ is phenyl substituted with 1, 2, or 3 independently selected substituent(s), at least one of which is $(C_3$-$C_6)$cycloalkylsulfonyl. In another embodiment, $R^2$ is phenyl substituted with 1, 2, or 3 independently selected substituent(s), at least one of which is $(C_1$-$C_4)$haloalkylsulfinyl. In another embodiment, $R^2$ is phenyl substituted with 1, 2, or 3 independently selected substituent(s), at least one of which is $(C_1$-$C_4)$haloalkylsulfonyl. In another embodiment, $R^2$ is phenyl substituted with 1, 2, or 3 independently selected substituent(s), at least one of which is $(C_1$-$C_4)$perhaloalkylsulfinyl. In another embodiment, $R^2$ is phenyl substituted with 1, 2, or 3 independently selected substituent(s), at least one of which is $(C_1$-$C_4)$perhaloalkylsulfonyl. In another embodiment, $R^2$ is phenyl substituted with 1, 2, or 3 independently selected substituent(s), at least one of which is —S(O)$_2$—$NR^6R^7$. In another embodiment, $R^2$ is phenyl substituted with 1, 2, or 3 independently selected substituent(s), at least one of which is —S(O)$_2$-phenyl. In another embodiment, $R^2$ is phenyl substituted with 1, 2, or 3 independently selected substituent(s), at least one of which is —S(O)$_2$-(5-, 6-, or 7-membered)heterocycloalkyl. In another embodiment, $R^2$ is phenyl substituted with 1, 2, or 3 independently selected substituent(s), at least one of which is —S(=O)(=$NR^8$)$(C_1$-$C_6)$alkyl. In another embodiment, $R^2$ is phenyl substituted with 1, 2, or 3 independently selected substituent(s), at least one of which is N,N-di$(C_1$-$C_6)$alkylaminosulfonyl.

In another embodiment, the present disclosure relates to a compound of formula (Ih) and the attendant definitions, wherein $R^2$ is monosubstituted phenyl substituted with halo, $(C_1$-$C_6)$alkyl, $(C_1$-$C_4)$haloalkyl, $(C_1$-$C_4)$perhaloalkyl, $(C_1$-$C_6)$alkoxy, $(C_1$-$C_4)$haloalkoxy, $(C_1$-$C_4)$perhaloalkoxy, —C(=O)OH, —C(=O)O$(C_1$-$C_6)$alkyl, —C(=O)$NR^4R^5$, —C(=O)-(5-, 6-, or 7-membered)heterocycloalkyl, (5-, 6-, or 7-membered)heterocycloalkyl, $(C_1$-$C_6)$alkylsulfanyl, $(C_1$-$C_4)$perhaloalkylsulfanyl, $(C_1$-$C_6)$alkylsulfinyl, $(C_1$-$C_6)$alkylsulfonyl, $(C_1$-$C_4)$haloalkylsulfinyl, $(C_1$-$C_4)$haloalkylsulfonyl, $(C_1$-$C_4)$perhaloalkylsulfinyl, $(C_1$-$C_4)$perhaloalkylsulfonyl, —S(O)$_2$—NH$_2$, —S(O)$_2$—$NR^6R^7$, —S(O)$_2$-phenyl, —S(O)$_2$-(5-, 6-, or 7-membered)heterocycloalkyl, —S(=O)(=$NR^8$)$(C_1$-$C_6)$alkyl, —$NR^4R^5$, N—$(C_1$-$C_6)$ alkylaminosulfonyl, or N,N-di$(C_1$-$C_6)$alkylaminosulfonyl.

In another embodiment, the present disclosure relates to a compound of formula (Ih) and the attendant definitions, wherein $R^2$ is disubstituted phenyl, each substituent being independently selected from halo, $(C_1$-$C_6)$alkyl, $(C_1$-$C_4)$ perhaloalkyl, $(C_1$-$C_6)$alkoxy, $(C_1$-$C_4)$haloalkoxy, $(C_1$-$C_4)$ perhaloalkoxy, —C(=O)OH, —C(=O)O$(C_1$-$C_6)$alkyl, —C(=O)$NR^4R^5$, —C(=O)-(5-, 6-, or 7-membered)heterocycloalkyl, (5-, 6-, or 7-membered)heterocycloalkyl, $(C_1$-$C_6)$alkylsulfanyl, $(C_1$-$C_4)$perhaloalkylsulfanyl, $(C_1$-$C_6)$ alkylsulfinyl, $(C_1$-$C_6)$alkylsulfonyl, $(C_1$-$C_4)$ haloalkylsulfinyl, $(C_1$-$C_4)$haloalkylsulfonyl, $(C_1$-$C_4)$ perhaloalkylsulfinyl, $(C_1$-$C_4)$perhaloalkylsulfonyl, —S(O)$_2$ —NH$_2$, —S(O)$_2$—$NR^6R^7$, —S(O)$_2$-phenyl, —S(O)$_2$-(5-, 6-, or 7-membered)heterocycloalkyl, —S(=O)(=$NR^8$)$(C_1$-$C_6)$alkyl, —$NR^4R^5$, N—$(C_1$-$C_6)$alkylaminosulfonyl, and N,N-di$(C_1$-$C_6)$alkylaminosulfonyl.

In another embodiment, the present disclosure relates to a compound of formula (Ih) and the attendant definitions, wherein $R^2$ is trisubstituted phenyl, each substituent being independently selected from halo, $(C_1$-$C_6)$alkyl, $(C_1$-$C_4)$ perhaloalkyl, $(C_1$-$C_6)$alkoxy, $(C_1$-$C_4)$haloalkoxy, $(C_1$-$C_4)$ perhaloalkoxy, —C(=O)OH, —C(=O)O$(C_1$-$C_6)$alkyl, —C(=O)$NR^4R^5$, —C(=O)-(5-, 6-, or 7-membered)heterocycloalkyl, (5-, 6-, or 7-membered)heterocycloalkyl, $(C_1$-$C_6)$alkylsulfanyl, $(C_1$-$C_4)$perhaloalkylsulfanyl, $(C_1$-$C_6)$ alkylsulfinyl, $(C_1$-$C_6)$alkylsulfonyl, $(C_1$-$C_4)$ haloalkylsulfinyl, $(C_1$-$C_4)$haloalkylsulfonyl, $(C_1$-$C_4)$ perhaloalkylsulfinyl, $(C_1$-$C_4)$perhaloalkylsulfonyl, —S(O)$_2$ —NH$_2$, —S(O)$_2$—$NR^6R^7$, —S(O)$_2$-phenyl, —S(O)$_2$-(5-, 6-, or 7-membered)heterocycloalkyl, —S(=O)(=$NR^8$)$(C_1$-$C_6)$alkyl, —$NR^4R^5$, N—$(C_1$-$C_6)$alkylaminosulfonyl, and N,N-di$(C_1$-$C_6)$alkylaminosulfonyl.

In one embodiment, the present disclosure relates to a compound of formula (Ih) and the attendant definitions, wherein $R^3$ is $(C_1$-$C_6)$alkyl. In another embodiment, $R^3$ is (5- or 6-membered)heteroaryl. In another embodiment, $R^3$ is phenyl. In another embodiment, $R^3$ is —C(=$NOR^9$)$R^{10}$ wherein $R^9$ is $(C_1$-$C_6)$alkyl, $(C_1$-$C_6)$alkyl substituted with phenyl or phenyl and $R^{10}$ is selected from $(C_1$-$C_6)$alkyl.

In another embodiment, the present disclosure relates to a compound of formula (Ih) and the attendant definitions, wherein $R^3$ is $(C_1$-$C_4)$alkyl. In another embodiment, $R^3$ is methyl, ethyl, propyl, or butyl. In another embodiment, $R^3$ is methyl, ethyl, or propyl. In another embodiment, $R^3$ is methyl, ethyl, or butyl. In another embodiment, $R^3$ is methyl, propyl, or butyl. In another embodiment, $R^3$ is ethyl, propyl, or butyl. In another embodiment, $R^3$ is methyl or ethyl. In another embodiment, $R^3$ is methyl or propyl. In another embodiment, $R^3$ is methyl or butyl. In another embodiment, $R^3$ is ethyl or propyl. In another embodiment, $R^3$ is ethyl or butyl. In another embodiment, $R^3$ is propyl or butyl. In another embodiment, $R^3$ is methyl. In another embodiment, $R^3$ is ethyl. In another embodiment, $R^3$ is propyl. In another embodiment, $R^3$ is iso-propyl. In another embodiment, $R^3$ is butyl. In another embodiment, $R^3$ is tert-butyl.

In another embodiment, the present disclosure relates to a compound of formula (Ih) and the attendant definitions, wherein $R^3$ is —C(=NOR$^9$)R$^{10}$ wherein $R^9$ is ($C_1$-$C_6$)alkyl and $R^{10}$ is ($C_1$-$C_6$)alkyl. In another embodiment, $R^3$ is —C(=NOR$^9$)R$^{10}$ wherein $R^9$ is ($C_1$-$C_6$)alkyl and $R^{10}$ is ($C_1$-$C_4$)alkyl. In another embodiment, $R^3$ is —C(=NOR$^9$)R$^{10}$ wherein $R^9$ is ($C_1$-$C_6$)alkyl and $R^{10}$ is methyl, ethyl or propyl. In another embodiment, $R^3$ is —C(=NOR$^9$)R$^{10}$ wherein $R^9$ is ($C_1$-$C_6$)alkyl and $R^{10}$ is methyl or ethyl. In another embodiment, $R^3$ is —C(=NOR$^9$)R$^{10}$ wherein $R^9$ is ($C_1$-$C_6$)alkyl and $R^{10}$ is methyl. In another embodiment, $R^3$ is —C(=NOR$^9$)R$^{10}$ wherein $R^9$ is ($C_1$-$C_6$)alkyl and $R^{10}$ is ethyl.

In another embodiment, the present disclosure relates to a compound of formula (Ih) and the attendant definitions, wherein $R^3$ is —C(=NOR$^9$)R$^{10}$ wherein $R^9$ is methyl, ethyl, propyl or butyl and $R^{10}$ is ($C_1$-$C_6$)alkyl. In another embodiment, $R^3$ is —C(=NOR$^9$)R$^{10}$ wherein $R^9$ is methyl, ethyl, propyl or butyl and $R^{10}$ is ($C_1$-$C_4$)alkyl. In another embodiment, $R^3$ is —C(=NOR$^9$)R$^{10}$ wherein $R^9$ is methyl, ethyl, propyl or butyl and $R^{10}$ is methyl, ethyl or propyl. In another embodiment, $R^3$ is —C(=NOR$^9$)R$^{10}$ wherein $R^9$ is methyl, ethyl, propyl or butyl and $R^{10}$ is methyl or ethyl. In another embodiment, $R^3$ is —C(=NOR$^9$)R$^{10}$ wherein $R^9$ is methyl, ethyl, propyl or butyl and $R^{10}$ is methyl. In another embodiment, $R^3$ is —C(=NOR$^9$)R$^{10}$ wherein $R^9$ is methyl, ethyl, propyl or butyl and $R^{10}$ is ethyl. In one embodiment, $R^3$ is —C(=NOR$^9$)R$^{10}$ wherein $R^9$ is methyl and $R^{10}$ is ($C_1$-$C_6$)alkyl. In another embodiment, $R^3$ is —C(=NOR$^9$)R$^{10}$ wherein $R^9$ is methyl and $R^{10}$ is ($C_1$-$C_4$)alkyl. In another embodiment, $R^3$ is —C(=NOR$^9$)R$^{10}$ wherein $R^9$ is methyl and $R^{10}$ is methyl, ethyl or propyl. In another embodiment, $R^3$ is —C(=NOR$^9$)R$^{10}$ wherein $R^9$ is methyl and $R^{10}$ is methyl or ethyl. In another embodiment, $R^3$ is —C(=NOR$^9$)R$^{10}$ wherein $R^9$ is methyl and $R^{10}$ is methyl. In another embodiment, $R^3$ is —C(=NOR$^9$)R$^{10}$ wherein $R^9$ is methyl and $R^{10}$ is ethyl. In one embodiment, $R^3$ is —C(=NOR$^9$)R$^{10}$ wherein $R^9$ is ethyl and $R^{10}$ is ($C_1$-$C_6$)alkyl. In another embodiment, $R^3$ is —C(=NOR$^9$)R$^{10}$ wherein $R^9$ is ethyl and $R^{10}$ is ($C_1$-$C_4$)alkyl. In another embodiment, $R^3$ is —C(=NOR$^9$)R$^{10}$ wherein $R^9$ is ethyl and $R^{10}$ is methyl, ethyl or propyl. In another embodiment, $R^3$ is —C(=NOR$^9$)R$^{10}$ wherein $R^9$ is ethyl and $R^{10}$ is methyl or ethyl. In another embodiment, $R^3$ is —C(=NOR$^9$)R$^{10}$ wherein $R^9$ is ethyl and $R^{10}$ is methyl. In another embodiment, $R^3$ is —C(=NOR$^9$)R$^{10}$ wherein $R^9$ is ethyl and $R^{10}$ is ethyl. In one embodiment, $R^3$ is —C(=NOR$^9$)R$^{10}$ wherein $R^9$ is propyl and $R^{10}$ is ($C_1$-$C_6$)alkyl. In another embodiment, $R^3$ is —C(=NOR$^9$)R$^{10}$ wherein $R^9$ is propyl and $R^{10}$ is ($C_1$-$C_4$)alkyl. In another embodiment, $R^3$ is —C(=NOR$^9$)R$^{10}$ wherein $R^9$ is propyl and $R^{10}$ is methyl, ethyl or propyl. In another embodiment, $R^3$ is —C(=NOR$^9$)R$^{10}$ wherein $R^9$ is propyl and $R^{10}$ is methyl or ethyl. In another embodiment, $R^3$ is —C(=NOR$^9$)R$^{10}$ wherein $R^9$ is propyl and $R^{10}$ is methyl. In another embodiment, $R^3$ is —C(=NOR$^9$)R$^{10}$ wherein $R^9$ is propyl and $R^{10}$ is ethyl. In one embodiment, $R^3$ is —C(=NOR$^9$)R$^{10}$ wherein $R^9$ is butyl and $R^{10}$ is ($C_1$-$C_6$)alkyl. In another embodiment, $R^3$ is —C(=NOR$^9$)R$^{10}$ wherein $R^9$ is butyl and $R^{10}$ is ($C_1$-$C_4$)alkyl. In another embodiment, $R^3$ is —C(=NOR$^9$)R$^{10}$ wherein $R^9$ is butyl and $R^{10}$ is methyl, ethyl or propyl. In another embodiment, $R^3$ is —C(=NOR$^9$)R$^{10}$ wherein $R^9$ is butyl and $R^{10}$ is methyl or ethyl. In another embodiment, $R^3$ is —C(=NOR$^9$)R$^{10}$ wherein $R^9$ is butyl and $R^{10}$ is methyl. In another embodiment, $R^3$ is —C(=NOR$^9$)R$^{10}$ wherein $R^9$ is butyl and $R^{10}$ is ethyl. In one embodiment, $R^3$ is —C(=NOR$^9$)R$^{10}$ wherein $R^9$ is tert-butyl and $R^{10}$ is ($C_1$-$C_6$)alkyl. In another embodiment, $R^3$ is —C(=NOR$^9$)R$^{10}$ wherein $R^9$ is tert-butyl and $R^{10}$ is ($C_1$-$C_4$)alkyl. In another embodiment, $R^3$ is —C(=NOR$^9$)R$^{10}$ wherein $R^9$ is tert-butyl and $R^{10}$ is methyl, ethyl or propyl. In another embodiment, $R^3$ is —C(=NOR$^9$)R$^{10}$ wherein $R^9$ is tert-butyl and $R^{10}$ is methyl or ethyl. In another embodiment, $R^3$ is —C(=NOR$^9$)R$^{10}$ wherein $R^9$ is tert-butyl and $R^{10}$ is methyl. In another embodiment, $R^3$ is —C(=NOR$^9$)R$^{10}$ wherein $R^9$ is tert-butyl and $R^{10}$ is ethyl. In one embodiment, $R^3$ is —C(=NOR$^9$)R$^{10}$ wherein $R^9$ is iso-butyl and $R^{10}$ is ($C_1$-$C_6$)alkyl. In another embodiment, $R^3$ is —C(=NOR$^9$)R$^{10}$ wherein $R^9$ is iso-butyl and $R^{10}$ is ($C_1$-$C_4$)alkyl. In another embodiment, $R^3$ is —C(=NOR$^9$)R$^{10}$ wherein $R^9$ is iso-butyl and $R^{10}$ is methyl, ethyl or propyl. In another embodiment, $R^3$ is —C(=NOR$^9$)R$^{10}$ wherein $R^9$ is iso-butyl and $R^{10}$ is methyl or ethyl. In another embodiment, $R^3$ is —C(=NOR$^9$)R$^{10}$ wherein $R^9$ is iso-butyl and $R^{10}$ is methyl. In another embodiment, $R^3$ is —C(=NOR$^9$)R$^{10}$ wherein $R^9$ is iso-butyl and $R^{10}$ is ethyl.

In another embodiment, the present disclosure relates to a compound of formula (Ih) and the attendant definitions, wherein $R^3$ is —C(=NOR$^9$)R$^{10}$ wherein at least one of $R^9$ and $R^{10}$ is methyl. In another embodiment, $R^3$ is —C(=NOR$^9$)R$^{10}$ wherein each of $R^9$ and $R^{10}$ is methyl. In another embodiment, $R^3$ is —C(=NOR$^9$)R$^{10}$ wherein one of $R^9$ and $R^{10}$ is methyl and the other is ethyl.

In another embodiment, the present disclosure relates to a compound of formula (Ih) and the attendant definitions, wherein $R^3$ is —C(=NOR$^9$)R$^{10}$ wherein $R^9$ is ($C_1$-$C_6$)alkyl substituted with phenyl and $R^{10}$ is ($C_1$-$C_6$)alkyl. In another embodiment, $R^3$ is —C(=NOR$^9$)R$^{10}$ wherein $R^9$ is ($C_1$-$C_6$)alkyl substituted with phenyl and $R^{10}$ is ($C_1$-$C_4$)alkyl. In another embodiment, $R^3$ is —C(=NOR$^9$)R$^{10}$ wherein $R^9$ is ($C_1$-$C_6$)alkyl substituted with phenyl and $R^{10}$ is methyl, ethyl or propyl. In another embodiment, $R^3$ is —C(=NOR$^9$)R$^{10}$ wherein $R^9$ is ($C_1$-$C_6$)alkyl substituted with phenyl and $R^{10}$ is methyl or ethyl. In another embodiment, $R^3$ is —C(=NOR$^9$)R$^{10}$ wherein $R^9$ is ($C_1$-$C_6$)alkyl substituted with phenyl and $R^{10}$ is methyl. In another embodiment, $R^3$ is —C(=NOR$^9$)R$^{10}$ wherein $R^9$ is phenyl and $R^{10}$ is ethyl.

In another embodiment, the present disclosure relates to a compound of formula (Ih) and the attendant definitions, wherein $R^3$ is —C(=NOR$^9$)R$^{10}$ wherein $R^9$ is ($C_1$-$C_4$)alkyl substituted with phenyl and $R^{10}$ is ($C_1$-$C_6$)alkyl. In one embodiment, $R^3$ is —C(=NOR$^9$)R$^{10}$ wherein $R^9$ is ($C_1$)alkyl substituted with phenyl and $R^{10}$ is ($C_1$-$C_6$)alkyl. In one embodiment, $R^3$ is —C(=NOR$^9$)R$^{10}$ wherein $R^9$ is ($C_2$)alkyl substituted with phenyl and $R^{10}$ is ($C_1$-$C_6$)alkyl. In one embodiment, $R^3$ is —C(=NOR$^9$)R$^{10}$ wherein $R^9$ is ($C_1$-$C_4$)alkyl substituted with phenyl and $R^{10}$ is ($C_1$-$C_4$)alkyl. In one embodiment, $R^3$ is —C(=NOR$^9$)R$^{10}$ wherein $R^9$ is ($C_1$)alkyl substituted with phenyl and $R^{10}$ is ($C_1$-$C_4$)alkyl. In one embodiment, $R^3$ is —C(=NOR$^9$)R$^{10}$ wherein $R^9$ is ($C_2$)alkyl substituted with phenyl and $R^{10}$ is ($C_1$-$C_4$)alkyl. In one embodiment, $R^3$ is —C(=NOR$^9$)R$^{10}$ wherein $R^9$ is ($C_1$-$C_4$)alkyl substituted with phenyl and $R^{10}$ is methyl, ethyl or propyl. In one embodiment, $R^3$ is —C(=NOR$^9$)R$^{10}$ wherein $R^9$ is ($C_1$)alkyl substituted with phenyl and $R^{10}$ is methyl, ethyl or propyl. In one embodiment, $R^3$ is —C(=NOR$^9$)R$^{10}$ wherein $R^9$ is ($C_2$)alkyl substituted with phenyl and $R^{10}$ is methyl, ethyl or propyl. In one embodiment, $R^3$ is —C(=NOR$^9$)R$^{10}$ wherein $R^9$ is ($C_1$-$C_4$)alkyl substituted with phenyl and $R^{10}$ is methyl or ethyl. In one embodiment, $R^3$ is —C(=NOR$^9$)R$^{10}$ wherein $R^9$ is ($C_1$)alkyl substituted with phenyl and $R^{10}$ is methyl or ethyl. In one embodiment, $R^3$ is —C(═NOR$^9$)R$^{10}$ wherein $R^9$ is (C$_2$)alkyl substituted with phenyl and $R^{10}$ is methyl or ethyl. In one embodiment, $R^3$ is —C(═NOR$^9$)R$^{10}$ wherein $R^9$ is (C$_1$-C$_4$)alkyl substituted with phenyl and $R^{10}$ is methyl. In one embodiment, $R^3$ is —C(═NOR$^9$)R$^{10}$ wherein $R^9$ is (C$_1$)alkyl substituted with phenyl and $R^{10}$ is methyl. In one embodiment, $R^3$ is —C(═NOR$^9$)R$^{10}$ wherein $R^9$ is (C$_2$)alkyl substituted with phenyl and $R^{10}$ is methyl. In one embodiment, $R^3$ is —C(═NOR$^9$)R$^{10}$ wherein $R^9$ is (C$_1$-C$_4$)alkyl substituted with phenyl and $R^{10}$ is ethyl. In one embodiment, $R^3$ is —C(═NOR$^9$)R$^{10}$ wherein $R^9$ is (C$_1$)alkyl substituted with phenyl and $R^{10}$ is ethyl. In one embodiment, $R^3$ is —C(═NOR$^9$)R$^{10}$ wherein $R^9$ is (C$_2$)alkyl substituted with phenyl and $R^{10}$ is ethyl.

In another embodiment, the present disclosure relates to a compound of formula (Ih) and the attendant definitions, wherein $R^3$ is —C(═NOR$^9$)R$^{10}$ wherein $R^9$ is phenyl and $R^{10}$ is (C$_1$-C$_6$)alkyl. In another embodiment, $R^3$ is —C(═NOR$^9$)R$^{10}$ wherein $R^9$ is phenyl and $R^{10}$ is (C$_1$-C$_4$)alkyl. In another embodiment, $R^3$ is —C(═NOR$^9$)R$^{10}$ wherein $R^9$ is phenyl and $R^{10}$ is methyl, ethyl or propyl. In another embodiment, $R^3$ is —C(═NOR$^9$)R$^{10}$ wherein $R^9$ is phenyl and $R^{10}$ is methyl or ethyl. In another embodiment, $R^3$ is —C(═NOR$^9$)R$^{10}$ wherein $R^9$ is phenyl and $R^{10}$ is methyl. In another embodiment, $R^3$ is —C(═NOR$^9$)R$^{10}$ wherein $R^9$ is phenyl and $R^{10}$ is ethyl.

In one embodiment, the present disclosure relates to a compound of formula (Ih) and the attendant definitions, wherein m is 1. In another embodiment, m is 2. In another embodiment, m is 3.

Another aspect of the disclosure provides a compound of formula (Ii)

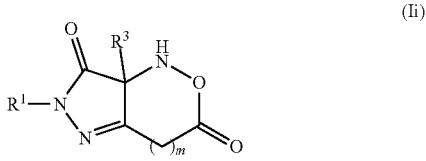

or a pharmaceutically acceptable salt thereof, wherein:
$R^1$ is H, (C$_1$-C$_6$)alkyl, (5- or 6-membered)heteroaryl, or phenyl, wherein said alkyl, heteroaryl and phenyl are unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(═O)OH, —C(═O)O(C$_1$-C$_6$)alkyl, —C(═O)O(5-methyl-2-oxo-2H-1,3-dioxol-4-ylmethyl), —C(═O)NR$^4$R$^5$, —C(═O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(═O)(═NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

$R^4$, $R^5$, $R^6$ and $R^7$ are each independently H or (C$_1$-C$_6$) alkyl;

$R^8$ is H, —(C═O)(C$_1$-C$_6$)alkyl or —(C═O)(C$_1$-C$_4$)perhaloalkyl;

$R^3$ is (C$_1$-C$_6$)alkyl, (5- or 6-membered)heteroaryl, phenyl or —C(═NOR$^9$)R$^{10}$ wherein $R^9$ is (C$_1$-C$_6$)alkyl, (C$_1$-C$_6$)alkyl substituted with phenyl or phenyl and $R^{10}$ are independently selected from (C$_1$-C$_6$)alkyl; and m is 0, 1 or 2, wherein when m is 2, the lactone ring is optionally fused to a phenyl ring, wherein said fused phenyl ring is unsubstituted or substituted with 1, 2, 3, 4, or 5 substituent(s) independently selected from halo, (C$_1$-C$_6$) alkyl, (C$_1$-C$_4$)haloalkyl, (C$_1$-C$_4$)perhaloalkyl, (C$_1$-C$_6$) alkoxy, (C$_1$-C$_4$)haloalkoxy, (C$_1$-C$_4$)perhaloalkoxy, —C(═O)OH, —C(═O)O(C$_1$-C$_6$)alkyl, —C(═O)NR$^4$R$^5$, —C(═O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(═O)(═NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In one embodiment, the present disclosure relates to a compound of formula (Ii) and the attendant definitions, wherein $R^1$ is H. In another embodiment, $R^1$ is (C$_1$-C$_6$)alkyl, wherein the alkyl is unsubstituted or substituted with 1, 2 or 3 independently selected substituents. In another embodiment, $R^1$ is (5- or 6-membered)heteroaryl, wherein the heteroaryl is unsubstituted or substituted with 1, 2, 3, 4, or 5 independently selected substituents. In another embodiment, $R^1$ is phenyl, wherein the phenyl is unsubstituted or substituted with 1, 2, 3, 4, or 5 independently selected substituents. In each of the embodiments listed in this paragraph, the substitutents are selected from among those disclosed above for $R^1$ in connection with formula (Ii).

In another embodiment, the present disclosure relates to a compound of formula (Ii) and the attendant definitions, wherein $R^1$ is (C$_1$-C$_4$)alkyl. In another embodiment, $R^1$ is methyl, ethyl, propyl, or butyl. In another embodiment, $R^1$ is methyl, ethyl, or propyl. In another embodiment, $R^1$ is methyl, ethyl, or butyl. In another embodiment, $R^1$ is methyl, propyl, or butyl. In another embodiment, $R^1$ is ethyl, propyl, or butyl. In another embodiment, $R^1$ is methyl or ethyl. In another embodiment, $R^1$ is methyl or propyl. In another embodiment, $R^1$ is methyl or butyl. In another embodiment, $R^1$ is ethyl or propyl. In another embodiment, $R^1$ is ethyl or butyl. In another embodiment, $R^1$ is propyl or butyl. In another embodiment, $R^1$ is methyl. In another embodiment, $R^1$ is ethyl. In another embodiment, $R^1$ is propyl. In another embodiment, $R^1$ is iso-propyl. In another embodiment, $R^1$ is butyl. In another embodiment, $R^1$ is tert-butyl. In each of the embodiments listed in this paragraph, the alkyl is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is —C(═O)OH, —C(═O)O(C$_1$-C$_6$)alkyl, —C(═O)OCH$_3$, —C(═O)OCH$_2$CH$_3$, —C(═O)O(5-methyl-2-oxo-2H-1,3-dioxol-4-ylmethyl), —C(═O)NR$^4$R$^5$, —C(═O)NH$_2$, —C(═O)NHCH$_3$, —C(═O)N(CH$_3$)$_2$, —NR$^4$R$^5$, —NH$_2$, —NHCH$_3$, (C$_1$-C$_6$)alkylsulfanyl, (C$_1$-C$_6$)alkylsulfinyl, (C$_1$-C$_6$)alkylsulfonyl, —S(O)$_2$—NH$_2$, —N—(C$_1$-C$_6$)alkylaminosulfonyl, or N,N-di(C$_1$-C$_6$)alkylaminosulfonyl or the substituents are independently selected from —C(═O)OH, —C(═O)O(C$_1$-C$_6$)alkyl, —C(═O)OCH$_3$, —C(═O)OCH$_2$CH$_3$, —C(═O)O(5-methyl-2-oxo-2H-1,3-dioxol-4-ylmethyl), —C(═O)

$NR^4R^5$, —C(=O)NH$_2$, —C(=O)NHCH$_3$, —C(=O)N(CH$_3$)$_2$, —NR$^4$R$^5$, —NH$_2$, —NHCH$_3$, (C$_1$-C$_6$)alkylsulfanyl, (C$_1$-C$_6$)alkylsulfinyl, (C$_1$-C$_6$)alkylsulfonyl, —S(O)$_2$—NH$_2$, —N—(C$_1$-C$_6$)alkylaminosulfonyl, or N,N-di(C$_1$-C$_6$)alkylaminosulfonyl.

In another embodiment, the present disclosure relates to a compound of formula (Ii) and the attendant definitions, wherein R$^1$ is (5- or 6-membered)heteroaryl, wherein the heteroaryl is unsubstituted or substituted with 1, 2 or 3 independently selected substituents, the substitutents being selected from among those disclosed above for R$^1$ in connection with formula (Ii). In another embodiment, R$^1$ is unsubstituted (5- or 6-membered)heteroaryl. In another embodiment, R$^1$ is monosubstituted (5- or 6-membered)heteroaryl. In another embodiment, R$^1$ is disubstituted (5- or 6-membered)heteroaryl. In another embodiment, R$^1$ is trisubstituted (5- or 6-membered)heteroaryl. In various embodiments of each of the above embodiments in this paragraph, the substituent is halo, (C$_1$-C$_6$)alkyl, (C$_1$-C$_6$)alkoxy, phenyl, —C(=O)NR$^4$R$^5$, (C$_1$-C$_6$)alkylsulfinyl, (C$_1$-C$_6$)alkylsulfonyl, and N,N-di(C$_1$-C$_6$)alkylaminosulfonyl.

In another embodiment, the present disclosure relates to a compound of formula (Ii) and the attendant definitions, wherein R$^1$ is unsubstituted phenyl. In another embodiment, R$^1$ is phenyl substituted with 1, 2 or 3 independently selected substituent(s), the substitutents being selected from among those disclosed above for R$^1$ in connection with formula (Ii). In another embodiment, R$^1$ is phenyl substituted with 1, 2, or 3 independently selected substituent(s), at least one of which is halo. In another embodiment, R$^1$ is phenyl substituted with 1, 2, or 3 independently selected substituent(s), at least one of which is (C$_1$-C$_6$)alkyl. In another embodiment, R$^1$ is phenyl substituted with 1, 2, or 3 independently selected substituent(s), at least one of which is (C$_1$-C$_4$)haloalkyl. In another embodiment, R$^1$ is phenyl substituted with 1, 2, or 3 independently selected substituent(s), at least one of which is (C$_1$-C$_4$)perhaloalkyl. In another embodiment, R$^1$ is phenyl substituted with 1, 2, or 3 independently selected substituent(s), at least one of which is (C$_1$-C$_6$)alkoxy. In another embodiment, R$^1$ is phenyl substituted with 1, 2, or 3 independently selected substituent(s), at least one of which is (C$_1$-C$_4$)perhaloalkoxy. In another embodiment, R$^1$ is phenyl substituted with 1, 2, or 3 independently selected substituent(s), at least one of which is —C(=O)OH. In another embodiment, R$^1$ is phenyl substituted with 1, 2, or 3 independently selected substituent(s), at least one of which is —C(=O)O(C$_1$-C$_6$)alkyl. In another embodiment, R$^1$ is phenyl substituted with 1, 2, or 3 independently selected substituent(s), at least one of which is —C(=O)NR$^4$R$^5$. In another embodiment, R$^1$ is phenyl substituted with 1, 2, or 3 independently selected substituent(s), at least one of which is —C(=O)NH(C$_1$-C$_6$)alkyl, wherein said alkyl is substituted with COOH. In another embodiment, R$^1$ is phenyl substituted with 1, 2, or 3 independently selected substituent(s), at least one of which is —C(=O)NH—(C$_1$-C$_6$)alkylsulfonyl. In another embodiment, R$^1$ is phenyl substituted with 1, 2, or 3 independently selected substituent(s), at least one of which is —C(=O)-(5-, 6-, or 7-membered)heterocycloalkyl. In another embodiment, R$^1$ is phenyl substituted with 1, 2, or 3 independently selected substituent(s), at least one of which is (5-, 6-, or 7-membered)heterocycloalkyl. In another embodiment, R$^1$ is phenyl substituted with 1, 2, or 3 independently selected substituent(s), at least one of which is (C$_1$-C$_6$)alkylsulfanyl. In another embodiment, R$^1$ is phenyl substituted with 1, 2, or 3 independently selected substituent(s), at least one of which is (C$_1$-C$_4$)perhaloalkylsulfanyl. In another embodiment, R$^1$ is phenyl substituted with 1, 2, or 3 independently selected substituent(s), at least one of which is (C$_1$-C$_6$)alkylsulfinyl. In another embodiment, R$^1$ is phenyl substituted with 1, 2, or 3 independently selected substituent(s), at least one of which is (C$_1$-C$_6$)alkylsulfonyl. In another embodiment, R$^1$ is phenyl substituted with 1, 2, or 3 independently selected substituent(s), at least one of which is (C$_3$-C$_6$)cycloalkylsulfonyl. In another embodiment, R$^1$ is phenyl substituted with 1, 2, or 3 independently selected substituent(s), at least one of which is (C$_1$-C$_4$)haloalkylsulfinyl. In another embodiment, R$^1$ is phenyl substituted with 1, 2, or 3 independently selected substituent(s), at least one of which is (C$_1$-C$_4$)haloalkylsulfonyl. In another embodiment, R$^1$ is phenyl substituted with 1, 2, or 3 independently selected substituent(s), at least one of which is (C$_1$-C$_4$)perhaloalkylsulfinyl. In another embodiment, R$^1$ is phenyl substituted with 1, 2, or 3 independently selected substituent(s), at least one of which is (C$_1$-C$_4$)perhaloalkylsulfonyl. In another embodiment, R$^1$ is phenyl substituted with 1, 2, or 3 independently selected substituent(s), at least one of which is —S(O)$_2$—NR$^6$R$^7$. In another embodiment, R$^1$ is phenyl substituted with 1, 2, or 3 independently selected substituent(s), at least one of which is —S(O)$_2$-phenyl. In another embodiment, R$^1$ is phenyl substituted with 1, 2, or 3 independently selected substituent(s), at least one of which is —S(O)$_2$-(5-, 6-, or 7-membered)heterocycloalkyl. In another embodiment, R$^1$ is phenyl substituted with 1, 2, or 3 independently selected substituent(s), at least one of which is —S(=O)(=NR$^8$)(C$_1$-C$_6$)alkyl. In another embodiment, R$^1$ is phenyl substituted with 1, 2, or 3 independently selected substituent(s), at least one of which is N,N-di(C$_1$-C$_6$)alkylaminosulfonyl.

In another embodiment, the present disclosure relates to a compound of formula (Ii) and the attendant definitions, wherein R$^1$ is monosubstituted phenyl substituted with halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, or N,N-di(C$_1$-C$_6$)alkylaminosulfonyl.

In another embodiment, the present disclosure relates to a compound of formula (Ii) and the attendant definitions, wherein R$^1$ is disubstituted phenyl, each substituent being independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In another embodiment, the present disclosure relates to a compound of formula (Ii) and the attendant definitions, wherein R$^1$ is trisubstituted phenyl, each substituent being independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)

perhaloalkoxy, —C(=O)OH, —C(=O)O($C_1$-$C_6$)alkyl, —C(=O)$NR^4R^5$, —C(=O)-(5-, 6-, or 7-membered)heterocycloalkyl, (5-, 6-, or 7-membered)heterocycloalkyl, ($C_1$-$C_6$)alkylsulfanyl, ($C_1$-$C_4$)perhaloalkylsulfanyl, ($C_1$-$C_6$)alkylsulfinyl, ($C_1$-$C_6$)alkylsulfonyl, ($C_1$-$C_4$)haloalkylsulfinyl, ($C_1$-$C_4$)haloalkylsulfonyl, ($C_1$-$C_4$)perhaloalkylsulfinyl, ($C_1$-$C_4$)perhaloalkylsulfonyl, —S(O)$_2$—NH$_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1$-$C_6$)alkyl, —$NR^4R^5$, N—($C_1$-$C_6$)alkylaminosulfonyl, and N,N-di($C_1$-$C_6$)alkylaminosulfonyl.

In one embodiment, the present disclosure relates to a compound of formula (Ii) and the attendant definitions, wherein $R^3$ is ($C_1$-$C_6$)alkyl. In another embodiment, $R^3$ is (5- or 6-membered)heteroaryl. In another embodiment, $R^3$ is phenyl. In another embodiment, $R^3$ is —C(=$NOR^9$)$R^{10}$ wherein $R^9$ is ($C_1$-$C_6$)alkyl, ($C_1$-$C_6$)alkyl substituted with phenyl or phenyl and $R^{10}$ is selected from ($C_1$-$C_6$)alkyl.

In another embodiment, the present disclosure relates to a compound of formula (Ii) and the attendant definitions, wherein $R^3$ is ($C_1$-$C_4$)alkyl. In another embodiment, $R^3$ is methyl, ethyl, propyl, or butyl. In another embodiment, $R^3$ is methyl, ethyl, or propyl. In another embodiment, $R^3$ is methyl, ethyl, or butyl. In another embodiment, $R^3$ is methyl, propyl, or butyl. In another embodiment, $R^3$ is ethyl, propyl, or butyl. In another embodiment, $R^3$ is methyl or ethyl. In another embodiment, $R^3$ is methyl or propyl. In another embodiment, $R^3$ is methyl or butyl. In another embodiment, $R^3$ is ethyl or propyl. In another embodiment, $R^3$ is ethyl or butyl. In another embodiment, $R^3$ is propyl or butyl. In another embodiment, $R^3$ is methyl. In another embodiment, $R^3$ is ethyl. In another embodiment, $R^3$ is propyl. In another embodiment, $R^3$ is iso-propyl. In another embodiment, $R^3$ is butyl. In another embodiment, $R^3$ is tert-butyl.

In another embodiment, the present disclosure relates to a compound of formula (Ii) and the attendant definitions, wherein $R^3$ is —C(=$NOR^9$)$R^{10}$ wherein $R^9$ is ($C_1$-$C_6$)alkyl and $R^{10}$ is ($C_1$-$C_6$)alkyl. In another embodiment, $R^3$ is —C(=$NOR^9$)$R^{10}$ wherein $R^9$ is ($C_1$-$C_6$)alkyl and $R^{10}$ is ($C_1$-$C_4$)alkyl. In another embodiment, $R^3$ is —C(=$NOR^9$)$R^{10}$ wherein $R^9$ is ($C_1$-$C_6$)alkyl and $R^{10}$ is methyl, ethyl or propyl. In another embodiment, $R^3$ is —C(=$NOR^9$)$R^{10}$ wherein $R^9$ is ($C_1$-$C_6$)alkyl and $R^{10}$ is methyl or ethyl. In another embodiment, $R^3$ is —C(=$NOR^9$)$R^{10}$ wherein $R^9$ is ($C_1$-$C_6$)alkyl and $R^{10}$ is methyl. In another embodiment, $R^3$ is —C(=$NOR^9$)$R^{10}$ wherein $R^9$ is ($C_1$-$C_6$)alkyl and $R^{10}$ is ethyl.

In another embodiment, the present disclosure relates to a compound of formula (Ii) and the attendant definitions, wherein $R^3$ is —C(=$NOR^9$)$R^{10}$ wherein $R^9$ is methyl, ethyl, propyl or butyl and $R^{10}$ is ($C_1$-$C_6$)alkyl. In another embodiment, $R^3$ is —C(=$NOR^9$)$R^{10}$ wherein $R^9$ is methyl, ethyl, propyl or butyl and $R^{10}$ is ($C_1$-$C_4$)alkyl. In another embodiment, $R^3$ is —C(=$NOR^9$)$R^{10}$ wherein $R^9$ is methyl, ethyl, propyl or butyl and $R^{10}$ is methyl, ethyl or propyl. In another embodiment, $R^3$ is —C(=$NOR^9$)$R^{10}$ wherein $R^9$ is methyl, ethyl, propyl or butyl and $R^{10}$ is methyl or ethyl. In another embodiment, $R^3$ is —C(=$NOR^9$)$R^{10}$ wherein $R^9$ is methyl, ethyl, propyl or butyl and $R^{10}$ is methyl. In another embodiment, $R^3$ is —C(=$NOR^9$)$R^{10}$ wherein $R^9$ is methyl, ethyl, propyl or butyl and $R^{10}$ is ethyl. In one embodiment, $R^3$ is —C(=$NOR^9$)$R^{10}$ wherein $R^9$ is methyl and $R^{10}$ is ($C_1$-$C_6$)alkyl. In another embodiment, $R^3$ is —C(=$NOR^9$)$R^{10}$ wherein $R^9$ is methyl and $R^{10}$ is ($C_1$-$C_4$)alkyl. In another embodiment, $R^3$ is —C(=$NOR^9$)$R^{10}$ wherein $R^9$ is methyl and $R^{10}$ is methyl, ethyl or propyl. In another embodiment, $R^3$ is —C(=$NOR^9$)$R^{10}$ wherein $R^9$ is methyl and $R^{10}$ is methyl or ethyl. In another embodiment, $R^3$ is —C(=$NOR^9$)$R^{10}$ wherein $R^9$ is methyl and $R^{10}$ is methyl. In another embodiment, $R^3$ is —C(=$NOR^9$)$R^{10}$ wherein $R^9$ is methyl and $R^{10}$ is ethyl. In one embodiment, $R^3$ is —C(=$NOR^9$)$R^{10}$ wherein $R^9$ is ethyl and $R^{10}$ is ($C_1$-$C_6$)alkyl. In another embodiment, $R^3$ is —C(=$NOR^9$)$R^{10}$ wherein $R^9$ is ethyl and $R^{10}$ is ($C_1$-$C_4$)alkyl. In another embodiment, $R^3$ is —C(=$NOR^9$)$R^{10}$ wherein $R^9$ is ethyl and $R^{10}$ is methyl, ethyl or propyl. In another embodiment, $R^3$ is —C(=$NOR^9$)$R^{10}$ wherein $R^9$ is ethyl and $R^{10}$ is methyl or ethyl. In another embodiment, $R^3$ is —C(=$NOR^9$)$R^{10}$ wherein $R^9$ is ethyl and $R^{10}$ is methyl. In another embodiment, $R^3$ is —C(=$NOR^9$)$R^{10}$ wherein $R^9$ is ethyl and $R^{10}$ is ethyl. In one embodiment, $R^3$ is —C(=$NOR^9$)$R^{10}$ wherein $R^9$ is propyl and $R^{10}$ is ($C_1$-$C_6$)alkyl. In another embodiment, $R^3$ is —C(=$NOR^9$)$R^{10}$ wherein $R^9$ is propyl and $R^{10}$ is ($C_1$-$C_4$)alkyl. In another embodiment, $R^3$ is —C(=$NOR^9$)$R^{10}$ wherein $R^9$ is propyl and $R^{10}$ is methyl, ethyl or propyl. In another embodiment, $R^3$ is —C(=$NOR^9$)$R^{10}$ wherein $R^9$ is propyl and $R^{10}$ is methyl or ethyl. In another embodiment, $R^3$ is —C(=$NOR^9$)$R^{10}$ wherein $R^9$ is propyl and $R^{10}$ is methyl. In another embodiment, $R^3$ is —C(=$NOR^9$)$R^{10}$ wherein $R^9$ is propyl and $R^{10}$ is ethyl. In one embodiment, $R^3$ is —C(=$NOR^9$)$R^{10}$ wherein $R^9$ is butyl and $R^{10}$ is ($C_1$-$C_6$)alkyl. In another embodiment, $R^3$ is —C(=$NOR^9$)$R^{10}$ wherein $R^9$ is butyl and $R^{10}$ is ($C_1$-$C_4$)alkyl. In another embodiment, $R^3$ is —C(=$NOR^9$)$R^{10}$ wherein $R^9$ is butyl and $R^{10}$ is methyl, ethyl or propyl. In another embodiment, $R^3$ is —C(=$NOR^9$)$R^{10}$ wherein $R^9$ is butyl and $R^{10}$ is methyl or ethyl. In another embodiment, $R^3$ is —C(=$NOR^9$)$R^{10}$ wherein $R^9$ is butyl and $R^{10}$ is methyl. In another embodiment, $R^3$ is —C(=$NOR^9$)$R^{10}$ wherein $R^9$ is butyl and $R^{10}$ is ethyl. In one embodiment, $R^3$ is —C(=$NOR^9$)$R^{10}$ wherein $R^9$ is tert-butyl and $R^{10}$ is ($C_1$-$C_6$)alkyl. In another embodiment, $R^3$ is —C(=$NOR^9$)$R^{10}$ wherein $R^9$ is tert-butyl and $R^{10}$ is ($C_1$-$C_4$)alkyl. In another embodiment, $R^3$ is —C(=$NOR^9$)$R^{10}$ wherein $R^9$ is tert-butyl and $R^{10}$ is methyl, ethyl or propyl. In another embodiment, $R^3$ is —C(=$NOR^9$)$R^{10}$ wherein $R^9$ is tert-butyl and $R^{10}$ is methyl or ethyl. In another embodiment, $R^3$ is —C(=$NOR^9$)$R^{10}$ wherein $R^9$ is tert-butyl and $R^{10}$ is methyl. In another embodiment, $R^3$ is —C(=$NOR^9$)$R^{10}$ wherein $R^9$ is tert-butyl and $R^{10}$ is ethyl. In one embodiment, $R^3$ is —C(=$NOR^9$)$R^{10}$ wherein $R^9$ is iso-butyl and $R^{10}$ is ($C_1$-$C_6$)alkyl. In another embodiment, $R^3$ is —C(=$NOR^9$)$R^{10}$ wherein $R^9$ is iso-butyl and $R^{10}$ is ($C_1$-$C_4$)alkyl. In another embodiment, $R^3$ is —C(=$NOR^9$)$R^{10}$ wherein $R^9$ is iso-butyl and $R^{10}$ is methyl, ethyl or propyl. In another embodiment, $R^3$ is —C(=$NOR^9$)$R^{10}$ wherein $R^9$ is iso-butyl and $R^{10}$ is methyl or ethyl. In another embodiment, $R^3$ is —C(=$NOR^9$)$R^{10}$ wherein $R^9$ is iso-butyl and $R^{10}$ is methyl. In another embodiment, $R^3$ is —C(=$NOR^9$)$R^{10}$ wherein $R^9$ is iso-butyl and $R^{10}$ is ethyl.

In another embodiment, the present disclosure relates to a compound of formula (Ii) and the attendant definitions, wherein $R^3$ is —C(=$NOR^9$)$R^{10}$ wherein at least one of $R^9$ and $R^{10}$ is methyl. In another embodiment, $R^3$ is —C(=$NOR^9$)$R^{10}$ wherein each of $R^9$ and $R^{10}$ is methyl. In another embodiment, $R^3$ is —C(=$NOR^9$)$R^{10}$ wherein one of $R^9$ and $R^{10}$ is methyl and the other is ethyl.

In another embodiment, the present disclosure relates to a compound of formula (Ii) and the attendant definitions, wherein $R^3$ is —C(=$NOR^9$)$R^{10}$ wherein $R^9$ is ($C_1$-$C_6$)alkyl substituted with phenyl and $R^{10}$ is ($C_1$-$C_6$)alkyl. In another embodiment, $R^3$ is —C(=$NOR^9$)$R^{10}$ wherein $R^9$ is ($C_1$-$C_6$)alkyl substituted with phenyl and $R^{10}$ is ($C_1$-$C_4$)alkyl. In another embodiment, $R^3$ is —C(=NOR$^9$)R$^{10}$ wherein R$^9$ is (C$_1$-C$_6$)alkyl substituted with phenyl and R$^{10}$ is methyl, ethyl or propyl. In another embodiment, $R^3$ is —C(=NOR$^9$)R$^{10}$ wherein R$^9$ is (C$_1$-C$_6$)alkyl substituted with phenyl and R$^{10}$ is methyl or ethyl. In another embodiment, $R^3$ is —C(=NOR$^9$)R$^{10}$ wherein R$^9$ is (C$_1$-C$_6$)alkyl substituted with phenyl and R$^{10}$ is methyl. In another embodiment, $R^3$ is —C(=NOR$^9$)R$^{10}$ wherein R$^9$ is phenyl and R$^{10}$ is ethyl.

In another embodiment, the present disclosure relates to a compound of formula (Ii) and the attendant definitions, wherein $R^3$ is —C(=NOR$^9$)R$^{10}$ wherein R$^9$ is (C$_1$-C$_4$)alkyl substituted with phenyl and R$^{10}$ is (C$_1$-C$_6$)alkyl. In one embodiment, $R^3$ is —C(=NOR$^9$)R$^{10}$ wherein R$^9$ is (C$_1$)alkyl substituted with phenyl and R$^{10}$ is (C$_1$-C$_6$)alkyl. In one embodiment, $R^3$ is —C(=NOR$^9$)R$^{10}$ wherein R$^9$ is (C$_2$)alkyl substituted with phenyl and R$^{10}$ is (C$_1$-C$_6$)alkyl. In one embodiment, $R^3$ is —C(=NOR$^9$)R$^{10}$ wherein R$^9$ is (C$_1$-C$_4$)alkyl substituted with phenyl and R$^{10}$ is (C$_1$-C$_4$)alkyl. In one embodiment, $R^3$ is —C(=NOR$^9$)R$^{10}$ wherein R$^9$ is (C$_1$)alkyl substituted with phenyl and R$^{10}$ is (C$_1$-C$_4$)alkyl. In one embodiment, $R^3$ is —C(=NOR$^9$)R$^{10}$ wherein R$^9$ is (C$_2$)alkyl substituted with phenyl and R$^{10}$ is (C$_1$-C$_4$)alkyl. In one embodiment, $R^3$ is —C(=NOR$^9$)R$^{10}$ wherein R$^9$ is (C$_1$-C$_4$)alkyl substituted with phenyl and R$^{10}$ is methyl, ethyl or propyl. In one embodiment, $R^3$ is —C(=NOR$^9$)R$^{10}$ wherein R$^9$ is (C$_1$)alkyl substituted with phenyl and R$^{10}$ is methyl, ethyl or propyl. In one embodiment, $R^3$ is —C(=NOR$^9$)R$^{10}$ wherein R$^9$ is (C$_2$)alkyl substituted with phenyl and R$^{10}$ is methyl, ethyl or propyl. In one embodiment, $R^3$ is —C(=NOR$^9$)R$^{10}$ wherein R$^9$ is (C$_1$-C$_4$)alkyl substituted with phenyl and R$^{10}$ is methyl or ethyl. In one embodiment, $R^3$ is —C(=NOR$^9$)R$^{10}$ wherein R$^9$ is (C$_1$)alkyl substituted with phenyl and R$^{10}$ is methyl or ethyl. In one embodiment, $R^3$ is —C(=NOR$^9$)R$^{10}$ wherein R$^9$ is (C$_2$)alkyl substituted with phenyl and R$^{10}$ is methyl or ethyl. In one embodiment, $R^3$ is —C(=NOR$^9$)R$^{10}$ wherein R$^9$ is (C$_1$-C$_4$)alkyl substituted with phenyl and R$^{10}$ is methyl. In one embodiment, $R^3$ is —C(=NOR$^9$)R$^{10}$ wherein R$^9$ is (C$_1$)alkyl substituted with phenyl and R$^{10}$ is methyl. In one embodiment, $R^3$ is —C(=NOR$^9$)R$^{10}$ wherein R$^9$ is (C$_2$)alkyl substituted with phenyl and R$^{10}$ is methyl. In one embodiment, $R^3$ is —C(=NOR$^9$)R$^{10}$ wherein R$^9$ is (C$_1$-C$_4$)alkyl substituted with phenyl and R$^{10}$ is ethyl. In one embodiment, $R^3$ is —C(=NOR$^9$)R$^{10}$ wherein R$^9$ is (C$_1$)alkyl substituted with phenyl and R$^{10}$ is ethyl. In one embodiment, $R^3$ is —C(=NOR$^9$)R$^{10}$ wherein R$^9$ is (C$_2$)alkyl substituted with phenyl and R$^{10}$ is ethyl.

In another embodiment, the present disclosure relates to a compound of formula (Ii) and the attendant definitions, wherein $R^3$ is —C(=NOR$^9$)R$^{10}$ wherein R$^9$ is phenyl and R$^{10}$ is (C$_1$-C$_6$)alkyl. In another embodiment, $R^3$ is —C(=NOR$^9$)R$^{10}$ wherein R$^9$ is phenyl and R$^{10}$ is (C$_1$-C$_4$)alkyl. In another embodiment, $R^3$ is —C(=NOR$^9$)R$^{10}$ wherein R$^9$ is phenyl and R$^{10}$ is methyl, ethyl or propyl. In another embodiment, $R^3$ is —C(=NOR$^9$)R$^{10}$ wherein R$^9$ is phenyl and R$^{10}$ is methyl or ethyl. In another embodiment, $R^3$ is —C(=NOR$^9$)R$^{10}$ wherein R$^9$ is phenyl and R$^{10}$ is methyl. In another embodiment, $R^3$ is —C(=NOR$^9$)R$^{10}$ wherein R$^9$ is phenyl and R$^{10}$ is ethyl.

In one embodiment, the present disclosure relates to a compound of formula (Ii) and the attendant definitions, wherein m is 1. In another embodiment, m is 2. In another embodiment, m is 3. In another embodiment, m is 2 and the lactone ring is not fused to a phenyl ring. In another embodiment, m is 2 and the lactone ring is fused to a phenyl ring, wherein said fused phenyl ring is unsubstituted or substituted with 1, 2, 3, 4, or 5 independently substituent(s), the substituent(s) being selected from among those disclosed above for m in connection with formula (Ii). In another embodiment, the fused phenyl ring is substituted with 1, 2, or 3 independently selected substituent(s), at least one of which is halo. In another embodiment, the fused phenyl ring is substituted with 1, 2, or 3 independently selected substituent(s), at least one of which is (C$_1$-C$_6$)alkyl. In another embodiment, the fused phenyl ring is substituted with 1, 2, or 3 independently selected substituent(s), at least one of which is (C$_1$-C$_4$)haloalkyl. In another embodiment, the fused phenyl ring is substituted with 1, 2, or 3 independently selected substituent(s), at least one of which is (C$_1$-C$_4$)perhaloalkyl. In another embodiment, the fused phenyl ring is substituted with 1, 2, or 3 independently selected substituent(s), at least one of which is (C$_1$-C$_6$)alkoxy. In another embodiment, the fused phenyl ring is substituted with 1, 2, or 3 independently selected substituent(s), at least one of which is (C$_1$-C$_4$)perhaloalkoxy. In another embodiment, the fused phenyl ring is substituted with 1, 2, or 3 independently selected substituent(s), at least one of which is —C(=O)OH. In another embodiment, the fused phenyl ring is substituted with 1, 2, or 3 independently selected substituent(s), at least one of which is —C(=O)O(C$_1$-C$_6$)alkyl. In another embodiment, the fused phenyl ring is substituted with 1, 2, or 3 independently selected substituent(s), at least one of which is —C(=O)NR$^4$R$^5$. In another embodiment, the fused phenyl ring is substituted with 1, 2, or 3 independently selected substituent(s), at least one of which is —C(=O)NH(C$_1$-C$_6$)alkyl, wherein said alkyl is substituted with COOH. In another embodiment, the fused phenyl ring is substituted with 1, 2, or 3 independently selected substituent(s), at least one of which is —C(=O)NH—(C$_1$-C$_6$)alkylsulfonyl. In another embodiment, the fused phenyl ring is substituted with 1, 2, or 3 independently selected substituent(s), at least one of which is —C(=O)-(5-, 6-, or 7-membered)heterocycloalkyl. In another embodiment, the fused phenyl ring is substituted with 1, 2, or 3 independently selected substituent(s), at least one of which is (5-, 6-, or 7-membered)heterocycloalkyl. In another embodiment, the fused phenyl ring is substituted with 1, 2, or 3 independently selected substituent(s), at least one of which is (C$_1$-C$_6$)alkylsulfanyl. In another embodiment, the fused phenyl ring is substituted with 1, 2, or 3 independently selected substituent(s), at least one of which is (C$_1$-C$_4$)perhaloalkylsulfanyl. In another embodiment, the fused phenyl ring is substituted with 1, 2, or 3 independently selected substituent(s), at least one of which is (C$_1$-C$_6$)alkylsulfinyl. In another embodiment, the fused phenyl ring is substituted with 1, 2, or 3 independently selected substituent(s), at least one of which is (C$_1$-C$_6$)alkylsulfonyl. In another embodiment, the fused phenyl ring is substituted with 1, 2, or 3 independently selected substituent(s), at least one of which is (C$_3$-C$_6$)cycloalkylsulfonyl. In another embodiment, the fused phenyl ring is substituted with 1, 2, or 3 independently selected substituent(s), at least one of which is (C$_1$-C$_4$)haloalkylsulfinyl. In another embodiment, the fused phenyl ring is substituted with 1, 2, or 3 independently selected substituent(s), at least one of which is (C$_1$-C$_4$)haloalkylsulfonyl. In another embodiment, the fused phenyl ring is substituted with 1, 2, or 3 independently selected substituent(s), at least one of which is (C$_1$-C$_4$)perhaloalkylsulfinyl. In another embodiment the fused phenyl ring is substituted with 1, 2, or 3 independently selected substituent(s), at least one of which is (C$_1$-C$_4$)perhaloalkylsulfonyl. In another embodiment, the fused phenyl ring is substituted with 1, 2, or 3 independently selected substituent(s), at least one of which is —S(O)$_2$—NR$^6$R$^7$. In another embodiment, the fused phenyl ring is substituted with 1, 2, or 3 independently selected substituent(s), at least one of which is —S(O)$_2$-phenyl. In another embodiment, the fused phenyl ring is substituted with 1, 2, or 3 independently selected substituent(s), at least one of which is —S(O)$_2$-(5-, 6-, or 7-membered)heterocycloalkyl. In another embodiment, the fused phenyl ring is substituted with 1, 2, or 3 independently selected substituent(s), at least one of which is —S(=O)(=NR$^8$)(C$_1$-C$_6$)alkyl. In another embodiment, the fused phenyl ring is substituted with 1, 2, or 3 independently selected substituent(s), at least one of which is N,N-di(C$_1$-C$_6$)alkylaminosulfonyl.

In another embodiment, the present disclosure relates to a compound of formula (Ii) and the attendant definitions, wherein the fused phenyl ring is a monosubstituted phenyl substituted with halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, or N,N-di(C$_1$-C$_6$)alkylaminosulfonyl.

In another embodiment, the present disclosure relates to a compound of formula (Ii) and the attendant definitions, wherein the fused phenyl ring is a disubstituted phenyl, each substituent being independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In another embodiment, the present disclosure relates to a compound of formula (Ii) and the attendant definitions, wherein the fused phenyl ring is a trisubstituted phenyl, each substituent being independently selected from halo, (C$_1$-C$_6$)alkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)perhaloalkylsulfanyl, (C$_1$-C$_6$)alkylsulfinyl, (C$_1$-C$_6$)alkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

Another aspect of the disclosure provides a compound of formula (Ij)

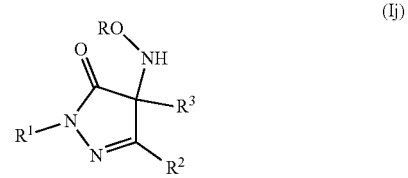

or a pharmaceutically acceptable salt thereof, wherein:
R$^1$ is (C$_1$-C$_6$)alkyl;
R$^2$ is phenyl, wherein said phenyl is unsubstituted or substituted with 1, 2, 3, 4, or 5 substituent(s) independently selected from halo, (C$_1$-C$_6$)alkyl, (C$_1$-C$_4$)haloalkyl, (C$_1$-C$_4$)perhaloalkyl, (C$_1$-C$_6$)alkoxy, (C$_1$-C$_4$)haloalkoxy, (C$_1$-C$_4$)perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, (C$_1$-C$_4$)haloalkylsulfanyl, (C$_1$-C$_4$)perhaloalkylsulfanyl, (C$_1$-C$_6$)alkylsulfinyl, (C$_1$-C$_6$)alkylsulfonyl, (C$_3$-C$_6$)cycloalkylsulfonyl, (C$_1$-C$_4$)haloalkylsulfinyl, (C$_1$-C$_4$)haloalkylsulfonyl, (C$_1$-C$_4$)perhaloalkylsulfinyl, (C$_1$-C$_4$)perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;
R$^4$, R$^5$, R$^6$ and R$^7$ are each independently H or (C$_1$-C$_6$)alkyl;
R$^8$ is H, —(C=O)(C$_1$-C$_6$)alkyl or —(C=O)(C$_1$-C$_4$)perhaloalkyl;
R$^3$ is (C$_1$-C$_6$)alkyl; and
R is 5-methyl-2-oxo-2H-1,3-dioxol-4-ylmethyl.

In one embodiment, the present disclosure relates to a compound of formula (Ij) and the attendant definitions, wherein R$^1$ is (C$_1$-C$_4$)alkyl. In another embodiment, R$^1$ is methyl, ethyl, propyl, or butyl. In another embodiment, R$^1$ is methyl, ethyl, or propyl. In another embodiment, R$^1$ is methyl, ethyl, or butyl. In another embodiment, R$^1$ is methyl, propyl, or butyl. In another embodiment, R$^1$ is ethyl, propyl, or butyl. In another embodiment, R$^1$ is methyl or ethyl. In another embodiment, R$^1$ is methyl or propyl. In another embodiment, R$^1$ is methyl or butyl. In another embodiment, R$^1$ is ethyl or propyl. In another embodiment, R$^1$ is ethyl or butyl. In another embodiment, R$^1$ is propyl or butyl. In another embodiment, R$^1$ is methyl. In another embodiment, R$^1$ is ethyl. In another embodiment, R$^1$ is propyl. In another embodiment, R$^1$ is iso-propyl. In another embodiment, R$^1$ is butyl. In another embodiment, R$^1$ is tert-butyl.

In one embodiment, the present disclosure relates to a compound of formula (Ij) and the attendant definitions, wherein R$^2$ is unsubstituted phenyl. In another embodiment, R$^2$ is phenyl substituted with 1, 2 or 3 independently selected substituent(s), the substitutents being selected from among those disclosed above for R$^2$ in connection with formula (Ij). In another embodiment, R$^2$ is phenyl substituted with 1, 2, or 3 independently selected substituent(s), at least one of which is halo. In another embodiment, R$^2$ is phenyl substituted with 1, 2, or 3 independently selected substituent(s), at least one of which is (C$_1$-C$_6$)alkyl. In another embodiment, R$^2$ is phenyl substituted with 1, 2, or 3 independently selected substituent(s), at least one of which is (C$_1$-C$_4$)haloalkyl. In another embodiment, R$^2$ is phenyl substituted with 1, 2, or 3 independently selected substituent(s), at least one of which is (C$_1$-C$_4$)perhaloalkyl. In another embodiment, R$^2$ is phenyl substituted with 1, 2, or 3 independently selected substituent(s), at least one of which is $(C_1-C_6)$ alkoxy. In another embodiment, $R^2$ is phenyl substituted with 1, 2, or 3 independently selected substituent(s), at least one of which is $(C_1-C_4)$perhaloalkoxy. In another embodiment, $R^2$ is phenyl substituted with 1, 2, or 3 independently selected substituent(s), at least one of which is —C(=O)OH. In another embodiment, $R^2$ is phenyl substituted with 1, 2, or 3 independently selected substituent(s), at least one of which is —C(=O)O($C_1-C_6$)alkyl. In another embodiment, $R^2$ is phenyl substituted with 1, 2, or 3 independently selected substituent(s), at least one of which is —C(=O)$NR^4R^5$. In another embodiment, $R^2$ is phenyl substituted with 1, 2, or 3 independently selected substituent(s), at least one of which is —C(=O)NH($C_1-C_6$)alkyl, wherein said alkyl is substituted with COOH. In another embodiment, $R^2$ is phenyl substituted with 1, 2, or 3 independently selected substituent(s), at least one of which is —C(=O)NH—($C_1-C_6$)alkylsulfonyl. In another embodiment, $R^2$ is phenyl substituted with 1, 2, or 3 independently selected substituent(s), at least one of which is —C(=O)-(5-, 6-, or 7-membered)heterocycloalkyl. In another embodiment, $R^2$ is phenyl substituted with 1, 2, or 3 independently selected substituent(s), at least one of which is (5-, 6-, or 7-membered)heterocycloalkyl. In another embodiment, $R^2$ is phenyl substituted with 1, 2, or 3 independently selected substituent(s), at least one of which is ($C_1-C_6$)alkylsulfanyl. In another embodiment, $R^2$ is phenyl substituted with 1, 2, or 3 independently selected substituent(s), at least one of which is ($C_1-C_4$)perhaloalkylsulfanyl. In another embodiment, $R^2$ is phenyl substituted with 1, 2, or 3 independently selected substituent(s), at least one of which is ($C_1-C_6$)alkylsulfinyl. In another embodiment, $R^2$ is phenyl substituted with 1, 2, or 3 independently selected substituent(s), at least one of which is ($C_1-C_6$)alkylsulfonyl. In another embodiment, $R^2$ is phenyl substituted with 1, 2, or 3 independently selected substituent(s), at least one of which is ($C_3-C_6$)cycloalkylsulfonyl. In another embodiment, $R^2$ is phenyl substituted with 1, 2, or 3 independently selected substituent(s), at least one of which is ($C_1-C_4$)haloalkylsulfinyl. In another embodiment, $R^2$ is phenyl substituted with 1, 2, or 3 independently selected substituent(s), at least one of which is ($C_1-C_4$)haloalkylsulfonyl. In another embodiment, $R^2$ is phenyl substituted with 1, 2, or 3 independently selected substituent(s), at least one of which is ($C_1-C_4$)perhaloalkylsulfinyl. In another embodiment, $R^2$ is phenyl substituted with 1, 2, or 3 independently selected substituent(s), at least one of which is ($C_1-C_4$)perhaloalkylsulfonyl. In another embodiment, $R^2$ is phenyl substituted with 1, 2, or 3 independently selected substituent(s), at least one of which is —S(O)$_2$—$NR^6R^7$. In another embodiment, $R^2$ is phenyl substituted with 1, 2, or 3 independently selected substituent(s), at least one of which is —S(O)$_2$-phenyl. In another embodiment, $R^2$ is phenyl substituted with 1, 2, or 3 independently selected substituent(s), at least one of which is —S(O)$_2$-(5-, 6-, or 7-membered)heterocycloalkyl. In another embodiment, $R^2$ is phenyl substituted with 1, 2, or 3 independently selected substituent(s), at least one of which is —S(=O)(=$NR^8$)($C_1-C_6$)alkyl. In another embodiment, $R^2$ is phenyl substituted with 1, 2, or 3 independently selected substituent(s), at least one of which is N,N-di($C_1-C_6$)alkylaminosulfonyl.

In another embodiment, the present disclosure relates to a compound of formula (Ij) and the attendant definitions, wherein $R^2$ is monosubstituted phenyl substituted with halo, ($C_1-C_6$)alkyl, ($C_1-C_4$)haloalkyl, ($C_1-C_4$)perhaloalkyl, ($C_1-C_6$)alkoxy, ($C_1-C_4$)haloalkoxy, ($C_1-C_4$)perhaloalkoxy, —C(=O)OH, —C(=O)O($C_1-C_6$)alkyl, —C(=O)$NR^4R^5$, —C(=O)-(5-, 6-, or 7-membered)heterocycloalkyl, (5-, 6-, or 7-membered)heterocycloalkyl, ($C_1-C_6$)alkylsulfanyl, ($C_1-C_4$)perhaloalkylsulfanyl, ($C_1-C_6$)alkylsulfinyl, ($C_1-C_4$)haloalkylsulfinyl, ($C_1-C_4$)haloalkylsulfonyl, ($C_1-C_4$)perhaloalkylsulfinyl, ($C_1-C_4$)perhaloalkylsulfonyl, —S(O)$_2$—NH$_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1-C_6$)alkyl, —$NR^4R^5$, N—($C_1-C_6$)alkylaminosulfonyl, or N,N-di($C_1-C_6$)alkylaminosulfonyl.

In another embodiment, the present disclosure relates to a compound of formula (Ij) and the attendant definitions, wherein $R^2$ is disubstituted phenyl, each substituent being independently selected from halo, ($C_1-C_6$)alkyl, ($C_1-C_4$)perhaloalkyl, ($C_1-C_6$)alkoxy, ($C_1-C_4$)haloalkoxy, ($C_1-C_4$)perhaloalkoxy, —C(=O)OH, —C(=O)O($C_1-C_6$)alkyl, —C(=O)$NR^4R^5$, —C(=O)-(5-, 6-, or 7-membered)heterocycloalkyl, (5-, 6-, or 7-membered)heterocycloalkyl, ($C_1-C_6$)alkylsulfanyl, ($C_1-C_4$)perhaloalkylsulfanyl, ($C_1-C_6$)alkylsulfinyl, ($C_1-C_6$)alkylsulfonyl, ($C_1-C_4$)haloalkylsulfinyl, ($C_1-C_4$)haloalkylsulfonyl, ($C_1-C_4$)perhaloalkylsulfinyl, ($C_1-C_4$)perhaloalkylsulfonyl, —S(O)$_2$—NH$_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1-C_6$)alkyl, —$NR^4R^5$, N—($C_1-C_6$)alkylaminosulfonyl, and N,N-di($C_1-C_6$)alkylaminosulfonyl.

In another embodiment, the present disclosure relates to a compound of formula (Ij) and the attendant definitions, wherein $R^2$ is trisubstituted phenyl, each substituent being independently selected from halo, ($C_1-C_6$)alkyl, ($C_1-C_4$)perhaloalkyl, ($C_1-C_6$)alkoxy, ($C_1-C_4$)haloalkoxy, ($C_1-C_4$)perhaloalkoxy, —C(=O)OH, —C(=O)O($C_1-C_6$)alkyl, —C(=O)$NR^4R^5$, —C(=O)-(5-, 6-, or 7-membered)heterocycloalkyl, (5-, 6-, or 7-membered)heterocycloalkyl, ($C_1-C_6$)alkylsulfanyl, ($C_1-C_4$)perhaloalkylsulfanyl, ($C_1-C_6$)alkylsulfinyl, ($C_1-C_6$)alkylsulfonyl, ($C_1-C_4$)haloalkylsulfinyl, ($C_1-C_4$)haloalkylsulfonyl, ($C_1-C_4$)perhaloalkylsulfinyl, ($C_1-C_4$)perhaloalkylsulfonyl, —S(O)$_2$—NH$_2$, —S(O)$_2$—$NR^6R^7$, —S(O)$_2$-phenyl, —S(O)$_2$-(5-, 6-, or 7-membered)heterocycloalkyl, —S(=O)(=$NR^8$)($C_1-C_6$)alkyl, —$NR^4R^5$, N—($C_1-C_6$)alkylaminosulfonyl, and N,N-di($C_1-C_6$)alkylaminosulfonyl.

In one embodiment, the present disclosure relates to a compound of formula (Ij) and the attendant definitions, wherein $R^3$ is ($C_1-C_4$)alkyl. In another embodiment, $R^3$ is methyl, ethyl, propyl, or butyl. In another embodiment, $R^3$ is methyl, ethyl, or propyl. In another embodiment, $R^3$ is methyl, ethyl, or butyl. In another embodiment, $R^3$ is methyl, propyl, or butyl. In another embodiment, $R^3$ is ethyl, propyl, or butyl. In another embodiment, $R^3$ is methyl or ethyl. In another embodiment, $R^3$ is methyl or propyl. In another embodiment, $R^3$ is methyl or butyl. In another embodiment, $R^3$ is ethyl or propyl. In another embodiment, $R^3$ is ethyl or butyl. In another embodiment, $R^3$ is propyl or butyl. In another embodiment, $R^3$ is methyl. In another embodiment, $R^3$ is ethyl. In another embodiment, $R^3$ is propyl. In another embodiment, $R^3$ is iso-propyl. In another embodiment, $R^3$ is butyl. In another embodiment, $R^3$ is tert-butyl.

Another aspect of the disclosure provides a compound of formula (Ik)

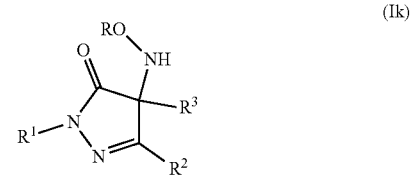

or a pharmaceutically acceptable salt thereof, wherein:

$R^1$ is (5-, 6- or 7-membered)heterocycloalkyl;

$R^2$ is phenyl, wherein said phenyl is unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)$(C_1-C_6)$alkyl, —NR$^4$R$^5$, N—$(C_1-C_6)$alkylaminosulfonyl, and N,N-di$(C_1-C_6)$alkylaminosulfonyl;

$R^4$, $R^5$, $R^6$ and $R^7$ are each independently H or $(C_1-C_6)$alkyl;

$R^8$ is H, —C(=O)$(C_1-C_6)$alkyl or —C(=O)$(C_1-C_4)$perhaloalkyl;

$R^3$ is $(C_1-C_6)$alkyl; and

R is hydrogen, —COH, —CO—$(C_1-C_6)$alkyl, —CO—$(C_2-C_4)$alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—$(C_1-C_6)$alkyl, —CO—NH$_2$, —CO—NH—$(C_1-C_4)$alkyl, or —CO—N$((C_1-C_4)$alkyl$)_2$, wherein said —$(C_1-C_6)$alkyl, —$(C_2-C_4)$alkenyl, phenyl, benzyl, cyclopentyl, cyclohexyl, -(5-, 6-, or 7-membered)heterocycloalkyl, benzyloxy, —O—$(C_1-C_6)$alkyl, —NH—$(C_1-C_4)$alkyl, or —N$((C_1-C_4)$alkyl$)_2$ can be unsubstituted or substituted with 1, 2 or 3 substituents selected from halo, —$(C_1-C_6)$alkyl, —$(C_2-C_4)$alkenyl, —$(C_2-C_3)$alkynyl, -(5- or 6-membered)heteroaryl, —O—$(C_1-C_6)$alkyl, —S—$(C_1-C_6)$alkyl, —C(halo)$_3$, —CH(halo)$_2$, —CH$_2$(halo), —CN, —NO$_2$, —NH$_2$, —NH—$(C_1-C_4)$alkyl, —N(—$(C_1-C_4)$alkyl)$_2$, —C(O)$(C_1-C_4)$alkyl, —C(O)O$(C_1-C_4)$alkyl, —OC(O)$(C_1-C_4)$alkyl, —OC(O)NH$_2$, —S(O)$(C_1-C_4)$alkyl, —S(O)$_2$$(C_1-C_4)$alkyl or 5-methyl-2-oxo-2H-1,3-dioxol-4-ylmethyl.

In one embodiment, the present disclosure relates to a compound of formula (Ik) and the attendant definitions, wherein $R^1$ is (5- or 6-membered)heterocycloalkyl. In another embodiment, $R^1$ is (5-membered)heterocycloalkyl. In another embodiment, $R^1$ is (6-membered)heterocycloalkyl. In another embodiment, $R^1$ is (7-membered)heterocycloalkyl. In another embodiment, $R^1$ is piperidinyl.

In one embodiment, the present disclosure relates to a compound of formula (Ik) and the attendant definitions, wherein $R^2$ is unsubstituted phenyl. In another embodiment, $R^2$ is phenyl substituted with 1, 2 or 3 independently selected substituent(s), the substitutents being selected from among those disclosed above for $R^2$ in connection with formula (Ik). In another embodiment, $R^2$ is phenyl substituted with 1, 2, or 3 independently selected substituent(s), at least one of which is halo. In another embodiment, $R^2$ is phenyl substituted with 1, 2, or 3 independently selected substituent(s), at least one of which is $(C_1-C_6)$alkyl. In another embodiment, $R^2$ is phenyl substituted with 1, 2, or 3 independently selected substituent(s), at least one of which is $(C_1-C_4)$haloalkyl. In another embodiment, $R^2$ is phenyl substituted with 1, 2, or 3 independently selected substituent(s), at least one of which is $(C_1-C_4)$perhaloalkyl. In another embodiment, $R^2$ is phenyl substituted with 1, 2, or 3 independently selected substituent(s), at least one of which is $(C_1-C_6)$alkoxy. In another embodiment, $R^2$ is phenyl substituted with 1, 2, or 3 independently selected substituent(s), at least one of which is $(C_1-C_4)$haloalkoxy. In another embodiment, $R^2$ is phenyl substituted with 1, 2, or 3 independently selected substituent(s), at least one of which is $(C_1-C_4)$perhaloalkoxy. In another embodiment, $R^2$ is phenyl substituted with 1, 2, or 3 independently selected substituent(s), at least one of which is —C(=O)OH. In another embodiment, $R^2$ is phenyl substituted with 1, 2, or 3 independently selected substituent(s), at least one of which is —C(=O)O$(C_1-C_6)$alkyl. In another embodiment, $R^2$ is phenyl substituted with 1, 2, or 3 independently selected substituent(s), at least one of which is —C(=O)NR$^4$R$^5$. In another embodiment, $R^2$ is phenyl substituted with 1, 2, or 3 independently selected substituent(s), at least one of which is —C(=O)NH$(C_1-C_6)$alkyl, wherein said alkyl is substituted with COOH. In another embodiment, $R^2$ is phenyl substituted with 1, 2, or 3 independently selected substituent(s), at least one of which is —C(=O)NH—$(C_1-C_6)$alkylsulfonyl. In another embodiment, $R^2$ is phenyl substituted with 1, 2, or 3 independently selected substituent(s), at least one of which is —C(=O)-(5-, 6-, or 7-membered)heterocycloalkyl. In another embodiment, $R^2$ is phenyl substituted with 1, 2, or 3 independently selected substituent(s), at least one of which is (5-, 6-, or 7-membered)heterocycloalkyl. In another embodiment, $R^2$ is phenyl substituted with 1, 2, or 3 independently selected substituent(s), at least one of which is $(C_1-C_6)$alkylsulfanyl. In another embodiment, $R^2$ is phenyl substituted with 1, 2, or 3 independently selected substituent(s), at least one of which is $(C_1-C_4)$perhaloalkylsulfanyl. In another embodiment, $R^2$ is phenyl substituted with 1, 2, or 3 independently selected substituent(s), at least one of which is $(C_1-C_6)$alkylsulfinyl. In another embodiment, $R^2$ is phenyl substituted with 1, 2, or 3 independently selected substituent(s), at least one of which is $(C_1-C_6)$alkylsulfonyl. In another embodiment, $R^2$ is phenyl substituted with 1, 2, or 3 independently selected substituent(s), at least one of which is $(C_3-C_6)$cycloalkylsulfonyl. In another embodiment, $R^2$ is phenyl substituted with 1, 2, or 3 independently selected substituent(s), at least one of which is $(C_1-C_4)$haloalkylsulfinyl. In another embodiment, $R^2$ is phenyl substituted with 1, 2, or 3 independently selected substituent(s), at least one of which is $(C_1-C_4)$haloalkylsulfonyl. In another embodiment, $R^2$ is phenyl substituted with 1, 2, or 3 independently selected substituent(s), at least one of which is $(C_1-C_4)$perhaloalkylsulfinyl. In another embodiment, $R^2$ is phenyl substituted with 1, 2, or 3 independently selected substituent(s), at least one of which is $(C_1-C_4)$perhaloalkylsulfonyl. In another embodiment, $R^2$ is phenyl substituted with 1, 2, or 3 independently selected substituent(s), at least one of which is —S(O)$_2$—NR$^6$R$^7$. In another embodiment, $R^2$ is phenyl substituted with 1, 2, or 3 independently selected substituent(s), at least one of which is —S(O)$_2$-phenyl. In another embodiment, $R^2$ is phenyl substituted with 1, 2, or 3 independently selected substituent(s), at least one of which is —S(O)$_2$-(5-, 6-, or 7-membered)heterocycloalkyl. In another embodiment, $R^2$ is phenyl substituted with 1, 2, or 3 independently selected substituent(s), at least one of which is —S(=O)(=NR$^8$)$(C_1-C_6)$alkyl. In another embodiment, $R^2$ is phenyl substituted with 1, 2, or 3 independently selected substituent(s), at least one of which is N,N-di$(C_1-C_6)$alkylaminosulfonyl.

In another embodiment, the present disclosure relates to a compound of formula (Ik) and the attendant definitions, wherein $R^2$ is monosubstituted phenyl substituted with halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O$(C_1-C_6)$alkyl, —C(=O)NR$^4$R$^5$, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$perhaloalkylsulfanyl, $(C_1-C_6)$alkylsulfinyl, $(C_1-C_6)$ alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, or N,N-di(C$_1$-C$_6$)alkylaminosulfonyl.

In another embodiment, the present disclosure relates to a compound of formula (Ik) and the attendant definitions, wherein R$^2$ is disubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In another embodiment, the present disclosure relates to a compound of formula (Ik) and the attendant definitions, wherein R$^2$ is trisubstituted phenyl, each substituent being independently selected from halo, $(C_1-C_6)$alkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O(C$_1$-C$_6$)alkyl, —C(=O)NR$^4$R$^5$, —C(=O)-(5-, 6-, or 7-membered)heterocycloalkyl, (5-, 6-, or 7-membered)heterocycloalkyl, (C$_1$-C$_6$)alkylsulfanyl, $(C_1-C_4)$perhaloalkylsulfanyl, $(C_1-C_6)$alkylsulfinyl, $(C_1-C_6)$alkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl.

In one embodiment, the present disclosure relates to a compound of formula (Ik) and the attendant definitions, wherein R$^3$ is $(C_1-C_4)$alkyl. In another embodiment, R$^3$ is methyl, ethyl, propyl, or butyl. In another embodiment, R$^3$ is methyl, ethyl, or propyl. In another embodiment, R$^3$ is methyl, ethyl, or butyl. In another embodiment, R$^3$ is methyl, propyl, or butyl. In another embodiment, R$^3$ is ethyl, propyl, or butyl. In another embodiment, R$^3$ is methyl or ethyl. In another embodiment, R$^3$ is methyl or propyl. In another embodiment, R$^3$ is methyl or butyl. In another embodiment, R$^3$ is ethyl or propyl. In another embodiment, R$^3$ is ethyl or butyl. In another embodiment, R$^3$ is propyl or butyl. In another embodiment, R$^3$ is methyl. In another embodiment, R$^3$ is ethyl. In another embodiment, R$^3$ is propyl. In another embodiment, R$^3$ is iso-propyl. In another embodiment, R$^3$ is butyl. In another embodiment, R$^3$ is tert-butyl.

In one embodiment, the present disclosure relates to a compound of formula (Ik) and the attendant definitions, wherein R is hydrogen, —CO-methyl, —CO-ethyl, —CO-benzyl, —CO-phenyl or 5-methyl-2-oxo-2H-1,3-dioxol-4-ylmethyl. In another embodiment, R is hydrogen or 5-methyl-2-oxo-2H-1,3-dioxol-4-ylmethyl. In another embodiment, R is hydrogen. In another embodiment, R is 5-methyl-2-oxo-2H-1,3-dioxol-4-ylmethyl. In another embodiment, R is —CO-methyl or —CO-ethyl. In another embodiment, R is —CO-methyl. In another embodiment, R is —CO-ethyl. In another embodiment, R is —CO-benzyl or —CO-phenyl. In another embodiments, R is —CO-benzyl. In another embodiment, R is —CO-phenyl. In another embodiment, R is —CO—NH$_2$. In each of the above embodiments in this paragraph, R is unsubstituted in one embodiment, monosubstituted in another embodiment, disubstituted with two independently selected substitutents in an additional embodiment, or trisubstituted with three independently selected substitutents in a further embodiment. In various embodiments of each of the above embodiments in this paragraph, the substituent is -halo, —NH$_2$, —NHCH$_3$, —CF$_3$ or —OCH$_3$ or the substituents are independently selected from -halo, —NH$_2$, —NHCH$_3$, —CF$_3$ or —OCH$_3$.

Table 1 provides representative compounds of the disclosure.

TABLE 1

Pyrazolone Derivative Compounds of the Disclosure

| Compound No. | Compound Structure | Compound Name |
| --- | --- | --- |
| 1 | 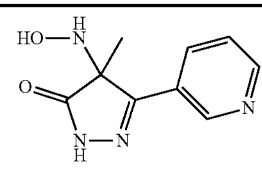 | 4-(Hydroxyamino)-4-methyl-3-(pyridin-3-yl)-4,5-dihydro-1H-pyrazol-5-one |
| 2 | 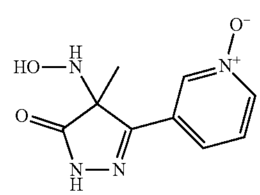 [SMILES: CC1(NO)C(=O)NN=C1c1ccc[n+]([O-])c1] | 3-[4-(Hydroxyamino)-4-methyl-5-oxo-4,5-dihydro-1H-pyrazol-3-yl]pyridin-1-ium-1-olate |
| 3 | 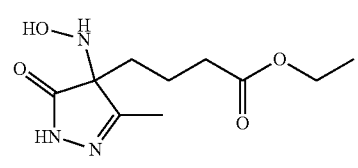 [SMILES: CCOC(=O)CCCC1(NO)C(=O)NN=C1C] | Ethyl 4-[4-(hydroxyamino)-3-methyl-5-oxo-4,5-dihydro-1H-pyrazol-4-yl]butanoate |

TABLE 1-continued

Pyrazolone Derivative Compounds of the Disclosure

| Compound No. | Compound Structure | Compound Name |
| --- | --- | --- |
| 4 | 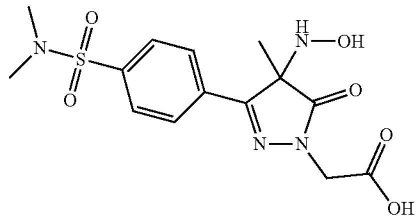 [SMILES: CN(C)S(=O)(=O)c1ccc(C2=NN(CC(=O)O)C(=O)C2(C)NO)cc1] | 2-{3-[4-(Dimethylsulfamoyl)phenyl]-4-(hydroxyamino)-4-methyl-5-oxo-4,5-dihydro-1H-pyrazol-1-yl}acetic acid |
| 5 | 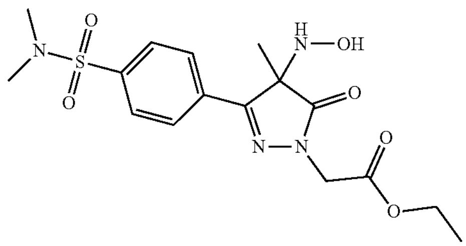 [SMILES: CCOC(=O)CN1N=C(c2ccc(S(=O)(=O)N(C)C)cc2)C(C)(NO)C1=O] | Ethyl 2-{3-[4-(dimethylsulfamoyl)phenyl]-4-(hydroxyamino)-4-methyl-5-oxo-4,5-dihydro-1H-pyrazol-1-yl}acetate |
| 6 | 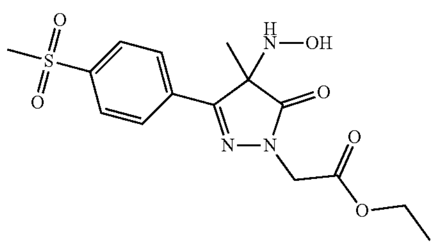 [SMILES: CCOC(=O)CN1N=C(c2ccc(S(C)(=O)=O)cc2)C(C)(NO)C1=O] | Ethyl 2-[4-(hydroxyamino)-3-(4-methanesulfonylphenyl)-4-methyl-5-oxo-4,5-dihydro-1H-pyrazol-1-yl]acetate |
| 7 | 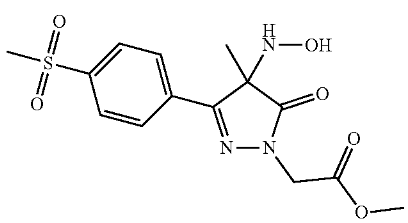 | Methyl 2-[4-(hydroxyamino)-3-(4-methanesulfonylphenyl)-4-methyl-5-oxo-4,5-dihydro-1H-pyrazol-1-yl]acetate |
| 8 | 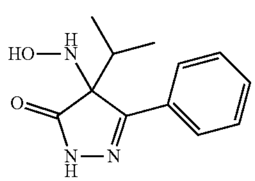 [SMILES: CC(C)C1(NO)C(=O)NN=C1c1ccccc1] | 4-(Hydroxyamino)-3-phenyl-4-(propan-2-yl)-4,5-dihydro-1H-pyrazol-5-one |
| 9 | 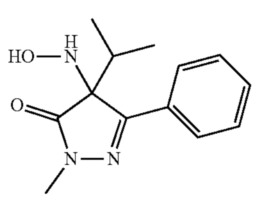 [SMILES: CC(C)C1(NO)C(=O)N(C)N=C1c1ccccc1] | 4-(Hydroxyamino)-1-methyl-3-phenyl-4-(propan-2-yl)-4,5-dihydro-1H-pyrazol-5-one |
| 10 | 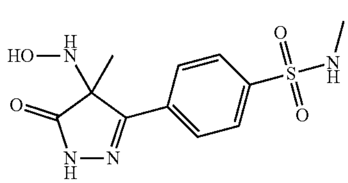 [SMILES: CNS(=O)(=O)c1ccc(C2=NNC(=O)C2(C)NO)cc1] | 4-[4-(Hydroxyamino)-4-methyl-5-oxo-4,5-dihydro-1H-pyrazol-3-yl]-N-methylbenzene-1-sulfonamide |

TABLE 1-continued

Pyrazolone Derivative Compounds of the Disclosure

| Compound No. | Compound Structure | Compound Name |
| --- | --- | --- |
| 11 | 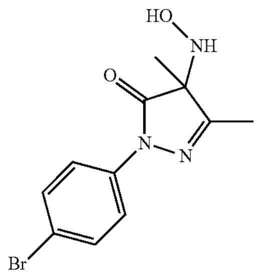 [SMILES: CC1=NN(c2ccc(Br)cc2)C(=O)C1(C)NO] | 1-(4-Bromophenyl)-4-(hydroxyamino)-3,4-dimethyl-4,5-dihydro-1H-pyrazol-5-one |
| 12 | 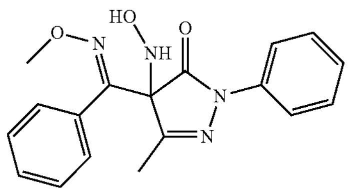 [SMILES: CO/N=C(\c1ccccc1)C1(NO)C(=O)N(c2ccccc2)N=C1C] | 4-(Hydroxyamino)-4-[(methoxyimino)(phenyl)methyl]-3-methyl-1-phenyl-4,5-dihydro-1H-pyrazol-5-one |
| 13 | 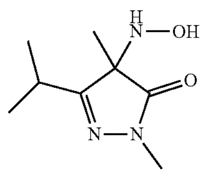 | 4-(Hydroxyamino)-1,4-dimethyl-3-(propan-2-yl)-4,5-dihydro-1H-pyrazol-5-one |
| 14 | 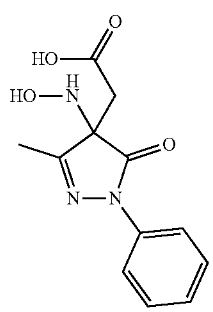 [SMILES: CC1=NN(c2ccccc2)C(=O)C1(CC(=O)O)NO] | 2-[4-(Hydroxyamino)-3-methyl-5-oxo-1-phenyl-4,5-dihydro-1H-pyrazol-4-yl]acetic acid |
| 15 | 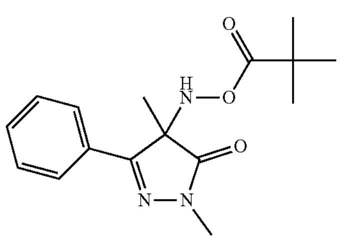 [SMILES: CN1N=C(c2ccccc2)C(C)(NOC(=O)C(C)(C)C)C1=O] | (1,4-Dimethyl-5-oxo-3-phenyl-4,5-dihydro-1H-pyrazol-4-yl)amino 2,2-dimethylpropanoate |
| 16 | 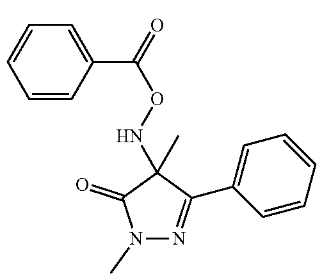 [SMILES: CN1N=C(c2ccccc2)C(C)(NOC(=O)c2ccccc2)C1=O] | (1,4-Dimethyl-5-oxo-3-phenyl-4,5-dihydro-1H-pyrazol-4-yl)amino benzoate |

TABLE 1-continued

Pyrazolone Derivative Compounds of the Disclosure

| Compound No. | Compound Structure | Compound Name |
|---|---|---|
| 17 | 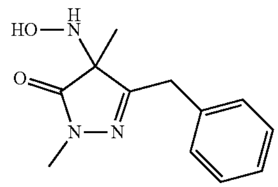 [SMILES: CN1N=C(Cc2ccccc2)C(C)(NO)C1=O] | 3-Benzyl-4-(hydroxyamino)-1,4-dimethyl-4,5-dihydro-1H-pyrazol-5-one |
| 18 | 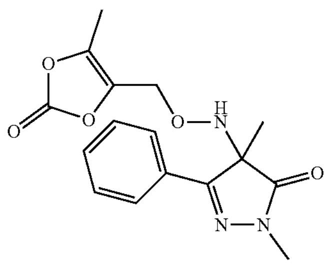 [SMILES: Cc1oc(=O)oc1CONC1(C)C(=O)N(C)N=C1c1ccccc1] | 1,4-Dimethyl-4-{[(5-methyl-2-oxo-2H-1,3-dioxol-4-yl)methoxy]amino}-3-phenyl-4,5-dihydro-1H-pyrazol-5-one |
| 19 | 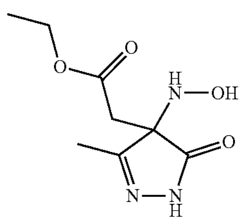 | Ethyl 2-[4-(hydroxyamino)-3-methyl-5-oxo-4,5-dihydro-1H-pyrazol-4-yl]acetate |
| 20 | 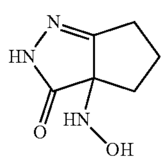 | 3a-(Hydroxyamino)-2H,3H,3aH,4H,5H,6H-cyclopenta[c]pyrazol-3-one |
| 21 | 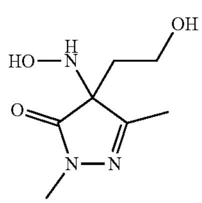 | 4-(Hydroxyamino)-4-(2-hydroxyethyl)-1,3-dimethyl-4,5-dihydro-1H-pyrazol-5-one |
| 22 | 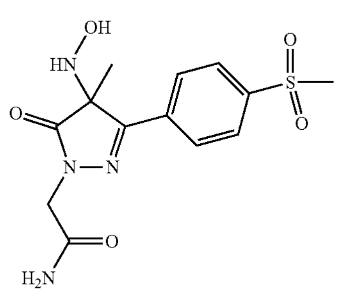 [SMILES: CC1(NO)C(=O)N(CC(N)=O)N=C1c1ccc(S(C)(=O)=O)cc1] | 2-[4-(Hydroxyamino)-3-(4-methanesulfonylphenyl)-4-methyl-5-oxo-4,5-dihydro-1H-pyrazol-1-yl]acetamide |
| 23 | 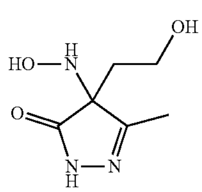 | 4-(Hydroxyamino)-4-(2-hydroxyethyl)-3-methyl-4,5-dihydro-1H-pyrazol-5-one |

TABLE 1-continued

Pyrazolone Derivative Compounds of the Disclosure

| Compound No. | Compound Structure | Compound Name |
|---|---|---|
| 24 | 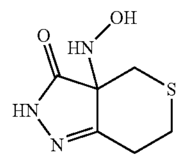 [SMILES: O=C1NN=C2CCSCC12NO] | 3a-(Hydroxyamino)-2H,3H,3aH,4H,6H,7H-thiopyrano[4,3-c]pyrazol-3-one |
| 25 | 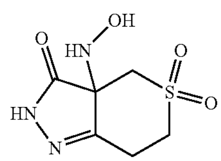 [SMILES: O=C1NN=C2CCS(=O)(=O)CC12NO] | 3a-(Hydroxyamino)-2H,3H,3aH,4H,6H,7H-5$\lambda^6$-thiopyrano[4,3-c]pyrazole-3,5,5-trione |
| 26 | 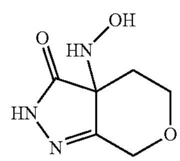 | 3a-(Hydroxyamino)-2H,3H,3aH,4H,5H,7H-pyrano[3,4-c]pyrazol-3-one |
| 27 | 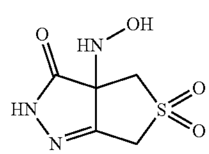 [SMILES: O=C1NN=C2CS(=O)(=O)CC12NO] | 3a-(Hydroxyamino)-2H,3H,3aH,4H,6H-5$\lambda^6$-thieno[3,4-c]pyrazole-3,5,5-trione |
| 28 | 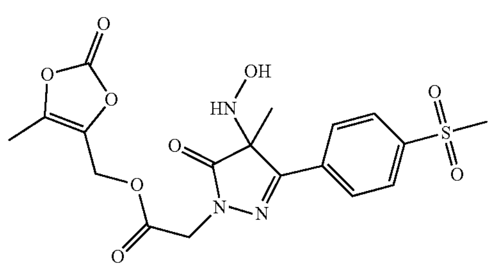 | (5-methyl-2-oxo-1,3-dioxol-4-yl)methyl 2-(4-(hydroxyamino)-4-methyl-3-(4-(methylsulfonyl)phenyl)-5-oxo-4,5-dihydro-1H-pyrazol-1-yl)acetate |
| 29 | 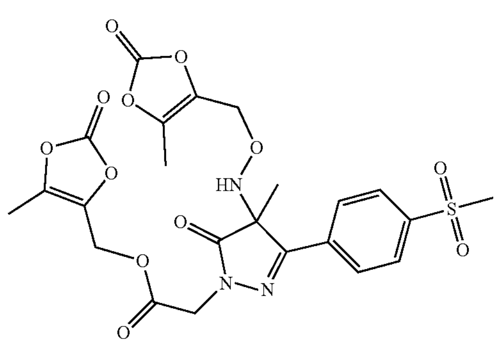 | (5-methyl-2-oxo-1,3-dioxol-4-yl)methyl 2-(4-methyl-4-(((5-methyl-2-oxo-1,3-dioxol-4-yl)methoxy)amino)-3-(4-(methylsulfonyl)phenyl)-5-oxo-4,5-dihydro-1H-pyrazol-1-yl)acetate |

TABLE 1-continued

Pyrazolone Derivative Compounds of the Disclosure

| Compound No. | Compound Structure | Compound Name |
|---|---|---|
| 30 | 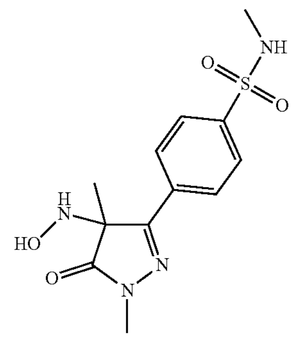 [SMILES: CNS(=O)(=O)c1ccc(C2=NN(C)C(=O)C2(C)NO)cc1] | 4-[4-(hydroxyamino)-1,4-dimethyl-5-oxo-4,5-dihydro-1H-pyrazol-3-yl]-N-methylbenzene-1-sulfonamide |
| 31 | 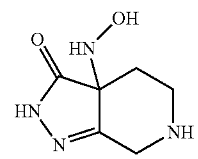 | 3a-(hydroxyamino)-2H,3H,3aH,4H,5H,6H,7H-pyrazolo[3,4-c]pyridin-3-one |
| 32 | 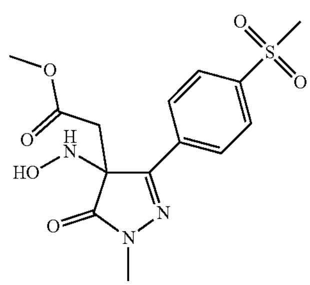 | methyl 2-[4-(hydroxyamino)-3-(4-methanesulfonylphenyl)-1-methyl-5-oxo-4,5-dihydro-1H-pyrazol-4-yl]acetate |
| 33 | 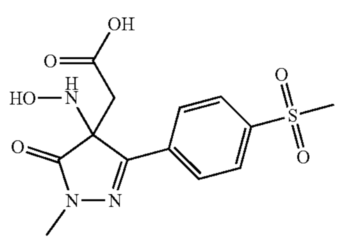 [SMILES: CN1N=C(c2ccc(S(C)(=O)=O)cc2)C(CC(=O)O)(NO)C1=O] | 2-[4-(hydroxyamino)-3-(4-methanesulfonylphenyl)-1-methyl-5-oxo-4,5-dihydro-1H-pyrazol-4-yl]acetic acid |
| 34 | 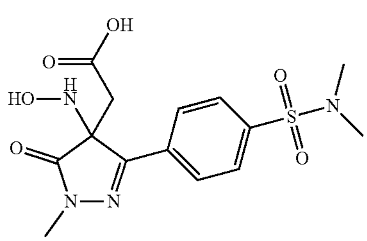 [SMILES: CN1N=C(c2ccc(S(=O)(=O)N(C)C)cc2)C(CC(=O)O)(NO)C1=O] | 2-{3-[4-(dimethylsulfamoyl)phenyl]-4-(hydroxyamino)-1-methyl-5-oxo-4,5-dihydro-1H-pyrazol-4-yl}acetic acid |
| 35 | 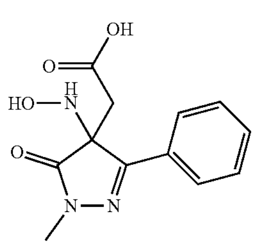 [SMILES: CN1N=C(c2ccccc2)C(CC(=O)O)(NO)C1=O] | 2-[4-(hydroxyamino)-1-methyl-5-oxo-3-phenyl-4,5-dihydro-1H-pyrazol-4-yl]acetic acid |

TABLE 1-continued

Pyrazolone Derivative Compounds of the Disclosure

| Compound No. | Compound Structure | Compound Name |
|---|---|---|
| 36 | 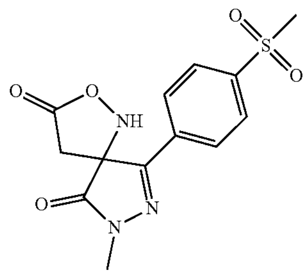 [SMILES: CN1N=C(c2ccc(S(C)(=O)=O)cc2)C2(CC(=O)ON2)C1=O] | 9-(4-methanesulfonylphenyl)-7-methyl-2-oxa-1,7,8-triazaspiro[4.4]non-8-ene-3,6-dione |
| 37 | 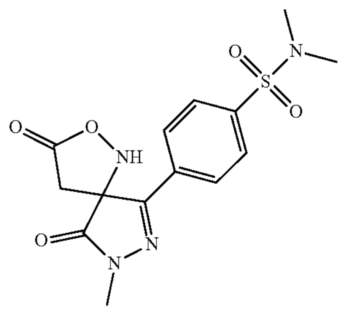 [SMILES: CN1N=C(c2ccc(S(=O)(=O)N(C)C)cc2)C2(CC(=O)ON2)C1=O] | N,N-dimethyl-4-{8-methyl-3,9-dioxo-2-oxa-1,7,8-triazaspiro[4.4]non-6-en-6-yl}benzene-1-sulfonamide |
| 38 | 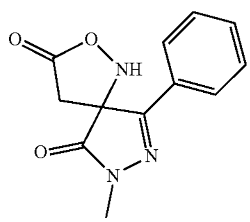 [SMILES: CN1N=C(c2ccccc2)C2(CC(=O)ON2)C1=O] | 7-methyl-9-phenyl-2-oxa-1,7,8-triazaspiro[4.4]non-8-ene-3,6-dione |
| 39 | 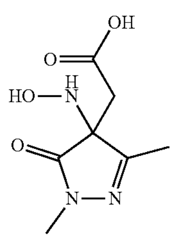 | 2-[4-(hydroxyamino)-1,3-dimethyl-5-oxo-4,5-dihydro-1H-pyrazol-4-yl]acetic acid |
| 40 | 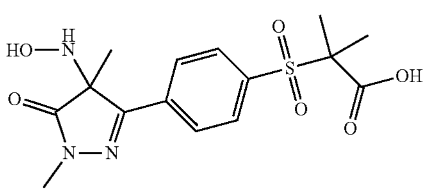 [SMILES: CN1N=C(c2ccc(S(=O)(=O)C(C)(C)C(=O)O)cc2)C(C)(NO)C1=O] | 2-{4-[4-(hydroxyamino)-1,4-dimethyl-5-oxo-4,5-dihydro-1H-pyrazol-3-yl]benzenesulfonyl}-2-methylpropanoic acid |
| 41 | 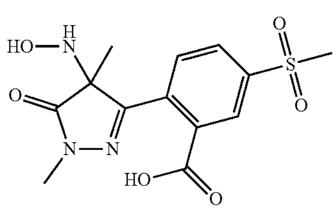 [SMILES: CN1N=C(c2ccc(S(C)(=O)=O)cc2C(=O)O)C(C)(NO)C1=O] | 2-[4-(hydroxyamino)-1,4-dimethyl-5-oxo-4,5-dihydro-1H-pyrazol-3-yl]-5-methanesulfonylbenzoic acid |

TABLE 1-continued

Pyrazolone Derivative Compounds of the Disclosure

| Compound No. | Compound Structure | Compound Name |
|---|---|---|
| 42 | 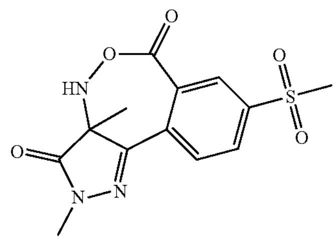 | 12-methanesulfonyl-4,6-dimethyl-8-oxa-3,4,7-triazatricyclo[8.4.0.0$^{2,6}$]tetradeca-1(14),2,10,12-tetraene-5,9-dione |
| 43 | 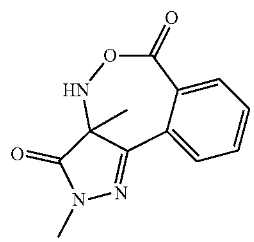 | 4,6-dimethyl-8-oxa-3,4,7-triazatricyclo[8.4.0.0$^{2,6}$]tetradeca-1(14),2,10,12-tetraene-5,9-dione |
| 44 | 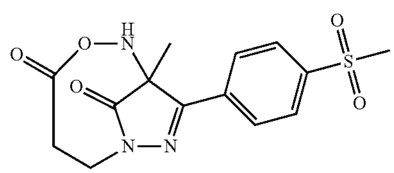 [SMILES: CC12NOC(=O)CCN(N=C1c1ccc(S(C)(=O)=O)cc1)C2=O] | 8-(4-methanesulfonylphenyl)-7-methyl-5-oxa-1,6,9-triazabicyclo[5.2.1]dec-8-ene-4,10-dione |
| 45 | 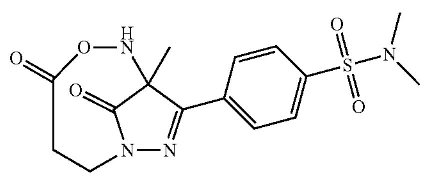 [SMILES: CN(C)S(=O)(=O)c1ccc(C2=NN3CCC(=O)ONC2(C)C3=O)cc1] | N,N-dimethyl-4-{7-methyl-4,10-dioxo-5-oxa-1,6,9-triazabicyclo[5.2.1]dec-8-en-8-yl}benzene-1-sulfonamide |
| 46 | 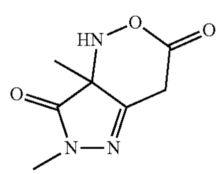 | 2,3a-dimethyl-2H,3H,3aH,4H,6H,7H-pyrazolo[4,3-c][1,2]oxazine-3,6-dione |
| 47 | 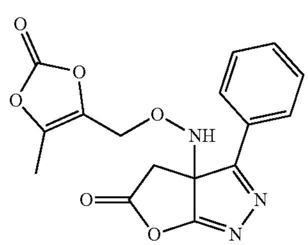 [SMILES: Cc1oc(=O)oc1CONC12CC(=O)OC1=NN=C2c1ccccc1] | 3a-(((5-methyl-2-oxo-1,3-dioxol-4-yl)methoxy)amino)-3-phenyl-3aH-furo[2,3-c]pyrazol-5(4H)-one |
| 48 | 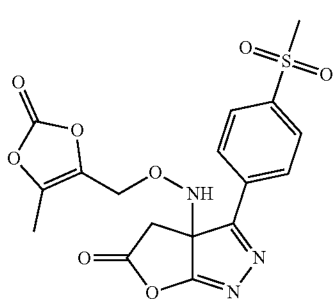 [SMILES: Cc1oc(=O)oc1CONC12CC(=O)OC1=NN=C2c1ccc(S(C)(=O)=O)cc1] | 3a-(((5-methyl-2-oxo-1,3-dioxol-4-yl)methoxy)amino)-3-(4-(methylsulfonyl)phenyl)-3aH-furo[2,3-c]pyrazol-5(4H)-one |

TABLE 1-continued

Pyrazolone Derivative Compounds of the Disclosure

| Compound No. | Compound Structure | Compound Name |
|---|---|---|
| 49 | 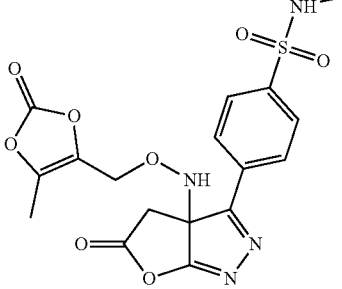 | N-methyl-4-(3a-(((5-methyl-2-oxo-1,3-dioxol-4-yl)methoxy)amino)-5-oxo-4,5-dihydro-3aH-furo[2,3-c]pyrazol-3-yl)benzenesulfonamide |
| 50 | 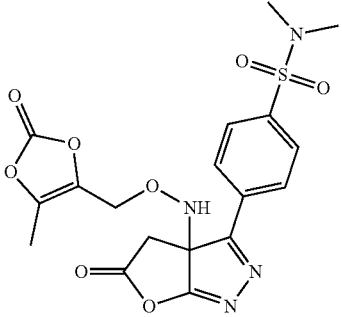 [SMILES: Cc1oc(=O)oc1CONC12CC(=O)OC1=NN=C2c1ccc(S(=O)(=O)N(C)C)cc1] | N,N-dimethyl-4-(3a-(((5-methyl-2-oxo-1,3-dioxol-4-yl)methoxy)amino)-5-oxo-4,5-dihydro-3aH-furo[2,3-c]pyrazol-3-yl)benzenesulfonamide |
| 51 | 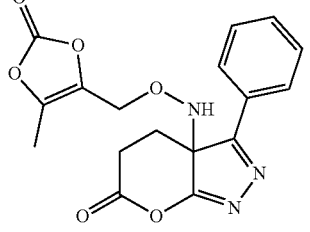 | 3a-(((5-methyl-2-oxo-1,3-dioxol-4-yl)methoxy)amino)-3-phenyl-4,5-dihydropyrano[2,3-c]pyrazol-6(3aH)-one |
| 52 | 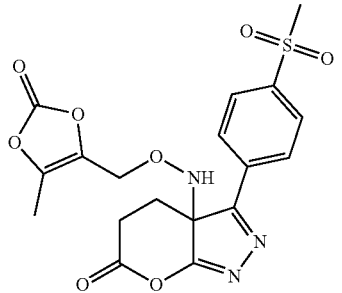 [SMILES: Cc1oc(=O)oc1CONC12CCC(=O)OC1=NN=C2c1ccc(S(C)(=O)=O)cc1] | 3a-(((5-methyl-2-oxo-1,3-dioxol-4-yl)methoxy)amino)-3-(4-(methylsulfonyl)phenyl)-4,5-dihydropyrano[2,3-c]pyrazol-6(3aH)-one |
| 53 | 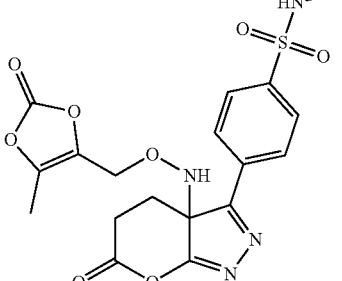 | N-methyl-4-(3a-(((5-methyl-2-oxo-1,3-dioxol-4-yl)methoxy)amino)-6-oxo-3a,4,5,6-tetrahydropyrano[2,3-c]pyrazol-3-yl)benzenesulfonamide |

TABLE 1-continued

Pyrazolone Derivative Compounds of the Disclosure

| Compound No. | Compound Structure | Compound Name |
|---|---|---|
| 54 | 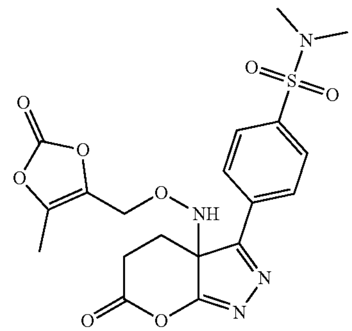 [SMILES: Cc1oc(=O)oc1CONC12CCC(=O)OC1=NN=C2c1ccc(S(=O)(=O)N(C)C)cc1] | N,N-dimethyl-4-(3a-(((5-methyl-2-oxo-1,3-dioxol-4-yl)methoxy)amino)-6-oxo-3a,4,5,6-tetrahydropyrano[2,3-c]pyrazol-3-yl)benzenesulfonamide |
| 55 | 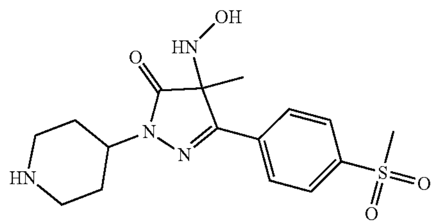 [SMILES: CC1(NO)C(=O)N(C2CCNCC2)N=C1c1ccc(S(C)(=O)=O)cc1] | 4-(Hydroxyamino)-3-(4-methanesulfonylphenyl)-4-methyl-1-(piperidin-4-yl)-4,5-dihydro-1H-pyrazol-5-one |
| 56 | 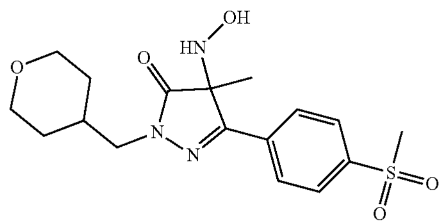 [SMILES: CC1(NO)C(=O)N(CC2CCOCC2)N=C1c1ccc(S(C)(=O)=O)cc1] | 4-(Hydroxyamino)-3-(4-methanesulfonylphenyl)-4-methyl-1-(oxan-4-ylmethyl)-4,5-dihydro-1H-pyrazol-5-one |

In particular embodiments, a compound from Table 1 is utilized as a pharmaceutically acceptable salt thereof.

3.3 Measuring Nitroxyl Donating Ability

Compounds are easily tested for nitroxyl donation by routine experiments. Although it is typically impractical to directly measure whether nitroxyl is donated, several analytical approaches are accepted as suitable for determining whether a compound donates nitroxyl. For example, the compound of interest can be placed in solution, for example in phosphate buffered saline ("PBS") or in a phosphate buffered solution at a pH of about 7.4, in a sealed container. After sufficient time for disassociation has elapsed, such as from several minutes to several hours, the headspace gas is withdrawn and analyzed to determine its composition, such as by gas chromatography and/or mass spectrometry. If the gas $N_2O$ is formed (which occurs by HNO dimerization), the test is positive for nitroxyl donation and the compound is deemed to be a nitroxyl donor.

Alternatively, the compound of interest can be placed in a solution of tris(4,6-dimethyl-3-sulfanatophenyl)phosphine trisodium salt (TXPTS) in e.g., a phosphate buffered solution at a pH of about 7.4. The amount of nitroxyl released from the compound of interest can be detected by monitoring the formation of TXPTS aza-ylide by $^1$H NMR. See Reisz et al., Org. Lett. 11:2719-2721 (2009), Reisz et al., J. Am. Chem. Soc. 133:11675-11685 (2011) and Guthrie et al., J. Org. Chem. 80:1338-1348 (2015). Accordingly, if TXPTS aza-ylide is formed, the test is positive for nitroxyl donation.

If desired, nitroxyl donation also can be detected by exposing the test compound to metmyoglobin ("$Mb^{3+}$"). See Bazylinski et al., J. Amer. Chem. Soc. 107(26):7982-7986 (1985). Nitroxyl reacts with $Mb^{3+}$ to form a $Mb^{2+}$—NO complex, which can be detected by changes in the ultraviolet/visible spectrum or by electron paramagnetic resonance ("EPR"). The $Mb^{2+}$—NO complex has an EPR signal centered around a g-value of about 2. Nitric oxide, on the other hand, reacts with $Mb^{3+}$ to form an $Mb^{3+}$—NO complex that has a negligible, if any, EPR signal. Accordingly, if a compound reacts with $Mb^{3+}$ to form a complex detectable by common methods, such as ultraviolet/visible or EPR, then the test is positive for nitroxyl donation.

The level of nitroxyl donating ability can be expressed as a percentage of a compound's theoretical stoichiometric maximum. A compound that donates a "significant level of nitroxyl" means, in various embodiments, a compound that donates about 40% or more, about 50% or more, about 60% or more, about 70% or more, about 80% or more, about 90% or more, or about 95% or more of its theoretical maximum amount of nitroxyl. In particular embodiments, a compound donates from about 70% to about 90% of its theoretical maximum amount of nitroxyl. In particular embodiments, a compound donates from about 85% to about 95% of its theoretical maximum amount of nitroxyl. In particular embodiments, a compound donates from about 90% to about 95% of its theoretical maximum amount of nitroxyl. Compounds that donate less than about 40%, or less than about 50%, of their theoretical maximum amount of nitroxyl are still nitroxyl donors and can be used in the methods disclosed. A compound that donates less than about 50% of its theoretical amount of nitroxyl can be used in the methods disclosed, but may require higher dosing levels as compared to a compound that donates a higher level of nitroxyl.

Testing for nitroxyl donation can be performed at a physiologically relevant pH. In particular embodiments, a compound of the disclosure is capable of donating nitroxyl at physiological pH (i.e., a pH of about 7.4) and physiological temperature (i.e., a temperature of about 37° C.) (together, "physiological conditions"). In particular embodiments, a compound of the disclosure can donate about 40% or more of its theoretical maximum (i.e., 100%) amount of nitroxyl under physiological conditions. In particular embodiments, a compound of the disclosure can donate about 50% or more of its theoretical maximum amount of nitroxyl under physiological conditions. In particular embodiments, a compound of the disclosure can donate about 60% or more of its theoretical maximum amount of nitroxyl under physiological conditions. In particular embodiments, a compound of the disclosure can donate about 70% or more of its theoretical maximum amount of nitroxyl under physiological conditions. In particular embodiments, a compound of the disclosure can donate about 80% or more of its theoretical maximum amount of nitroxyl under physiological conditions. In particular embodiments, a compound of the disclosure can donate about 90% or more of its theoretical maximum amount of nitroxyl under physiological conditions.

It will be understood that a compound of the disclosure might also donate a limited amount of nitric oxide, so long as the amount of nitroxyl donation exceeds the amount of nitric oxide donation. In certain embodiments, a compound of the disclosure can donate about 25 mole % or less of nitric oxide under physiological conditions. In particular embodiments, a compound of the disclosure can donate about 20 mole % or less of nitric oxide under physiological conditions. In particular embodiments, a compound of the disclosure can donate about 15 mole % or less of nitric oxide under physiological conditions. In particular embodiments, a compound of the disclosure can donate about 10 mole % or less of nitric oxide under physiological conditions. In particular embodiments, a compound of the disclosure can donates about 5 mole % or less of nitric oxide under physiological conditions. In particular embodiments, a compound of the disclosure can donate about 2 mole % or less of nitric oxide under physiological conditions. In particular embodiments, a compound of the disclosure can donate an insignificant amount (e.g., about 1 mole % or less) of nitric oxide under physiological conditions.

3.4 Pharmaceutical Compositions

The disclosure also encompasses pharmaceutical compositions comprising at least one compound of formula (Ia), (Ib), (Ic), (Id), (Ie), (If), (Ig), (Ih), (Ii), (Ij) or (Ik) or a compound from Table 1 and at least one pharmaceutically acceptable excipient. Examples of pharmaceutically acceptable excipients include those described above, such as carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and any combination thereof. The selection and use of pharmaceutically acceptable excipients is taught, e.g., in Troy, Ed., *Remington: The Science and Practice of Pharmacy*, 21$^{st}$ Ed. (Lippincott Williams & Wilkins, Baltimore, Md., 2005).

In one embodiment, the at least one pharmaceutically acceptable excipient is selected from lactose, microcrystalline cellulose, croscarmellose, or any mixture thereof. In another embodiment, the at least one pharmaceutically acceptable excipient is selected from lactose, microcrystalline cellulose, croscarmellose sodium, or any mixture thereof. Lactose, the naturally-occurring disaccharide of galactose and glucose, being available in a range of varieties, e.g., granulated, sieved, milled, spray dried, and anhydrous, is a well-accepted excipient for medical and pharmaceutical uses. Reilly, "Pharmaceutical Necessities," pp. 1015-1050 in *Remington: The Science and Practice of Pharmacy* (Gennaro, ed., 20$^{th}$ ed., Lippincott, Williams & Wilkins, Baltimore, Md., 2000). Microcrystalline cellulose is disclosed to be a most resourceful excipient because of the profusion of grades available for different needs and its physical properties that support a variety of functional requirements, e.g., as a bulking agent, disintegrant, binder, lubricant, glidant, and/or stability enhancer. Baboota et al., "Microcrystalline cellulose as a versatile excipient in drug research," *J. Young Pharmacists* 1:6-12 (2009). Croscarmellose is an internally cross-linked carboxymethylcellulose; croscarmellose sodium is the sodium salt of an internally cross-linked, at least partially O-(carboxymethylated) cellulose. Either form of this excipient has reduced water solubility, attributed to the cross-linking, thus providing, inter alia, enhanced dissolution characteristics. Boylan et al., pp. 2623-2624 in *Encyclopedia of Pharmaceut. Technol.* (1$^{st}$ ed., Marcel Dekker, New York, 1988).

The pharmaceutical compositions can be formulated for administration in solid or liquid form, including those adapted for the following: (1) oral administration, for example, as drenches (for example, aqueous or non-aqueous solutions or suspensions), tablets (for example, those targeted for buccal, sublingual and systemic absorption), caplets, boluses, powders, granules, pastes for application to the tongue, hard gelatin capsules, soft gelatin capsules, mouth sprays, troches, lozenges, pellets, syrups, suspensions, elixirs, liquids, emulsions and microemulsions; or (2) parenteral administration by, for example, subcutaneous, intramuscular, intravenous or epidural injection as, for example, a sterile solution or suspension. The pharmaceutical compositions can be for immediate, sustained or controlled release.

In one particular embodiment, the pharmaceutical composition is formulated for intravenous administration. In another embodiment, the pharmaceutical composition is formulated for intravenous administration by continuous infusion.

In another embodiment, the pharmaceutical composition is formulated for oral administration. In another embodiment, the pharmaceutical composition is formulated for oral administration as a liquid dosage form. In another embodiment, the pharmaceutical composition is formulated for oral administration in solid dosage form. In particular embodiments where the pharmaceutical composition is formulated as an oral liquid or solid dosage form, polyethylene glycol, such as polyethylene glycol 300 ("PEG300"), polyethylene glycol 400 ("PEG400"), and mixtures thereof, can serve as an excipient.

The pharmaceutical composition can be prepared as any appropriate unit dosage form, such as capsule, sachet, tablet, powder, granule, solution, suspension in an aqueous liquid, suspension in a non-aqueous liquid, oil-in-water liquid emulsion, water-in-oil liquid emulsion, liposomes or bolus. In one embodiment, the pharmaceutical composition is formulated as a tablet. In another embodiment, the pharmaceutical composition is formulated as a capsule.

Tablets can be made by compression or molding, optionally with one or more accessory ingredients. Compressed tablets can be prepared by compressing in a suitable machine the therapeutic agent or agents in a free-flowing form such as a powder or granules, optionally mixed with a binder, lubricant, inert diluent, preservative, surface-active or dispersing agent. Molded tablets can be made by molding in a suitable machine a mixture of the powdered compound moistened with an inert liquid diluent. The tablets can be optionally coated or scored and can be formulated so as to provide slow or controlled release of the active ingredient therein. Methods of formulating such slow or controlled release compositions of pharmaceutically active ingredients, such as the therapeutic agents herein and other compounds known in the art, are known in the art and disclosed in issued U.S. patents, some of which include, but are not limited to, U.S. Pat. Nos. 4,369,174, 4,842,866, and the references cited therein. Coatings can be used for delivery of compounds to the intestine (see, e.g., U.S. Pat. Nos. 6,638,534, 5,217,720, 6,569,457, and the references cited therein). An artisan will recognize that in addition to tablets, other dosage forms can be formulated to provide slow or controlled release of the active ingredient. Such dosage forms include, but are not limited to, capsules, granulations and gel-caps.

Pharmaceutical compositions suitable for topical administration include, without limitation, lozenges comprising the ingredients in a flavored basis, such as sucrose, acacia and tragacanth; and pastilles comprising the active ingredient in a flavored basis or in an inert basis, such as gelatin and glycerin.

Various embodiments of pharmaceutical compositions suitable for parenteral administration include, without limitation, either aqueous sterile injection solutions or non-aqueous sterile injection solutions, each containing, for example, anti-oxidants, buffers, bacteriostats and solutes that render the formulation isotonic with the blood of the intended recipient; and aqueous sterile suspensions and non-aqueous sterile suspensions, each containing, for example, suspending agents and thickening agents. The formulations can be presented in unit-dose or multi-dose containers, for example, sealed ampules or vials, and can be stored in a freeze dried (lyophilized) condition requiring only the addition of a sterile liquid carrier, such as water, immediately prior to use.

Pharmaceutical compositions administered parenterally can be administered in an acidic, neutral or basic solution. In one embodiment, pharmaceutical compositions are formulated in an acidic solution having a pH of from about 4 to about 5, for instance, a pH of about 4, about 4.5, about 4.8, or about 5, including values there between. While a pH of about 4 has generally been considered optimal for formulating nitroxyl donating compositions to achieve adequate stability of the compound, it has been discovered that formulating under such acidic conditions can potentially cause or exacerbate venous irritation following parenteral administration. The amount of irritation can be attenuated by formulating the pharmaceutical compositions in less acidic or even neutral solutions. Accordingly, in particular embodiments, a pharmaceutical composition formulated for parenteral use at a pH of from about 5 to about 6.2 (e.g., pH of about 5, about 5.5, about 5.8, about 6, or about 6.2, including values there between).

3.5 Methods of Use

In one aspect, the disclosure provides a method of increasing in vivo nitroxyl levels, comprising administering to a patient in need thereof an effective amount of a compound or a pharmaceutical composition as disclosed herein. In various embodiments, the patient has, is suspected of having, or is at risk of having or developing a condition that is responsive to nitroxyl therapy.

In particular embodiments, the disclosure provides a method of treating, preventing or delaying the onset and/or development of a condition, comprising administering to a patient (including a patient identified as in need of such treatment, prevention or delay) an effective amount of a compound or a pharmaceutical composition as disclosed herein. Identifying a patient in need thereof can be in the judgment of a physician, clinical staff, emergency response personnel or other health care professional and can be subjective (e.g., opinion) or objective (e.g., measurable by a test or diagnostic method).

Particular conditions embraced by the methods disclosed herein include, without limitation, cardiovascular diseases, ischemia/reperfusion injury, and pulmonary hypertension.

3.5.1 Cardiovascular Diseases

In one embodiment, the disclosure provides a method of treating a cardiovascular disease, comprising administering an effective amount of a compound or a pharmaceutical composition as disclosed herein to a patient in need thereof.

Examples of cardiovascular diseases and symptoms that can usefully be treated with the compounds and compositions disclosed herein include cardiovascular diseases that are responsive to nitroxyl therapy, coronary obstructions, coronary artery disease ("CAD"), angina, heart attack, myocardial infarction, high blood pressure, ischemic cardiomyopathy and infarction, pulmonary congestion, pulmonary edema, cardiac fibrosis, valvular heart disease, pericardial disease, circulatory congestive states, peripheral edema, ascites, Chagas' disease, ventricular hypertrophy, heart valve disease, heart failure, diastolic heart failure, systolic heart failure, congestive heart failure, acute congestive heart failure, acute decompensated heart failure, and cardiac hypertrophy.

3.5.1.1 Heart Failure

The compounds and compositions of the disclosure can be used to treat patients suffering from heart failure. The heart failure can be of any type or form, including any of the heart failures disclosed herein. Nonlimiting examples of heart failure include early stage heart failure, Class I, II, III and IV heart failure, acute heart failure, congestive heart failure ("CHF") and acute CHF. In one embodiment, the compounds and compositions of the disclosure can be used to treat acute decompensated heart failure.

In embodiments where the compounds and pharmaceutical compositions of the disclosure are used to treat patients suffering from heart failure, another active agent that treats heart failure can also be administered. In one such embodiment, the compound or pharmaceutical composition of the disclosure can be administered in conjunction with a positive inotrope such as a beta-agonist. Examples of beta-agonists include, without limitation, dopamine, dobutamine, isoproterenol, analogs of such compounds and derivatives of such compounds. In another embodiment, the compound or pharmaceutical composition of the disclosure can be administered in conjunction with a beta-adrenergic receptor antagonist (also referred to herein as beta-antagonist or beta-blocker). Examples of beta-antagonists include, without limitation, propranolol, metoprolol, bisoprolol, bucindolol, and carvedilol.

Compounds of the disclosure compounds can be administered as pharmaceutical formulations to patients in need of modulating in vivo nitroxyl levels. For instance, a pharmaceutical formulation comprising a compound of the disclosure can be administered to a patient intravenously.

3.5.1.2 Ischemia/Reperfusion Injury

In another embodiment, the disclosed subject matter provides a method of treating, preventing or delaying the onset and/or development of ischemia/reperfusion injury, comprising administering an effective amount of a compound or pharmaceutical composition as disclosed herein to a subject in need thereof.

In a particular embodiment, the method is for preventing ischemia/reperfusion injury. In a particular embodiment, a compound or pharmaceutical composition of the disclosure is administered prior to the onset of ischemia. In a particular embodiment, a pharmaceutical composition of the disclosure is administered prior to procedures in which myocardial ischemia can occur, for example an angioplasty or surgery, such as a coronary artery bypass graft surgery. In a particular embodiment, a pharmaceutical composition of the disclosure is administered after ischemia but before reperfusion. In a particular embodiment, a pharmaceutical composition of the disclosure is administered after ischemia and reperfusion.

In another embodiment, a pharmaceutical composition of the disclosure can be administered to a patient who is at risk for an ischemic event. In a particular embodiment, a pharmaceutical composition of the disclosure is administered to a patient at risk for a future ischemic event, but who has no present evidence of ischemia. The determination of whether a patient is at risk for an ischemic event can be performed by any method known in the art, such as by examining the patient or the patient's medical history. In a particular embodiment, the patient has had a prior ischemic event. Thus, the patient can be at risk of a first or subsequent ischemic event. Examples of patients at risk for an ischemic event include patients with known hypercholesterolemia, EKG changes associated with ischemia (e.g., peaked or inverted T-waves or ST segment elevations or depression in an appropriate clinical context), abnormal EKG not associated with active ischemia, elevated CKMB, clinical evidence of ischemia (e.g., crushing sub-sternal chest pain or arm pain, shortness of breath and/or diaphoresis), prior history of myocardial infarction ("MI"), elevated serum cholesterol, sedentary lifestyle, angiographic evidence of partial coronary artery obstruction, echocardiographic evidence of myocardial damage, or any other evidence of a risk for a future ischemic event. Examples of ischemic events include, without limitation, MI and neurovascular ischemia, such as a cerebrovascular accident ("CVA").

In another embodiment, the subject of treatment is an organ that is to be transplanted. In a particular embodiment, a pharmaceutical composition of the disclosure can be administered prior to reperfusion of the organ in a transplant recipient. In a particular embodiment, a pharmaceutical composition of the disclosure can be administered prior to removal of the organ from the donor, for example through the perfusion cannulas used in the organ removal process. If the organ donor is a live donor, for example a kidney donor, the compounds or pharmaceutical compositions of the disclosure can be administered to the organ donor. In a particular embodiment, the compounds or pharmaceutical compositions of the disclosure are administered by storing the organ in a solution comprising the compound or pharmaceutical composition. For example, a compound or pharmaceutical composition of the disclosure can be included in the organ preservation solution, such as the University of Wisconsin "UW" solution, which is a solution comprising hydroxyethyl starch substantially free of ethylene glycol, ethylene chlorohydrin and acetone (see U.S. Pat. No. 4,798,824). In a particular embodiment, a pharmaceutical composition of the disclosure that is administered is such that ischemia/reperfusion injury to the tissues of the organ is reduced upon reperfusion in the recipient of transplanted organ. In a particular embodiment, the method reduces tissue necrosis (the size of infarct) in at-risk tissues.

Ischemia/reperfusion injury can damage tissues other than those of the myocardium and the disclosed subject matter embraces methods of treating or preventing such damage. In various embodiments, the ischemia/reperfusion injury is non-myocardial. In particular embodiments, the method reduces injury from ischemia/reperfusion in the tissue of the brain, liver, gut, kidney, bowel, or any part of the body other than the myocardium. In another embodiment, the patient is at risk for such injury. Selecting a person at risk for non-myocardial ischemia could include a determination of the indicators used to assess risk for myocardial ischemia. However, other factors can indicate a risk for ischemia/reperfusion in other tissues. For example, surgery patients often experience surgery related ischemia. Thus, patients scheduled for surgery could be considered at risk for an ischemic event. The following risk factors for stroke (or a subset of these risk factors) could demonstrate a patient's risk for ischemia of brain tissue: hypertension, cigarette smoking, carotid artery stenosis, physical inactivity, diabetes mellitus, hyperlipidemia, transient ischemic attack, atrial fibrillation, CAD, CHF, past MI, left ventricular dysfunction with mural thrombus, and mitral stenosis. Ingall, *Postgrad. Med.* 107(6):34-50 (2000). Further, complications of untreated infectious diarrhea in the elderly can include myocardial, renal, cerebrovascular and intestinal ischemia. Slotwiner-Nie et al., *Gastroenterol. Clin. N. Amer.* 30(3): 625-635 (2001). Alternatively, patients could be selected based on risk factors for ischemic bowel, kidney and/or liver disease. For example, treatment would be initiated in elderly patients at risk of hypotensive episodes (such as surgical blood loss). Thus, patients presenting with such an indication would be considered at risk for an ischemic event. In another embodiment, the patient has any one or more of the conditions listed herein, such as diabetes mellitus and hypertension. Other conditions that can result in ischemia, such as cerebral arteriovenous malformation, could demonstrate a patient's risk for an ischemic event.

3.5.2 Pulmonary Hypertension

In another embodiment, a compounds or pharmaceutical composition of the disclosure can be used to prevent or delay the onset and/or development of pulmonary hypertension. In one such embodiment, a compounds or pharmaceutical composition of the disclosure can be used to prevent or delay the onset and/or development of pulmonary arterial hypertension ("PAH").

In another embodiment, the disclosed subject matter provides a method of reducing mean pulmonary arterial pressure ("MPAP"), comprising administering an effective amount of a compound or a pharmaceutical composition disclosed herein to a patient in need thereof. In another embodiment, the MPAP is reduced by up to about 50%. In another embodiment, the MPAP is reduced by up to about 25%. In another embodiment, the MPAP is reduced by up to about 20%. In another embodiment, the MPAP is reduced by up to about 15%. In another embodiment, the MPAP is reduced by up to 10%. In another embodiment, the MPAP is reduced by up to about 5%. In another embodiment, the MPAP is reduced to be from about 12 mmHg to about 16 mmHg. In another embodiment, the MPAP is reduced to be about 15 mmHg.

3.6 Administration Modes, Regimens and Dose Levels

The compounds and pharmaceutical compositions of the disclosure can be administered via parenteral (e.g., subcutaneous, intramuscular, intravenous or intradermal) administration. In certain embodiments, the compound or pharmaceutical composition is administered by intravenous infusion. In other embodiments, the compounds and pharmaceutical compositions of the disclosure can be administered by oral administration.

When a pharmaceutical composition comprising a compound of the disclosure is administered, dosages are expressed based on the amount of active pharmaceutical ingredient, i.e., the amount of compound(s) of the disclosure present in the pharmaceutical composition.

In a variety of embodiments, including various oral administration embodiments, the compounds or pharmaceutical compositions of the disclosure are administered according to a weight-based daily dosing regimen, either as a single daily dose ("QD") or in multiple divided doses administered, e.g., twice a day ("BID"), 3 times a day ("TID"), or four times a day ("QID").

In certain embodiments, the compound or pharmaceutical composition of the disclosure is administered in a dose of at least about 0.5 mg/kg/d, at least about 0.75 mg/kg/d, at least about 1.0 mg/kg/d, at least about 1.5 mg/kg/d, at least about 2 mg/kg/d, at least about 2.5 mg/kg/d, at least about 3 mg/kg/d, at least about 4 mg/kg/d, at least about 5 mg/kg/d, at least about 7.5 mg/kg/d, at least about 10 mg/kg/d, at least about 12.5 mg/kg/d, at least about 15 mg/kg/d, at least about 17.5 mg/kg/d, at least about 20 mg/kg/d, at least about 25 mg/kg/d, at least about 30 mg/kg/d, at least about 35 mg/kg/d, at least about 40 mg/kg/d, at least about 45 mg/kg/d, at least about 50 mg/kg/d, at least about 60 mg/kg/d, at least about 70 mg/kg/d, at least about 80 mg/kg/d, at least about 90 mg/kg/d, or at least about 100 mg/kg/d.

In certain embodiments, the compound or pharmaceutical composition of the disclosure is administered at a dose of no more than about 100 mg/kg/d, no more than about 100 mg/kg/d, no more than about 90 mg/kg/d, no more than about 80 mg/kg/d, no more than about 80 mg/kg/d, no more than about 75 mg/kg/d, no more than about 70 mg/kg/d, no more than about 60 mg/kg/d, no more than about 50 mg/kg/d, no more than about 45 mg/kg/d, no more than about 40 mg/kg/d, no more than about 35 mg/kg/d, no more than about 30 mg/kg/d.

In a variety of embodiments, the dose is from about 0.001 mg/kg/d to about 10,000 mg/kg/d. In certain embodiments, the dose is from about 0.01 mg/kg/d to about 1,000 mg/kg/d. In certain embodiments, the dose is from about 0.01 mg/kg/d to about 100 mg/kg/d. In certain embodiments, the dose is from about 0.01 mg/kg/d to about 10 mg/kg/d. In certain embodiments, the dose is from about 0.1 mg/kg/d to about 1 mg/kg/d. In certain embodiments, the dose is less than about 1 g/kg/d.

In certain embodiments, a compound or pharmaceutical composition of the disclosure is administered in a dose range in which the low end of the range is any amount from about 0.1 mg/kg/day to about 90 mg/kg/day and the high end of the range is any amount from about 1 mg/kg/day to about 100 mg/kg/day (e.g., from about 0.5 mg/kg/day to about 2 mg/kg/day in one series of embodiments and from about 5 mg/kg/day to about 20 mg/kg/day in another series of embodiments).

In particular embodiments, the compound or pharmaceutical composition of the disclosure is administered in a dose range of about 3 to about 30 mg/kg, administered QD, BID, or TID.

In certain embodiments, compounds or pharmaceutical compositions of the disclosure are administered according to a flat (i.e., non-weight-based) dosing regimen, either QD or in multiple divided doses administered, e.g., BID, TID, or QID.

In various embodiments, the compound or pharmaceutical composition of the disclosure is administered at a dose of at least about 0.01 grams/day (g/d), at least about 0.05 g/d, at least about 0.1 g/d, at least about 0.5 g/d, at least about 1 g/d, at least about 1.5 g/d, at least about 2.0 g/d, at least about 2.5 g/d, at least about 3.0 g/d, or at least about 3.5 g/d.

In various embodiments, the compound or pharmaceutical composition of the disclosure is administered at a dose of no more than about 5 g/d, no more than about 4.5 g/d, no more than about 4 g/d, no more than about 3.5 g/d, no more than about 3 g/d, no more than about 2.5 g/d, or no more than about 2 g/d.

In certain embodiments, the compound or pharmaceutical composition of the disclosure is administered in a dose of about 0.01 grams per day to about 4.0 grams per day. In certain embodiments, a compound or pharmaceutical composition of the disclosure can be administered at a dose in which the low end of the range is any amount from about 0.1 mg/day to about 400 mg/day and the high end of the range is any amount from about 1 mg/day to about 4000 mg/day. In certain embodiments, the compound or pharmaceutical composition is administered in a dose of about 5 mg/day to about 100 mg/day. In various embodiments, the compound or pharmaceutical composition is administered at a dose of from about 150 mg/day to about 500 mg/day.

The dosing interval for parenteral or oral administration can be adjusted according to the needs of the patient. For longer intervals between administrations, extended release or depot formulations can be used.

For intravenous administration, the dose can usefully be expressed per unit time, either as a fixed amount per unit time or as a weight-based amount per unit time.

In various embodiments, a compound or pharmaceutical composition of the disclosure is administered intravenously in an amount of at least about 0.1 µg/kg/min, at least about 0.2 µg/kg/min, at least about 0.3 µg/kg/min, at least about 0.4 µg/kg/min, at least about 0.5 µg/kg/min, at least about 1 µg/kg/min, at least about 2.5 µg/kg/min, at least about 5 µg/kg/min, at least about 7.5 µg/kg/min, at least about 10 µg/kg/min, at least about 11 µg/kg/min, at least about 12 µg/kg/min, at least about 13 µg/kg/min, at least about 14 µg/kg/min, at least about 15 µg/kg/min, at least about 16 µg/kg/min, at least about 17 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36

μg/kg/min, at least about 37 μg/kg/min, at least about 38 μg/kg/min, at least about 39 μg/kg/min, or at least about 40 μg/kg/min.

In various embodiments, the compound or pharmaceutical composition of the present disclosure is administered intravenously in an amount of no more than about 100 μg/kg/min, no more than about 90 μg/kg/min, no more than about 80 μg/kg/min, no more than about 70 μg/kg/min, no more than about 60 μg/kg/min, no more than about 50 μg/kg/min, no more than about 49 μg/kg/min, no more than about 48 μg/kg/min, no more than about 47 μg/kg/min, no more than about 46 μg/kg/min, no more than about 45 μg/kg/min, no more than about 44 μg/kg/min, no more than about 43 μg/kg/min, no more than about 42 μg/kg/min, no more than about 41 μg/kg/min, no more than about 40 μg/kg/min, no more than about 39 μg/kg/min, no more than about 38 μg/kg/min, no more than about 37 μg/kg/min, no more than about 36 μg/kg/min, no more than about 35 μg/kg/min, no more than about 34 μg/kg/min, no more than about 33 μg/kg/min, no more than about 32 μg/kg/min, no more than about 31 μg/kg/min, or no more than about 30 μg/kg/min.

In some embodiments, the compound or pharmaceutical composition of the present disclosure is administered intravenously in an amount ranging from about 0.1 μg/kg/min to about 100 μg/kg/min, about 1 μg/kg/min to about 100 μg/kg/min, about 2.5 μg/kg/min to about 100 μg/kg/min, about 5 μg/kg/min to about 100 μg/kg/min, about 10 μg/kg/min to about 100 μg/kg/min, about 1.0 μg/kg/min to about 80 μg/kg/min, from about 10.0 μg/kg/min to about 70 μg/kg/min, from about 20 μg/kg/min to about 60 μg/kg/min, from about 15 μg/kg/min to about 50 μg/kg/min, from about 0.01 μg/kg/min to about 1.0 μg/kg/min, from about 0.01 μg/kg/min to about 10 μg/kg/min, from about 0.1 μg/kg/min to about 1.0 μg/kg/min, from about 0.1 μg/kg/min to about 10 μg/kg/min, from about 1.0 μg/kg/min to about 5 μg/kg/min, from about 70 μg/kg/min to about 100 μg/kg/min, or from about 80 μg/kg/min to about 90 μg/kg/min.

In particular embodiments, the compound or pharmaceutical composition of the present disclosure is administered intravenously in an amount ranging from about 10 μg/kg/min to about 50 μg/kg/min, about 20 μg/kg/min to about 40 μg/kg/min, about 25 μg/kg/min to about 35 μg/kg/min, or about 30 μg/kg/min to about 40 μg/kg/min. In particular embodiments, a compound or pharmaceutical composition of the present disclosure is administered intravenously in an amount of from about 20 μg/kg/min to about 30 μg/kg/min.

A compound or pharmaceutical composition as disclosed herein can be administered prior to, at substantially the same time with, or after administration of an additional therapeutic agent. The administration regimen can include pretreatment and/or co-administration with the additional therapeutic agent. In such case, the compound or pharmaceutical composition and the additional therapeutic agent can be administered simultaneously, separately, or sequentially.

Examples of administration regimens include without limitation: administration of each compound, pharmaceutical composition or therapeutic agent in a sequential manner; and co-administration of each compound, pharmaceutical composition or therapeutic agent in a substantially simultaneous manner (e.g., as in a single unit dosage form) or in multiple, separate unit dosage forms for each compound, pharmaceutical composition or therapeutic agent.

It will be appreciated by those in the art that the "effective amount" or "dose" ("dose level") will depend on various factors such as the particular administration mode, administration regimen, compound, and pharmaceutical composition selected, as well as the particular condition and patient being treated. For example, the appropriate dose level can vary depending upon the activity, rate of excretion and potential for toxicity of the specific compound or pharmaceutical composition employed; the age, body weight, general health, gender and diet of the patient being treated; the frequency of administration; the other therapeutic agent(s) being co-administered; and the type and severity of the condition.

3.7 Kits Comprising the Compounds or Pharmaceutical Compositions

The disclosure provides kits comprising a compound or a pharmaceutical composition disclosed herein. In a particular embodiment, the kit comprises a compound or a pharmaceutical composition disclosed herein, each in dry form, and a pharmaceutically acceptable liquid diluent.

In particular embodiments, either a compound in dry form or a pharmaceutical composition in dry form contains about 2.0% or less water by weight, about 1.5% or less water by weight, about 1.0% or less water by weight, about 0.5% or less water by weight, about 0.3% or less water by weight, about 0.2% or less water by weight, about 0.1% or less water by weight, about 0.05% or less water by weight, about 0.03% or less water by weight, or about 0.01% or less water by weight.

Pharmaceutically acceptable liquid diluents are known in the art and include but are not limited to sterile water, saline solutions, aqueous dextrose, glycerol, glycerol solutions, and the like. Other examples of suitable liquid diluents are disclosed by Naim, "Solutions, Emulsions, Suspensions and Extracts," pp. 721-752 in *Remington: The Science and Practice of Pharmacy*, 20th Ed. (Lippincott Williams & Wilkins, Baltimore, Md., 2000).

In one embodiment, the kit further comprises instructions for using the compound or pharmaceutical composition. The instructions can be in any appropriate form, such as written or electronic form. In another embodiment, the instructions can be written instructions. In another embodiment, the instructions are contained in an electronic storage medium (e.g., magnetic diskette or optical disk). In another embodiment, the instructions include information as to the compound or pharmaceutical composition and the manner of administering the compound or pharmaceutical composition to a patient. In another embodiment, the instructions relate to a method of use disclosed herein (e.g., treating, preventing and/or delaying onset and/or development of a condition selected from cardiovascular diseases, ischemia/reperfusion injury, pulmonary hypertension and other conditions responsive to nitroxyl therapy).

In another embodiment, the kit further comprises suitable packaging. Where the kit comprises more than one compound or pharmaceutical composition, the compounds or pharmaceutical compositions can be packaged patiently in separate containers, or combined in one container when cross-reactivity and shelf life permit.

Should there be doubt over the agreement of a depicted chemical structure and a chemical name, the chemical name governs.

4. EXAMPLES

The following examples are presented for illustrative purposes and should not serve to limit the scope of the disclosed subject matter.

4.1 Synthesis of Pyrazolone Derivative Compounds

The compounds disclosed herein can be made according to the methods disclosed below or by procedures known in the art. Starting materials for the reactions can be commercially available or can be prepared by known procedures or obvious modifications thereof. For example, some of the starting materials are available from commercial suppliers such as Sigma-Aldrich (St. Louis, Mo.). Others can be prepared by procedures or obvious modifications thereof disclosed in standard reference texts such as *March's Advanced Organic Chemistry* (John Wiley and Sons) and *Larock's Comprehensive Organic Transformations* (VCH Publishers).

The following "General Methods" were employed in specific steps of the compound syntheses disclosed in the Examples, which Examples appear after the General Methods. Throughout the General Methods, "R" represents the phenyl substituent or substituents that may be present on phenyl in a specific synthesis, "R'" is $(C_1-C_4)$alkyl, and "R''" is $(C_1-C_6)$alkyl, $(C_3-C_6)$cycloalkyl, $(C_1-C_4)$haloalkyl, $(C_1-C_4)$perhaloalkyl, $—NH_2$, $—N(H)—(C_1-C_6)$alkyl, or $—N—[(C_1-C_6)alkyl]_2$.

General Method 1: Pyrazolone Synthesis

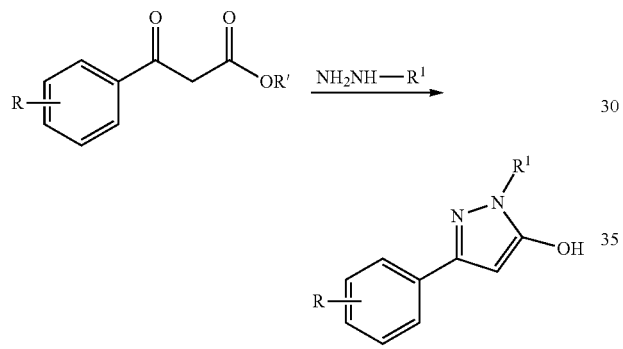

To a solution of the beta-ketoester (1 equiv) in ethanol (5 vol) was added a hydrazine derivative, e.g., $(C_1-C_6)$alkyl-, substituted phenyl-, or unsubstituted phenyl-hydrazine, such as methyl hydrazine, (1.1 equiv) with stirring. The reaction was heated to reflux until analysis showed substantially complete consumption of the starting material (about 3 hours). The reaction was allowed to cool to a temperature of about 25° C. and the solid that formed was collected by filtration, washed with cold ethanol (2 vol), and dried under reduced pressure. Alternatively, after concentration, the compound could be isolated by chromatography, e.g., by silica gel column chromatography.

General Method 2: Bromination by Process A

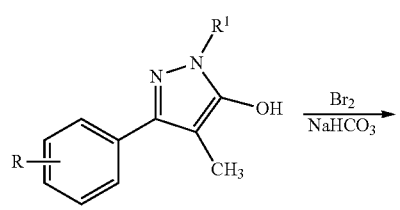

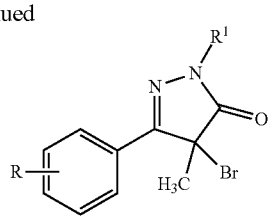

To a solution of the pyrazolone (1 equiv) in dichloromethane ("DCM"):water (1:1, 50 vol) was added sodium bicarbonate (1 equiv). The biphasic reaction mixture was vigorously stirred while bromine (1 equiv) was added dropwise. Stirring was continued for about 5 minutes before the reaction mixture was transferred to a separating funnel and shaken until a clear, colorless aqueous layer resulted. The organic layer was removed, dried over magnesium sulfate, filtered, and concentrated under reduced pressure to provide the brominated product.

General Method 2b: Bromination by Process B

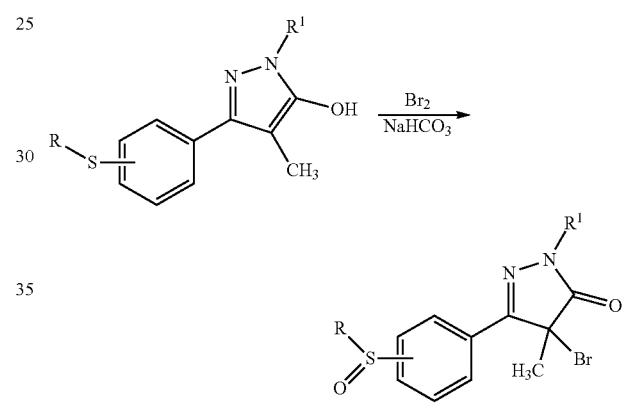

To a solution of the pyrazolone (1 equiv) in DCM:water (1:1, 50 vol) was added sodium bicarbonate (2 equiv). The biphasic reaction mixture was vigorously stirred while bromine (2 equiv) was added dropwise. Stirring was continued for about 5 minutes before the reaction mixture was transferred to a separating funnel and shaken until a clear, colorless aqueous layer resulted. The organic layer was removed, dried over magnesium sulfate, filtered and concentrated under reduced pressure to provide the brominated product.

General Method 3: Bromine Displacement

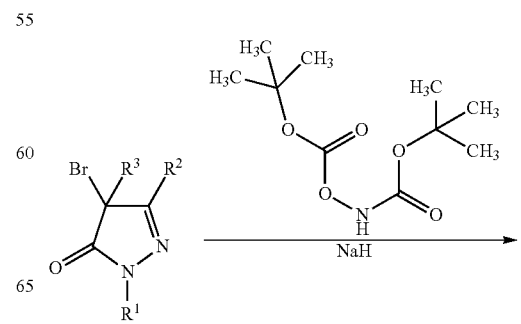

145

-continued

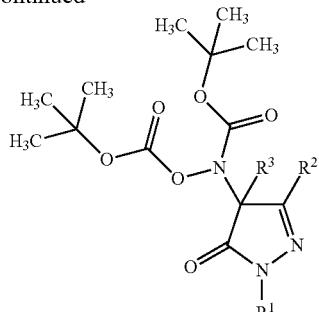

To a solution of N,O-di-BOC-hydroxylamine (1 equiv) in DMF (5 vol) was added sodium hydride (1.2 equiv, 60% dispersion). The reaction mixture was allowed to stand for about 1 hour after which time a brominated pyrazolone, e.g., the brominated pyrazolone synthesized in General Method 2 (1 equiv) was added as a solution in DMF (5 vol). Stirring was continued until substantially complete consumption of the bromide was achieved as determined by LC-MS (in about 1-24 hours). The mixture was diluted with diethyl ether (30 vol), washed with ammonium chloride (1×20 vol), washed with water (3×30 vol), and washed with brine (2×30 vol). The organic portion was dried over sodium sulfate, filtered, and concentrated under reduced pressure. As required, purification was carried out by silica gel column chromatography eluting with heptanes:ethyl acetate gradients.

General Method 4: Deprotection

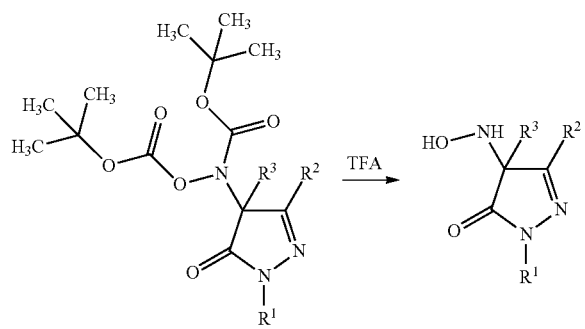

To a solution of the bis-BOC pyrazolone derivative from General Method 3 (1 equiv) in DCM (10 vol) was added trifluoroacetic acid ("TFA", 10 equiv). The reaction mixture was stirred at a temperature of about 25° C. until substantially complete consumption of the starting material was achieved as determined by LC-MS. The solvent was removed under reduced pressure and, as required, the product was purified by a standard method(s) including silica gel column chromatography or reverse phase HPLC.

146

General Method 5: Nitroso Aldol

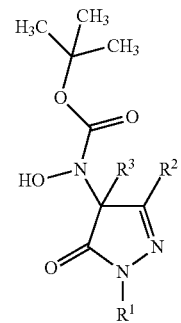

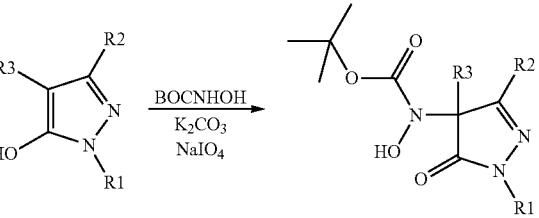

To a solution of a pyrazolone (1 equiv) in ethanol (28 vol) and water (28 vol) was added tert-butyl N-hydroxycarbamate (1.2 equiv) and potassium carbonate (0.35 equiv). Sodium periodate (1.2 equiv) was added and the reaction mixture was stirred at a temperature of about 25° C. for 30 minutes. Additional aliquots of tert-butyl N-hydroxycarbamate (1.2-3.6 equiv) and sodium periodate (1.2-3.6 equiv) were added at 30 minute intervals until reaction completion as determined by LC-MS. The white solid was removed by filtration and the resulting filtrate concentrated under reduced pressure. The product was then used directly or purified using standard methods.

General Method 6: Alkylation

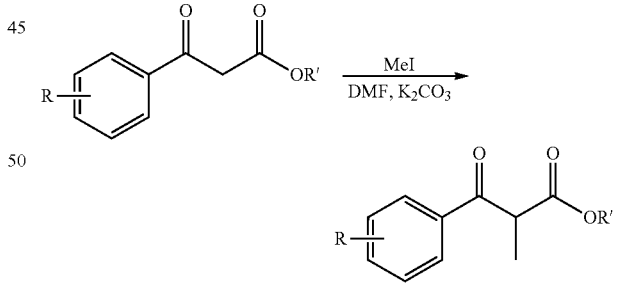

To a solution of the beta ketoester (1 equiv.) in DMF (10-20 vol) was added potassium carbonate (1 equiv.) and methyl iodide (1.1 equiv). The resulting reaction mixture was stirred for 3 hours at room temperature (or until complete consumption of the starting material was observed by LC-MS). Water (10 vol) was added and the resulting solution was extracted into DCM (3×20 vol). The combined organic extracts were washed with brine (10 vol), dried over sodium sulfate, filtered and concentrated in vacuo to afford a yellow oil which was either used directly or purified using standard methods.

General Method 7: Synthesis of Compounds of Formula (Ig)

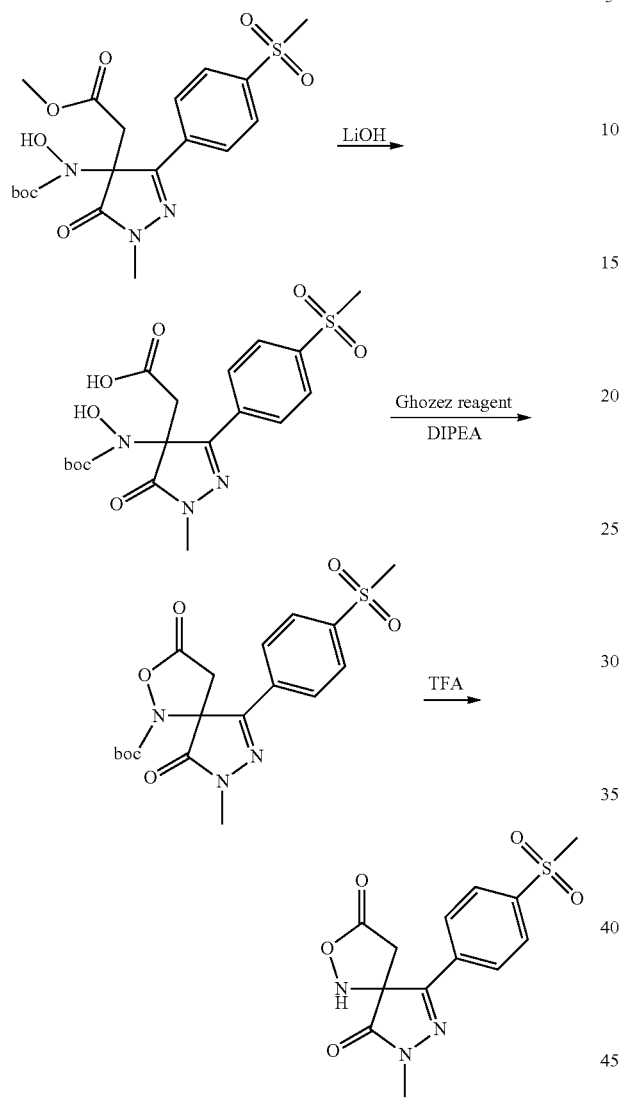

To a solution of methyl 2-(4-{[(tert-butoxy)carbonyl](hydroxy)amino}-3-(4-methanesulfonylphenyl)-1-methyl-5-oxo-4,5-dihydro-1H-pyrazol-4-yl)acetate in THF:water (1:1 v:v) is added LiOH and the reaction mixture is stirred at room temperature until complete consumption of the starting material is observed by LC-MS. The THF is removed in vacuo and the resulting suspension is acidified to pH 1 using 1N HCl solution and extracted into ethyl acetate. The organic layers are dried over magnesium sulfate, filtered and concentrated in vacuo to yield the acid which is purified by standard methods or used directly in the synthesis of the corresponding acid chloride.

To a stirred solution of 2-(4-{[(tert-butoxy)carbonyl](hydroxy)amino}-3-(4-methanesulfonylphenyl)-1-methyl-5-oxo-4,5-dihydro-1H-pyrazol-4-yl)acetic acid in DCM at room temperature is added 1-chloro-N,N,2-trimethylprop-1-en-1-amine (Ghosez reagent). The reaction mixture is stirred under nitrogen for 30 minutes, whereupon N,N-diethylethanamine is added and stirring continued for 18 hours after which time the reaction mixture is diluted with DCM and the organics are washed with water. The organic layer is separated and the aqueous layer extracted with DCM. The organic layers are combined, washed with brine and dried over sodium sulfate, filtered and concentrated under reduced pressure to give the required oxazolidinone 9-(4-Methanesulfonylphenyl)-7-methyl-2-oxa-1,7,8-triazaspiro[4.4]non-8-ene-3,6-dione is synthesized according to General Method 4 and is purified by standard methods including low pH HPLC.

General Method 8: Synthesis of Compounds of Formula (Ih)

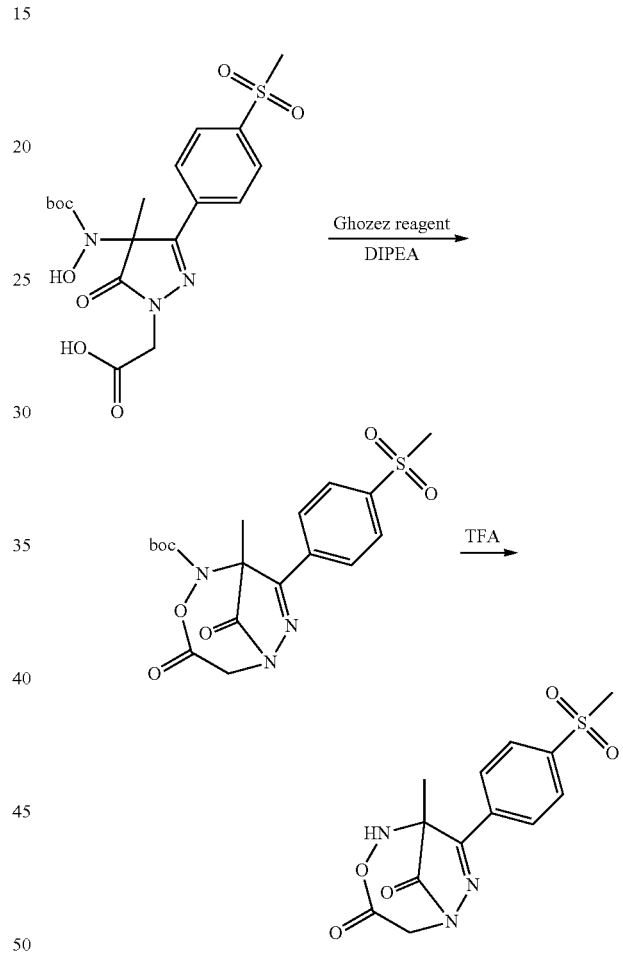

To a stirred solution of 2-(4-{[(tert-butoxy)carbonyl](hydroxy)amino}-3-(4-methanesulfonylphenyl)-4-methyl-5-oxo-4,5-dihydro-1H-pyrazol-1-yl)acetic acid in DCM at room temperature is added 1-chloro-N,N,2-trimethylprop-1-en-1-amine (Ghosez reagent). The reaction mixture is stirred under nitrogen for 30 minutes, whereupon N,N-diethylethanamine is added and stirring continued for 18 hours after which time the reaction mixture is diluted with DCM and the organics are washed with water. The organic layer is separated and the aqueous layer extracted with DCM. The organic layers are combined, washed with brine and dried over sodium sulfate, filtered and concentrated under reduced pressure to give the required cyclised compound.

7-(4-Methanesulfonylphenyl)-6-methyl-4-oxa-1,5,8-triazabicyclo[4.2.1]non-7-ene-3,9-dione is synthesized from tert-butyl 7-(4-methanesulfonylphenyl)-6-methyl-3,9-dioxo-4-oxa-1,5,8-triazabicyclo[4.2.1]non-7-ene-5-carboxylate according to General Method 4 and purified by standard methods General Method 9: Synthesis of Compounds of Formula (Ii)

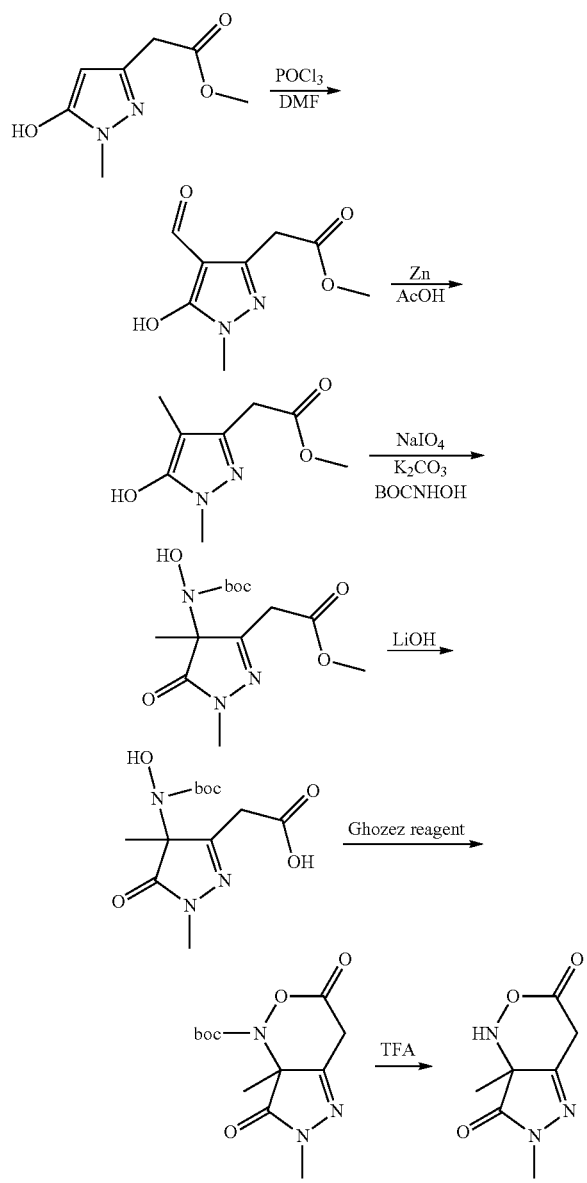

To a solution of methyl 2-(5-hydroxy-1-methyl-1H-pyrazol-3-yl)acetate in DMF is added phosphorus oxychloride and the reaction mixture is heated to 65° C. for 2.5 hours. The reaction mixture is subsequently cooled to room temperature, diluted with water and allowed to stand at room temperature for 17 hours. The resulting filtrate is filtered giving a solid which is washed with water and dried in vacuo An acetic acid suspension of methyl 2-(4-formyl-5-hydroxy-1-methyl-H-pyrazol-3-yl)acetate and powdered zinc is heated at 65° C. until reaction is complete by LCMS (~3 hours). The reaction mixture is allowed to cool to room temperature before the zinc is removed by filtration, washed with acetic acid and the solvent removed in vacuo to yield the desired compound.

Methyl 2-(4-{[(tert-butoxy)carbonyl](hydroxy)amino}-1,4-dimethyl-5-oxo-4,5-dihydro-1H-pyrazol-3-yl)acetate is synthesized from methyl 2-(5-hydroxy-1,4-dimethyl-1H-pyrazol-3-yl)acetate according to General Method 5 and is purified via standard methods To a solution of methyl 2-(4-{[(tert-butoxy)carbonyl](hydroxy)amino}-1,4-dimethyl-5-oxo-4,5-dihydro-1H-pyrazol-3-yl)acetate in THF:water (1:1 v:v) is added LiOH and the reaction mixture is stirred at room temperature until complete consumption of the starting material is observed by LC-MS. The THF is removed in vacuo and the resulting suspension is acidified to pH 1 using 1N HCl solution and is extracted into ethyl acetate. The organic layers are dried over magnesium sulfate, filtered and concentrated in vacuo to yield the acid which is purified by standard methods or used directly in the synthesis of the corresponding acid chloride To a stirred solution of 2-(4-{[(tert-butoxy)carbonyl](hydroxy)amino}-1,4-dimethyl-5-oxo-4,5-dihydro-1H-pyrazol-3-yl)acetic acid in DCM at room temperature is added 1-chloro-N,N,2-trimethylprop-1-en-1-amine (Ghosez reagent). The reaction mixture is stirred under nitrogen for 30 minutes, whereupon N,N-diethylethanamine is added and stirring continued for 18 hours after which time the reaction mixture is diluted with DCM and the organics are washed with water. The organic layer is separated and the aqueous layer extracted with DCM. The organic layers are combined, washed with brine and dried over sodium sulfate, filtered and concentrated under reduced pressure to give the required pyrazolo oxazine.

2,3a-Dimethyl-2H,3H,3aH,4H,6H,7H-pyrazolo[4,3-c][1,2]oxazine-3,6-dione is synthesized from tert-butyl 2,3a-dimethyl-3,6-dioxo-2H,3H,3aH,4H,6H,7H-pyrazolo[4,3-c][1,2]oxazine-4-carboxylate according to General Method 4 and purified by standard methods including low pH HPLC.

Example 1: Compound 1 [4-(Hydroxyamino)-4-methyl-3-(pyridin-3-yl)-4,5-dihydro-1H-pyrazol-5-one]

1.1 2-Methyl-3-oxo-3-(pyridin-3-yl)propanoate

2-Methyl-3-oxo-3-(pyridin-3-yl)propanoate was synthesized from methyl 3-oxo-3-(pyridin-3-yl)propanoate according to General Method 6 and was purified by silica gel chromatography eluting with 0-40% Heptane:Ethyl acetate to yield the title compound as a yellow oil (1.505 g, 98% yield). LC-MS $t_R$=0.78 min, [M+H]$^+$=194, $^1$H NMR (500 MHz, Methanol-d4) δ 9.15-9.11 (m, 1H), 8.77-8.74 (m, 1H), 8.43-8.38 (m, 1H), 7.63-7.57 (m, 1H), 4.66 (q, J=7.0 Hz, 1H), 3.67 (s, 3H), 1.44 (d, J=7.0 Hz, 3H).

1.2 4-Methyl-3-(pyridin-3-yl)-1H-pyrazol-5-ol

4-Methyl-3-(pyridin-3-yl)-1H-pyrazol-5-ol was synthesized from 2-methyl-3-oxo-3-(pyridin-3-yl)propanoate and hydrazine hydrate according to General Method 1 and was used directly without additional purification (994 mg, 74% yield). [M+H]$^+$=176, $^1$H NMR (500 MHz, DMSO-d6) δ 11.90 (br.s, 1H), 9.62 (br. s, 1H), 8.76 (d, J=1.6 Hz, 1H), 8.53 (dd, J=4.7, 1.3 Hz, 1H), 7.98-7.87 (m, 1H), 7.48 (dd, J=7.8, 4.8 Hz, 1H), 2.00 (s, 3H).

1.3 Tert-Butyl N-hydroxy-N-[4-methyl-5-oxo-3-(pyridin-3-yl)-4,5-dihydro-1H-pyrazol-4-yl]carbamate tert-Butyl N-hydroxy-N-[4-methyl-5-oxo-3-(pyridin-3-yl)-4,5-dihydro-1H-pyrazol-4-yl]carbamate was synthesized from 4-methyl-3-(pyridin-3-yl)-1H-pyrazol-5-ol according to General Method 5 and was purified by silica gel chromatography eluting with a gradient of 0-100% ethyl acetate:Heptane to yield the title compound as a white powder (1.38 g, 88% yield). LC-MS $t_R$=2.39 min, [M+H]$^+$=307, $^1$H NMR (500 MHz, Methanol-d4) δ 9.07 (d, J=1.8 Hz, 1H), 8.59 (dd, J=4.9, 1.5 Hz, 1H), 8.36-8.30 (m, 1H), 7.52 (dd, J=8.1, 4.9 Hz, 1H), 1.67 (s, 3H), 1.30 (s, 9H).

1.4 4-(Hydroxyamino)-4-methyl-3-(pyridin-3-yl)-4,5-dihydro-H-pyrazol-5-one

To a solution of tert-butyl N-hydroxy-N-[4-methyl-5-oxo-3-(pyridin-3-yl)-4,5-dihydro-1H-pyrazol-4-yl]carbamate (313 mg, 0.9 mmol) in DCM (5 mL) was added HCl (2.25 mL of a 4M solution in 1,4 dioxane) and the reaction mixture was stirred at room temperature for 18 hours, after which time the resulting suspension was filtered and washed with diethyl ether (2×10 mL). The precipitate was dried for 18 hours at room temperature in vacuo to afford the title compound as a yellow powder (217 mg, 100% yield). LC-MS $t_R$=0.62 min, [M+H]$^+$=207, $^1$H NMR (500 MHz, DMSO-d6) δ 11.96 (s, 1H), 9.32 (s, 1H), 8.98-8.88 (m, 2H), 8.08 (dd, J=7.9, 5.9 Hz, 1H), 1.25 (s, 3H).

Example 2: Compound 2 [3-[4-(Hydroxyamino)-4-methyl-5-oxo-4,5-dihydro-1H-pyrazol-3-yl]pyridin-1-ium-1-olate]

2.1 3-(4-{[(tert-Butoxy)carbonyl](hydroxy)amino}-4-methyl-5-oxo-4,5-dihydro-1H-pyrazol-3-yl)pyridin-1-ium-1-olate To a solution of tert-butyl N-hydroxy-N-[4-methyl-5-oxo-3-(pyridin-3-yl)-4,5-dihydro-1H-pyrazol-4-yl]carbamate (1.07 g, 3.06 mmol) in DCM (30 mL) cooled to 0° C. was added 3-chlorobenzenecarboperoxoic acid (792 mg, 4.59 mmol) and the reaction mixture was stirred for 18 hours at room temperature after which time a white precipitate was collected and was washed with DCM (2×100 mL) and ethyl acetate (50 mL) before purification by acidic reverse phase C18 chromatography to yield the desired compound as a white solid (305 mg, 25% yield). $^1$H NMR (500 MHz, Methanol-d4) δ 8.86-8.80 (m, 1H), 8.40-8.33 (m, 1H), 8.11-8.05 (m, 1H), 7.67-7.58 (m, 1H), 1.65 (s, 3H), 1.33 (s, 9H).

2.2 3-[4-(Hydroxyamino)-4-methyl-5-oxo-4,5-dihydro-1H-pyrazol-3-yl]pyridin-1-ium-1-olate 3-[4-(Hydroxyamino)-4-methyl-5-oxo-4,5-dihydro-1H-pyrazol-3-yl]pyridin-1-ium-1-olate was synthesized from 3-(4-{[(tert-butoxy)carbonyl](hydroxy)amino}-4-methyl-5-oxo-4,5-dihydro-1H-pyrazol-3-yl)pyridin-1-ium-1-olate according to General Method 4 and was triturated with heptanes:DCM followed by lyophilisation from acetonitrile water (1:1 v:v) to yield the title compound as an off white solid (105 mg, 55% yield). [M+H]$^+$=223, $^1$H NMR (500 MHz, DMSO-d6) δ 11.70 (s, 1H), 8.74 (s, 1H), 8.27 (d, J=6.5 Hz, 1H), 7.82 (d, J=8.1 Hz, 1H), 7.77 (s, 1H), 7.49 (dd, J=8.0, 6.5 Hz, 1H), 6.57 (br. s, 1H), 1.18 (s, 3H).

Example 3: Compound 3 [Ethyl 4-[4-(hydroxyamino)-3-methyl-5-oxo-4,5-dihydro-1H-pyrazol-4-yl]butanoate]

3.1 6-Ethyl 1-methyl 2-acetylhexanedioate

To a suspension of methyl 3-oxobutanoate (0.93 mL, 8.61 mmol) and potassium carbonate (1.67 g, 12.06 mmol) in DMF (10 mL) was added ethyl 4-bromobutanoate (1.61 mL, 11.2 mmol) and the mixture was stirred at room temperature for 18 hours, after which time, the mixture was partitioned between ethyl acetate (30 mL) and water (20 mL). The organic layer was separated, the aqueous layer extracted into ethyl acetate (2×30 mL) and the combined organic layers were washed with brine (20 mL), dried over sodium sulfate, filtered and concentrated under reduced pressure to yield the crude product as a viscous yellow oil which was purified by silica gel chromatography eluting with a gradient of 0-20% ethyl acetate:Heptane to yield the title compound as an orange oil (1.05 g, 53% yield). $^1$H NMR (250 MHz, Chloroform-d) δ 4.12 (q, J=7.1 Hz, 2H), 3.73 (s, 3H), 3.44 (t, J=7.3 Hz, 1H), 2.32 (t, J=7.3 Hz, 2H), 2.23 (s, 3H), 1.94-1.81 (m, 2H), 1.68-1.55 (m, 2H), 1.24 (t, J=7.1 Hz, 3H).

3.2 Ethyl 4-(5-hydroxy-3-methyl-1H-pyrazol-4-yl)butanoate

Ethyl 4-(5-hydroxy-3-methyl-1H-pyrazol-4-yl)butanoate was synthesized from 6-ethyl 1-methyl 2-acetylhexanedioate and hydrazine hydrate according to General Method 1 and was isolated as a white solid and used directly without additional purification (572 mg, 59% yield). $^1$H NMR (500 MHz, Methanol-d4) δ 4.10 (q, J=7.1 Hz, 2H), 2.35-2.27 (m, 4H), 2.12 (s, 3H), 1.82-1.74 (m, 2H), 1.24 (t, J=7.1 Hz, 3H).

3.3 Ethyl 4-(4-{[(tert-butoxy)carbonyl](hydroxy)amino}-3-methyl-5-oxo-4,5-dihydro-1H-pyrazol-4-yl)butanoate Ethyl 4-(4-{[(tert-butoxy)carbonyl](hydroxy)amino}-3-methyl-5-oxo-4,5-dihydro-1H-pyrazol-4-yl)butanoate was synthesized from ethyl 4-(5-hydroxy-3-methyl-1H-pyrazol-4-yl)butanoate according to General Method 5 and was purified by silica gel chromatography eluting with a gradient of 0-100% ethyl acetate:Heptane to afford the title as a yellow powder (435 mg, 73% yield). [M+Na]$^+$=366, $^1$H NMR (500 MHz, Methanol-d4) δ 4.11 (q, J=7.1 Hz, 2H), 2.42-2.27 (m, 2H), 2.01-1.93 (m, 5H), 1.56-1.46 (m, 2H), 1.42 (s, 9H), 1.24 (t, J=7.1 Hz, 3H).

3.4 Ethyl 4-[4-(hydroxyamino)-3-methyl-5-oxo-4,5-dihydro-1H-pyrazol-4-yl]butanoate Ethyl 4-[4-(hydroxyamino)-3-methyl-5-oxo-4,5-dihydro-1H-pyrazol-4-yl]butanoate was synthesized from ethyl 4-(4-{[(tert-butoxy)carbonyl](hydroxy)amino}-3-methyl-5-oxo-4,5-dihydro-1H-pyrazol-4-yl)butanoate according to General Method 4 and was purified by silica gel chromatography eluting with ethyl acetate:Heptane (0-100%) to afford the title compound as an orange gum (86 mg, 60% yield). LC-MS $t_R$=1.25 min, [M+H]$^+$=244, $^1$H NMR (500 MHz, DMSO-d6) δ 10.79 (s, 1H), 7.46 (br.s, 1H), 6.17 (br.s, 1H), 4.03 (q, J=7.1 Hz, 2H), 2.30-2.17 (m, 2H), 1.93 (s, 3H), 1.47-1.33 (m, 2H), 1.25-1.19 (m, 2H), 1.16 (t, J=7.1 Hz, 3H).

Example 4: Compound 4 [2-{3-[4-(Dimethylsulfamoyl)phenyl]-4-(hydroxyamino)-4-methyl-5-oxo-4,5-dihydro-1H-pyrazol-1-yl}acetic acid]

4.1 Ethyl 3-[4-(dimethylsulfamoyl)phenyl]-2-methyl-3-oxopropanoate

Ethyl 3-[4-(dimethylsulfamoyl)phenyl]-2-methyl-3-oxopropanoate was synthesized from ethyl 3-[4-(dimethylsulfamoyl)phenyl]-3-oxopropanoate according to General Method 6 and was purified by silica gel chromatography eluting with heptane:ethyl acetate (0-100%) to yield the title compound as a white solid (1.67 g, 82% yield). LC-MS $t_R$=1.03 min, M+H]$^+$=300, $^1$H NMR (500 MHz, Methanol-d4) δ 8.21 (d, J=8.4 Hz, 2H), 7.95-7.91 (m, 2H), 4.67 (q, J=7.0 Hz, 1H), 3.68 (s, 3H), 2.73 (s, 6H), 1.45 (d, J=7.1 Hz, 3H).

4.2 Tert-Butyl 2-{3-[4-(dimethylsulfamoyl)phenyl]-5-hydroxy-4-methyl-1H-pyrazol-1-yl}acetate To a solution of methyl 3-[4-(dimethylsulfamoyl)phenyl]-2-methyl-3-oxopropanoate (835 mg, 2.79 mmol) min ethanol (13 mL) was added triethylamine (0.39 mL, 2.79 mmol) and tert-butyl 2-hydrazinylacetate hydrochloride (560 mg, 2.79 mmol) and the resulting yellow solution was heated to 80° C. for 18 hours. After 18 hours the reaction mixture was concentrated under reduced pressure and the residue was partitioned between ethyl acetate (40 mL) and 1M HCl (40 mL). The organic layer was separated and the aqueous layer re-extracted into ethyl acetate (2×40 mL). The organic layers were combined, washed with water (50 mL) and brine (50 mL), dried over sodium sulfate, filtered and concentrated under reduced pressure to give the crude product as a glass which was purified by silica gel chromatography eluting with ethyl acetate:Heptane (0-100%) to yield the title compound as a colourless oil (593 mg, 48% yield). LC-MS $t_R$=1.06 min, [M+H]$^+$=396, $^1$H NMR (500 MHz, Methanol-d4) δ 7.88-7.83 (m, 4H), 4.67 (s, 2H), 2.72 (s, 6H), 2.10 (s, 3H), 1.49 (s, 9H).

4.3 Tert-Butyl 2-(4-{[(tert-butoxy)carbonyl](hydroxy)amino}-3-[4-(dimethylsulfamoyl)phenyl]-4-methyl-5-oxo-4,5-dihydro-H-pyrazol-1-yl)acetate tert-Butyl 2-(4-{[(tert-butoxy)carbonyl](hydroxy)amino}-3-[4-(dimethylsulfamoyl)phenyl]-4-methyl-5-oxo-4,5-dihydro-1H-pyrazol-1-yl)acetate was synthesized from tert-butyl 2-{3-[4-(dimethylsulfamoyl)phenyl]-5-hydroxy-4-methyl-1H-pyrazol-1-yl}acetate according to General Method 5 and was purified by silica gel chromatography eluting with ethyl acetate:Heptane (0-50%) to yield the title compound as a colourless glass (332 mg, 48% yield). LC-MS $t_R$=1.22 min, [M+Na]$^+$=549, $^1$H NMR (500 MHz, Methanol-d4) δ 8.18 (d, J=8.6 Hz, 2H), 7.86 (d, J=8.6 Hz, 2H), 4.67 (d, J=17.5 Hz, 1H), 4.31 (d, J=17.5 Hz, 1H), 2.71 (s, 6H), 1.76 (s, 3H), 1.51 (s, 9H), 1.26 (s, 9H).

4.4 2-{3-[4-(Dimethylsulfamoyl)phenyl]-4-(hydroxyamino)-4-methyl-5-oxo-4,5-dihydro-1H-pyrazol-1-yl}acetic acid 2-{3-[4-(Dimethylsulfamoyl)phenyl]-4-(hydroxyamino)-4-methyl-5-oxo-4,5-dihydro-1H-pyrazol-1-yl}acetic acid was synthesized from tert-butyl 2-(4-{[(tert-butoxy)carbonyl](hydroxy)amino}-3-[4-(dimethylsulfamoyl)phenyl]-4-methyl-5-oxo-4,5-dihydro-1H-pyrazol-1-yl)acetate according to General Method 4 and was and azeotroped with DCM followed by heptane, to give the crude product as an orange oil. The title compound was isolated as a white solid via low pH preparative HPLC (128 mg, 60% yield). LC-MS $t_R$=1.8 min, [M+H]$^+$=371, $^1$H NMR (500 MHz, DMSO-d6) δ 13.10 (br.s, 1H), 8.28 (d, J=8.6 Hz, 2H), 7.83 (d, J=8.6 Hz, 2H), 7.71 (s, 1H), 6.67 (s, 1H), 4.55 (d, J=17.6 Hz, 1H), 4.42 (d, J=17.7 Hz, 1H), 2.65 (s, 6H), 1.28 (s, 3H).

Example 5: Compound 5 [Ethyl 2-{3-[4-(dimethylsulfamoyl)phenyl]-4-(hydroxyamino)-4-methyl-5-oxo-4,5-dihydro-1H-pyrazol-1-yl}acetate]

5.1 Ethyl 2-{3-[4-(dimethylsulfamoyl)phenyl]-5-hydroxy-4-methyl-1H-pyrazol-1-yl}acetate To a solution of methyl 3-[4-(dimethylsulfamoyl)phenyl]-2-methyl-3-oxopropanoate (835 mg, 2.79 mmol) and trimethylamine (0.39 mL, 2.79 mmol) in ethanol (15 mL) was added methyl 2-hydrazinylacetate hydrochloride (588 mg, 4.18 mmol) and the resulting yellow solution was heated at 80° C. for 18 hours. The reaction mixture was concentrated under reduced pressure and the residue partitioned between ethyl acetate (40 mL) and 1M HCl (40 mL). The organic layer was separated and the aqueous layer re-extracted into ethyl acetate (2×40 mL). The organic layers were combined, washed with water (50 mL) brine (50 mL) and dried over sodium sulfate, filtered and concentrated under reduced pressure to give the crude product as a colourless oil which was purified by silica gel chromatography eluting with heptane:ethyl acetate (0-100%) to yield the title compound as an off white solid (496 mg, 45% yield). LC-MS $t_R$=0.98 min, [M+H]$^+$=368, $^1$H NMR (500 MHz, Methanol-d4) δ 7.86 (s, 4H), 4.78 (s, 2H), 4.24 (q, J=7.1 Hz, 2H), 2.72 (s, 6H), 2.10 (s, 3H), 1.29 (t, J=7.1 Hz, 3H).

5.2 Ethyl 2-(4-{[(tert-butoxy)carbonyl](hydroxy)amino}-3-[4-(dimethylsulfamoyl)phenyl]-4-methyl-5-oxo-4,5-dihydro-1H-pyrazol-1-yl)acetate Ethyl 2-(4-{[(tert-butoxy)carbonyl](hydroxy)amino}-3-[4-(dimethylsulfamoyl)phenyl]-4-methyl-5-oxo-4,5-dihydro-1H-pyrazol-1-yl)acetate was synthesized from ethyl 2-{3-[4-(dimethylsulfamoyl)phenyl]-5-hydroxy-4-methyl-1H-pyrazol-1-yl}acetate according to General Method 5 and was purified by silica gel chromatography eluting with heptane:ethyl acetate (0-60%) to yield the title compound as a white solid (524 mg, 77% yield). LC-MS $t_R$=1.13 min, [M+Na]$^+$=521, $^1$H NMR (500 MHz, Methanol-d4) δ 8.20-8.15 (m, 2H), 7.88-7.84 (m, 2H), 4.78 (d, J=17.6 Hz, 1H), 4.43 (d, J=17.6 Hz, 1H), 4.25 (q, J=7.1 Hz, 2H), 2.71 (s, 6H), 1.75 (s, 3H), 1.33-1.26 (m, 12H).

5.3 Ethyl 2-{3-[4-(dimethylsulfamoyl)phenyl]-4-(hydroxyamino)-4-methyl-5-oxo-4,5-dihydro-1H-pyrazol-1-yl}acetate Ethyl 2-{3-[4-(dimethylsulfamoyl)phenyl]-4-(hydroxyamino)-4-methyl-5-oxo-4,5-dihydro-1H-pyrazol-1-yl}acetate was synthesized from ethyl 2-(4-{[(tert-butoxy)carbonyl](hydroxy)amino}-3-[4-(dimethylsulfamoyl)phenyl]-4-methyl-5-oxo-4,5-dihydro-1H-pyrazol-1-yl)acetate according to General Method 4 and was purified by silica gel chromatography eluting with heptane:ethyl acetate (0-100%) to yield the title compound as an off white solid (280 mg, 74% yield). LC-MS $t_R$=2.51 min, [M+H]$^+$=399, $^1$H NMR (500 MHz, DMSO-d6) δ 8.30-8.26 (m, 2H), 7.85-7.82 (m, 2H), 7.73 (d, J=2.5 Hz, 1H), 6.70 (d, J=2.6 Hz, 1H), 4.67 (d, J=17.7 Hz, 1H), 4.55 (d, J=17.7 Hz, 1H), 4.16 (q, J=7.1 Hz, 2H), 2.65 (s, 6H), 1.29 (s, 3H), 1.21 (t, J=7.1 Hz, 3H).

Example 6: Compound 6 [Ethyl 2-[4-(hydroxyamino)-3-(4-methanesulfonylphenyl)-4-methyl-5-oxo-4,5-dihydro-1H-pyrazol-1-yl]acetate]

6.1 Ethyl 2-{5-hydroxy-4-methyl-3-[4-(methylsulfanyl)phenyl]-1H-pyrazol-1-yl}acetate To a solution of methyl 2-methyl-3-[4-(methylsulfanyl)phenyl]-3-oxopropanoate (3.5 g, 14.69 mmol) and trimethylamine (2.05 ml, 14.69 mmol) in ethanol (30 mL) was added methyl 2-hydrazinylacetate hydrochloride (3.1 g, 22.03 mmol) and the resulting yellow solution was heated at 80° C. for 18 hours. The reaction mixture was concentrated under reduced pressure and the residue partitioned between ethyl acetate (40 mL) and 1M HCl (40 mL). The organic layer was separated and the aqueous layer re-extracted into ethyl acetate (2×40 mL). The organic layers were combined, washed with water (50 mL) brine (50 mL) and dried over sodium sulfate, filtered and concentrated under reduced pressure to give the crude product as a colourless oil which was purified by silica gel chromatography eluting with heptane:ethyl acetate (0-85%) to yield the title compound as an off white glass (2.199 g, 43% yield. $^1$H NMR (500 MHz, Methanol-d4) δ 7.53-7.50 (m, 2H), 7.38-7.35 (m, 2H), 4.69 (s, 2H), 4.23 (q, J=7.1 Hz, 2H), 2.52 (s, 3H), 2.02 (s, 3H), 1.28 (t, J=7.1 Hz, 3H).

6.2 Ethyl 2-(4-{[(tert-butoxy)carbonyl](hydroxy)amino}-4-methyl-3-[4-(methylsulfanyl)phenyl]-5-oxo-4,5-dihydro-H-pyrazol-1-yl)acetate Ethyl 2-(4-{[(tert-butoxy)carbonyl](hydroxy)amino}-4-methyl-3-[4-(methylsulfanyl)phenyl]-5-oxo-4,5-dihydro-1H-pyrazol-1-yl)acetate was synthesized from ethyl 2-{5-hydroxy-4-methyl-3-[4-(methylsulfanyl)phenyl]-1H-pyrazol-1-yl}acetate according to General Method 5 and was purified by silica gel chromatography eluting with DCM:ethyl acetate (0-100%) to yield the title compound as a white solid (2.1 g, 74% yield). LC-MS $t_R$=1.23 min, [M+Na]$^+$=460, $^1$H NMR (500 MHz, Methanol-d4) δ 7.89-7.83 (m, 2H), 7.34-7.27 (m, 2H), 4.74 (d, J=17.5 Hz, 1H), 4.34 (d, J=17.5 Hz, 1H), 4.25 (q, J=7.1 Hz, 2H), 2.52 (s, 3H), 1.72 (s, 3H), 1.30 (t, J=7.1 Hz, 3H), 1.26 (s, 9H).

6.3 Ethyl 2-(4-{[(tert-butoxy)carbonyl](hydroxy)amino}-3-(4-methanesulfonylphenyl)-4-methyl-5-oxo-4,5-dihydro-H-pyrazol-1-yl)acetate To a solution of ethyl 2-(4-{[(tert-butoxy)carbonyl](hydroxy)amino}-4-methyl-3-[4-(methylsulfanyl)phenyl]-5-oxo-4,5-dihydro-1H-pyrazol-1-yl)acetate (2.1 g, 4.75 mmol) in 1,4 dioxane (25 mL) cooled to 0° C. was added a solution of oxone (4.38 g, 7.13 mmol) in water (25 mL) and the reaction mixture was stirred for 1 hour, whilst warming to room temperature. The reaction mixture was filtered and the solid was washed with ethyl acetate (100 mL). The filtrate was diluted with water (25 mL) and the organic layer was separated. The aqueous layer was extracted into ethyl acetate (2×50 mL), the organic layers were combined, washed with brine (50 mL), dried over sodium sulfate, filtered and concentrated under reduced pressure. The crude product was purified by silica gel chromatography eluting with heptane:ethyl acetate (0-70%) to yield the title compound as a white solid (1.74 g, 77% yield). $^1$H NMR (500 MHz, Methanol-d4) δ 8.21-8.17 (m, 2H), 8.06-8.01 (m, 2H), 4.78 (d, J=17.6 Hz, 1H), 4.43 (d, J=17.6 Hz, 1H), 4.25 (q, J=7.1 Hz, 2H), 3.16 (s, 3H), 1.74 (s, 3H), 1.30 (t, J=7.1 Hz, 3H), 1.28 (s, 9H).

6.4 Ethyl 2-[4-(hydroxyamino)-3-(4-methanesulfonylphenyl)-4-methyl-5-oxo-4,5-dihydro-1H-pyrazol-1-yl]acetate Ethyl 2-[4-(hydroxyamino)-3-(4-methanesulfonylphenyl)-4-methyl-5-oxo-4,5-dihydro-1H-pyrazol-1-yl]acetate was synthesized from ethyl 2-(4-{[(tert butoxy)carbonyl](hydroxy)amino}-3-(4-methanesulfonylphenyl)-4-methyl-5-oxo-4,5-dihydro-1H-pyrazol-1-yl)acetate according to General Method 4 and was purified by silica gel chromatography eluting with heptane:ethyl acetate (0-100%) to yield the title compound as a white solid (201 mg, 83% yield). LC-MS $t_R$=2.07 min, [M+H]$^+$=370, $^1$H NMR (500 MHz, DMSO-d6) δ 8.29 (d, J=8.6 Hz, 2H), 8.02 (d, J=8.6 Hz, 2H), 7.75 (s, 1H), 6.71 (br.s, 1H), 4.67 (d, J=17.7 Hz, 1H), 4.56 (d, J=17.7 Hz, 1H), 4.16 (q, J=7.1 Hz, 2H), 3.26 (s, 3H), 1.28 (s, 3H), 1.21 (t, J=7.1 Hz, 3H).

Example 7: Compound 7 [Methyl 2-[4-(hydroxyamino)-3-(4-methanesulfonylphenyl)-4-methyl-5-oxo-4,5-dihydro-1H-pyrazol-1-yl]acetate]

7.1 Methyl 2-{5-hydroxy-4-methyl-3-[4-(methylsulfanyl)phenyl]-1H-pyrazol-1-yl}acetate To a solution of methyl 2-methyl-3-[4-(methylsulfanyl)phenyl]-3-oxopropanoate (3.5 g, 14.69 mmol) and trimethylamine (2.05 ml, 14.69 mmol) in ethanol (30 mL) was added methyl 2-hydrazinylacetate hydrochloride (3.1 g, 22.03 mmol) and the resulting yellow solution was heated at 80° C. for 18 hours. The reaction mixture was concentrated under reduced pressure and the residue partitioned between ethyl acetate (40 mL) and 1M HCl (40 mL). The organic layer was separated and the aqueous layer re-extracted into ethyl acetate (2×40 mL). The organic layers were combined, washed with water (50 mL) brine (50 mL) and dried over sodium sulfate, filtered and concentrated under reduced pressure to give the crude product as a colourless oil which was purified by silica gel chromatography eluting with heptane:ethyl acetate (0-85%) to yield the title compound as an off white glass (0.684 g, 14% yield). $^1$H NMR (500 MHz, Methanol-d4) δ 7.54-7.50 (m, 2H), 7.38-7.35 (m, 2H), 4.71 (s, 2H), 3.77 (s, 3H), 2.52 (s, 3H), 2.02 (s, 3H).

7.2 Methyl 2-(4-{[(tert-butoxy)carbonyl](hydroxy)amino}-4-methyl-3-[4-(methylsulfanyl)phenyl]-5-oxo-4,5-dihydro-H-pyrazol-1-yl)acetate Methyl 2-(4-{[(tert-butoxy)carbonyl](hydroxy)amino}-4-methyl-3-[4-(methylsulfanyl)phenyl]-5-oxo-4,5-dihydro-1H-pyrazol-1-yl)acetate was synthesized from methyl 2-{5-hydroxy-4-methyl-3-[4-(methylsulfanyl)phenyl]-1H-pyrazol-1-yl}acetate according to General Method 5 and was purified by silica gel chromatography eluting with heptane:ethyl acetate (0-50%) followed by purification by silica gel chromatography eluting with ethyl acetate:DCM (0-80%) to yield the title compound as a white solid (589 mg, 63% yield). LC-MS $t_R$=1.17 min, [M+Na]$^+$=446, $^1$H NMR (500 MHz, Methanol-d4) δ 7.86 (d, J=8.7 Hz, 2H), 7.34-7.27 (m, 2H), 4.76 (d, J=17.6 Hz, 1H), 4.36 (d, J=17.6 Hz, 1H), 3.79 (s, 3H), 2.52 (s, 3H), 1.72 (s, 3H), 1.26 (s, 9H).

7.3 Methyl 2-(4-{[(tert-butoxy)carbonyl](hydroxy)amino}-3-(4-methanesulfonylphenyl)-4-methyl-5-oxo-4,5-dihydro-H-pyrazol-1-yl)acetate To a solution of methyl 2-(4-{[(tert-butoxy)carbonyl](hydroxy)amino}-4-methyl-3-[4-(methylsulfanyl)phenyl]-5-oxo-4,5-dihydro-1H-pyrazol-1-yl)acetate (589 mg, 1.29 mmol) in 1,4 dioxane (6 mL) at 0° C. was added a solution of oxone (1.59 g, 2.59 mmol) in water (6 mL) and the reaction mixture was stirred for 2 hours at room temperature. The reaction mixture was filtered and the solid was washed with ethyl acetate (30 mL). The filtrate was washed with water (15 mL) and the organic layer was separated. The aqueous layer was re-extracted with ethyl acetate (2×30 mL), the organic layers were combined, washed with brine (30 mL), dried over sodium sulfate, filtered and concentrated under reduced pressure to yield the crude product as a yellow gum which was purified by silica gel chromatography eluting with heptane:ethyl acetate (0-70%) to yield the title compound as a white gum (591 mg, 86% yield). LC-MS $t_R$=1.01 min, [M+Na]$^+$=478, $^1$H NMR (500 MHz, Methanol-d4) δ 8.21-8.17 (m, 2H), 8.06-8.01 (m, 2H), 4.80 (d, J=17.6 Hz, 1H), 4.46 (d, J=17.6 Hz, 1H), 3.80 (s, 3H), 3.16 (s, 3H), 1.75 (s, 3H), 1.28 (s, 9H).

7.4 Methyl 2-[4-(hydroxyamino)-3-(4-methanesulfonylphenyl)-4-methyl-5-oxo-4,5-dihydro-1H-pyrazol-1-yl]acetate Methyl 2-[4-(hydroxyamino)-3-(4-methanesulfonylphenyl)-4-methyl-5-oxo-4,5-dihydro-1H-pyrazol-1-yl]acetate was synthesized from methyl 2-(4-{[(tert-butoxy)carbonyl](hydroxy)amino}-3-(4-methanesulfonylphenyl)-4-methyl-5-oxo-4,5-dihydro-1H-pyrazol-1-yl)acetate according to General Method 4 and was azeotroped with DCM followed by heptane to yield the crude product as a white solid. The crude product was purified by low pH preparative HPLC and isolated by lyophilisation to yield the title compound as a white solid (52 mg, 66% yield). LC-MS $t_R$=1.79 min, [M+H]$^+$=356, $^1$H NMR (500 MHz, DMSO-d6) δ 8.29 (d, J=8.6 Hz, 2H), 8.02 (d, J=8.6 Hz, 2H), 7.75 (d, J=2.2 Hz, 1H), 6.71 (d, J=1.7 Hz, 1H), 4.70 (d, J=17.7 Hz, 1H), 4.59 (d, J=17.7 Hz, 1H), 3.70 (s, 3H), 3.26 (s, 3H), 1.28 (s, 3H).

Example 8: Compound 8 [4-(Hydroxyamino)-3-phenyl-4-(propan-2-yl)-4,5-dihydro-1H-pyrazol-5-one]

8.1 3-Phenyl-4-(propan-2-yl)-1H-pyrazol-5-ol

To a solution of methyl 2-benzoyl-3-methylbutanoate (0.5 g, 2.27 mmol) in ethanol (3 mL) was added hydrazine hydrate (113.64 μl, 2.5 mmol) and the reaction mixture was heated to 80° C. for 19 hours. The reaction mixture was allowed to cool to room temperature and acetic acid (0.3 mL) was added and the reaction mixture was heated to 80° C. for 23 hours. Additional hydrazine hydrate (51.65 μl, 1.14 mmol) and 0.2 mL of acetic acid were added and the reaction mixture was heated to 80° C. for 20 hours. Upon cooling, the reaction mixture was concentrated in vacuo and the product was purified by silica gel chromatography eluting with heptanes:ethyl acetate (0-100%) to yield the title compound as an off white solid (467 mg, 90% yield). $^1$H NMR (250 MHz, DMSO-d6) δ 7.52-7.32 (m, 5H), 2.92-2.73 (m, 1H), 1.20 (d, J=7.0 Hz, 6H).

8.2 Tert-Butyl N-hydroxy-N-[5-oxo-3-phenyl-4-(propan-2-yl)-4,5-dihydro-1H-pyrazol-4-yl]carbamate tert-Butyl N-hydroxy-N-[5-oxo-3-phenyl-4-(propan-2-yl)-4,5-dihydro-1H-pyrazol-4-yl]carbamate was synthesized from 3-phenyl-4-(propan-2-yl)-1H-pyrazol-5-ol according to General Method 5 and was purified by silica gel chromatography eluting with heptanes:ethyl acetate (0-70%) to yield the title compound as an off white solid (185 mg, 44% yield). LC-MS $t_R$=1.06 min, [M+Na]$^+$=356, $^1$H NMR (250 MHz, DMSO-d6) δ 11.32 (s, 1H), 10.06 (s, 1H), 7.92-7.75 (m, 2H), 7.42 (dd, J=5.2, 1.9 Hz, 3H), 2.63-2.54 (m, 1H), 1.24 (s, 9H), 1.09 (d, J=6.5 Hz, 3H), 0.70 (d, J=7.0 Hz, 3H).

8.3 4-(Hydroxyamino)-3-phenyl-4-(propan-2-yl)-4,5-dihydro-H-pyrazol-5-one 4-(Hydroxyamino)-3-phenyl-4-(propan-2-yl)-4,5-dihydro-1H-pyrazol-5-one was synthesized from tert-butyl N-hydroxy-N-[5-oxo-3-phenyl-4-(propan-2-yl)-4,5-dihydro-1H-pyrazol-4-yl]carbamate according to General Method 4. Purification was carried out by azeotroping with heptanes (10 mL) and ethyl acetate (10 mL) followed by lyophilisation from acetonitrile:water (1:1) to yield the title compound as a yellow solid (112 mg, 86% yield). LC-MS $t_R$=2.15 min, [M+H]$^+$=234, $^1$H NMR (250 MHz, DMSO-d6) δ 11.32 (s, 1H), 8.08-7.95 (m, 2H), 7.61 (s, 1H), 7.47-7.38 (m, 3H), 6.34 (s, 1H), 2.10-1.96 (m, 1H), 0.90 (d, J=6.8 Hz, 3H), 0.64 (d, J=6.9 Hz, 3H).

Example 9: Compound 9 [4-(Hydroxyamino)-1-methyl-3-phenyl-4-(propan-2-yl)-4,5-dihydro-1H-pyrazol-5-one]

9.1 1-Methyl-3-phenyl-4-(propan-2-yl)-1H-pyrazol-5-ol

To a solution of methyl 2-benzoyl-3-methylbutanoate (0.5 g, 2.27 mmol) in ethanol (3 mL) was added methylhydrazine (179.49 μl, 3.41 mmol) and the reaction mixture was heated to 80° C. for 3 hours. The reaction was cooled to room temperature and acetic acid (0.3 mL) was added and the reaction was heated to 80° C. for 40 hours. The reaction was cooled to room temperature and the solvent removed in vacuo. Purification was performed by silica gel chromatography eluting with ethyl acetate:heptanes (0-60%) to afford the title compound as a yellow solid (0.183 g, 15% yield)

9.2 Tert-Butyl N-hydroxy-N-[1-methyl-5-oxo-3-phenyl-4-(propan-2-yl)-4,5-dihydro-1H-pyrazol-4-yl]carbamate tert-Butyl N-hydroxy-N-[1-methyl-5-oxo-3-phenyl-4-(propan-2-yl)-4,5-dihydro-1H-pyrazol-4-yl]carbamate was synthesized from 1-methyl-3-phenyl-4-(propan-2-yl)-1H-pyrazol-5-ol according to General Method 5 and was purified by silica gel chromatography eluting with heptanes:ethyl acetate (0-70%) to yield the title compound as an off white solid (68 mg, 23% yield). LC-MS $t_R$=1.15 min, [M+Na]$^+$=370, $^1$H NMR (250 MHz, Chloroform-d) δ 7.89

(dd, J=6.6, 3.0 Hz, 2H), 7.50-7.32 (m, 3H), 7.16 (s, 1H), 3.38 (s, 3H), 2.90-2.73 (m, 1H), 1.31 (s, 9H), 1.18 (d, J=6.5 Hz, 3H), 0.83 (d, J=7.0 Hz, 3H).

9.3 4-(Hydroxyamino)-1-methyl-3-phenyl-4-(propan-2-yl)-4,5-dihydro-H-pyrazol-5-one 4-(Hydroxyamino)-1-methyl-3-phenyl-4-(propan-2-yl)-4,5-dihydro-1H-pyrazol-5-one was synthesized from tert-butyl N-hydroxy-N-[1-methyl-5-oxo-3-phenyl-4-(propan-2-yl)-4,5-dihydro-1H-pyrazol-4-yl]carbamate according to General Method 4 and was purified by silica gel chromatography eluting with heptanes:ethyl acetate (0-80%) to yield the title compound as a white solid (69 mg, Quant yield). LC-MS $t_R$=2.5 min, [M+H]$^+$=248, $^1$H NMR (250 MHz, DMSO-d6) δ 8.08-7.96 (m, 2H), 7.65 (d, J=2.2 Hz, 1H), 7.49-7.32 (m, 3H), 6.49 (d, J=2.1 Hz, 1H), 3.27 (s, 3H), 2.11-1.99 (m, 1H), 0.90 (d, J=6.8 Hz, 3H), 0.62 (d, J=6.9 Hz, 3H).

Example 10: Compound 10 [4-[4-(Hydroxyamino)-4-methyl-5-oxo-4,5-dihydro-1H-pyrazol-3-yl]-N-methylbenzene-1-sulfonamide]

10.1 4-Bromo-N-methylbenzene-1-sulfonamide

To a solution of 4-bromobenzene-1-sulfonyl chloride (3 g, 11.74 mmol) in DCM (20 mL) at 0° C. was added methylamine (29 mL of a 2M solution in THF, 58.7 mmol) and the reaction mixture and stirred at room temperature for 18 hours. The reaction mixture was diluted with DCM (100 mL) and washed with ammonium chloride solution (20 mL). The organic layer was collected and dried over magnesium sulfate, filtered and concentrated in vacuo. The resulting emulsion was purified by silica gel chromatography eluting with 0-40% Heptane:ethyl acetate to yield the desired compound as a white solid (2.7 g, 92% yield). $^1$H NMR (250 MHz, DMSO-d6) δ 7.91-7.79 (m, 2H), 7.79-7.65 (m, 2H), 7.56 (s, 1H), 2.43 (s, 3H).

10.2 Ethyl-3-ethoxy-3-[4-(methylsulfamoyl)phenyl]prop-2-enoate

Synthesis was carried out according to the method detailed in Tetrahedron Letters 54 (2013) 7065-7068.

A flask containing lithium chloride (50.9 mg, 1.2 mmol), 4-bromo-N-methylbenzene-1-sulfonamide (100 mg, 0.4 mmol), N-cyclohexyl-N-methylcyclohexanamine (93.38 µl, 0.44 mmol), ethyl-3-ethoxyprop-2-enoate (172.92 mg, 1.2 mmol) in 1,4-dioxane (2 mL) was degassed by passing a stream of nitrogen through the mixture for 10 minutes. palladium-tri-tert-butylphosphane (12.26 mg, 0.02 mmol) was added, and reaction mixture was heated at reflux under nitrogen for 16 hours. The brown mixture was cooled and partitioned between ethyl acetate (10 mL) and water (3 mL). The layers were separated, and the organic layer was washed sequentially with saturated ammonium chloride solution (5 mL) and brine (5 mL), followed by drying over sodium sulfate. The mixture was filtered, and the filtrate was concentrated under reduced pressure to give an oil which was purified by silica gel chromatography eluting with 10-50% ethyl acetate in heptane to afford the desired compound as an orange oil (54 mg, 43% yield). LC-MS $t_R$=1.1 min, [M+H]$^+$=314, $^1$H NMR (500 MHz, DMSO-d6) δ 7.89-7.79 (m, 4H), 7.76 (d, J=8.4 Hz, 1H), 7.56 (d, J=8.4 Hz, 1H), 5.84 (s, 1H), 4.12 (q, J=7.1 Hz, 2H), 4.03 (q, J=7.0 Hz, 2H), 2.43 (s, 3H), 1.30 (t, J=7.0 Hz, 3H), 1.23 (t, J=7.1 Hz, 3H).

10.3 Ethyl 3-[4-(methylsulfamoyl)phenyl]-3-oxopropanoate

To a solution of ethyl-3-ethoxy-3-[4-(methylsulfamoyl)phenyl]prop-2-enoate (1.1 g, 3.51 mmol) in dichloroethane (40 mL) was added 6 M HCl (3.2 mL), and the biphasic mixture was stirred vigorously for 15 hours at room temperature. The layers were then separated and the dichloroethane layer was dried over sodium sulfate. The mixture was filtered, and the filtrate concentrated to afford an orange oil which was seen to be a mixture of keto/enol form by NMR (0.92 g, 92% yield, 4:1 keto/enol). $^1$H NMR Keto form (250 MHz, DMSO-d6) δ 8.20-8.12 (m, 2H), 7.97-7.89 (m, 2H), 7.68 (q, J=5.0 Hz, 1H), 4.27 (s, 2H), 4.13 (q, J=7.1 Hz, 2H), 2.45 (d, J=5.0 Hz, 3H), 1.18 (t, J=7.1 Hz, 3H). $^1$H NMR (250 MHz, DMSO-d6) δ 8.09 (d, J=8.7 Hz, 2H), 7.86 (d, J=8.7 Hz, 2H), 7.60 (d, J=5.0 Hz, 1H), 6.09 (s, 1H), 4.27 (s, 13H), 2.45 (d, J=5.0 Hz, 3H), 1.29 (t, J=7.1 Hz, 3H).

10.4 Ethyl 2-methyl-3-[4-(methylsulfamoyl)phenyl]-3-oxopropanoate

Ethyl 2-methyl-3-[4-(methylsulfamoyl)phenyl]-3-oxopropanoate was synthesized from ethyl 3-[4-(methylsulfamoyl)phenyl]-3-oxopropanoate according to General Method 6 and was purified by silica gel chromatography eluting with heptane:ethyl acetate (20-60%) yielding the title compound as yellow oil (0.25 g, 87% yield). LC-MS $t_R$=0.86 min, [M+H]$^+$=268, $^1$H NMR (250 MHz, DMSO-d6) δ 8.23-8.13 (m, 2H), 7.97-7.89 (m, 2H), 7.67 (br. s, 1H), 4.76 (q, J=7.0 Hz, 1H), 4.07 (q, J=7.1 Hz, 2H), 2.45 (d, J=2.2 Hz, 3H), 1.35 (d, J=7.0 Hz, 3H), 1.08 (t, J=7.1 Hz, 3H).

10.5 4-(5-Hydroxy-4-methyl-1H-pyrazol-3-yl)-N-methylbenzene-1-sulfonamide 4-(5-Hydroxy-4-methyl-1H-pyrazol-3-yl)-N-methylbenzene-1-sulfonamide was synthesized from ethyl 2-methyl-3-[4-(methylsulfamoyl)phenyl]-3-oxopropanoate according to General Method 1 and was purified by trituration from heptane:ethyl acetate (1:1, v:v) to yield the title compound as an off white solid (0.17 g, 77% yield). LC-MS $t_R$=1.07 min, [M+H]$^+$=300, $^1$H NMR (250 MHz, DMSO-d6) δ 7.87-7.73 (m, 4H), 2.45 (s, 3H), 2.04 (s, 3H).

10.6 Tert-Butyl N-hydroxy-N-{4-methyl-3-[4-(methylsulfamoyl)phenyl]-5-oxo-4,5-dihydro-1H-pyrazol-4-yl}carbamate tert-Butyl N-hydroxy-N-{4-methyl-3-[4-(methylsulfamoyl)phenyl]-5-oxo-4,5-dihydro-1H-pyrazol-4-yl}carbamate was synthesized from 4-(5-hydroxy-4-methyl-1H-pyrazol-3-yl)-N-methylbenzene-1-sulfonamide according to General Method 5 and was purified by silica gel chromatography eluting with heptane:ethyl acetate (0-90%) yielding the title compound as an off white solid (183 mg, 69% yield). LC-MS $t_R$=0.88 min, [M−H]$^−$=397. $^1$H NMR (500 MHz, DMSO-d6) δ 11.72 (s, 1H), 10.26 (s, 1H), 8.02 (d, J=8.6 Hz, 2H), 7.83 (d, J=8.6 Hz, 2H), 7.53 (s, 1H), 2.42 (s, 3H), 1.52 (s, 3H), 1.20 (s, 9H).

10.7 4-[4-(Hydroxyamino)-4-methyl-5-oxo-4,5-dihydro-1H-pyrazol-3-yl]-N-methylbenzene-1-sulfonamide 4-[4-(Hydroxyamino)-4-methyl-5-oxo-4,5-dihydro-1H-pyrazol-3-yl]-N-methylbenzene-1-sulfonamide was synthesized from tert-butyl N-hydroxy-N-{4-methyl-3-[4-(methylsulfamoyl)phenyl]-5-oxo-4,5-dihydro-1H-pyrazol-4-yl}carbamate according to General Method 4 and was purified by acidic reverse phase HPLC yielding the title compound as a white solid (84 mg, 62% yield). LC-MS $t_R$=2.53 min, [M+H]$^+$=299, $^1$H NMR (500 MHz, DMSO-d6) δ 11.62 (s, 1H), 8.23 (d, J=8.6 Hz, 2H), 7.84 (d, J=8.6 Hz, 2H), 7.65 (s, 1H), 7.53 (q, J=5.0 Hz, 1H), 2.55 (s, 1H), 2.45 (d, J=5.0 Hz, 3H), 1.22 (s, 3H).

Example 11: Compound 11 [1-(4-Bromophenyl)-4-(hydroxyamino)-3,4-dimethyl-4,5-dihydro-1H-pyrazol-5-one]

11.1 4-Bromo-1-(4-bromophenyl)-3,4-dimethyl-4,5-dihydro-1H-pyrazol-5-one

4-Bromo-1-(4-bromophenyl)-3,4-dimethyl-4,5-dihydro-1H-pyrazol-5-one was synthesized from 3,4-dimethyl-1-phenyl-1H-pyrazol-5-ol according to General Method 2 and was used directly without purification (901 mg, 58% yield). LC-MS $t_R$=2.26 min, [M+H]$^+$=346

11.2 1-(4-Bromophenyl)-4-{[(tert-butoxy)carbonyl]({[(tert-butoxy)carbonyl]oxy})amino}-3,4-dimethyl-4,5-dihydro-1H-pyrazol-5-one 1-(4-Bromophenyl)-4-{[(tert-butoxy)carbonyl]({[(tert-butoxy)carbonyl]oxy})amino}-3,4-dimethyl-4,5-dihydro-1H-pyrazol-5-one was synthesized from 4-Bromo-1-(4-bromophenyl)-3,4-dimethyl-4,5-dihydro-1H-pyrazol-5-one according to General Method 3 and was purified by silica gel chromatography eluting with heptane:ethyl acetate (9:1) followed by neutral preparative HPLC to yield the title compound as an off white solid (450 mg, 35% yield). LC-MS $t_R$=2.58 min, [M-BOC]$^+$=297, $^1$H NMR (500 MHz, Chloroform-d) δ 7.79 (d, J=8.8 Hz, 2H), 7.65 (d, J=8.8 Hz, 2H), 1.52 (s, 9H), 1.49 (s, 3H), 1.28 (s, 9H).

11.3 1-(4-Bromophenyl)-4-(hydroxyamino)-3,4-dimethyl-4,5-dihydro-1H-pyrazol-5-one 1-(4-Bromophenyl)-4-(hydroxyamino)-3,4-dimethyl-4,5-dihydro-1H-pyrazol-5-one was synthesized from 1-(4-bromophenyl)-4-{[(tert-butoxy)carbonyl]({[(tert-butoxy)carbonyl]oxy})amino}-3,4-dimethyl-4,5-dihydro-1H-pyrazol-5-one according to General Method 4 and was purified by reverse phase C18 chromatography eluting with water:acetonitrile to yield the title compound as a yellow solid (145 mg, 95% yield). LC-MS $t_R$=1.81 min, [M+H]$^+$=299, $^1$H NMR (500 MHz, DMSO-d6) δ 7.89-7.79 (m, 2H), 7.72 (d, J=2.7 Hz, 1H), 7.66-7.55 (m, 2H), 6.54 (d, J=2.6 Hz, 1H), 2.12 (s, 3H), 1.15 (s, 3H).

Example 12: Compound 12 [4-(Hydroxyamino)-4-[(methoxyimino)(phenyl)methyl]-3-methyl-1-phenyl-4,5-dihydro-1H-pyrazol-5-one]

12.1 4-[(Methoxyimino)(phenyl)methyl]-3-methyl-1-phenyl-1H-pyrazol-5-ol

To a suspension of 4-benzoyl-3-methyl-1-phenyl-1H-pyrazol-5-ol (5 g, 17.97 mmol) in methanol (50 mL) was added O-Methyl hydroxylamine HCl (1.5 g, 17.97 mmol) and sodium bicarbonate (1.51 g, 17.97 mmol). The reaction mixture was heated to reflux for 1 hour then allowed to cool to room temperature. The reaction mixture was concentrated in vacuo, redissolved in DCM (20 mL), filtered and concentrated in vacuo yielding a yellow solid which was purified by silica gel chromatography eluting with heptanes:ethyl acetate (50-75%) to yield the title compound as an off white solid (4.6 g, 73% yield). LC-MS $t_R$=1.89 min, [M+H]$^+$=308, $^1$H NMR (500 MHz, Chloroform-d) δ 7.80 (d, J=7.6 Hz, 2H), 7.58-7.27 (m, 8H), 4.15 (s, 3H), 3.86 (s, 1H), 1.67 (s, 3H).

12.2 4-Bromo-4-[(methoxyimino)(phenyl)methyl]-3-methyl-1-phenyl-4,5-dihydro-1H-pyrazol-5-one 4-Bromo-4-[(methoxyimino)(phenyl)methyl]-3-methyl-1-phenyl-4,5-dihydro-1H-pyrazol-5-one was synthesized from 4-[(methoxyimino)(phenyl)methyl]-3-methyl-1-phenyl-1H-pyrazol-5-ol according to General Method 2 and was used directly without additional purification (1.26 g, 88% yield). LC-MS $t_R$=2.31 min, [M+H]$^+$=388, $^1$H NMR (500 MHz, Chloroform-d) δ 7.88 (ddd, J=20.7, 8.7, 1.0 Hz, 2H), 7.61-7.33 (m, 7H), 7.27-7.19 (m, 1H), 3.91 (d, J=24.0 Hz, 3H), 2.34 (d, J=34.9 Hz, 3H).

12.3 4-{[(tert-butoxy)carbonyl]({[(tert-butoxy)carbonyl]oxy})amino}-4-[(methoxyimino)(phenyl)methyl]-3-methyl-1-phenyl-4,5-dihydro-1H-pyrazol-5-one 4-{[(tert-Butoxy)carbonyl]({[(tert-butoxy)carbonyl]oxy})amino}-4-[(methoxyimino)(phenyl)methyl]-3-methyl-1-phenyl-4,5-dihydro-1H-pyrazol-5-one was synthesized from 4-bromo-4-[(methoxyimino)(phenyl)methyl]-3-methyl-1-phenyl-4,5-dihydro-1H-pyrazol-5-one according to General Method 3 and was purified by silica gel chromatography eluting with heptanes:DCM (50-100%) to yield the title compound as an off white solid (950 mg, 54% yield). LC-MS $t_R$=2.57 min, [M+Na]$^+$=561.

12.4 4-(Hydroxyamino)-4-[(methoxyimino)(phenyl)methyl]-3-methyl-1-phenyl-4,5-dihydro-1H-pyrazol-5-one 4-(Hydroxyamino)-4-[(methoxyimino)(phenyl)methyl]-3-methyl-1-phenyl-4,5-dihydro-1H-pyrazol-5-one was synthesized from 4-{[(tert-butoxy)carbonyl]({[(tert-butoxy)carbonyl]oxy})amino}-4-[(methoxyimino)(phenyl)methyl]-3-methyl-1-phenyl-4,5-dihydro-1H-pyrazol-5-one according to General Method 4 and was purified by silica gel chromatography eluting with heptanes:ethyl acetate (20-50%) to yield the title compound as an off white solid (254 mg, 54% yield). LC-MS $t_R$=2.00 min, [M+H]$^+$=339, $^1$H NMR (500 MHz, DMSO-d6) δ 8.00 (d, J=2.7 Hz, 1H), 7.75-7.66 (m, 2H), 7.45-7.38 (m, 2H), 7.36 (dd, J=5.0, 1.7 Hz, 3H), 7.19 (td, J=5.7, 2.5 Hz, 3H), 6.59 (d, J=2.7 Hz, 1H), 3.77 (s, 3H), 2.16 (s, 3H).

Example 13: Compound 13 [4-(Hydroxyamino)-1,4-dimethyl-3-(propan-2-yl)-4,5-dihydro-1H-pyrazol-5-one]

13.1 1-Methyl-3-(propan-2-yl)-1H-pyrazol-5-ol

To ethyl 4-methyl-3-oxopentanoate (10 g, 63.21 mmol) cooled to 0° C. by an ice bath was added methylhydrazine (3.33 mL, 63.21 mmol) dropwise over 3 minutes with stirring. On complete addition, the reaction was subjected to sonication for 5 minutes whereupon 1-methyl-3-(propan-2-yl)-1H-pyrazol-5-ol precipitated from solution. The reaction mixture was diluted in ethanol (25 mL) and concentrated in vacuo to yield the pyrazolone as an off white solid, which was triturated with heptane (50 mL) and concentrated in vacuo to yield the desired compound as an off white solid (8.1 g, 91% yield). $^1$H NMR (500 MHz, DMSO-d6) δ 10.60 (s, 1H), 5.14 (s, 1H), 3.41 (s, 3H), 2.65 (p, J=6.9 Hz, 1H), 1.10 (d, J=6.8 Hz, 6H).

13.2 5-Hydroxy-1-methyl-3-(propan-2-yl)-1H-pyrazole-4-carbaldehyde

1-Methyl-3-(propan-2-yl)-1H-pyrazol-5-ol (1 g, 7.13 mmol) was dissolved in dimethyl formamide dimethyl acetal (3 mL) and stirred at room temperature for 90 minutes, after which time LC-MS showed complete consumption of the starting material. The reaction vessel was stood overnight before concentrating in vacuo to yield the intermediate as a yellow solid. $^1$H NMR (500 MHz, Chloroform-d) δ 7.52 (s, 1H), 4.11 (s, 3H), 3.62 (s, 3H), 3.54 (s, 3H), 3.02 (dq, J=13.8, 7.4, 6.9 Hz, 1H), 1.51 (s, 3H), 1.49 (s, 3H). The solid was taken up in 6N HCL (5 mL) and stirred for 18 hours and the resulting orange oil was concentrated in vacuo and used directly without purification (1.0 g, 83% yield). $^1$H NMR (250 MHz, DMSO-d6) δ 9.71 (s, 1H), 8.82 (s, 2H), 3.45 (s, 3H), 3.20 (m, 1H), 1.14 (d, J=6.9 Hz, 6H).

13.3 1,4-Dimethyl-3-(propan-2-yl)-H-pyrazol-5-ol

To an acetic acid (50 mL) suspension of 5-hydroxy-1-methyl-3-(propan-2-yl)-1H-pyrazole-4-carbaldehyde (2.8 g, 16.65 mmol) was added powdered zinc (16.33 g, 0.25 mol) and the resulting reaction mixture was heated at 65° C. for 2.5 hours until reaction was complete by LCMS. The reaction was cooled to room temperature, filtered, washed with cyclohexane and the solvent removed in vacuo to yield a yellow solid (1.23 g, 48% yield). LC-MS $t_R$=0.8 min, [M+H]$^+$=155.

13.4 4-Bromo-1,4-dimethyl-3-(propan-2-yl)-4,5-dihydro-H-pyrazol-5-one

4-Bromo-1,4-dimethyl-3-(propan-2-yl)-4,5-dihydro-1H-pyrazol-5-one was synthesized from 1,4-dimethyl-3-(propan-2-yl)-1H-pyrazol-5-ol according to General Method 2 and was used directly without purification (1.72 g, 93% yield). LC-MS $t_R$=1.19 min, [M+H]$^+$=235.

13.5 4-{[(tert-Butoxy)carbonyl]({[(tert-butoxy)carbonyl]oxy})amino}-1,4-dimethyl-3-(propan-2-yl)-4,5-dihydro-H-pyrazol-5-one 4-{[(tert-Butoxy)carbonyl]({[(tert-butoxy)carbonyl]oxy})amino}-1,4-dimethyl-3-(propan-2-yl)-4,5-dihydro-1H-pyrazol-5-one was synthesized from 4-bromo-1,4-dimethyl-3-(propan-2-yl)-4,5-dihydro-1H-pyrazol-5-one according to General Method 3 and was purified by silica gel chromatography eluting with heptanes:ethyl acetate (0-80%) to yield the title compound as a yellow oil (650 mg, 10% yield). LC-MS $t_R$=1.51 min, [M+Na]$^+$=408.

13.6 4-(Hydroxyamino)-1,4-dimethyl-3-(propan-2-yl)-4,5-dihydro-H-pyrazol-5-one 4-(Hydroxyamino)-1,4-dimethyl-3-(propan-2-yl)-4,5-dihydro-1H-pyrazol-5-one was synthesized from 4-{[(tert-butoxy)carbonyl]({[(tert-butoxy)carbonyl]oxy})amino}-1,4-dimethyl-3-(propan-2-yl)-4,5-dihydro-1H-pyrazol-5-one according to General Method 4 and was purified by silica gel chromatography eluting with heptanes:ethyl acetate (0-100%) to yield the title compound as a yellow solid (121 mg, 39% yield). LC-MS $t_R$=1.20 min, [M+H]$^+$=186, $^1$H NMR (500 MHz, DMSO-d6) δ 7.43 (s, 1H), 3.13 (s, 3H), 2.77 (p, J=6.9 Hz, 1H), 1.18 (d, J=6.9 Hz, 3H), 1.14 (d, J=6.9 Hz, 3H), 1.05 (s, 3H).

Example 14: Compound 14 [2-[4-(Hydroxyamino)-3-methyl-5-oxo-1-phenyl-4,5-dihydro-1H-pyrazol-4-yl]acetic acid]

14.1 2-(4-{[(tert-butoxy)carbonyl](hydroxy)amino}-3-methyl-5-oxo-1-phenyl-4,5-dihydro-1H-pyrazol-4-yl)acetic acid 2-(4-{[(tert-Butoxy)carbonyl](hydroxy)amino}-3-methyl-5-oxo-1-phenyl-4,5-dihydro-1H-pyrazol-4-yl)acetic acid was synthesized from 2-(5-hydroxy-3-methyl-1-phenyl-1H-pyrazol-4-yl)acetic acid according to General Method 5 and was purified by low pH preparative HPLC (71 mg, 51% yield). $^1$H NMR (250 MHz, Methanol-d4) δ 7.86-7.79 (m, 2H), 7.43-7.34 (m, 2H), 7.23-7.13 (m, 1H), 3.29-3.00 (m, 2H), 2.18 (s, 3H), 1.34 (s, 9H).

14.2 2-[4-(Hydroxyamino)-3-methyl-5-oxo-1-phenyl-4,5-dihydro-1H-pyrazol-4-yl]acetic Acid 2-[4-(Hydroxyamino)-3-methyl-5-oxo-1-phenyl-4,5-dihydro-1H-pyrazol-4-yl]acetic acid was synthesized from 2-(4-{[(tert-butoxy)carbonyl](hydroxy)amino}-3-methyl-5-oxo-1-phenyl-4,5-dihydro-1H-pyrazol-4-yl)acetic acid according to General Method 4 and was purified by low pH preparative HPLC (17 mg, 34% yield). LC-MS $t_R$=2.72 min, [M+H]$^+$=264, $^1$H NMR (500 MHz, DMSO-d6) δ 7.88 (d, J=7.7 Hz, 2H), 7.78 (s, 1H), 7.50-7.44 (m, 2H), 7.22 (t, J=7.4 Hz, 1H), 6.62 (s, 1H), 2.73 (d, J=4.1 Hz, 2H), 2.17 (s, 3H).

Example 15: Compound 15 [(1,4-Dimethyl-5-oxo-3-phenyl-4,5-dihydro-1H-pyrazol-4-yl)amino 2,2-dimethylpropanoate]

15.1 Tert-Butyl N-(1,4-dimethyl-5-oxo-3-phenyl-4,5-dihydro-H-pyrazol-4-yl)-N-hydroxycarbamate tert-Butyl N-(1,4-dimethyl-5-oxo-3-phenyl-4,5-dihydro-1H-pyrazol-4-yl)-N-hydroxycarbamate was synthesized from 1,4-dimethyl-3-phenyl-1H-pyrazol-5-ol according to General Method 5 and was purified by silica gel chromatography eluting with heptanes:ethyl acetate (0-50%) to yield the title compound as a white solid (361 mg, 11% yield). LC-MS $t_R$=1.09 min, [M+Na]$^+$=342, $^1$H NMR (500 MHz, Methanol-d4) δ 7.97-7.91 (m, 2H), 7.47-7.40 (m, 3H), 3.38 (s, 3H), 1.65 (s, 3H), 1.25 (s, 9H).

15.2 [(tert-Butoxy)carbonyl](1,4-dimethyl-5-oxo-3-phenyl-4,5-dihydro-H-pyrazol-4-yl)amino 2,2-dimethylpropanoate To a solution of tert-butyl N-(1,4-dimethyl-5-oxo-3-phenyl-4,5-dihydro-1H-pyrazol-4-yl)-N-hydroxycarbamate (479 mg, 1.27 mmol) and N,N-diethylethanamine (194 μL, 1.4 mmol) in DCM (9 mL) cooled to 0° C. was added and 2,2-dimethylpropanoyl chloride (157 μL, 1.27 mmol) and the reaction mixture was allowed to warm to room temperature for 18 hours. After 18 hours the reaction was retreated with N,N-diethylethanamine (194 μL, 1.4 mmol) and 2,2- dimethylpropanoyl chloride (157 µL, 1.27 mmol) and stirring continued for 4 hours at room temperature. After 4 hours the reaction mixture was retreated with N,N-diethylethanamine (194 µL, 1.4 mmol) and 2,2-dimethylpropanoyl chloride (157 µL, 1.27 mmol) and stirring continued for 18 hours at room temperature. The reaction mixture was partitioned between DCM (20 mL) and water (20 mL) and the organic layer was separated. The aqueous layer was re-extracted with DCM (2×20 mL), the organic layers combined and washed with brine (20 mL) before being dried over sodium sulfate, filtered and concentrated under reduced pressure. The crude product was purified by silica gel chromatography eluting with ethyl acetate:heptane (0-20%) to yield the title product as an orange oil (519 mg, 81% yield). $^1$H NMR (500 MHz, Methanol-d4) δ 8.35-7.79 (m, 2H), 7.45 (s, 3H), 3.40 (s, 3H), 1.65-1.52 (m, 3H), 1.42-1.29 (m, 18H).

15.3 (1,4-Dimethyl-5-oxo-3-phenyl-4,5-dihydro-1H-pyrazol-4-yl)amino 2,2-dimethylpropanoate (1,4-Dimethyl-5-oxo-3-phenyl-4,5-dihydro-1H-pyrazol-4-yl)amino 2,2-dimethylpropanoate was synthesized from [(tert-butoxy)carbonyl](1,4-dimethyl-5-oxo-3-phenyl-4,5-dihydro-1H-pyrazol-4-yl)amino 2,2-dimethylpropanoate according to General Method 4 and was purified by silica gel chromatography eluting with heptanes:ethyl acetate (0-50%) followed by lyophilisation to yield the title compound as a white solid (276 mg, 88% yield). LC-MS $t_R$=1.23 min, [M+H]$^+$=304, $^1$H NMR (250 MHz, Methanol-d4) δ 8.34 (s, 1H), 8.16-8.04 (m, 2H), 7.50-7.37 (m, 3H), 3.38 (s, 3H), 1.46 (s, 3H), 1.01 (s, 9H).

Example 16: Compound 16 [(1,4-Dimethyl-5-oxo-3-phenyl-4,5-dihydro-1H-pyrazol-4-yl)amino benzoate]

16.1 [(tert-Butoxy)carbonyl](1,4-dimethyl-5-oxo-3-phenyl-4,5-dihydro-H-pyrazol-4-yl)amino benzoate To a solution of tert-butyl N-(1,4-dimethyl-5-oxo-3-phenyl-4,5-dihydro-1H-pyrazol-4-yl)-N-hydroxycarbamate (479 mg, 1.27 mmol) and N,N-diethylethanamine (194 µL, 1.4 mmol) in DCM (9 mL) cooled to 0° C. was added benzoyl chloride (148 µL, 1.27 mmol), and the reaction mixture was allowed to warm to room temperature for 18 hours. After 18 hours the reaction was retreated with N,N-diethylethanamine (194 µL, 1.4 mmol) and benzoyl chloride (148 µL, 1.27 mmol) and stirring continued for 4 hours at room temperature. The reaction mixture was partitioned between DCM (20 mL) and water (20 mL) and the organic layer was separated. The aqueous layer was re-extracted with DCM (2×20 mL), the organic layers combined and washed with brine (20 mL) before being dried over sodium sulfate, filtered and concentrated under reduced pressure. The crude product was purified by silica gel chromatography eluting with ethyl acetate:heptane (0-50%) to yield the title product as an orange glass (515 mg, 86% yield). $^1$H NMR (500 MHz, Methanol-d4) δ 8.42-7.88 (m, 4H), 7.77-7.70 (m, 1H), 7.64-7.57 (m, 2H), 7.57-7.39 (m, 3H), 3.43 (s, 3H), 1.72-1.61 (m, 3H), 1.29 (s, 9H).

16.2 (1,4-Dimethyl-5-oxo-3-phenyl-4,5-dihydro-1H-pyrazol-4-yl)amino benzoate (1,4-Dimethyl-5-oxo-3-phenyl-4,5-dihydro-1H-pyrazol-4-yl)amino benzoate was synthesized from [(tert-butoxy)carbonyl](1,4-dimethyl-5-oxo-3-phenyl-4,5-dihydro-H-pyrazol-4-yl)amino benzoate according to General Method 4 and was purified by silica gel chromatography eluting with heptanes:ethyl acetate (0-50%) to yield the title compound as a white solid (346 mg, 93% yield). LC-MS $t_R$=1.23 min, [M+Na]$^+$=346, $^1$H NMR (500 MHz, DMSO-d6) δ 8.92 (s, 1H), 8.10-8.02 (m, 2H), 7.67-7.59 (m, 3H), 7.52-7.41 (m, 5H), 3.37 (s, 3H), 1.46 (s, 3H).

Example 17: Compound 17 [3-benzyl-4-(hydroxyamino)-1,4-dimethyl-4,5-dihydro-1H-pyrazol-5-one]

17.1 3-Benzyl-1-methyl-1H-pyrazol-5-ol

3-Benzyl-1-methyl-1H-pyrazol-5-ol was synthesized from ethyl 3-oxo-4-phenylbutanoate according to General Method 1 and was used directly without purification (4.9 g, Quant. yield). $^1$H NMR (500 MHz, Chloroform-d) δ 7.35-7.21 (5H, m), 3.71 (2H, s), 3.30 (3H, s), 3.08 (2H, s).

17.2 3-Benzyl-5-hydroxy-1-methyl-1H-pyrazole-4-carbaldehyde

To a solution of 3-benzyl-1-methyl-4,5-dihydro-1H-pyrazol-5-one (4.9 g, 24.21 mmol) in DMF (12 mL) was added phosphorus oxychloride (1.58 mL, 16.95 mmol) and the reaction mixture was heated to 65° C. for 2.5 hours. The reaction mixture was diluted with water (25 mL) and allowed to stand at room temperature for two days. The solution was filtered to remove the precipitate and the filtrate was washed with diethyl ether (3×60 mL) and the organic layer washed with brine (10 mL). The resulting solution was dried over magnesium sulfate, filtered and concentrated under vacuum to give a brown oil which was purified by silica gel chromatography eluting with heptane:ethyl acetate (0-100%), followed by methanol in ethyl acetate (0-20%) to yield the title compound as a yellow solid (0.53 g, 10% yield). $^1$H NMR (500 MHz, DMSO-d6) δ 9.65 (1H, s), 7.14-7.26 (5H, m), 3.99 (2H, s), 3.47 (3H, s).

17.3 3-Benzyl-1,4-dimethyl-1H-pyrazol-5-ol

An acetic acid (15 mL) suspension of 3-benzyl-5-hydroxy-1-methyl-1H-pyrazole-4-carbaldehyde (0.53 g, 2.23 mmol) and powdered zinc (1.46 g, 22.3 mmol) was heated at 65° C. for 18 hours. The reaction mixture was retreated with zinc (1.46 g, 22.3 mmol) and stirred at 65° C. for 2 hours. The reaction mixture was filtered over glass fibre filter paper whilest hot (55° C.) and the zinc was washed with acetic acid (60 mL). The filtrate concentrated in vacuo and azeotroped with toluene to afford a brown solid, (650 mg, Quant. yield). LC-MS $t_R$=0.9 min, [M+H]$^+$=203.

17.4 Tert-Butyl N-(3-benzyl-1,4-dimethyl-5-oxo-4,5-dihydro-H-pyrazol-4-yl)-N-hydroxycarbamate tert-Butyl N-(3-benzyl-1,4-dimethyl-5-oxo-4,5-dihydro-1H-pyrazol-4-yl)-N-hydroxycarbamate was synthesized from 3-benzyl-1,4-dimethyl-1H-pyrazol-5-ol according to General Method 5 and was purified by silica gel chromatography eluting with heptanes:ethyl acetate (0-100%) to yield the title compound as a yellow oil (294 mg, 37% yield). LC-MS $t_R$=1.06 min, [M+Na]$^+$=356. $^1$H NMR (250 MHz, Chloroform-d) δ 7.36-7.27 (m, 5H), 6.80 (s, 1H), 3.68 (d, J=6.5 Hz, 2H), 3.29 (s, 3H), 1.40 (s, 3H), 1.35 (s, 9H).

17.5 3-Benzyl-4-(hydroxyamino)-1,4-dimethyl-4,5-dihydro-H-pyrazol-5-one

3-Benzyl-4-(hydroxyamino)-1,4-dimethyl-4,5-dihydro-1H-pyrazol-5-one was synthesized from tert-butyl N-(3-benzyl-1,4-dimethyl-5-oxo-4,5-dihydro-1H-pyrazol-4-yl)-N-hydroxycarbamate according to General Method 4 and was purified by silica gel chromatography eluting with heptanes:ethyl acetate (0-100%) followed by lyophilisation from acetonitrile:water (1:1) to yield the title compound as a yellow solid (117 mg, 59% yield). LC-MS $t_R$=2.94 min, [M+H]$^+$=234. $^1$H NMR (250 MHz, DMSO-d6) δ 7.65 (s, 1H), 7.39-7.13 (m, 6H), 3.73 (d, J=4.2 Hz, 2H), 3.10 (s, 3H), 0.89 (s, 3H).

Example 18: Compound 18 [1,4-Dimethyl-4-{[(5-methyl-2-oxo-2H-1,3-dioxol-4-yl)methoxy]amino}-3-phenyl-4,5-dihydro-1H-pyrazol-5-one]

18.1 Tert-Butyl N-(1,4-dimethyl-5-oxo-3-phenyl-4,5-dihydro-1H-pyrazol-4-yl)-N-[(5-methyl-2-oxo-2H-1,3-dioxol-4-yl)methoxy]carbamate To a solution of tert-butyl N-(1,4-dimethyl-5-oxo-3-phenyl-4,5-dihydro-1H-pyrazol-4-yl)-N-hydroxycarbamate (361 mg, 1.13 mmol) in DMF (1 mL) cooled to 0° C. was added sodium hydride (60%, 45 mg, 1.13 mmol) and the reaction mixture was stirred for 15 minutes. Sodium iodide (169 mg, 1.13 mmol) and 4-(chloromethyl)-5-methyl-1,3-dioxol-2-one (123 μL, 1.13 mmol) were added and the reaction mixture was heated at 60° C. for 1 hour. The reaction mixture was quenched by the addition of saturated ammonium chloride solution (10 mL) and was diluted with ethyl acetate (10 mL). The organic layer was separated and the aqueous layer was re-extracted with ethyl acetate (10 mL). The organic layers were combined, washed with brine (10 mL), dried over sodium sulfate, filtered and concentrated under reduced pressure. The product was purified by silica gel chromatography eluting with heptanes:ethyl acetate (0-50%) to yield the title compound as an off white solid (91 mg, 13% yield). $^1$H NMR (500 MHz, DMSO-d6) δ 7.78-7.67 (m, 2H), 7.59-7.41 (m, 3H), 5.38-5.23 (m, 1H), 5.14-5.02 (m, 1H), 2.03-1.93 (m, 3H), 1.70-1.60 (m, 3H), 1.38-1.22 (m, 3H), 1.21-1.04 (m, 9H).

18.2 1,4-Dimethyl-4-{[(5-methyl-2-oxo-2H-1,3-dioxol-4-yl)methoxy]amino}-3-phenyl-4,5-dihydro-1H-pyrazol-5-one 1,4-Dimethyl-4-{[(5-methyl-2-oxo-2H-1,3-dioxol-4-yl)methoxy]amino}-3-phenyl-4,5-dihydro-1H-pyrazol-5-one was synthesized from tert-butyl N-(1,4-dimethyl-5-oxo-3-phenyl-4,5-dihydro-1H-pyrazol-4-yl)-N-[(5-methyl-2-oxo-2H-1,3-dioxol-4-yl)methoxy]carbamate according to General Method 4 and was purified by silica gel chromatography eluting with heptanes:ethyl acetate (0-50%) followed by low pH preparative HPLC to yield the title compound as a white solid (23 mg, 20% yield). LC-MS $t_R$=2.94 min, [M+H]$^+$=234. $^1$H NMR (500 MHz, DMSO-d6) δ 8.03-7.94 (m, 2H), 7.73 (s, 1H), 7.49-7.41 (m, 3H), 4.20 (d, J=14.4 Hz, 1H), 4.10 (d, J=14.4 Hz, 1H), 3.30 (s, 3H), 1.98 (s, 3H), 1.29 (s, 3H).

Example 19: Compound 19 [Ethyl 2-[4-(hydroxyamino)-3-methyl-5-oxo-4,5-dihydro-1H-pyrazol-4-yl]acetate]

19.1 Ethyl 2-(5-hydroxy-3-methyl-1H-pyrazol-4-yl)acetate

Ethyl 2-(5-hydroxy-3-methyl-1H-pyrazol-4-yl)acetate was synthesized from 1,4-diethyl 2-acetylbutanedioate according to General Method 1 and was isolated as a white solid and used directly without additional purification (781 mg, 91% yield). LC-MS $t_R$=0.64 min, [M+H]$^+$=185.

19.2 Ethyl 2-(4-{[(tert-butoxy)carbonyl](hydroxy)amino}-3-methyl-5-oxo-4,5-dihydro-1H-pyrazol-4-yl)acetate Ethyl 2-(4-{[(tert-butoxy)carbonyl](hydroxy)amino}-3-methyl-5-oxo-4,5-dihydro-1H-pyrazol-4-yl)acetate was synthesized from ethyl 2-(5-hydroxy-3-methyl-1H-pyrazol-4-yl)acetate according to General Method 5 and was purified by silica gel chromatography eluting with heptanes:ethyl acetate (0-100%) to yield the title compound as an off white solid (174 mg, 13% yield). $^1$H NMR (250 MHz, DMSO-d6) δ 10.91 (s, 1H), 9.88 (s, 1H), 4.06-3.92 (m, 2H), 2.99 (d, J=13.9 Hz, 1H), 2.71 (d, J=13.9 Hz, 1H), 1.92 (s, 3H), 1.35 (s, 9H), 1.13 (t, J=7.1 Hz, 3H).

19.3 Ethyl 2-[4-(hydroxyamino)-3-methyl-5-oxo-4,5-dihydro-1H-pyrazol-4-yl]acetate Ethyl 2-[4-(hydroxyamino)-3-methyl-5-oxo-4,5-dihydro-1H-pyrazol-4-yl]acetate was synthesized from ethyl 2-(4-{[(tert-butoxy)carbonyl](hydroxy)amino}-3-methyl-5-oxo-4,5-dihydro-1H-pyrazol-4-yl)acetate according to General Method 4 and was purified by silica gel chromatography eluting with heptanes:ethyl acetate (0-100%) followed by lyophilisation to yield the title compound as an off white solid (66 mg, 57% yield). m/z=[M+H]$^+$=215.95, $^1$H NMR (250 MHz, DMSO-d6) δ 10.81 (s, 1H), 7.57 (d, J=3.0 Hz, 1H), 6.26 (d, J=3.0 Hz, 1H), 3.98 (q, J=7.1 Hz, 2H), 2.54 (s, 2H), 1.93 (s, 3H), 1.11 (t, J=7.1 Hz, 3H).

Example 20: Compound 20 [3a-(Hydroxyamino)-2H,3H,3aH,4H,5H,6H-cyclopenta[c]pyrazol-3-one]

20.1 2H, 4H, 5H, 6H-Cyclopenta[c]pyrazol-3-ol

A solution of methyl 2-oxocyclopentane-1-carboxylate and methyl hydrazine in ethanol was heated to 70° C. for 2 hours. The solvent was removed to afford the intermediate imine as a yellow oil which was re-dissolved in ethanol (5 mL) and heated at 75° C. for 2 hours. The resulting solid was removed by filtration and washed with ethanol to afford 61 mg (7%) of the title compound as a white solid. The remaining yellow filtrate irradiated in a microwave at 170° C. for 1 hour. The resulting solid was isolated by filtration and washed with heptanes to afford an additional crop of the title compound as a yellow solid (125 mg, 14%). $^1$H NMR (500 MHz, DMSO-d6) δ 10.20 (s, 2H), 2.39-2.31 (m, 6H).

20.2 Tert-Butyl N-hydroxy-N-{3-oxo-2H, 3H, 3aH, 4H, 5H, 6H-cyclopenta[c]pyrazol-3a-yl}carbamate tert-Butyl N-hydroxy-N-{3-oxo-2H,3H,3aH,4H,5H,6H-cyclopenta[c]pyrazol-3a-yl}carbamate was synthesized from 2H,4H,5H,6H-Cyclopenta[c]pyrazol-3-ol according to General Method 5 and was purified by silica gel chromatography eluting with heptanes:ethyl acetate (0-100%) to yield the title compound as an off white solid (227 mg, 88% yield). LC-MS $t_R$=0.76 min, [M+Na]$^+$=278, $^1$H NMR (250 MHz, DMSO-d6) δ 10.80 (s, 1H), 9.67 (s, 1H), 2.45-2.02 (m, 6H), 1.37 (s, 9H).

20.3 3a-(Hydroxyamino)-2H, 3H, 3aH, 4H, 5H, 6H-cyclopenta[c]pyrazol-3-one

To a solution of tert-butyl N-hydroxy-N-{3-oxo-2H,3H,3aH,4H,5H,6H-cyclopenta[c]pyrazol-3a-yl}carbamate (100 mg, 0.39 mmol) in DCM (1 mL) was added HCl (0.98 mL of a 4M solution in 1,4-dioxane) and the reaction mixture was stirred at room temperature for 3 hours. The solvent was removed in vacuo to give an off-white solid which was dried in vacuo (49 mg, 81% yield). LC-MS $t_R$=0.64 min, [M+H]$^+$=156, $^1$H NMR (250 MHz, DMSO-d6) δ 2.40-2.18 (m, 2H), 2.12-1.91 (m, 2H), 1.88-1.67 (m, 1H), 1.66-1.41 (m, 1H).

Example 21: Compound 21 [4-(Hydroxyamino)-4-(2-hydroxyethyl)-1,3-dimethyl-4,5-dihydro-1H-pyrazol-5-one]

21.1
4-(2-Hydroxyethyl)-1,3-dimethyl-1H-pyrazol-5-ol 4-(2-Hydroxyethyl)-1,3-dimethyl-1H-pyrazol-5-ol was synthesized from 3-acetyloxolan-2-one according to General Method 1 and isolated as a white solid (3.69 g, Quant. yield). $^1$H NMR (250 MHz, Chloroform-d) δ 3.79 (d, J=5.4 Hz, 2H), 3.40 (s, 3H), 2.50 (t, J=5.4 Hz, 2H), 2.07 (s, 3H).

21.2 Tert-Butyl N-hydroxy-N-[4-(2-hydroxyethyl)-1,3-dimethyl-5-oxo-4,5-dihydro-1H-pyrazol-4-yl]carbamate tert-Butyl N-hydroxy-N-[4-(2-hydroxyethyl)-1,3-dimethyl-5-oxo-4,5-dihydro-1H-pyrazol-4-yl]carbamate was synthesized from 4-(2-hydroxyethyl)-1,3-dimethyl-1H-pyrazol-5-ol according to General Method 5 and was purified by silica gel chromatography eluting with heptanes:ethyl acetate (20-100%) followed by trituration from heptane:ethyl acetate to yield the title compound as a white solid (770 mg, 41% yield). LC-MS $t_R$=0.82 min, [M+Na]$^+$=310, $^1$H NMR (250 MHz, DMSO-d6) δ 9.77 (s, 1H), 4.62 (s, 1H), 3.32-3.22 (m, 2H), 3.08 (s, 3H), 2.05-1.95 (m, 2H), 1.89 (s, 3H), 1.32 (s, 9H).

21.3 4-(Hydroxyamino)-4-(2-hydroxyethyl)-1,3-dimethyl-4,5-dihydro-H-pyrazol-5-one To a solution of tert-butyl N-hydroxy-N-[4-(2-hydroxyethyl)-1,3-dimethyl-5-oxo-4,5-dihydro-1H-pyrazol-4-yl] carbamate (170 mg, 0.58 mmol) in DCM (2 mL) was added HCl (0.94 mL of a 4M solution in 1,4-dioxane) and the resulting yellow solution was stirred at room temperature for 20 hours. The reaction mixture was concentrated in vacuo to afford a colourless oil which was azeotroped with DCM (10 mL) followed by diethyl ether (10 mL) and heptanes to afford a sticky white solid, which was lyophilised from acetonitrile:water (1:1) to afford the title compound as a glass (107 mg, Quant. yield). LC-MS $t_R$=0.54 min, [M+H]$^+$=188, $^1$H NMR (500 MHz, DMSO-d6) δ 3.26-3.18 (m, 2H), 3.11 (s, 3H), 2.01 (s, 3H), 1.74 (t, J=6.8 Hz, 2H).

Example 22: Compound 22 [2-[4-(Hydroxyamino)-3-(4-methanesulfonylphenyl)-4-methyl-5-oxo-4,5-dihydro-1H-pyrazol-1-yl]acetamide]

22.1 2-(4-{[(tert-Butoxy)carbonyl](hydroxy)amino}-3-(4-methanesulfonylphenyl)-4-methyl-5-oxo-4,5-dihydro-1H-pyrazol-1-yl)acetic Acid To a solution of ethyl 2-(4-{[(tert-butoxy)carbonyl](hydroxy)amino}-3-(4-methanesulfonylphenyl)-4-methyl-5-oxo-4,5-dihydro-1H-pyrazol-1-yl)acetate (300 mg, 0.64 mmol) in water:THF (10 mL, 1:1) was added lithium hydroxide (45.91 mg, 1.92 mmol) and the reaction mixture was stirred at room temperature for 1.5 hours. The THF was removed in vacuo and the reaction mixture was partitioned between ethyl acetate (20 mL) and water (5 mL). The biphasic mixture was acidified to pH 1 by the addition of 1N HCl and the desired product was extracted into ethyl acetate. The acidic aqueous solution was re-extracted with ethyl acetate (3×15 mL) and the organics were combined, dried over magnesium sulfate, filtered and concentrated in vacuo to afford the title compound as a white solid (292 mg, 94% yield). LC-MS $t_R$=0.93 min, [M+Na]$^+$=464, $^1$H NMR (500 MHz, DMSO-d6) δ 10.41 (s, 1H), 8.08 (d, J=8.7 Hz, 2H), 8.03 (d, J=8.7 Hz, 2H), 4.64 (d, J=17.6 Hz, 1H), 4.36 (d, J=17.6 Hz, 1H), 3.26 (s, 3H), 1.91 (s, 1H), 1.59 (s, 3H), 1.20 (s, 9H).

22.2 Tert-Butyl N-[1-(carbamoylmethyl)-3-(4-methanesulfonylphenyl)-4-methyl-5-oxo-4,5-dihydro-1H-pyrazol-4-yl]-N-hydroxycarbamate To a solution of 2-(4-{[(tert-butoxy)carbonyl](hydroxy)amino}-3-(4-methanesulfonylphenyl)-4-methyl-5-oxo-4,5-dihydro-1H-pyrazol-1-yl)acetic acid (120 mg, 0.22 mmol) in DCM (3 mL) at room temperature was added 1-chloro-N,N,2-trimethylprop-1-en-1-amine (73.72 μl, 0.56 mmol) and stirring was continued under nitrogen for 1 hour to form tert-butyl N-[1-(2-chloro-2-oxoethyl)-3-(4-methanesulfonylphenyl)-4-methyl-5-oxo-4,5-dihydro-1H-pyrazol-4-yl]-N-hydroxycarbamate which was used directly to form the primary amide The solution containing the acid chloride was diluted with THF (1 mL) and added dropwise to an ice cooled ammonia solution (1.11 mL of a 0.5M solution in THF). The reaction mixture was allowed to warm to room temperature and stirring continued for 20 hours. The solvent was removed in vacuo and DCM (10 mL) was added. The resulting slurry was filtered to remove any solid and the filtrate was concentrated in vacuo to afford a white solid which was redissolved in ethyl acetate (30 mL) and washed with water (3×15 mL). The organic layer was dried over magnesium sulfate, filtered and concentrated in vacuo to afford a colourless oil. The oil was re-dissolved in ethyl acetate (20 mL) and washed with water (3×20 mL). The organic layer was isolated, dried over magnesium sulfate, filtered and concentrated in vacuo to afford the title compound as a white solid (85 mg, 27% yield). LC-MS $t_R$=0.91 min, [M+Na]$^+$=463

22.3 2-[4-(Hydroxyamino)-3-(4-methanesulfonylphenyl)-4-methyl-5-oxo-4,5-dihydro-1H-pyrazol-1-yl]acetamide 2-[4-(Hydroxyamino)-3-(4-methanesulfonylphenyl)-4-methyl-5-oxo-4,5-dihydro-1H-pyrazol-1-yl]acetamide was synthesized from tert-butyl N-[1-(carbamoylmethyl)-3-(4-methanesulfonylphenyl)-4-methyl-5-oxo-4,5-dihydro-1H-pyrazol-4-yl]-N-hydroxycarbamate according to General Method 4 and was purified via low pH preparative HPLC to yield the title compound as a white solid (12 mg, 57% yield). LC-MS $t_R$=2.33 min, [M+H]$^+$=341, $^1$H NMR (250 MHz, DMSO-d6) δ 8.27 (d, J=8.7 Hz, 2H), 8.01 (d, J=8.7 Hz, 2H), 7.83 (s, 1H), 7.31 (d, J=8.6 Hz, 2H), 6.70 (s, 1H), 4.32 (d, J=17.0 Hz, 2H) 4.39 (d, J=16.8 Hz, 1H), 4.25 (d, J=16.9 Hz, 1H), 3.25 (s, 3H), 1.29 (s, 3H).

Example 23: Compound 23 [4-(Hydroxyamino)-4-(2-hydroxyethyl)-3-methyl-4,5-dihydro-1H-pyrazol-5-one]

23.1 4-(2-Hydroxyethyl)-3-methyl-1H-pyrazol-5-ol 4-(2-Hydroxyethyl)-3-methyl-1H-pyrazol-5-ol was synthesized from 3-acetyloxolan-2-one and hydrazine hydrate according to General Method 1 and was isolated as a white solid via filtration and used directly without any additional purification, (4.7 g, 85% yield). $^1$H NMR (250 MHz, DMSO-d6) δ 3.40 (t, J=7.3 Hz, 2H), 2.35 (t, J=7.3 Hz, 2H), 2.04 (s, 3H).

23.2 Tert-Butyl N-hydroxy-N-[4-(2-hydroxyethyl)-3-methyl-5-oxo-4,5-dihydro-H-pyrazol-4-yl]carbamate tert-Butyl N-hydroxy-N-[4-(2-hydroxyethyl)-3-methyl-5-oxo-4,5-dihydro-1H-pyrazol-4-yl]carbamate was synthesized from 4-(2-hydroxyethyl)-3-methyl-1H-pyrazol-5-ol according to General Method 5 and was purified by trituration from heptane:ethyl acetate to yield the title compound as a white solid (491 mg, 64% yield). LC-MS $t_R$=0.72 min, [M+Na]$^+$=296

23.3 4-(Hydroxyamino)-4-(2-hydroxyethyl)-3-methyl-4,5-dihydro-H-pyrazol-5-one 4-(Hydroxyamino)-4-(2-hydroxyethyl)-3-methyl-4,5-dihydro-1H-pyrazol-5-one was synthesized from tert-butyl N-hydroxy-N-[4-(2-hydroxyethyl)-3-methyl-5-oxo-4,5-dihydro-1H-pyrazol-4-yl]carbamate according to General Method 4 and was azeotroped from heptane:ethyl acetate (1:1) to yield the title compound as a white solid (54 mg, 85% yield). LC-MS $t_R$=0.2 min, [M+H]$^+$=174, $^1$H NMR (250 MHz, Methanol-d4) δ 3.60-3.34 (m, 2H), 2.08 (s, 3H), 1.81 (td, J=6.8, 1.0 Hz, 2H), 1H NMR (250 MHz, DMSO-d6) δ 10.49 (s, 1H), 3.44-3.25 (m, 2H), 1.97 (s, 3H), 1.66 (td, J=7.3, 2.4 Hz, 2H).

Example 24: Compound 24 [3a-(Hydroxyamino)-2H,3H,3aH,4H,6H,7H-thiopyrano[4,3-c]pyrazol-3-one]

24.1 2H, 4H, 6H, 7H-Thiopyrano[4,3-c]pyrazol-3-ol 2H,4H,6H,7H-thiopyrano[4,3-c]pyrazol-3-ol was synthesized from methyl 4-oxothiane-3-carboxylate according to General Method 1 and was isolated as a white solid which was washed with ethanol (100 mL) to afford the title compound (1.95 g, 87% yield). LC-MS $t_R$=1.60 min, [M+H]$^+$=157, $^1$H NMR (500 MHz, DMSO-d6) δ 3.36 (s, 5H), 2.78 (t, J=5.8 Hz, 2H), 2.68 (t, J=5.7 Hz, 2H).

24.2 Tert-Butyl N-hydroxy-N-{3-oxo-2H,3H,3aH,4H,6H,7H-thiopyrano[4,3-c]pyrazol-3a-yl}carbamate tert-Butyl N-hydroxy-N-{3-oxo-2H,3H,3aH,4H,6H,7H-thiopyrano[4,3-c]pyrazol-3a-yl}carbamate was synthesized from 2H,4H,6H,7H-thiopyrano[4,3-c]pyrazol-3-ol according to General Method 5 and was purified via trituration from diethyl ether (~40 mL) to afford the title compound as a white solid (1.126 g, 41% yield). LC-MS $t_R$=0.82 min, [M+Na]$^+$=310, $^1$H NMR (250 MHz, Chloroform-d) δ 8.42 (s, 1H), 6.44 (s, 1H), 3.56 (d, J=14.1 Hz, 1H), 2.87-2.80 (m, 3H), 2.68-2.62 (m, 2H), 1.39 (s, 9H).

24.3 3a-(Hydroxyamino)-2H, 3H,3aH,4H,6H,7H-thiopyrano[4,3-c]pyrazol-3-one 3a-(Hydroxyamino)-2H,3H,3aH,4H,6H,7H-thiopyrano[4,3-c]pyrazol-3-one was synthesized from tert-butyl N-hydroxy-N-{3-oxo-2H,3H,3aH,4H,6H,7H-thiopyrano[4,3-c]pyrazol-3a-yl}carbamate according to General Method 4 and was isolated via trituration from heptane followed by lyophilisation from acetonitrile:water (1:1) to yield the title compound as a white solid (108 mg, 83% yield). LC-MS $t_R$=1.04 min, [M+H]$^+$=188, $^1$H NMR (250 MHz, DMSO-d6) δ 11.09 (s, 1H), 7.68 (s, 1H), 6.16 (s, 1H), 2.96-2.83 (m, 1H), 2.79-2.63 (m, 5H).

Example 25: Compound 25 [3a-(Hydroxyamino)-2H,3H,3aH,4H,6H,7H-5λ$^6$-thiopyrano[4,3-c]pyrazole-3,5,5-trione]

25.1 Tert-Butyl N-hydroxy-N-{3,5,5-trioxo-2H,3H,3aH,4H,6H,7H-5λ$^6$,1,2-[1λ$^6$]thiopyrano[4,3-c]pyrazol-3a-yl}carbamate To a vigorously stirred solution of tert-butyl N-hydroxy-N-{3-oxo-2H,3H,3aH,4H,6H,7H-thiopyrano[4,3-c]pyrazol-3a-yl}carbamate (0.5 g, 1.74 mmol) in 1,4-dioxane:water (10 mL, 1:1, vv) was added Oxone (2.14 g, 3.48 mmol) and the reaction mixture was stirred at room temperature for 4 hours. The solids were removed by filtration and washed with ethyl acetate (50 mL). The layers were separated and the aqueous layer was re-extracted with ethyl acetate (3×10 mL). The combined organic layers were washed with water (3×30 mL) and the organic layer was washed with brine (10 mL), dried over magnesium sulfate, filtered and concentrated in vacuo to afford the title compound as a white solid (460 mg, 83% yield). LC-MS $t_R$=0.97 min, [M−H]$^-$=269, $^1$H NMR (250 MHz, Chloroform-d) δ 8.56 (s, 1H), 6.79 (s, 1H), 4.20 (dd, J=14.9, 3.8 Hz, 1H), 3.54-3.11 (m, 4H), 3.09-2.93 (m, 1H), 1.48 (s, 9H).

25.2 3a-(Hydroxyamino)-2H,3H,3aH,4H,6H,7H-5λ$^6$-thiopyrano[4,3-c]pyrazole-3,5,5-trione 3a-(Hydroxyamino)-2H,3H,3aH,4H,6H,7H-5λ$^6$-thiopyrano[4,3-c]pyrazole-3,5,5-trione was synthesized tert-butyl N-hydroxy-N-{3-oxo-2H,3H,3aH,4H,6H,7H-thiopyrano[4,3-c]pyrazol-3a-yl}carbamate according to General Method 4 and was isolated via trituration from DCM to yield the title compound as a white solid (145 mg, 46% yield). LC-MS $t_R$=0.18 min, [M+H]$^+$=220, $^1$H NMR (250 MHz, Deuterium Oxide) δ 3.75 (d, J=14.6 Hz, 1H), 3.66-3.39 (m, 3H), 3.36-3.19 (m, 1H), 3.15-3.01 (m, 1H).

Example 26: Compound 26 [3a-(Hydroxyamino)-2H,3H,3aH,4H,5H,7H-pyrano[3,4-c]pyrazol-3-one]

26.1 2H, 4H, 5H, 7H-Pyrano[3,4-c]pyrazol-3-ol 2H,4H,5H,7H-pyrano[3,4-c]pyrazol-3-ol was synthesized from ethyl 3-oxooxane-4—according to General Method 1 and the resulting solid was isolated via filtration and was washed with ethanol (2×5 mL) to yield the title compound as a white solid (322 mg, 78% yield). $^1$H NMR (500 MHz, Methanol-d4) δ 4.56 (s, 2H), 3.84 (t, J=5.6 Hz, 2H), 2.45 (t, J=5.6 Hz, 2H).

26.2 Tert-Butyl N-hydroxy-N-{3-oxo-2H, 3H, 3aH, 4H, 5H, 7H-pyrano[3,4-c]pyrazol-3a-yl}carbamate tert-Butyl N-hydroxy-N-{3-oxo-2H,3H,3aH,4H,5H,7H-pyrano[3,4-c]pyrazol-3a-yl}carbamate was synthesized from 2H,4H,5H,7H-pyrano[3,4-c]pyrazol-3-ol according to General Method 5 and was purified by silica gel chromatography eluting with heptanes:ethyl acetate (0-70%) to yield the title compound as a white solid. (473 mg, 79%, purity 99%). $^1$H NMR (500 MHz, Methanol-d4) δ 4.29 (d, J=11.9 Hz, 1H), 4.18 (d, J=11.9 Hz, 1H), 3.87-3.75 (m, 2H), 2.83 (d, J=14.3 Hz, 1H), 1.78 (ddd, J=14.2, 11.0, 5.4 Hz, 1H), 1.42 (s, 9H).

26.3 3a-(Hydroxyamino)-2H, 3H, 3aH,4H,5H,7H-pyrano[3,4-c]pyrazol-3-one 3a-(Hydroxyamino)-2H,3H,3aH,4H,5H,7H-pyrano[3,4-c]pyrazol-3-one was synthesized from tert-butyl N-hydroxy-N-{3-oxo-2H,3H,3aH,4H,5H,7H-pyrano[3,4-c]pyrazol-3a-yl}carbamate according to General Method 4 and was azeotroped with DCM followed by heptane. The resulting gum was lyophilised to afford the title compound as a yellow powder (305 mg, 99% yield). LC-MS $t_R$=0.46 min, [M+H]$^+$=172, $^1$H NMR (500 MHz, DMSO-d6) δ 11.21 (s, 1H), 7.62 (br.s, 1H), 6.54 (br.s, 1H), 4.27 (d, J=11.9 Hz, 1H), 4.20 (d, J=11.9 Hz, 1H), 3.75-3.62 (m, 2H), 1.79 (d, J=14.1 Hz, 1H), 1.59 (ddd, J=14.1, 12.1, 5.2 Hz, 1H).

Example 27: Compound 27 [3a-(Hydroxyamino)-2H,3H,3aH,4H,6H-5λ$^6$-thieno[3,4-c]pyrazole-3,5,5-trione]

27.1 2H, 4H, 6H-Thieno[3,4-c]pyrazol-3-ol 2H,4H,6H-Thieno[3,4-c]pyrazol-3-ol was synthesized from methyl 4-oxotetrahydrothiophene-3-carboxylate and hydrazine hydrate according to General Method 1 and the resulting solid was isolated by filtration and was washed with ethanol (2×5 mL) to yield the title compound as an off white solid (129 mg, 29% yield). $^1$H NMR (500 MHz, Methanol-d4) δ 3.89-3.83 (m, 2H), 3.75-3.70 (m, 2H).

27.2 Tert-Butyl N-hydroxy-N-{3-oxo-2H,3H,3aH, 4H,6H-thieno[3,4-c]pyrazol-3a-yl}carbamate tert-Butyl N-hydroxy-N-{3-oxo-2H,3H,3aH,4H,6H-thieno[3,4-c]pyrazol-3a-yl}carbamate was synthesized from 2H,4H,6H-thieno[3,4-c]pyrazol-3-ol according to General Method 5 and was purified by silica gel chromatography eluting with heptanes:ethyl acetate (0-60%) to yield the title compound as a white solid (183 mg, 72% yield). LC-MS $t_R$=0.81 min, [M+Na]$^+$=296, $^1$H NMR (500 MHz, Methanol-d4) δ 3.66 (d, J=11.9 Hz, 1H), 3.49 (dd, J=12.0, 4.8 Hz, 2H), 2.88 (d, J=12.0 Hz, 1H), 1.47 (s, 9H).

27.3 Tert-Butyl N-hydroxy-N-{3,5,5-trioxo-2H, 3H,3aH, 4H,6H-5λ$^6$1,2-[1λ$^6$]thieno[3,4-c]pyrazol-3a-yl}carbamate To a vigorously stirred solution of tert-butyl N-hydroxy-N-{3-oxo-2H,3H,3aH,4H,6H-thieno[3,4-c]pyrazol-3a-yl}carbamate (113 mg, 0.41 mmol) in 1,4-dioxane:water (4 mL, 1:1, vv) was added Oxone (373.6 mg, 0.61 mmol) and the reaction mixture was stirred at room temperature for 4 hours. The solids were removed by filtration and washed with ethyl acetate (20 mL). The layers were separated and the aqueous layer was re-extracted with ethyl acetate (3×10 mL). The combined organic layers were washed with water (3×10 mL) and the organic layer was washed with brine (10 mL), dried over magnesium sulfate, filtered and concentrated in vacuo. The resulting oil was purified by silica gel chromatography eluting with heptanes:ethyl acetate (0-70%) to afford the title compound as a white solid (80 mg, 62% yield). LC-MS $t_R$=0.76 min, [M–H]$^-$=304, $^1$H NMR (500 MHz, Methanol-d4) δ 4.40 (d, J=14.1 Hz, 1H), 4.18 (s, 1H), 3.45 (d, J=14.0 Hz, 1H), 1.48 (s, 9H).

27.4 3a-(Hydroxyamino)-2H,3H,3aH,4H,6H-5λ$^6$-thieno[3,4-c]pyrazole-3,5,5-trione 3a-(Hydroxyamino)-2H,3H,3aH,4H,6H-5λ$^6$-thieno[3,4-c]pyrazole-3,5,5-trione was synthesized from tert-butyl N-hydroxy-N-{3,5,5-trioxo-2H,3H,3aH,4H,6H-5λ$^6$,1,2-[1λ$^6$]thieno[3,4-c]pyrazol-3a-yl}carbamate according to General Method 4 and was purified by silica gel chromatography eluting with heptanes:ethyl acetate (0-100%) to yield the title compound as a white solid (201 mg, 83% yield). LC-MS $t_R$=0.45 min, [M+H]$^+$=206, $^1$H NMR (500 MHz, DMSO-d6) δ 11.67 (s, 1H), 8.08 (br. s, 1H), 6.85 (br. s, 1H), 4.35 (d, J=14.1 Hz, 1H), 4.26 (d, J=14.1 Hz, 1H), 3.55 (d, J=13.8 Hz, 1H), 3.41 (d, J=13.7 Hz, 1H).

Example 28: Compound 28 [(5-Methyl-2-oxo-2H-1,3-dioxol-4-yl)methyl 2-[4-(hydroxyamino)-3-(4-methanesulfonylphenyl)-4-methyl-5-oxo-4,5-dihydro-1H-pyrazol-1-yl]acetate]

28.1 (5-Methyl-2-oxo-2H-1,3-dioxol-4-yl)methyl 2-(4-{[(tert-butoxy)carbonyl](hydroxy)amino}-3-(4-methanesulfonylphenyl)-4-methyl-5-oxo-4,5-dihydro-1H-pyrazol-1-yl)acetate To a solution of 2-(4-{[(tert-butoxy)carbonyl](hydroxy)amino}-3-(4-methanesulfonylphenyl)-4-methyl-5-oxo-4,5-dihydro-1H-pyrazol-1-yl)acetic acid (150 mg, 0.31 mmol) in DCM (3 mL) at room temperature was added 1-chloro-N,N,2-trimethylprop-1-en-1-amine (123.26 μl, 0.93 mmol). The reaction mixture was stirred under nitrogen for 30 minutes at room temperature to form tert-butyl N-[1-(2-chloro-2-oxoethyl)-3-(4-methanesulfonylphenyl)-4-methyl-5-oxo-4,5-dihydro-1H-pyrazol-4-yl]-N-hydroxycarbamate which was used directly in the formation of the corresponding ester.

To the solution containing the afore synthesized acid chloride cooled to 0° C. was added 4-(hydroxymethyl)-5-methyl-2H-1,3-dioxol-2-one (323 μl, 2.48 mmol). The reaction mixture was warmed to room temperature and stirred for 6 hours, after which time the reaction mixture was diluted with DCM (10 mL) and quenched with water (10 mL). The organic layer was isolated and the aqueous layer was re-extracted with DCM (3×10 mL). The combined organic layers were washed with water (10 mL), brine (10 mL), dried over magnesium sulfate, filtered and concentrated in vacuo. The resulting oil was purified by silica gel chromatography eluting with heptanes:ethyl acetate (0-80%) to afford the title compound as a pale yellow oil (92 mg, 20% yield). LC-MS $t_R$=1.06 min, [M+Na]$^+$=576.

28.2 (5-Methyl-2-oxo-2H-1,3-dioxol-4-yl)methyl 2-[4-(hydroxyamino)-3-(4-methanesulfonylphenyl)-4-methyl-5-oxo-4,5-dihydro-H-pyrazol-1-yl]acetate (5-Methyl-2-oxo-2H-1,3-dioxol-4-yl)methyl 2-[4-(hydroxyamino)-3-(4-methanesulfonylphenyl)-4-methyl-5-oxo-4,5-dihydro-1H-pyrazol-1-yl]acetate was synthesized from (5-methyl-2-oxo-2H-1,3-dioxol-4-yl)methyl 2-(4-{[(tert-butoxy)carbonyl](hydroxy)amino}-3-(4-methanesulfonylphenyl)-4-methyl-5-oxo-4,5-dihydro-1H-pyrazol-1-yl)acetate according to General Method 4 and was purified via low pH preparative HPLC to yield the title compound as a white solid (21 mg, 50% yield). LC-MS $t_R$=0.97 min, [M+H]$^+$=454, $^1$H NMR (250 MHz, DMSO-d6) δ 8.28 (d, J=8.7 Hz, 2H), 8.02 (d, J=8.6 Hz, 2H), 7.76 (d, J=2.5 Hz, 1H), 6.72 (d, J=2.5 Hz, 1H), 5.08 (s, 2H), 4.70 (dd, J=17.8, 12.6 Hz, 2H), 3.26 (s, 3H), 2.16 (s, 3H), 1.28 (s, 3H).

Example 29: Compound 29 [(5-Methyl-2-oxo-2H-1,3-dioxol-4-yl)methyl 2-[3-(4-methanesulfonylphenyl)-4-methyl-4-{[(5-methyl-2-oxo-2H-1,3-dioxol-4-yl)methoxy]amino}-5-oxo-4,5-dihydro-1H-pyrazol-1-yl]acetate]

29.1 (5-Methyl-2-oxo-2H-1,3-dioxol-4-yl)methyl 2-(4-{[(tert-butoxy)carbonyl][(5-methyl-2-oxo-2H-1,3-dioxol-4-yl) methoxy]amino}-3-(4-methanesulfonylphenyl)-4-methyl-5-oxo-4,5-dihydro-1H-pyrazol-1-yl)acetate To a solution of 2-(4-{[(tert-Butoxy)carbonyl](hydroxy)amino}-3-(4-methanesulfonylphenyl)-4-methyl-5-oxo-4,5-dihydro-1H-pyrazol-1-yl)acetic acid (50 mg, 0.11 mmol) and potassium carbonate (17.22 mg, 0.12 mmol) in DMF (1 mL) was added 4-(chloromethyl)-5-methyl-1,3-dioxol-2-one (13.61 μl, 0.12 mmol) and the mixture was stirred at room temperature for 17 hours. 4-(chloromethyl)-5-methyl-1,3-dioxol-2-one (13.61 μl, 0.12 mmol) was added and the reaction continued at room temperature for 170 minutes. Potassium carbonate (17.22 mg, 0.12 mmol) was added and the reaction stirred for an additional 2 hours. The reaction mixture was diluted with ethyl acetate (10 mL) and washed with water (10 mL). The aqueous layer was re-extracted with ethyl acetate (3×10 mL), the organics were combined, dried over magnesium sulfate, filtered and concentrated in vacuo to afford the title compound as a yellow oil (46 mg, 53% yield). LC-MS $t_R$=1.17 min, [M+Na]$^+$=688.

29.2 (5-Methyl-2-oxo-2H-1,3-dioxol-4-yl)methyl 2-[3-(4-methanesulfonylphenyl)-4-methyl-4-{[(5-methyl-2-oxo-2H-1,3-dioxol-4-yl)methoxy]amino}-5-oxo-4,5-dihydro-H-pyrazol-1-yl]acetate (5-Methyl-2-oxo-2H-1,3-dioxol-4-yl)methyl 2-[3-(4-methanesulfonylphenyl)-4-methyl-4-{[(5-methyl-2-oxo-2H-1,3-dioxol-4-yl)methoxy]amino}-5-oxo-4,5-dihydro-1H-pyrazol-1-yl]acetate was synthesized from (5-methyl-2-oxo-2H-1,3-dioxol-4-yl)methyl 2-(4-{[(tert-butoxy)carbonyl][(5-methyl-2-oxo-2H-1,3-dioxol-4-yl)methoxy]amino}-3-(4-methanesulfonylphenyl)-4-methyl-5-oxo-4,5-dihydro-1H-pyrazol-1-yl)acetate according to General Method 4 and was purified via low pH preparative HPLC to yield the title compound as a white solid (10 mg, 30% yield). LC-MS $t_R$=3.62 min, [M+Na]$^+$=588, $^1$H NMR (250 MHz, DMSO-d6) δ 8.19 (d, J=8.7 Hz, 2H), 8.00 (d, J=8.7 Hz, 2H), 7.94 (s, 1H), 5.08 (s, 2H), 4.72 (dd, J=17.8, 7.2 Hz, 2H), 4.18 (dd, J=14.6, 6.4 Hz, 2H), 3.24 (s, 3H), 2.16 (s, 3H), 2.02 (s, 3H), 1.36 (s, 3H).

Example 30: Compound 30 [4-[4-(Hydroxyamino)-1,4-dimethyl-5-oxo-4,5-dihydro-1H-pyrazol-3-yl]-N-methylbenzene-1-sulfonamide]

30.1 4-(5-Hydroxy-1,4-dimethyl-1H-pyrazol-3-yl)-N-methylbenzene-1-sulfonamide 4-(5-Hydroxy-1,4-dimethyl-1H-pyrazol-3-yl)-N-methylbenzene-1-sulfonamide was synthesized from ethyl 2-methyl-3-[4-(methylsulfamoyl)phenyl]-3-oxopropanoate and methyl hydrazine according to General Method 1 and was purified by trituration from heptane:ethyl acetate (1:1, v:v) to yield the title compound as an off white solid (0.17 g, 10% yield). LC-MS $t_R$=0.82 min, [M+H]$^+$=282.

30.2 Tert-Butyl N-{1,4-dimethyl-3-[4-(methylsulfamoyl)phenyl]-5-oxo-4,5-dihydro-1H-pyrazol-4-yl}-N-hydroxycarbamate tert-Butyl N-{1,4-dimethyl-3-[4-(methylsulfamoyl)phenyl]-5-oxo-4,5-dihydro-1H-pyrazol-4-yl}-N-hydroxycarbamate was synthesized from 4-(5-hydroxy-1,4-dimethyl-1H-pyrazol-3-yl)-N-methylbenzene-1-sulfonamide according to General Method 5 and was purified by silica gel chromatography eluting with heptane:ethyl acetate (0-90%) yielding the title compound as a yellow solid (50 mg, 20% yield). LC-MS $t_R$=1.00 min, [M+Na]$^+$=435.

30.3 4-[4-(Hydroxyamino)-1,4-dimethyl-5-oxo-4,5-dihydro-1H-pyrazol-3-yl]-N-methylbenzene-1-sulfonamide 4-[4-(Hydroxyamino)-1,4-dimethyl-5-oxo-4,5-dihydro-1H-pyrazol-3-yl]-N-methylbenzene-1-sulfonamide was synthesized from tert-butyl N-{1,4-dimethyl-3-[4-(methylsulfamoyl)phenyl]-5-oxo-4,5-dihydro-1H-pyrazol-4-yl}-N-hydroxycarbamate according to General Method 4 and was purified by acidic reverse phase HPLC yielding the title compound as a white solid (84 mg, 62% yield). LC-MS $t_R$=2.82 min, [M+H]$^+$=313, $^1$H NMR (500 MHz, DMSO-d6) δ 8.24 (d, J=7.9 Hz, 2H), 7.86 (d, J=7.9 Hz, 2H), 7.69 (s, 1H), 7.54 (d, J=5.0 Hz, 1H), 6.66 (s, 1H), 3.33 (s, 3H), 2.45 (d, J=5.0 Hz, 3H), 1.25 (s, 3H).

Example 31: Compound 31 [3a-(hydroxyamino)-2H,3H,3aH,4H,5H,6H,7H-pyrazolo[3,4-c]pyridine-3-one]

31.1 1-tert-Butyl 3-hydroxy-2H,4H,5H,6H,7H-pyrazolo[3,4-c]pyridine-6-carboxylate 1-tert-Butyl 3-hydroxy-2H,4H,5H,6H,7H-pyrazolo[3,4-c]pyridine-6-carboxylate was synthesized from 1-tert-butyl 4-ethyl 3-oxopiperidine-1,4-dicarboxylate and hydrazine hydrate according to General Method 1 and the resulting solid was purified by silica gel chromatography eluting with heptanes:ethyl acetate (20-100%), followed by methanol:ethyl acetate (0-20%) to afford the title compound as a yellow solid (223 mg, 31% yield). LC-MS $t_R$=0.88 min, [M+H]$^+$=240, $^1$H NMR (250 MHz, Chloroform-d) δ 4.44 (s, 2H), 3.60 (s, 2H), 2.44 (s, 2H), 1.47 (s, 9H).

31.2 Tert-Butyl 3a-{[(tert-butoxy)carbonyl](hydroxy)amino}-3-oxo-2H,3H,3aH,4H,5H,6H,7H-pyrazolo[3,4-c]pyridine-6-carboxylate tert-Butyl 3a-{[(tert-butoxy)carbonyl](hydroxy)amino}-3-oxo-2H,3H,3aH,4H,5H,6H,7H-pyrazolo[3,4-c]pyridine-6-carboxylate was synthesized from 1-tert-butyl 3-hydroxy-2H,4H,5H,6H,7H-pyrazolo[3,4-c]pyridine-6-carboxylate according to General Method 5 and was purified by silica gel chromatography eluting with heptanes:ethyl acetate (0-70%) to yield the title compound as a colourless oil (133 mg, 62% yield). LC-MS $t_R$=1.03 min, [M+Na]$^+$=393, 1H NMR (250 MHz, Chloroform-d) δ 8.82 (s, 1H), 7.31 (s, 1H), 4.74 (d, J=11.4 Hz, 1H), 4.21-4.03 (m, 1H), 3.73 (d, J=13.7 Hz, 1H), 3.34-3.12 (m, 1H), 2.87 (d, J=14.2 Hz, 1H), 1.73-1.54 (m, 1H), 1.47 (s, 9H), 1.45 (s, 9H)

31.3 3a-(Hydroxyamino)-2H,3H,3aH,4H,5H,6H,7H-pyrazolo[3,4-c]pyridin-3-one 3a-(Hydroxyamino)-2H,3H,3aH,4H,5H,6H,7H-pyrazolo[3,4-c]pyridin-3-one was synthesized from tert-butyl 3a-{[(tert-butoxy)carbonyl](hydroxy)amino}-3-oxo-2H,3H,3aH,4H,5H,6H,7H-pyrazolo[3,4-c]pyridine-6-carboxylate according to General Method 4 and dried by lyophilisation to yield the TFA salt of the title compound as a yellow solid (42 mg, 83% yield). LC-MS $t_R$=0.58 min, [M+H]$^+$=170, $^1$H NMR (250 MHz, DMSO-d6) δ 11.53 (s, 1H), 9.11 (s, 2H), 7.75 (s, 1H), 6.67 (s, 1H), 4.12-3.87 (m, 2H), 3.28-3.09 (m, 2H), 2.03-1.91 (m, 1H), 1.78-1.58 (m, 1H).

Example 32: Compound 32 [Methyl 2-[4-(hydroxyamino)-3-(4-methanesulfonylphenyl)-1-methyl-5-oxo-4,5-dihydro-1H-pyrazol-4-yl]acetate]

32.1 1,4-Dimethyl 2-(4-methanesulfonylbenzoyl)butanedioate

To a suspension of methyl 3-(4-methanesulfonylphenyl)-3-oxopropanoate (3 g, 11.71 mmol) in DMF (30 mL) was added potassium carbonate (1.62 g, 11.71 mmol) and methyl bromoacetate (1.19 mL, 11.71 mmol). The resulting reaction mixture was stirred for 18 hours at room temperature. Water (50 mL) was added and the resulting solution was extracted into ethyl acetate (4×100 mL). The combined organic extracts were washed with brine (100 mL), dried over sodium sulfate, filtered and concentrated in vacuo to afford an orange gum which was purified by silica gel chromatography eluting with heptanes:ethyl acetate (0-40%) to afford the title compound as a colourless gum (2.83 g, 56% yield). LC-MS tR=3.34 min, [M+Na]$^+$=351, $^1$H NMR (500 MHz, Chloroform-d) δ 8.21 (d, J=8.5 Hz, 2H), 8.08 (d, J=8.5 Hz, 2H), 4.88 (dd, J=9.0, 5.4 Hz, 1H), 3.69 (s, 3H), 3.68 (s, 3H), 3.21 (d, J=9.0 Hz, 1H), 3.09 (s, 3H), 3.07 (d, J=5.6 Hz, 1H).

32.2 Methyl 2-[5-hydroxy-3-(4-methanesulfonylphenyl)-1-methyl-1H-pyrazol-4-yl]acetate Methyl 2-[5-hydroxy-3-(4-methanesulfonylphenyl)-1-methyl-1H-pyrazol-4-yl]acetate was synthesized from 1,4-dimethyl 2-(4-methanesulfonylbenzoyl)butanedioate and methyl hydrazine according to General Method 1 and the resulting solid was triturated from DCM to afford the title compound as an off-white solid (210 mg, 9% yield). LC-MS $t_R$=2.66 min, [M+H]$^+$=325, $^1$H NMR (500 MHz, Methanol-d4) δ 8.08 (d, J=8.4 Hz, 2H), 7.66 (d, J=8.4 Hz, 2H), 3.62 (s, 3H), 3.57 (s, 3H), 3.33 (s, 2H), 3.18 (s, 3H).

32.3 Methyl 2-(4-{[(tert-butoxy)carbonyl](hydroxy)amino}-3-(4-methanesulfonylphenyl)-1-methyl-5-oxo-4,5-dihydro-1H-pyrazol-4-yl)acetate Methyl 2-(4-{[(tert-butoxy)carbonyl](hydroxy)amino}-3-(4-methanesulfonylphenyl)-1-methyl-5-oxo-4,5-dihydro-1H-pyrazol-4-yl)acetate was synthesized from methyl 2-[5-hydroxy-3-(4-methanesulfonylphenyl)-1-methyl-1H-pyrazol-4-yl]acetate according to General Method 5 and was purified by silica gel chromatography eluting with heptanes:ethyl acetate (0-75%) to yield the title compound as an orange oil (95 mg, 41% yield). LC-MS $t_R$=3.34 min, [M+Na]$^+$=478, $^1$H NMR (500 MHz, Methanol-d4) δ 8.16-8.13 (m, 2H), 8.04-8.01 (m, 2H), 3.52 (s, 3H), 3.39 (s, 3H), 3.16 (s, 3H), 1.31 (s, 9H).

32.4 Methyl 2-[4-(hydroxyamino)-3-(4-methanesulfonylphenyl)-1-methyl-5-oxo-4,5-dihydro-1H-pyrazol-4-yl]acetate Methyl 2-[4-(hydroxyamino)-3-(4-methanesulfonylphenyl)-1-methyl-5-oxo-4,5-dihydro-1H-pyrazol-4-yl]acetate was synthesized from methyl 2-(4-{[(tert-butoxy)carbonyl](hydroxy)amino}-3-(4-methanesulfonylphenyl)-1-methyl-5-oxo-4,5-dihydro-1H-pyrazol-4-yl)acetate according to General Method 4 and the excess TFA was removed using DCM/heptane azeotropes. The crude product was purified by low pH preparative HPLC and isolated by lyophilisation to yield the title compound as a white powder (17 mg, 29% yield). LC-MS $t_R$=2.63 min, [M+H]$^+$=356, $^1$H NMR (500 MHz, DMSO-d6) δ 8.21-8.18 (m, 2H), 8.00-7.97 (m, 2H), 7.78 (d, J=2.6 Hz, 1H), 6.73 (d, J=2.5 Hz, 1H), 3.43 (s, 3H), 3.32 (s, 3H), 3.26 (s, 3H), 2.91 (s, 2H).

Example 33: Compound 55 [4-(Hydroxyamino)-3-(4-methanesulfonylphenyl)-4-methyl-1-(piperidin-4-yl)-4,5-dihydro-1H-pyrazol-5-one]

33.1 Tert-Butyl 4-[5-hydroxy-3-(4-methanesulfonylphenyl)-4-methyl-1H-pyrazol-1-yl]piperidine-1-carboxylate To solution of methyl 3-(4-methanesulfonylphenyl)-2-methyl-3-oxopropanoate (500 mg, 1.85 mmol) and tert-butyl 4-hydrazinylpiperidine-1-carboxylate hydrochloride (512.26 mg, 2.03 mmol) in ethanol (6 mL) was added triethylamine (0.26 mL, 1.85 mmol) and the reaction mixture was heated to 80° C. for 19 hours in a sealed tube. The reaction mixture was allowed to cool to room temperature and concentrated under reduced pressure. The resulting crude compound was purified by silica gel chromatography eluting with 0-100% heptanes:ethyl acetate to yield the title compound as a white foam (0.55 g, 68% yield). LC-MS $t_R$=1.06 min, [M−H]$^-$=434.

33.2 Tert-Butyl 4-(4-{[(tert-butoxy)carbonyl](hydroxy)amino}-3-(4-methanesulfonylphenyl)-4-methyl-5-oxo-4,5-dihydro-H-pyrazol-1-yl)piperidine-1-carboxylate tert-Butyl 4-(4-{[(tert-butoxy)carbonyl](hydroxy)amino}-3-(4-methanesulfonylphenyl)-4-methyl-5-oxo-4,5-dihydro-1H-pyrazol-1-yl)piperidine-1-carboxylate was synthesized from tert-butyl 4-[5-hydroxy-3-(4-methanesulfonylphenyl)-4-methyl-1H-pyrazol-1-yl]piperidine-1-carboxylate according to General Method 5 and was purified by silica gel chromatography eluting with 40-80% ethyl acetate:Heptane to yield the title compound as a white foam (0.61 g, 85% yield). LC-MS $t_R$=1.20 min, [M+Na]$^+$=589. $^1$H NMR (500 MHz, Chloroform-d) δ 8.16-8.12 (m, 2H), 8.02-7.98 (m, 2H), 7.84 (s, 1H), 4.02-3.97 (m, 2H), 3.80 (dd, J=13.8, 7.4 Hz, 1H), 3.57 (dd, J=13.8, 6.6 Hz, 1H), 3.40 (tdd, J=11.7, 7.0, 2.2 Hz, 2H), 3.07 (s, 3H), 2.19-2.08 (m, 1H), 1.77-1.59 (m, 9H), 1.50-1.37 (m, 2H), 1.31 (s, 9H).

33.3 4-(Hydroxyamino)-3-(4-methanesulfonylphenyl)-4-methyl-1-(piperidin-4-yl)-4,5-dihydro-1H-pyrazol-5-one 4-(Hydroxyamino)-3-(4-methanesulfonylphenyl)-4-methyl-1-(piperidin-4-yl)-4,5-dihydro-1H-pyrazol-5-one was synthesized from tert-butyl 4-(4-{[(tert-butoxy)carbonyl](hydroxy)amino}-3-(4-methanesulfonylphenyl)-4-methyl-5-oxo-4,5-dihydro-1H-pyrazol-1-yl)piperidine-1-carboxylate according to General Method 4 and was purified by low pH preparative HPLC to yield the title compound as a white powder (10 mg, 5% yield). LC-MS $t_R$=0.97 min, [M+H]$^+$=367, $^1$H NMR (500 MHz, DMSO-d6) δ 8.40 (br. s, 1H), 8.26 (d, J=8.7 Hz, 2H), 8.04 (d, J=8.6 Hz, 2H), 7.71 (d, J=2.6 Hz, 1H), 6.67 (d, J=2.6 Hz, 1H), 4.45-4.35 (m, 1H), 3.43-3.37 (m, 2H), 3.26 (s, 3H), 3.15-3.06 (m, 2H), 2.22-2.03 (m, 2H), 2.02-1.94 (m, 1H), 1.91-1.83 (m, 1H), 1.25 (s, 3H).

Example 34: Compound 56 [4-(Hydroxyamino)-3-(4-methanesulfonylphenyl)-4-methyl-1-(oxan-4-ylmethyl)-4,5-dihydro-1H-pyrazol-5-one]

34.1 3-(4-Methanesulfonylphenyl)-4-methyl-1-(oxan-4-ylmethyl)-1H-pyrazol-5-ol To solution of methyl 3-(4-methanesulfonylphenyl)-2-methyl-3-oxopropanoate (725 mg, 2.68 mmol) and (oxan-4-ylmethyl)hydrazine hydrochloride (491.68 mg, 2.95 mmol) in ethanol (6 mL) was added triethylamine (0.37 mL, 2.68 mmol) and the reaction mixture was heated to 80° C. for 19 hours in a sealed tube. The reaction mixture was allowed to cool to room temperature and concentrated under reduced pressure. The resulting crude compound was purified by silica gel chromatography eluting with 0-100% heptanes:ethyl acetate to yield the title compound as an off white foam (0.49 g, 45% yield). LC-MS $t_R$=0.88 min, [M+H]+=351, $^1$H NMR (250 MHz, DMSO-d6) δ 7.97-7.83 (m, 4H), 4.10 (s, 1H), 3.84 (d, J=6.9 Hz, 3H), 3.30-3.25 (m, 2H), 3.22 (s, 3H), 3.18 (d, J=2.9 Hz, 2H), 2.09 (s, 3H), 2.05-1.95 (m, 1H), 1.53-1.39 (m, 2H), 1.26 (qd, J=12.0, 4.4 Hz, 2H).

34.2 Tert-Butyl N-hydroxy-N-[3-(4-methanesulfonylphenyl)-4-methyl-1-(oxan-4-ylmethyl)-5-oxo-4,5-dihydro-H-pyrazol-4-yl]carbamate tert-Butyl N-hydroxy-N-[3-(4-methanesulfonylphenyl)-4-methyl-1-(oxan-4-ylmethyl)-5-oxo-4,5-dihydro-1H-pyrazol-4-yl]carbamate was synthesised from 3-(4-methanesulfonylphenyl)-4-methyl-1-(oxan-4-ylmethyl)-1H-pyrazol-5-ol according to General Method 5 and was purified by silica gel chromatography eluting with 40-80% ethyl acetate:heptane to yield the title compound as an off white foam (0.3 g, 45% yield). LC-MS $t_R$=1.05 min, [M+Na]$^+$=504, $^1$H NMR (500 MHz, Chloroform-d) δ 8.05 (d, J=8.7 Hz, 2H), 7.94-7.89 (m, 2H), 7.50 (s, 1H), 4.20 (ddt, J=11.4, 8.2, 4.1 Hz, 2H), 3.00 (s, 3H), 2.88-2.74 (m, 2H), 1.93 (d, J=10.6 Hz, 1H), 1.80 (t, J=12.1 Hz, 2H), 1.65 (s, 3H), 1.63-1.57 (m, 4H), 1.42 (s, 9H).

34.3 4-(Hydroxyamino)-3-(4-methanesulfonylphenyl)-4-methyl-1-(oxan-4-ylmethyl)-4,5-dihydro-1H-pyrazol-5-one 4-(Hydroxyamino)-3-(4-methanesulfonylphenyl)-4-methyl-1-(oxan-4-ylmethyl)-4,5-dihydro-1H-pyrazol-5-one was synthesized from tert-butyl N-hydroxy-N-[3-(4-methanesulfonylphenyl)-4-methyl-1-(oxan-4-ylmethyl)-5-oxo-4,5-dihydro-1H-pyrazol-4-yl]carbamate according to General Method 4 and was purified by low pH preparative HPLC to yield the title compound as a white powder (205 mg, 85% yield). LC-MS $t_R$=2.01 min, [M+H]$^+$=382, $^1$H NMR (500 MHz, DMSO-d6) δ 8.28 (d, J=8.6 Hz, 2H), 8.01 (d, J=8.6 Hz, 2H), 7.70 (d, J=2.4 Hz, 1H), 6.59 (d, J=2.2 Hz, 1H), 3.87-3.78 (m, 2H), 3.67-3.55 (m, 2H), 3.28-3.20 (m, 5H), 2.04-1.94 (m, 1H), 1.63-1.52 (m, 2H), 1.31-1.16 (m, 5H).

4.2 Example 35: Nitroxyl Production from Pyrazolone Derivative Compounds as Determined via $N_2O$ Quantification in the Headspace Protocol Nitrous oxide ($N_2O$) is produced via the dimerization and dehydration of HNO, and is the most common marker for nitroxyl production (Fukuto et al., *Chem. Res. Toxicol.* 18:790-801 (2005)). Nitroxyl, however, can also be partially quenched by oxygen to provide a product that does not produce $N_2O$ (see Mincione et al., *J. Enzyme Inhibition* 13:267-284 (1998); and Scozzafava et al., *J. Med. Chem.* 43:3677-3687 (2000)). Using either nitrous oxide gas or Angeli's salt ("AS") as a standard, the relative amounts of $N_2O$ released from compounds of the disclosure is examined via gas chromatography ("GC") headspace analysis.

A procedure for determining the relative amounts of $N_2O$ released from compounds of the disclosure is as follows. GC is performed on an Agilent gas chromatograph equipped with a split injector (10:1 splitting), microelectron capture detector, and a HP-MOLSIV 30 m×0.32 mm×25 μm molecular sieve capillary column. Helium is used as the carrier (4 mL/min) gas and nitrogen is used as the make-up (20 mL/min) gas. The injector oven and the detector oven are kept at 200° C. and 325° C., respectively. All nitrous oxide analyses are performed with the column oven held at a constant temperature of 200° C.

All gas injections are made using an automated headspace analyzer. Vial pressurization is 15 psi. The analyzer's sample oven, sampling valve, and transfer line are kept at 40° C., 45° C., and 50° C., respectively. The oven stabilization, vial pressurization, loop fill, loop equilibration, and sample injection times are 1.00 min., 0.20 min., 0.20 min., 0.05 min., and 1.00 min., respectively.

All determinations use a batch of nominal 20 mL headspace vials with volumes pre-measured for sample uniformity (actual vial volume varied by <2.0% relative standard deviation (n=6)). The average vial volume for the batch is determined from six randomly-selected vials by calculating the weight difference between the capped and sealed empty (i.e., air-filled) vial and the capped and sealed deionized water-filled vial using the known density of deionized water, then averaging. Blanks are prepared by sealing and capping 2 vials then purging each for 20 seconds with a gentle argon stream. Nitroxyl standards are prepared by sealing and capping four vials then purging each for 1 minute with a gentle stream, from a gas cylinder, of a 3000 ppm nitroxyl standard.

"Standards" are prepared by, in duplicate, accurately weighing 10±0.5 mg of a compound of formula (Ia), (Ib), (Ic), (Id), (Ie), (If), (Ig), (Ih), (Ii) or (Ij) or a compound from Table 1 and adding it to each 4 mL vial. Using an auto pipette, 1 mL of argon-purged anhydrous DMF (Sigma-Aldrich) is added to each 4 mL vial to form a stock solution for each sample and the vials are capped and shaken and/or sonicated to insure complete dissolution upon visual observation. Using an auto pipette, 20 mL vials are charged with 5 mL of PBS (purged for at least 30 min. with argon prior to use), purged with argon for at least 20 sec., and sealed with a rubber septum. Using a 50 μL syringe, 50 μL of the stock solution is injected into each 20 mL vial containing the PBS.

Samples are prepared as follows. In duplicate, 18±1 mg of each sample is accurately weighed into each 4 mL vial. Using an auto pipette, 1 mL of argon-purged anhydrous DMF is added to each 4 mL vial to form a sample stock solution for each sample and the vials are capped and shaken and/or sonicated to insure complete sample dissolution upon visual observation. Using an auto pipette, 20 mL vials are charged with 5 mL of PBS (purged for at least 30 min. with argon prior to use), purged with argon for at least 20 sec., and sealed with a rubber septum. The vials are equilibrated for at least 10 min. at 37° C. in a dry block heater. Thereafter, using a 50 μL syringe, 50 μL of a sample stock solution is injected into each 20 mL vial containing the PBS. The vials are then held at 37° C. in the dry block heater for a time period such that the sum of the time spent in the dry block heater plus the time spent in the automated headspace analyzer oven before sample injection equals the desired incubation time.

Another procedure for determining the relative amounts of $N_2O$ released from compounds of the disclosure is as follows. GC is performed on a Varian CP-3800 instrument equipped with a 1041 manual injector, electron capture detector, and a 25 m 5 Å molecular sieve capillary column. Grade 5.0 nitrogen is used as both the carrier (8 mL/min) and the make-up (22 mL/min) gas. The injector oven and the detector oven are kept at 200° C. and 300° C., respectively. All nitrous oxide analyses are performed with the column oven held at a constant temperature of 150° C. All gas injections are made using a 100 μL gas-tight syringe with a sample-lock. Samples are prepared in 15 mL amber headspace vials with volumes pre-measured for sample uniformity (actual vial volume ranges from 15.19 to 15.20 mL). Vials are charged with 5 mL of PBS containing diethylenetriamine pentaacetic anhydride ("DTPAN"), purged with argon, and sealed with a rubber septum. The vials are equilibrated for at least 10 minutes at 37° C. in a dry block heater. A 10 mM stock solution of AS is prepared in 10 mM sodium hydroxide, and solutions of the nitroxyl donors are prepared in either acetonitrile or methanol and used immediately after preparation. From these stock solutions, 50 μL is introduced into individual thermally-equilibrated headspace vials using a 100 μL gas-tight syringe with a sample-lock to provide final substrate concentrations of 0.1 mM. Substrates are then incubated for 90 minutes or 360 minutes. The headspace (60 μL) is then sampled and injected five successive times into the GC apparatus using the gas-tight syringe with a sample lock. This procedure is repeated for 2 or more vials per donor.

4.3 Example 36: Nitroxyl Production from Pyrazolone Derivative Compounds as Determined Via $^1$H NMR Protocol Using TXPTS The $^1$H NMR protocol is based on an HPLC protocol developed by S. Bruce King and coworkers (Reisz et al., *Org. Lett.* 11:2719-2721 (2009), Reisz et al., *J. Am. Chem. Soc.* 133:11675-11685 (2011) and Guthrie et al., *J. Org. Chem.* 80:1338-1348 (2015)). According to this procedure, the amount of HNO released from a pyrazolone derivative compound is determined by reacting the compound with the triarylphosphine TXPTS and monitoring the resulting aza-ylide formation. Scheme 1 shows the conversion of compound of formula (Ia) to its corresponding pyrazol-5-ol (II) and HNO (trapped as one molecule of aza-ylide and one molecule of phosphine oxide).

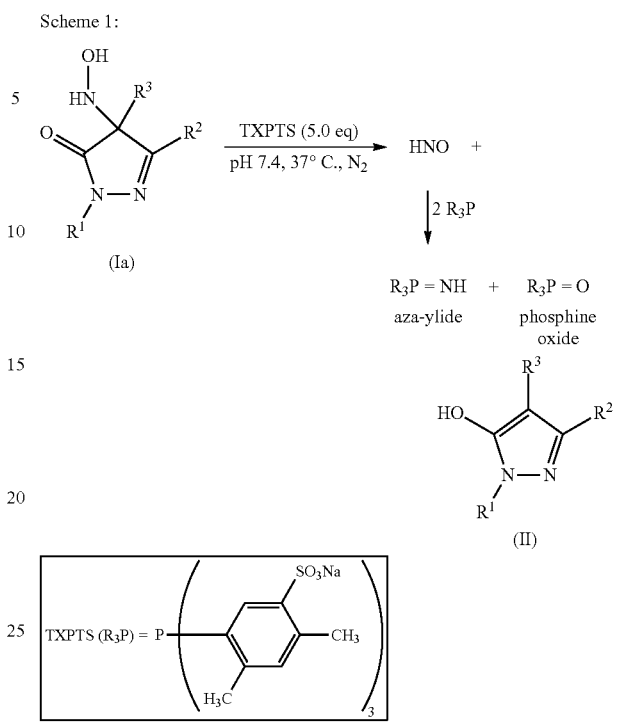

The procedure for determining the amount of HNO released from compounds of the disclosure is as follows.

Tris(4,6-dimethyl-3-sulfanatophenyl)phosphine trisodium salt (TXPTS) is of reagent grade and is used without further purification. Synthetic TXPTS aza-ylide is obtained through the amidation of TXPTS using hydroxylamine O-sulfonic acid in water (Armstrong et al., *Org. Lett.* 7:713-716 (2005)). All other materials are of reagent grade and used without further purification.

All $^1$H NMR spectra are obtained in an adjusted-to pH 7.4 solution containing 0.25 M phosphate buffer, 0.2 mM of the metal chelator diethylenetriaminepentaacetic acid ("DTPAC"), and 10% $D_2O$ on a Bruker Avance 250 MHz FT-NMR spectrometer using a 1 second presaturation pulse to suppress the water signal. To a nitrogen-purged NMR solution (1.00 mL) containing TXPTS (3.3 mg, 5 mM) is added a pyrazolone derivative compound (10 μL of 100 mM in methanol-$d_4$) to give 1 mM as the initial concentration of the pyrazolone derivative compound. The solution is briefly mixed, about 0.5 mL is transferred to a nitrogen-purged NMR tube and an initial $^1$H NMR spectrum (time=0) is obtained. Thereafter, the sample is internally incubated at 37° C. and $^1$H NMR spectra are collected at regular intervals for 8 hours.

The HNO donating pyrazolone derivative compound, by-product (e.g., (II) in Scheme 1), and TXPTS aza-ylide concentrations, determined from NMR spectra taken over 8 hours, are plotted as a function of time, and each data set is fitted to a single exponential function. The NMR half-lives for the disappearance of the HNO donating pyrazolone derivative compound and the appearance of by-product and TXPTS aza-ylide are determined from the respective plots.

4.4 Example 37: In Vitro Plasma Stability of Pyrazolone Derivative Compounds in Plasma A procedure for determining in vitro plasma stability of compounds of the disclosure is as follows. The assay system comprises plasma from rat, dog or human (at least 3 donors, male, pooled) at pH 7.4, and (ii) an anticoagulant (sodium heparin or sodium citrate). Each test compound (5 µM) is incubated in plasma at 37° C. on a THERMOMIXER® with shaking. Three samples (n=3) are taken at each of seven sampling time points: 0, 10, 30, 60, 90, 180 and 360 minutes. The samples are immediately combined with 3 volumes (i.e., 3 times the volume of plasma) of acetonitrile containing 1% formic acid and an internal standard to terminate the reaction. AB SCIEX API 3000 LC-MS/MS analysis of the test compounds is performed without a standard curve. Plasma half-lives ($T_{1/2}$) of the test compounds are determined from graphs of the percent remaining values using the peak area response ratio.

4.4 Example 38: Solid-State Stability of Pyrazolone Derivative Compounds

A procedure for determining solid-state stability of the compounds of the disclosure is as follows. Solid, powdered samples of test compounds are sealed in double polyethylene bags and stored at 40° C., 75% relative humidity ("RH") for up to 3 months. Initially and after 1 month, 2 months, and 3 months of storage, the samples are analyzed for purity, as determined by high performance liquid chromatography ("HPLC"). Additionally, test compounds are admixed at a level of 50% by weight with one of the following excipients before stability testing: lactose, microcrystalline cellulose, or croscarmellose sodium. The resulting admixtures are also stored as described above then analyzed for purity of the pyrazolone derivative component, as determined by HPLC. The HPLC apparatus comprises a quaternary or binary pump, an auto sampler, a thermostated column compartment, and a UV/visible detector. The HPLC measurement conditions are as follows:

Column: Zorbax Eclipse XDB-C18, 2.1×50 mm, 3.5 µm (Agilent Technologies, Santa Clara, Calif.)
Injection Volume: 2 µL
Detection Wavelength: 220 nm
Mobile Phase A: 0.1% by volume formic acid ("FA") in water
Mobile Phase B: 0.1% by volume FA in acetonitrile
Diluent: About 0.2 mg sample/mL acetonitrile
Gradient:

| Time (min) | % A | % B |
|---|---|---|
| 0 | 99 | 1 |
| 15 | 70 | 30 |
| 20 | 99 | 1 |
| 23 | 99 | 1 |

Flow Rate: 0.8 mL/min
Column Temperature: 25° C.

4.5 Example 39: Separation of Pyrazolone Derivative Compound Enantiomers

The pyrazolone ring carbon atom of each pyrazolone derivative compound that is not bonded to oxo is optically active; thus, these compounds can exist as, inter alia, enantiomers. The enantiomers of a pyrazolone derivative compound can be separated by, e.g., chiral preparative supercritical fluid chromatography ("SFC") using the following procedure. A CHIRALPAK IA (250 mm×20 mm×5 µm) SFC semi-prep column (Daicel Corp., Osaka, Japan) eluting with 25% methanol (plus diethylamine):75% carbon dioxide can be used. The flow rate is 50 mL/min. UV detection at 215 nm is used.

In one embodiment, a pyrazolone derivative compound of the disclosure is present as a racemic mixture. In another embodiment, a pyrazolone derivative compound of the disclosure is present as a substantially pure enantiomer, for example, in about 90% or greater enantiomeric excess in one embodiment, in about 92% or greater enantiomeric excess in another embodiment, in about 94% or greater enantiomeric excess in another embodiment, in about 95% or greater enantiomeric excess in another embodiment, in about 96% or greater enantiomeric excess in another embodiment, in about 97% or greater enantiomeric excess in another embodiment, in about 98% or greater enantiomeric excess in another embodiment, in about 99% or greater enantiomeric excess in another embodiment, in about 99.5% or greater enantiomeric excess in another embodiment, and in about 99.8% or greater enantiomeric excess in another embodiment.

4.6 Example 40: Pharmacodynamic Activity of Pyrazolone Derivative Compounds in Dogs The effect of compounds of the disclosure on blood pressure in freely moving telemetered normal beagle dogs (n=3) after single oral doses is evaluated. The animals are surgically implanted with a pressure transducer equipped telemetry transmitter. The transmitter assembly is secured internally and a fluid-filled catheter is placed into the abdominal aorta to allow for collection of cardiovascular data. To evaluate cardiovascular effects, 3 dogs are given single oral doses of a test compound (100% PEG300 in gelatin capsules) at a concentration of 100 mg/mL and at doses of 30 mg/kg. Systemic blood pressure and heart rate are evaluated continuously for 2 hr before and for 24 hr after dosing. To compare the pharmacodynamic activity for all tested compounds, the mean systolic blood pressure (SBP) decrease during the first 2 hr post-dose is determined relative to the baseline SBP (30-120 min pre-dose).

4.7 Example 41: Pharmacokinetic Activity of Pyrazolone Derivative Compounds in Rats Male Sprague-Dawley rats (n=3/group) were assigned to Groups 1 to 6. Group 1 was administered an intravenous bolus dose of 1 mg/kg a test compound in 30% polyethyleneglycol-200 (PEG-200): 10% DMSO in saline. Serial samples of blood were collected at 0.05, 0.15, 0.75, 1.5, 3, 6, 10 and 24 hours via an implanted jugular vein catheter. Groups 2-6 received oral gavage doses of a test compound, formulated in 100% PEG300 (10 mg/kg). Rats from groups 2-6 were sacrificed at 0.25, 2, 6, 10 or 24 hours post-dose and blood samples (1 mL via cardiac puncture) were collected into chilled tubes containing $K_2EDTA$ as the anticoagulant. CSF and brain tissue were also collected at these time points. Blood samples were immediately centrifuged at 3000 g for 5 minutes under refrigerated conditions (4° C.). Plasmas and CSF samples were mixed with an aqueous solution of ascorbic acid to reach a final concentration of 2%. Brain, plasma and CSF samples were stored at −80° C. until analysis. The test compound and by-product concentrations were determined by LC-MS/MS. The eluent from a reversed-phase gradient (water/acetonitrile both containing 0.1% v/v formic acid) on a 1290 UHPLC system (Agilent Technologies, Stockport, UK) was introduced by positive electrospray ionization into an API6500 mass spectrometer (AB Sciex, Warrington, UK) and analyzed by multiple reaction monitoring (MRM). The lower limit of quantification (LLOQ) was in the range 1-10 ng/mL for the test compound and by-products. The mean plasma concentration-time data for each group were used to calculate pharmacokinetic parameters of the test compound and by-products with the software program Phoenix WinNonlin version 6.4 (Certara L. P., Princeton, N.J.).

Following IV administration of Compound 6, a high plasma clearance (41±2 ml/min/kg) and a moderate volume of distribution (1.1±0.1 L/kg) resulted in a short half-life of 0.4±0.01 h. A mean $C_0$ of 110±10 ng/mL was observed.

Following PO administration of Compound 6, a mean $C_{max}$ of 8 ng/mL was observed at a median $T_{max}$ of 0.25 h. There were insufficient data points to calculate PK parameters.

A $C_{max}$ at 0.25 h of 8±2 ng/g and 26±18 ng/mL was observed in brain and CSF samples, respectively. This resulted in a mean brain:plasma ratio of 1.1 (0.25 h), and a mean CSF:plasma ratio of 4 (0.25-2 h).

The product of ester hydrolysis, 2-[4-(hydroxyamino)-3-(4-methanesulfonylphenyl)-4-methyl-5-oxo-4,5-dihydro-1H-pyrazol-1-yl]acetic acid (Compound 6a), was the major drug-related component observed in the samples. A plasma $C_{max}$ of Compound 6a of 5215 ng/mL (700-fold the concentration of parent compound) was observed at a median $T_{max}$ of 0.25 h following PO administration, rising to 2000-fold the concentration of parent compound by 2 h. A $C_{max}$ at 2 h of 85±22 ng/g and 107±33 ng/mL was observed in brain and CSF samples, respectively. The amount in brain was low, suggesting the concentration may be restricted to the vasculature around the brain.

The products of HNO release ethyl 2-[5-hydroxy-3-(4-methanesulfonylphenyl)-4-methyl-1H-pyrazol-1-yl]acetate plus ester hydrolysis and HNO release 2-[5-hydroxy-3-(4-methanesulfonylphenyl)-4-methyl-1H-pyrazol-1-yl]acetic acid), were detected at much lower levels in plasma, brain and CSF.

In conclusion, it is apparent that Compound 6 was very well absorbed after oral dosing. It was then rapidly metabolized at the ester function thus limiting brain exposure of Compound 6 whilst concomitantly revealing the carboxylic acid prodrug (Compound 6a), which itself was restricted to the periphery.

Traces of Compound 6 and Compound 6a were observed when analyzing brain samples; however, these were at such low levels that it is believed that these levels are due to contamination of the brain samples with blood.

While the invention has been disclosed in some detail by way of illustration and example for purposes of clarity of understanding, it is apparent to those in the art that various changes may be made and equivalents may be substituted without departing from the true spirit and scope of the invention. Therefore, the description and examples should not be construed as limiting the scope of the invention.

All references, publications, patents, and patent applications disclosed herein are hereby incorporated by reference in their entirety.

What is claimed is:
1. A compound of formula (Ie)

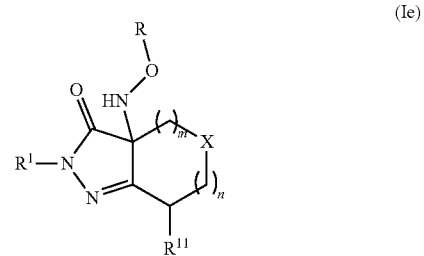

or a pharmaceutically acceptable salt thereof, wherein:
$R^1$ is H, $(C_1-C_6)$alkyl, (5- or 6-membered)heteroaryl or phenyl, wherein said alkyl, heteroaryl, and phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)O(5-methyl-2-oxo-2H-1,3-dioxol-4-ylmethyl), —C(=O)NR⁴R⁵, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)($C_1-C_6$)alkyl, —NR⁴R⁵, N—($C_1-C_6$)alkylaminosulfonyl, and N,N-di($C_1-C_6$)alkylaminosulfonyl;
X is CH₂, O, NH, N($C_1-C_6$)alkyl, N(C=O)($C_1-C_6$)alkyl, N(CO)phenyl, S, SO, or SO₂, wherein said phenyl is unsubstituted to substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR⁴R⁵, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)₂—NH₂, —S(O)₂—NR⁶R⁷, —S(O)₂-phenyl, —S(O)₂-(5-, 6-, or 7-membered)heterocycloalkyl, —S(=O)(=NR⁸)($C_1-C_6$)alkyl, —NR⁴R⁵, N—($C_1-C_6$)alkylaminosulfonyl, and N,N-di($C_1-C_6$)alkylaminosulfonyl;
m is 0, 1, 2, 3, 4, or 5;
n is 0, 1, 2, 3, 4, or 5;
$R^{11}$ is H, $(C_1-C_6)$alkyl or phenyl, wherein said alkyl and said phenyl are unsubstituted or substituted with 1, 2, 3, 4, or 5 substituent(s) independently selected from halo, $(C_1-C_6)$alkyl, $(C_1-C_4)$haloalkyl, $(C_1-C_4)$perhaloalkyl, $(C_1-C_6)$alkoxy, $(C_1-C_4)$haloalkoxy, $(C_1-C_4)$perhaloalkoxy, —C(=O)OH, —C(=O)O($C_1-C_6$)alkyl, —C(=O)NR⁴R⁵, —C(=O)-(5-, 6-, or 7-membered)heterocycloalkyl, (5-, 6-, or 7-membered)heterocycloalkyl, $(C_1-C_6)$alkylsulfanyl, $(C_1-C_4)$haloalkylsulfanyl, $(C_1-C_4)$perhaloalkylsulfanyl, $(C_1-C_6)$alkylsulfinyl, $(C_1-C_6)$alkylsulfonyl, $(C_3-C_6)$cycloalkylsulfonyl, $(C_1-C_4)$haloalkylsulfinyl, $(C_1-C_4)$haloalkylsulfonyl, $(C_1-C_4)$perhaloalkylsulfinyl, $(C_1-C_4)$perhaloalkylsulfonyl, —S(O)$_2$—NH$_2$, —S(O)$_2$—NR$^6$R$^7$, —S(O)$_2$-phenyl, —S(O)$_2$-(5-, 6-, or 7-membered)heterocycloalkyl, —S(=O)(=NR$^8$)(C$_1$-C$_6$)alkyl, —NR$^4$R$^5$, N—(C$_1$-C$_6$)alkylaminosulfonyl, and N,N-di(C$_1$-C$_6$)alkylaminosulfonyl;

R$^4$, R$^5$, R$^6$ and R$^7$ are each independently H or (C$_1$-C$_6$)alkyl; R$^8$ is H, —(C=O)(C$_1$-C$_6$)alkyl or —(C=O)(C$_1$-C$_4$)perhaloalkyl; and R is hydrogen, —COH, —CO—(C$_1$-C$_6$)alkyl, —CO—(C$_2$-C$_4$)alkenyl, —CO-phenyl, —CO-benzyl, —CO— cyclopentyl, —CO-cyclohexyl, —CO-(5-, 6-, or 7-membered)heterocycloalkyl, —CO-benzyloxy, —CO—O—(C$_1$-C$_6$)alkyl, —CO—NH$_2$, —CO—NH—(C$_1$-C$_4$)alkyl, or —CO—N((C$_1$-C$_4$)alkyl)$_2$, wherein said —(C$_1$-C$_6$)alkyl, —(C$_2$-C$_4$)alkenyl, phenyl, benzyl, cyclopentyl, cyclohexyl, -(5-, 6-, or 7-membered)heterocycloalkyl, benzyloxy, —O—(C$_1$-C$_6$)alkyl, —NH—(C$_1$-C$_4$)alkyl, or —N((C$_1$-C$_4$)alkyl)$_2$ can be unsubstituted or substituted with 1, 2 or 3 substituents selected from the group consisting of halo, —(C$_1$-C$_6$)alkyl, —(C$_2$-C$_4$)alkenyl, —(C$_2$-C$_3$)alkynyl, -(5- or 6-membered)heteroaryl, —O—(C$_1$-C$_6$)alkyl, —S—(C$_1$-C$_6$)alkyl, —C(halo)$_3$, —CH(halo)$_2$, —CH$_2$(halo), —CN, —NO$_2$, —NH$_2$, —NH—(C$_1$-C$_4$)alkyl, —N(—(C$_1$-C$_4$)alkyl)$_2$, —C(O)(C$_1$-C$_4$)alkyl, —C(O)O(C$_1$-C$_4$)alkyl, —OC(O)(C$_1$-C$_4$)alkyl, —OC(O)NH$_2$, —S(O)(C$_1$-C$_4$)alkyl, —S(O)$_2$(C$_1$-C$_4$)alkyl and 5-methyl-2-oxo-2H-1,3-dioxol-4-ylmethyl.

2. The compound of claim 1, wherein R$^{11}$ is H or (C$_1$-C$_6$)alkyl.

3. The compound of claim 1, wherein R$^{11}$ is H.

4. The compound of claim 1, wherein R is hydrogen, —CO—(C$_1$-C$_6$)alkyl, —CO— phenyl, —CO-benzyl, —CO—NH$_2$ or 5-methyl-2-oxo-2H-1,3-dioxol-4-ylmethyl.

5. The compound of claim 1, wherein R is hydrogen.

6. The compound of claim 4, wherein R$^1$ is H or (C$_1$-C$_6$)alkyl.

7. The compound of claim 1, wherein R$^1$ is H.

8. The compound of claim 1, wherein X is CH$_2$, O, NH, N(C$_1$-C$_6$)alkyl, S, SO, or SO$_2$.

9. The compound of claim 8, wherein X is CH$_2$.

10. The compound of claim 1, wherein m is 0, 1 or 2.

11. The compound of claim 10, wherein m is 1.

12. The compound of claim 1, wherein n is 0, 1 or 2.

13. The compound of claim 12, wherein n is 1.

14. The compound of claim 1, wherein X is CH$_2$, O, NH, N(C$_1$-C$_6$)alkyl, S, SO, or SO$_2$; and n is 0, 1 or 2.

15. The compound of claim 1, wherein m is 0, 1 or 2; and n is 0, 1 or 2.

16. The compound of claim 1, wherein X is CH$_2$, O, S, SO, or SO$_2$; m is 0, 1 or 2; and n is 0, 1 or 2.

17. The compound of claim 1, wherein the compound is

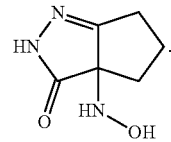

18. A pharmaceutical composition comprising the compound of claim 1, and at least one pharmaceutically acceptable excipient.

19. A method of treating a cardiovascular disease, comprising administering an effective amount of the compound of claim 1 to a patient in need thereof.

* * * * *